(12) United States Patent
Olsen et al.

(10) Patent No.: US 7,879,893 B2
(45) Date of Patent: Feb. 1, 2011

(54) LIGANDS FOR THE HISB10 $ZN^{2+}$ SITES OF THE R-STATE INSULIN HEXAMER

(75) Inventors: Helle Birk Olsen, Allerod (DK); Niels C. Kaarsholm, Vanlose (DK); Peter Madsen, Bagsvaerd (DK); Soren Ostergaard, Bronshoj (DK); Svend Ludvigsen, Lyuge (DK); Palle Jakobsen, Vaerlose (DK); Anders Klarskov Petersen, Naerum (DK); Dorte Bjerre Steensgaard, Copenhagen (DK)

(73) Assignee: Novo Nordisk A/S, Bagsvaerd (DK)

( * ) Notice: Subject to any disclaimer, the term of this patent is extended or adjusted under 35 U.S.C. 154(b) by 1083 days.

(21) Appl. No.: 10/332,541

(22) PCT Filed: Sep. 13, 2002

(86) PCT No.: PCT/DK02/00595

§ 371 (c)(1),
(2), (4) Date: May 14, 2003

(87) PCT Pub. No.: WO03/027081

PCT Pub. Date: Apr. 3, 2003

(65) Prior Publication Data

US 2003/0229120 A1   Dec. 11, 2003

Related U.S. Application Data

(60) Provisional application No. 60/396,051, filed on Jul. 10, 2002, provisional application No. 60/323,925, filed on Sep. 21, 2001.

(30) Foreign Application Priority Data

Sep. 14, 2001 (DK) .............................. 2001 01337
Jul. 5, 2002 (DK) .............................. 2002 01066

(51) Int. Cl.
*A61K 31/41* (2006.01)
*A61K 31/40* (2006.01)
*C07D 257/00* (2006.01)
*C07D 209/82* (2006.01)

(52) U.S. Cl. .................. 514/381; 514/411; 548/253; 548/444

(58) Field of Classification Search .................. 514/14, 514/381, 411; 530/304; 548/253, 444
See application file for complete search history.

(56) References Cited

U.S. PATENT DOCUMENTS 5,646,120 A * 7/1997 Sumner-Smith et al. ...... 514/14
5,830,999 A 11/1998 Dunn ........................ 530/303

FOREIGN PATENT DOCUMENTS

GB        2105191      3/1983
WO    WO 00/29013   * 5/2000

OTHER PUBLICATIONS du Vigneaud et al. "A Synthetic Preparation Possessing Biological Properties Associated with Arginine-Vasopressin" Journal of the American Chemical Society 1954, 4751-4752.*
Brenna et al. "A New Two Step Route to 1-Hydroxy-9H-3-Carbazolecarboxylic Acid Derivatives from 3-Formylindole. Application to the Synthesis of Mukonine" Tetrahedron 1998, 1585-1588.*
McMurry, John "Organic Chemistry—Fourth Edition" Brooks/Cole Publishing Company, 1996, pp. 946-947 and 1076-1082.*
Brown et al. "Chemistry: The Central Science—7th Edition" Prentice Hall, 1997, pp. 463-465 and 901-902.*
Patani and LaVoie "Bioisosterism: A Rational Approach in Drug Design" Chem. Rev. 1996, 3147-3176.*
Choi et al., Biochemistry, vol. 32, pp. 11638-11645 (1993).
Huang et al., Biochemistry, vol 36, pp. 9878-9888 (1997).
McGraw, S.E. et al., "Testing of Insulin Hexamer-Stabilizing Ligands Using Theoretical Binding, Microcalorimetry, and Nuclear Magnetic Resonance (NMR) Line Broadening Techniques", Pharmaceutical Research, vol. 7, No. 6, 1990, pp. 600-605.

* cited by examiner

*Primary Examiner*—Joseph R Kosack
(74) *Attorney, Agent, or Firm*—Rosemarie R. Wilk-Orescan

(57) ABSTRACT

The present invention relates to novel ligands for the $His^{B10}$ $Zn^{2+}$ sites of the R-state insulin hexamer having the formula A-B-C-D-X (III), wherein: A is a chemical group which reversibly binds to a $His^{B10}$ $Zn^{2+}$ sites of an insulin hexamer; B is a linker; C is a fragment consisting of 0 to 5 neutral amino acids; D is a fragment comprising 1 to 20 positively charged groups independently selected from amino or guanidino groups; and X is —OH, —$NH_2$ or a diamino group. The present invention also relates to R-state insulin hexamers comprising such ligands, and aqueous insulin preparations comprising such R-state insulin hexamers.

67 Claims, 3 Drawing Sheets

SEQUENCE LISTING

```
<160> NUMBER OF SEQ ID NOS: 62

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Xaa = Benzotriazol-5-oyl

<400> SEQUENCE: 1

Xaa Gly Gly Arg Arg Arg Arg Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Xaa = Benzotriazol-5-oyl

<400> SEQUENCE: 2

Xaa Gly Gly Arg Arg Arg Arg
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Xaa = Benzotriazol-5-oyl
<220> FEATURE:
<221> NAME/KEY: MOD_RES
<222> LOCATION: (2)..(2)
<223> OTHER INFORMATION: Xaa = Aminobenzoic acid

<400> SEQUENCE: 3

Xaa Xaa Gly Gly Arg Arg Arg Arg Arg
1               5
```

```
<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Xaa = Aminobenzoic acid

<400> SEQUENCE: 4

Xaa Gly Gly Arg Arg Arg Arg Arg
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: XAA = BENZOTRIAZOL-5-OYL

<400> SEQUENCE: 5

Xaa Gly Gly Arg Arg Arg Arg Arg Arg
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: XAA = BENZOTRIAZOL-5-OYL

<400> SEQUENCE: 6

Xaa Gly Gly Arg Arg Arg
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: XAA = BENZOTRIAZOL-5-OYL

<400> SEQUENCE: 7

Xaa Gly Arg Arg Arg Arg Arg
1               5

<210> SEQ ID NO 8
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: XAA = BENZOTRIAZOL-5-OYL

<400> SEQUENCE: 8

Xaa Gly Gly Gly Arg Arg Arg Arg
1               5

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: XAA = BENZOTRIAZOL-5-OYL
<220> FEATURE:
<221> NAME/KEY: MOD_RES
<222> LOCATION: (2)..(2)
<223> OTHER INFORMATION: Xaa = 4-aminobenzoic acid

<400> SEQUENCE: 9

Xaa Xaa Gly Gly Arg Arg Arg Arg Arg Arg
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: XAA = BENZOTRIAZOL-5-OYL
<220> FEATURE:
<221> NAME/KEY: MOD_RES
<222> LOCATION: (2)..(2)
<223> OTHER INFORMATION: Xaa = 4-aminobenzoic acid

<400> SEQUENCE: 10

Xaa Xaa Gly Gly Arg Arg Arg Arg Arg
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: XAA = BENZOTRIAZOL-5-OYL
<220> FEATURE:
<221> NAME/KEY: MOD_RES
<222> LOCATION: (2)..(2)
<223> OTHER INFORMATION: Xaa = 4-aminobenzoic acid

<400> SEQUENCE: 11

Xaa Xaa Gly Gly Arg Arg Arg Arg
1               5
```

```
<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: XAA = BENZOTRIAZOL-5-OYL
<220> FEATURE:
<221> NAME/KEY: MOD_RES
<222> LOCATION: (2)..(2)
<223> OTHER INFORMATION: Xaa = 4-aminobenzoic acid

<400> SEQUENCE: 12

Xaa Xaa Gly Gly Arg Arg Arg
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: XAA = BENZOTRIAZOL-5-OYL
<220> FEATURE:
<221> NAME/KEY: MOD_RES
<222> LOCATION: (2)..(2)
<223> OTHER INFORMATION: Xaa = 4-aminobenzoic acid

<400> SEQUENCE: 13

Xaa Xaa Arg Arg Arg Arg Arg
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: XAA = BENZOTRIAZOL-5-OYL
<220> FEATURE:
<221> NAME/KEY: MOD_RES
<222> LOCATION: (2)..(2)
<223> OTHER INFORMATION: 4Apac

<400> SEQUENCE: 14

Xaa Xaa Gly Gly Arg Arg Arg Arg Arg
1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: XAA = BENZOTRIAZOL-5-OYL
<220> FEATURE:
<221> NAME/KEY: MOD_RES
```

```
<222> LOCATION: (2)..(2)
<223> OTHER INFORMATION: 4Apac

<400> SEQUENCE: 15

Xaa Xaa Gly Gly Arg Arg Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: XAA = BENZOTRIAZOL-5-OYL
<220> FEATURE:
<221> NAME/KEY: MOD_RES
<222> LOCATION: (2)..(2)
<223> OTHER INFORMATION: 4Apac

<400> SEQUENCE: 16

Xaa Xaa Gly Gly Arg Arg Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: XAA = BENZOTRIAZOL-5-OYL
<220> FEATURE:
<221> NAME/KEY: MOD_RES
<222> LOCATION: (2)..(2)
<223> OTHER INFORMATION: 4Apac

<400> SEQUENCE: 17

Xaa Xaa Arg Arg Arg Arg Arg
1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: XAA = BENZOTRIAZOL-5-OYL
<220> FEATURE:
<221> NAME/KEY: MOD_RES
<222> LOCATION: (2)..(2)
<223> OTHER INFORMATION: 4Apac

<400> SEQUENCE: 18

Xaa Xaa Arg Arg Arg Arg
1               5

<210> SEQ ID NO 19
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Xaa = 4-aminobenzoic acid

<400> SEQUENCE: 19

Xaa Gly Gly Arg Arg Arg Arg Arg
1               5

<210> SEQ ID NO 20
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(20)
<223> OTHER INFORMATION: This region may encompass 1-20 Arg residues

<400> SEQUENCE: 20

Arg Arg Arg Arg Arg Arg Arg Arg Arg Arg Arg Arg Arg Arg Arg Arg
1               5                   10                  15

Arg Arg Arg Arg
            20

<210> SEQ ID NO 21
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: This region may encompass 0-5 Gly residues
<220> FEATURE:
<221> NAME/KEY: MOD_RES
<222> LOCATION: (6)..(25)
<223> OTHER INFORMATION: This region may encompass 1-20 Arg residues

<400> SEQUENCE: 21

Gly Gly Gly Gly Gly Arg Arg Arg Arg Arg Arg Arg Arg Arg Arg Arg
1               5                   10                  15

Arg Arg Arg Arg Arg Arg Arg Arg Arg
            20                  25

<210> SEQ ID NO 22
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aminobenzoic acid and this residue may or may
      not be present
<220> FEATURE:
<221> NAME/KEY: MOD_RES
<222> LOCATION: (2)..(6)
<223> OTHER INFORMATION: This region may encompass 0-5 Gly residues
<220> FEATURE:
<221> NAME/KEY: MOD_RES
<222> LOCATION: (7)..(26)
```

-continued

```
<223> OTHER INFORMATION: This region may encompass 1-20 Arg residues

<400> SEQUENCE: 22

Xaa Gly Gly Gly Gly Gly Arg Arg Arg Arg Arg Arg Arg Arg Arg
1               5                   10                  15

Arg Arg Arg Arg Arg Arg Arg Arg Arg
            20                  25

<210> SEQ ID NO 23
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-Aminobenzoic acid and this residue may or may
      not be present
<220> FEATURE:
<221> NAME/KEY: MOD_RES
<222> LOCATION: (2)..(6)
<223> OTHER INFORMATION: This region may encompass 0-5 Gly residues
<220> FEATURE:
<221> NAME/KEY: MOD_RES
<222> LOCATION: (7)..(26)
<223> OTHER INFORMATION: This region may encompass 1-20 Arg residues

<400> SEQUENCE: 23

Xaa Gly Gly Gly Gly Gly Arg Arg Arg Arg Arg Arg Arg Arg Arg
1               5                   10                  15

Arg Arg Arg Arg Arg Arg Arg Arg Arg
            20                  25

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: XAA = BENZOTRIAZOL-5-OYL
<220> FEATURE:
<221> NAME/KEY: MOD_RES
<222> LOCATION: (2)..(2)
<223> OTHER INFORMATION: Xaa = 4-aminobenzoic acid

<400> SEQUENCE: 24

Xaa Xaa Gly Arg Arg Arg Arg Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Gly Arg Arg Arg Arg Arg
1               5

<210> SEQ ID NO 26
<211> LENGTH: 5
```

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Arg Arg Arg Arg
1               5

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Arg Arg Arg
1

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Arg Arg Arg Arg Arg Arg Arg Arg Arg Arg Arg
1               5                   10

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Arg Arg Arg Arg Arg Arg Arg
1               5

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Arg Arg Arg Arg Arg Arg Arg Arg Arg
1               5                   10

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Arg Arg Arg Arg Arg Arg Arg Arg
```

-continued

```
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Arg Arg Arg Arg Arg Arg
1               5

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Arg Arg Arg Arg Arg Arg Arg Arg Arg Arg
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Arg Arg Arg Arg Arg Arg Arg Arg Arg Arg Arg Arg
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Arg Arg Arg Arg Arg Arg Arg Arg Arg Arg Arg Arg Arg
1               5                   10

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Arg Arg Arg Arg Arg Arg Arg Arg Arg Arg Arg Arg Arg Arg
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 37

Arg Arg Arg Arg Arg Arg Arg Arg Arg Arg Arg Arg Arg Arg Arg Arg
1               5                   10                  15

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Arg Arg Arg Arg Arg Arg Arg Arg Arg Arg Arg Arg Arg Arg Arg
1               5                   10                  15

Arg

<210> SEQ ID NO 39
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Arg Arg Arg Arg Arg Arg Arg Arg Arg Arg Arg Arg Arg Arg Arg
1               5                   10                  15

Arg Arg

<210> SEQ ID NO 40
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Arg Arg Arg Arg Arg Arg Arg Arg Arg Arg Arg Arg Arg Arg Arg Arg
1               5                   10                  15

Arg Arg Arg

<210> SEQ ID NO 41
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Arg Arg Arg Arg Arg Arg Arg Arg Arg Arg Arg Arg Arg Arg Arg
1               5                   10                  15

Arg Arg Arg Arg
            20

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic

```
                              peptide

<400> SEQUENCE: 42

Lys Lys Lys Lys Lys Lys
1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Lys Lys Lys Lys Lys
1               5

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Lys Lys Lys Lys
1

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Lys Lys Lys Lys Lys Lys Lys
1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Lys Lys Lys Lys Lys Lys Lys Lys
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Lys Lys Lys Lys Lys Lys Lys Lys
1               5

<210> SEQ ID NO 48
```

-continued

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Lys Lys Lys Lys Lys Lys Lys Lys Lys Lys
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Lys Lys Lys Lys Lys Lys Lys Lys Lys Lys Lys
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Lys Lys Lys Lys Lys Lys Lys Lys Lys Lys Lys Lys
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Lys Lys Lys Lys Lys Lys Lys Lys Lys Lys Lys Lys Lys
1               5                   10

<210> SEQ ID NO 52
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Lys Lys Lys Lys Lys Lys Lys Lys Lys Lys Lys Lys Lys Lys
1               5                   10

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53
```

Lys Lys Lys Lys Lys Lys Lys Lys Lys Lys Lys Lys Lys Lys Lys
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Lys Lys Lys Lys Lys Lys Lys Lys Lys Lys Lys Lys Lys Lys Lys Lys
1               5                   10                  15

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Lys Lys Lys Lys Lys Lys Lys Lys Lys Lys Lys Lys Lys Lys Lys Lys
1               5                   10                  15

Lys

<210> SEQ ID NO 56
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Lys Lys Lys Lys Lys Lys Lys Lys Lys Lys Lys Lys Lys Lys Lys Lys
1               5                   10                  15

Lys Lys

<210> SEQ ID NO 57
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Lys Lys Lys Lys Lys Lys Lys Lys Lys Lys Lys Lys Lys Lys Lys Lys
1               5                   10                  15

Lys Lys Lys

<210> SEQ ID NO 58
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Lys Lys Lys Lys Lys Lys Lys Lys Lys Lys Lys Lys Lys Lys Lys Lys
1               5                   10                  15

```
Lys Lys Lys Lys
            20

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Arg Arg Arg Arg Arg Arg
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Xaa = 4-aminobenzoic acid

<400> SEQUENCE: 60

Xaa Gly Gly Arg Arg Arg Arg Arg Arg
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Xaa = 4-aminobenzoic acid

<400> SEQUENCE: 61

Xaa Gly Gly Arg Arg Arg Arg
1               5

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Xaa = 4-aminobenzoic acid

<400> SEQUENCE: 62

Xaa Gly Gly Arg Arg Arg
1               5
```

LIGANDS FOR THE HISB10 ZN$^{2+}$ SITES OF THE R-STATE INSULIN HEXAMER

CROSS-REFERENCE TO RELATED APPLICATIONS

This application claims priority from application serial no. PCT/DK02/00595 filed on Sep. 13, 2002 under 35 U.S.C. 120 and claims priority under 35 U.S.C. 119 of Danish application no. PA 2001 01337 filed on Sep. 14, 2001, Danish application no. PA 2002 01066 filed on Jul. 5, 2002, U.S. application Ser. No. 60/323,925, filed 21 Sep. 2001, U.S. application Ser. No. 60/396,051, filed 10 Jul. 2002, the contents of which are fully incorporated herein by reference.

FIELD OF THE INVENTION

The present invention discloses novel ligands for the His10 Zn$^{2+}$ sites of the R-state insulin hexamer, R-state insulin hexamers comprising such ligands, and aqueous insulin preparations comprising such R-state insulin hexamers. The novel preparations release insulin slowly following subcutaneous injection.

BACKGROUND OF THE INVENTION

Insulin Allostery. The insulin hexamer is an allosteric protein that exhibits both positive and negative cooperativity and half-of-the-sites reactivity in ligand binding. This allosteric behaviour consists of two interrelated allosteric transitions designated $L^A_0$ and $L^B_0$, three interconverting allosteric conformation states (eq. 1),

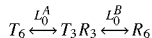

(1)

designated $T_6$, $T_3R_3$, and $R_6$ and two classes of allosteric ligand binding sites designated as the phenolic pockets and the His$^{B10}$ anion sites. These allosteric sites are associated only with insulin subunits in the R conformation.

Insulin Hexamer Structures and Ligand Binding. The T- to R-transition of the insulin hexamer involves transformation of the first nine residues of the B chain from an extended conformation in the T-state to an α-helical conformation in the R-state. This coil-to-helix transition causes the N-terminal residue, Phe$^{B1}$, to undergo an ~30 Å change in position. This conformational change creates hydrophobic pockets (the phenolic pockets) at the sub-unit interfaces (three in $T_3R_3$, and six in $R_6$), and the new B-chain helices form 3-helix bundles (one in $T_3R_3$ and two in $R_6$) with the bundle axis aligned along the hexamer three-fold symmetry axis. The His$^{B10}$ Zn$^{2+}$ in each $R_3$ unit is forced to change coordination geometry from octahedral to either tetrahedral (monodentate ligands) or pentahedran (bidentate ligands). Formation of the helix bundle creates a narrow hydrophobic tunnel in each $R_3$ unit that extends from the surface ~12 Å down to the His$^{B10}$ metal ion. This tunnel and the His$^{B10}$ Zn$^{2+}$ ion form the anion binding site.

Hexamer Ligand Binding and Stability of Insulin Formulations. The in vivo role of the T to R transition is unknown. However, the addition of allosteric ligands (e.g. phenol and chloride ion) to insulin preparations is widely used. Hexamerization is driven by coordination of Zn$^{2+}$ at the His$^{B10}$ sites to give $T_6$, and the subsequent ligand-mediated transition of $T_6$ to $T_3R_3$ and to $R_6$ is known to greatly enhance the physical and chemical stability of the resulting formulations.

Ligand Binding and Long Acting Insulin Formulations. Although the conversion of $T_6$ to $T_3R_3$ and $R_6$ improves the stability of the preparation, the rate of absorption following subcutaneous injection of a soluble hexameric preparation is not much affected by the addition of phenol and chloride.

Putative events following injection of a soluble hexameric preparation. The small molecule ligands initially diffuse away from the protein. The affinity of the ligands for insulin may help to slow this process. On the other hand, the affinity of Zn$^{2+}$ for e.g. albumin and the large effective space available for diffusion of the lipophilic phenol will tend to speed up the separation. In about 10-15 minutes after injection, the distribution of insulin species in the subcutaneous tissue will roughly correspond to that of a zinc-free insulin preparation at the same dilution. Then, the equilibrium distribution of species at this point will determine the observed absorption rate. In this regimen, absorption rates vary between about 1 hour (for rapid-acting insulin analogues, such as Asp$^{B28}$ human insulin) and about 4 hours (Co$^{3+}$-hexamer).

Current Approaches Toward Slow Acting Insulins. The inherent limitation of the absorption half-life to about 4 hours for a soluble human insulin hexamer necessitates further modifications to obtain the desired protraction. Traditionally, this has been achieved by the use of preparations wherein the constituent insulin is in the form of a crystalline and/or amorphous precipitate. In this type of formulation, the dissolution of the precipitate in the subcutaneous depot becomes rate-limiting for the absorption. NPH and Ultralente belong to this category of insulin preparations where crystallization/precipitation is effected by the addition of protamine and excessive zinc ion, respectively.

Another approach involves the use of insulin derivatives where the net charge is increased to shift the isoelectric point, and hence the pH of minimum solubility, from about 5.5 to the physiological range. Such preparations may be injected as clear solutions at slightly acidic pH. The subsequent adjustment of the pH to neutral induces crystallization/precipitation in the subcutaneous depot and dissolution again becomes rate-limiting for the absorption. Gly$^{A21}$Arg$^{B31}$Arg$^{B32}$ human insulin belongs to this category of insulin analogues.

Most recently, a series of soluble insulin derivatives with a hydrophobic moiety covalently attached to the side chain of Lys$^{B29}$ have been synthesized. These derivatives may show prolonged action profile due to various mechanisms including albumin binding (e.g. B29-N$^ε$-myristoyl-des(B30) human insulin), extensive protein self-association and/or stickiness (e.g. B29-N$^ε$-(N-lithocholyl-γ-glutamyl)-des (B30) human insulin) induced by the attached hydrophobic group.

SUMMARY OF THE INVENTION

The present invention provides novel ligands for the His$^{B10}$ Zn$^{2+}$ sites of the R-state insulin hexamer. The ligands stabilize the hexamers and modify solubility in the neutral range. The resulting preparations release insulin slowly following subcutaneous injection. In comparison with earlier slow release preparations, the present ligands work to modify the timing of both human insulin and insulin mutants/analogues. The ligands alone or in combination with new ligands for the phenol cavity also confer increased physical and chemical stability of the resulting preparations. Moreover, the preparations release active insulin more reproducibly that e.g. NPH preparations.

DEFINITIONS

The following is a detailed definition of the terms used to describe the invention:

"Halogen" designates an atom selected from the group consisting of F, Cl, Br and I.

The term "$C_1$-$C_6$-alkyl" as used herein represents a saturated, branched or straight hydrocarbon group having from 1 to 6 carbon atoms. Representative examples include, but are not limited to, methyl, ethyl, n-propyl, isopropyl, butyl, isobutyl, sec-butyl, tert-butyl, n-pentyl, isopentyl, neopentyl, tert-pentyl, n-hexyl, isohexyl and the like.

The term "$C_1$-$C_6$-alkylene" as used herein represents a saturated, branched or straight bivalent hydrocarbon group having from 1 to 6 carbon atoms. Representative examples include, but are not limited to, methylene, 1,2-ethylene, 1,3-propylene, 1,2-propylene, 1,4-butylene, 1,5-pentylene, 1,6-hexylene, and the like.

The term "$C_2$-$C_6$-alkenyl" as used herein represents a branched or straight hydrocarbon group having from 2 to 6 carbon atoms and at least one double bond. Examples of such groups include, but are not limited to, vinyl, 1-propenyl, 2-propenyl, iso-propenyl, 1,3-butadienyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 2,4-hexadienyl, 5-hexenyl and the like.

The term "$C_2$-$C_6$-alkynyl" as used herein represents a branched or straight hydrocarbon group having from 2 to 6 carbon atoms and at least one triple bond. Examples of such groups include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 2,4-hexadienyl and the like.

The term "$C_1$-$C_6$-alkoxy" as used herein refers to the radical —O—$C_1$-$C_6$-alkyl, wherein $C_1$-$C_6$-alkyl is as defined above. Representative examples are methoxy, ethoxy, n-propoxy, isopropoxy, butoxy, sec-butoxy, tert-butoxy, pentoxy, isopentoxy, hexoxy, isohexoxy and the like.

The term "$C_3$-$C_8$-cycloalkyl" as used herein represents a saturated, carbocyclic group having from 3 to 8 carbon atoms. Representative examples are cyclopropyl, cyclobutyl, cyclopentyl, cyclohexyl, cycloheptyl, cyclooctyl and the like.

The term "$C_{4-8}$-cycloalkenyl" as used herein represents a non-aromatic, carbocyclic group having from 4 to 8 carbon atoms containing one or two double bonds. Representative examples are 1-cyclopentenyl, 2-cyclopentenyl, 3-cyclopentenyl, 1-cyclohexenyl, 2-cyclohexenyl, 3-cyclohexenyl, 2-cycloheptenyl, 3-cycloheptenyl, 2-cyclooctenyl, 1,4-cyclooctadienyl and the like.

The term "heterocyclyl" as used herein represents a non-aromatic 3 to 10 membered ring containing one or more heteroatoms selected from nitrogen, oxygen and sulphur and optionally containing one or two double bonds. Representative examples are pyrrolidinyl, piperidyl, piperazinyl, morpholinyl, thiomorpholinyl, aziridinyl, tetrahydrofuranyl and the like.

The term "aryl" as used herein is intended to include carbocyclic, aromatic ring systems such as 6 membered monocyclic and 9 to 14 membered bi- and tricyclic, carbocyclic, aromatic ring systems. Representative examples are phenyl, biphenylyl, naphthyl, anthracenyl, phenanthrenyl, fluorenyl, indenyl, azulenyl and the like. Aryl is also intended to include the partially hydrogenated derivatives of the ring systems enumerated above. Non-limiting examples of such partially hydrogenated derivatives are 1,2,3,4-tetrahydronaphthyl, 1,4-dihydronaphthyl and the like.

The term "arylene" as used herein is intended to include divalent, carbocyclic, aromatic ring systems such as 6 membered monocyclic and 9 to 14 membered bi- and tricyclic, divalent, carbocyclic, aromatic ring systems. Representative examples are phenylene, biphenylylene, naphthylene, anthracenylene, phenanthrenylene, fluorenylene, indenylene, azulenylene and the like. Arylene is also intended to include the partially hydrogenated derivatives of the ring systems enumerated above. Non-limiting examples of such partially hydrogenated derivatives are 1,2,3,4-tetrahydronaphthylene, 1,4-dihydronaphthylene and the like.

The term "aryloxy" as used herein denotes a group —O-aryl, wherein aryl is as defined above.

The term "aroyl" as used herein denotes a group —C(O)-aryl, wherein aryl is as defined above.

The term "heteroaryl" as used herein is intended to include aromatic, heterocyclic ring systems containing one or more heteroatoms selected from nitrogen, oxygen and sulphur such as 5 to 7 membered monocyclic and 8 to 14 membered bi- and tricyclic aromatic, heterocyclic ring systems containing one or more heteroatoms selected from nitrogen, oxygen and sulphur. Representative examples are furyl, thienyl, pyrrolyl, pyrazolyl, 3-oxopyrazolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuryl, benzothienyl, indazolyl, benzimidazolyl, benzthiazolyl, benzisothiazolyl, benzoxazolyl, benzisoxazolyl, purinyl, quinazolinyl, quinolizinyl, quinolinyl, isoquinolinyl, quinoxalinyl, naphthyridinyl, pteridinyl, carbazolyl, azepinyl, diazepinyl, acridinyl, thiazolidinyl, 2-thiooxothiazolidinyl and the like. Heteroaryl is also intended to include the partially hydrogenated derivatives of the ring systems enumerated above. Non-limiting examples of such partially hydrogenated derivatives are 2,3-dihydrobenzofuranyl, pyrrolinyl, pyrazolinyl, indolinyl, oxazolidinyl, oxazolinyl, oxazepinyl and the like.

The term "heteroarylene" as used herein is intended to include divalent, aromatic, heterocyclic ring systems containing one or more heteroatoms selected from nitrogen, oxygen and sulphur such as 5 to 7 membered monocyclic and 8 to 14 membered bi- and tricyclic aromatic, heterocyclic ring systems containing one or more heteroatoms selected from nitrogen, oxygen and sulphur. Representative examples are furylene, thienylene, pyrrolylene, oxazolylene, thiazolylene, imidazolylene, isoxazolylene, isothiazolylene, 1,2,3-triazolylene, 1,2,4-triazolylene, pyranylene, pyridylene, pyridazinylene, pyrimidinylene, pyrazinylene, 1,2,3-triazinylene, 1,2,4-triazinylene, 1,3,5-triazinylene, 1,2,3-oxadiazolylene, 1,2,4-oxadiazolylene, 1,2,5-oxadiazolylene, 1,3,4-oxadiazolylene, 1,2,3-thiadiazolylene, 1,2,4-thiadiazolylene, 1,2,5-thiadiazolylene, 1,3,4-thiadiazolylene, tetrazolylene, thiadiazinylene, indolylene, isoindolylene, benzofurylene, benzothienylene, indazolylene, benzimidazolylene, benzthiazolylene, benzisothiazolylene, benzoxazolylene, benzisoxazolylene, purinylene, quinazolinylene, quinolizinylene, quinolinylene, isoquinolinylene, quinoxalinylene, naphthyridinylene, pteridinylene, carbazolylene, azepinylene, diazepinylene, acridinylene and the like. Heteroaryl is also intended to include the partially hydrogenated derivatives of the ring systems enumerated above. Non-limiting examples of such partially hydrogenated derivatives are 2,3- dihydrobenzofuranylene, pyrrolinylene, pyrazolinylene, indolinylene, oxazolidinylene, oxazolinylene, oxazepinylene and the like.

"Aryl-$C_1$-$C_6$-alkyl", "heteroaryl-$C_1$-$C_6$-alkyl", "aryl-$C_2$-$C_6$-alkenyl" etc. is intended to mean $C_1$-$C_6$-alkyl or $C_2$-$C_6$-alkenyl as defined above, substituted by an aryl or heteroaryl as defined above, for example:

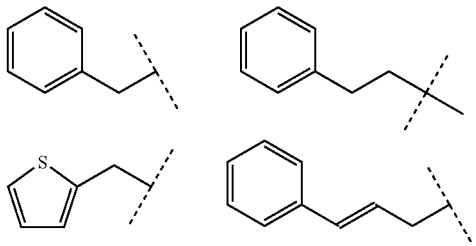

The term "optionally substituted" as used herein means that the groups in question are either unsubstituted or substituted with one or more of the substituents specified. When the groups in question are substituted with more than one substituent the substituents may be the same or different.

Furthermore, when polycyclic structures are substituted with one or more substituents, it is intended that substitutions at any available position in either of the rings that are part of the polycyclic structure are included.

Certain of the above defined terms may occur more than once in the structural formulae, and upon such occurrence each term shall be defined independently of the other.

Furthermore, when using the terms "independently are" and "independently selected from" it should be understood that the groups in question may be the same or different.

The term "treatment" as used herein means the management and care of a patient for the purpose of combating a disease, disorder or condition. The term is intended to include the delaying of the progression of the disease, disorder or condition, the alleviation or relief of symptoms and complications, and/or the cure or elimination of the disease, disorder or condition. The patient to be treated is preferably a mammal, in particular a human being.

The term "fragment" as used herein is intended to mean a bivalent chemical group The term "Neutral amino acid" as used herein is intended to mean any natural (codable) and non-natural amino acid, including α- or β-aminocarboxylic acids, including D-isomers of these (when applicable) without charges at physiologically relevant pH in the side chain, such as glycine, alanine, β-alanine, valine, leucine, isoleucine, phenylalanine, tyrosine, aspargine, glutamine, cysteine, methionine, 3-aminobenzoic acid, 4-aminobenzoic acid or the like.

The term "positively charged group" as used herein is intended to mean any pharmaceutically acceptable group that contains a positive charge at physiologically relevant pH, such as amino (primary, secondary and tertiary), ammonium and guanidino groups.

The term "α amino acid" as used herein is intended to mean mean any natural (codable) and non-natural α-aminocarboxylic acid, including D-isomers of these.

The term "β amino acid" as used herein is intended to mean any β-aminocarboxylic acid, such as β-alanine, isoserine or the like.

When in the specification or claims mention is made of groups of compounds such as carboxylates, dithiocarboxylates, phenolates, thiophenolates, alkylthiolates, sulfonamides, imidazoles, triazoles, 4-cyano-1,2,3-triazoles, benzimidazoles, benzotriazoles, purines, thiazolidinediones, tetrazoles, 5-mercaptotetrazoles, rhodanines, N-hydroxyazoles, hydantoines, thiohydantoines, naphthoic acids and salicylic acids, these groups of compounds are intended to include also derivatives of the compounds from which the groups take their name.

The term human insulin as used herein refers to naturally produced insulin or recombinantly produced insulin. Recombinant human insulin may be produced in any suitable host cell, for example the host cells may be bacterial, fungal (including yeast), insect, animal or plant cells. The expression "insulin derivative" as used herein (and related expressions) refers to human insulin or an analogue thereof in which at least one organic substituent is bound to one or more of the amino acids.

By "analogue of human insulin" as used herein (and related expressions) is meant human insulin in which one or more amino acids have been deleted and/or replaced by other amino acids, including non-codeable amino acids, or human insulin comprising additional amino acids, i.e. more than 51 amino acids, such that the resulting analogue possesses insulin activity.

The term "phenolic compound" or similar expressions as used herein refers to a chemical compound in which a hydroxyl group is bound directly to a benzene or substituted benzene ring. Examples of such compounds include, but are not limited to, phenol, o-cresol, m-cresol and p-cresol.

The term "physiologically relevant pH" as used herein is intended to mean a pH of about 7.1 to 7.9.

When calculating the ratio between precipitated and dissolved insulin in dual-acting insulin composition, i.e. a composition containing both rapid-acting insulin and insulin with a prolonged action, the term "precipitated insulin" as used herein is intended to mean insulin monomer which is part of a hexamer to which a ligand of the present invention is bound at physiologically relevant pH as defined above. Similarly the term "dissolved insulin" as used herein is intended to mean insulin which is not precipitated as defined above.

| Abbreviations: | |
|---|---|
| 4H3N | 4-hydroxy-3-nitrobenzoic acid |
| Abz | Aminobenzoic acid |
| AcOH | acetic acid |
| BT | Benzotriazol-5-oyl |
| DMF | N,N-Dimethylformamide |
| DMSO | Dimethylsulfoxide |
| DIC | Diisopropylcarbodiimide |
| EDAC | 1-ethyl-3-(3'-dimethylamino-propyl)carbodiimide, hydrochloride |
| Fmoc | 9H-Fluorene-9-ylmethoxycarbonyl |
| G, Gly | Glycine |
| HOAt | 1-hydroxy-7-azabenzotriazole |
| HOBT | 1-Hydroxybenzotriazole |
| K, Lys | Lysine |
| NMP | N-methyl-2-pyrrolidone |
| Pbf | 2,2,4,6,7-pentamethyldihydrobenzofuran-5-sulfonyl |
| Pmc | 2,2,5,7,8-pentamethylchroman-6-sulfonyl |
| R, Arg | Arginine |
| TFA | Trifluoroacetic acid |

Abbreviations for non-natural amino acid residues:

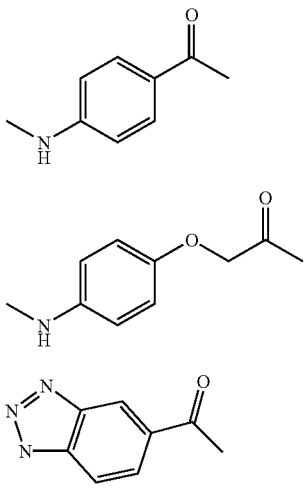

DESCRIPTION OF THE INVENTION

Figure 1:
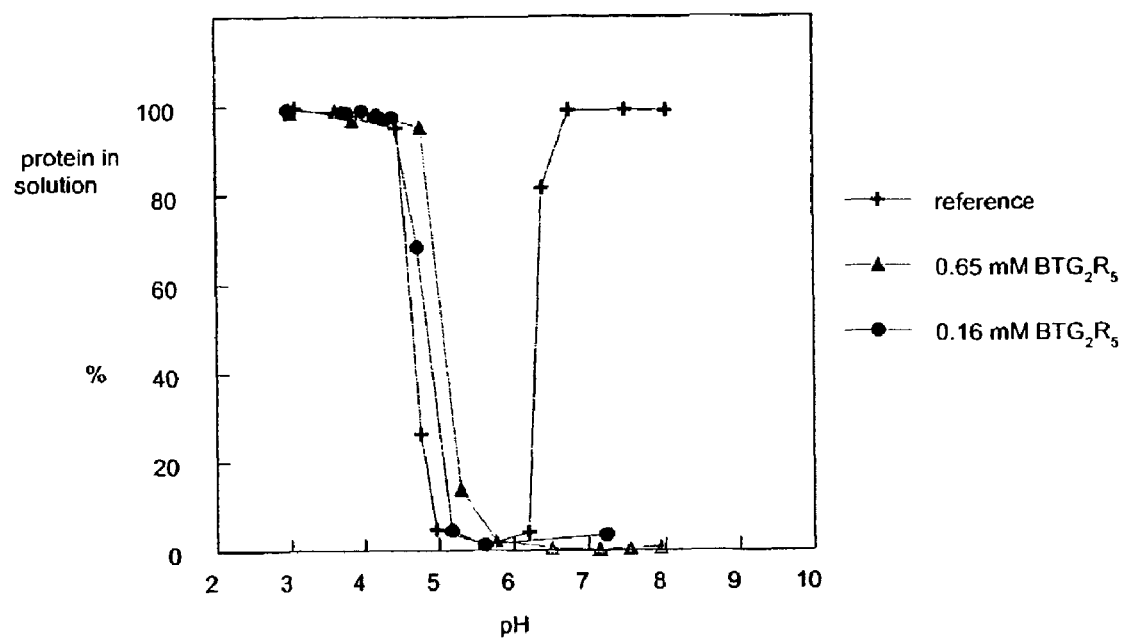
FIG. 1: Effect of BTG$_2$R$_5$—NH$_2$ (SEQ ID NO: 1) on pH-solubility profile of an insulin preparation.

The present invention is based on the discovery that the two known ligand binding sites of the R-state insulin hexamer can be used to obtain an insulin preparation having prolonged action designed for flexible injection regimes including once-daily, based on insulin molecules of any kind, e.g. human Insulin or AspB28 human insulin.

The basic concept underlying the present invention involves reversible attachment of a ligand to the His$^{B10}$ Zn$^{2+}$ site of the R-state hexamer. A suitable ligand binds to the hexamer metal site with one end while other moieties are covalently attachment to the other end. On this basis, prolonged action via modification of preparation solubility may be obtained in a number of ways. However, all cases involve the same point of protein-ligand attachment and the delivery of human insulin (or analogues or derivatives thereof) as the active species.

The anions currently used in insulin formulations as allosteric ligands for the R-state hexamers (notably chloride ion) bind only weakly to the His$^{B10}$ anion site. The present invention, which is based on the discovery of suitable higher affinity ligands for these anion sites, provides ligands which are extended to modify timing via changes in hexamer solubility as outlined above.

Most ligand binding sites in proteins are highly asymmetric. Because the His$^{B10}$ Zn$^{2+}$ sites reside on the three-fold symmetry axis, these sites posses a symmetry that is unusual, but not unique. Several other proteins have highly symmetric ligand binding sites.

The His$^{B10}$ Zn$^{2+}$ site consists of a tunnel or cavity with a triangular-shaped cross-section that extends ~12 Å from the surface of the hexamer down to the His$^{B10}$ Zn$^{2+}$ ion. The diameter of the tunnel varies along its length and, depending on the nature of the ligand occupying the site, the opening can be capped over by the Asn$^{B3}$ and Phe$^{B1}$ side chains. The walls of the tunnel are made up of the side chains of the amino acid residues along one face each of the three α-helices. The side chains from each helix that make up the lining of the tunnel are Phe$^{B1}$, Asn$^{B3}$, and Leu$^{B6}$. Therefore, except for the zinc ion, which is coordinated to three His$^{B10}$ residues and is positioned at the bottom of the tunnel, the site is principally hydrophobic. Depending on the ligand structure, it may be possible for substituents on the ligand to make H-bonding interactions with Asn$^{B3}$ and with the peptide linkage to Cys$^{B7}$.

The present invention originates from a search for compounds with suitable binding properties by using novel UV-visible and fluorescence based competition assays described herein which are based on the displacement of chromophoric ligands from the R-state His$^{B10}$-Zn$^{2+}$ site by the incoming ligand in question. These compounds will be referred to as "starter compounds" in the following. These assays are easily transformed into a high-throughput format capable of handling libraries from the initial search of compound databases.

These starter compounds provide the starting point for the task of constructing a chemical handle that allows for attachment of the positively charged fragment D (see below).

Thus, from the structure-activity relationship (SAR) information obtained from the binding assay(s) it will be apparent for those skilled in the art to modify the starter compounds in question by introduction of a chemical group that will allow for coupling to a peptide containing e.g. one or more arginine or lysine residues. These chemical groups include carboxylic acid (amide bond formation with the peptide), carbaldehyde (reductive alkylation of the peptide), sulfonyl chloride (sulphonamide formation with the peptide) or the like.

The decision where and how to introduce this chemical group can be made in various ways. For example: From the SAR of a series of closely related starter compounds, a suitable position in the starter compound can be identified and the chemical group can be attached to this position, optionally using a spacer group, using synthesis procedures known to those skilled in the art.

Alternatively, this chemical group can be attached (optionally using a spacer group using and synthesis procedures known to those skilled in the art) to a position on the starter compound remote from the Zn$^{2+}$-binding functionality The zinc-binding ligands of the present invention are characterised by the following formula (I):

wherein:
A is a functionality capable of reversibly coordinating to a His$^{B10}$ Zn$^{2+}$ site of an insulin hexamer;
B is a valence bond or a non-naturally occurring amino acid residue containing an aromatic ring;
C is a valence bond or a fragment consisting of 1 to 5 neutral α- or β-amino acids;
D is a fragment containing 1 to 20 positively charged groups independently selected from amino or guanidino groups, preferably a fragment consisting of 1 to 20 basic amino acids independently selected from the group consisting of Lys and Arg and D-isomers of these; and
X is OH, NH$_2$ or a diamino group.

The length of the zinc-binding ligand should be such that it extends from the His$^{B10}$ Zn$^{2+}$ site to beyond the hexamer surface.

A is preferably a chemical structure selected from the group consisting of carboxylates, dithiocarboxylates, phenolates, thiophenolates, alkylthiolates, sulfonamides, imidazoles, triazoles, benzimidazoles, benzotriazoles, purines, thiazolidinediones, naphthoic acids and salicylic acids.

More preferably, A comprises a benzotriazole, a 3-hydroxy 2-napthoic acid, a salicylic acid, a tetrazole or a thiazolidinedione structure.

A is advantageously selected from one of the following chemical structures:

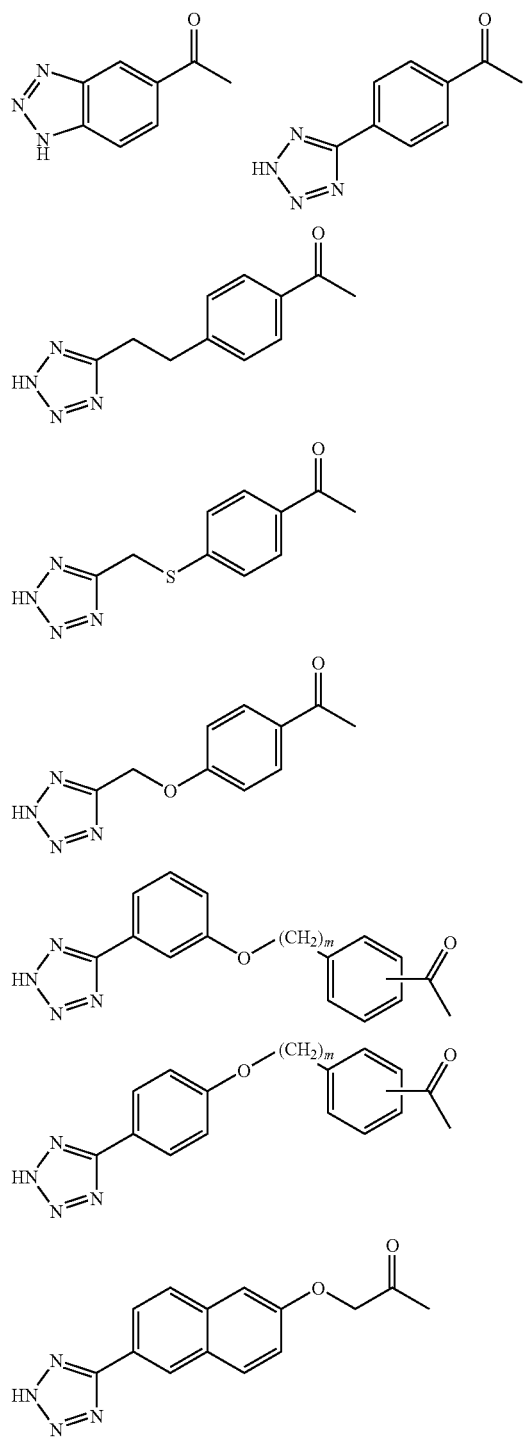

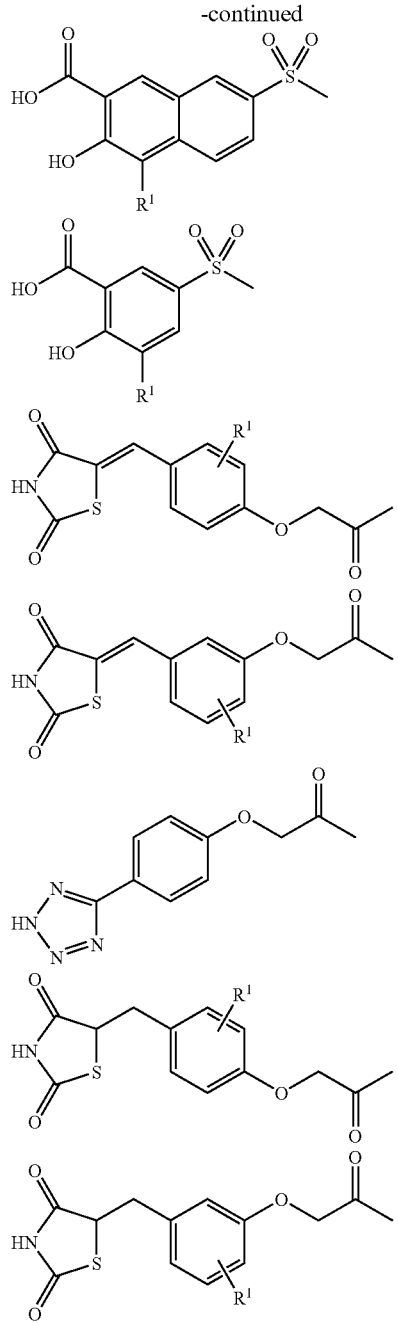

wherein
R[1] is hydrogen, fluoro, chloro, bromo or iodo,
m is 0 or 1.
B is preferably a valence bond or one of the following amino acid residues:

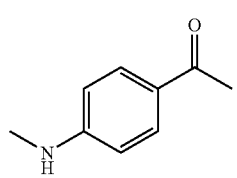

-continued

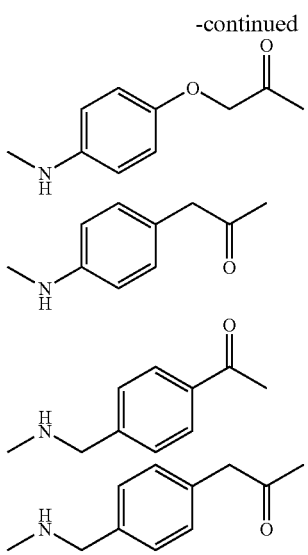

C is preferably a valence bond or a fragment consisting of 1 to 5 amino acids independently selected from the group consisting of neutral amino acids, more preferably from the group of amino acids consisting of Gly, Ala, Thr, and Ser.

In a particular preferred embodiment, C consists of 1-5 Gly residues or 1-5 Ala residues.

D preferably consists of 1-10 Arg residues.

X is preferably OH, $NH_2$ or

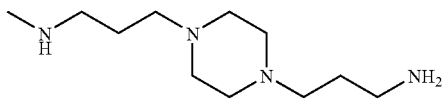

The most preferred specific zinc-binding ligands of the present invention are:

Benzotriazol-5-ylcarbonyl-Gly-Gly-Arg-Arg-Arg-Arg-Arg-Arg-NH₂ (SEQ ID NO: 5)
Benzotriazol-5-ylcarbonyl-Gly-Gly-Arg-Arg-Arg-Arg-Arg-NH₂ (SEQ ID NO: 1)
Benzotriazol-5-ylcarbonyl-Gly-Gly-Arg-Arg-Arg-Arg-NH₂ (SEQ ID NO: 2)
Benzotriazol-5-ylcarbonyl-Gly-Gly-Arg-Arg-Arg-NH₂ (SEQ ID NO: 6)
Benzotriazol-5-ylcarbonyl-Gly-Arg-Arg-Arg-Arg-Arg-NH₂ (SEQ ID NO: 7)
Benzotriazol-5-ylcarbonyl-Gly-Gly-Gly-Arg-Arg-Arg-Arg-NH₂ (SEQ ID NO: 8)
Benzotriazol-5-ylcarbonyl-4-Abz-Gly-Gly-Arg-Arg-Arg-Arg-Arg-NH₂ (SEQ ID NO: 9)
Benzotriazol-5-ylcarbonyl-4-Abz-Gly-Gly-Arg-Arg-Arg-Arg-NH₂ (SEQ ID NO: 10)
Benzotriazol-5-ylcarbonyl-4-Abz-Gly-Gly-Arg-Arg-Arg-NH₂ (SEQ ID NO: 11)
Benzotriazol-5-ylcarbonyl-4-Abz-Gly-Gly-Arg-Arg-NH₂ (SEQ ID NO: 12)
Benzotriazol-5-ylcarbonyl-4-Abz-Arg-Arg-Arg-Arg-NH₂ (SEQ ID NO: 13)
Benzotriazol-5-ylcarbonyl-4-Apac-Gly-Gly-Arg-Arg-Arg-Arg-Arg-NH₂ (SEQ ID NO: 14)
Benzotriazol-5-ylcarbonyl-4-Apac-Gly-Gly-Arg-Arg-Arg-Arg-NH₂ (SEQ ID NO: 15)
Benzotriazol-5-ylcarbonyl-4-Apac-Gly-Gly-Arg-Arg-Arg-NH₂ (SEQ ID NO: 16)
Benzotriazol-5-ylcarbonyl-4-Apac-Arg-Arg-Arg-Arg-Arg-NH₂ (SEQ ID NO: 17)
Benzotriazol-5-ylcarbonyl-4-Apac-Arg-Arg-Arg-Arg-NH₂ (SEQ ID NO: 18)
Benzotriazol-5-ylcarbonyl-4-Apac-Arg-Arg-Arg-NH₂ [4-(2,4-Dioxothiazolidin-5-ylidenemethyl)phenoxy]acetyl-4-Abz-Gly-Gly-Arg-Arg-Arg-Arg-Arg-NH₂ (SEQ ID NO: 19)
[3-(2,4-Dioxothiazolidin-5-ylidenemethyl)phenoxy]acetyl-4-Abz-Gly-Gly-Arg-Arg-Arg-Arg-Arg-NH₂ (SEQ ID NO: 19)
4-(2H-Tetrazol-5-yl)benzoyl-Abz-Gly-Gly-Arg-Arg-Arg-Arg-Arg-NH₂ (SEQ ID NO: 19)

In another embodiment the invention provides a zinc-binding ligand of the following general formula (II)

$$A-B-C-D-X \quad (II)$$

wherein:
A is a chemical group which reversibly binds to a His$^{B10}$ $Zn^{2+}$ site of an insulin hexamer;
B is a linker selected from
A valence bond
A chemical group $G^B$ of the formula —$B^1$—$B^2$—C(O)—, —$B^1$—$B^2$—$SO_2$—, —$B^1$—$B^2$—$CH_2$—, or —$B^1$—$B^2$—NH—; wherein $B^1$ is a valence bond, —O—, —S—, or —$NR^6$—;
$B^2$ is a valence bond, $C_1$-$C_{18}$-alkylene, $C_2$-$C_{18}$-alkenylene, $C_2$-$C_{18}$-alkynylene, arylene, heteroarylene, —$C_1$-$C_{18}$-alkyl-aryl-, —$C_2$-$C_{18}$-alkenyl-aryl-, —$C_2$-$C_{18}$-alkynyl-aryl-, —C(═O)—$C_1$-$C_{18}$-alkyl-C(═O), —C(═O)—$C_1$-$C_{18}$-alkenyl-C(═O)—, —C(═O)—$C_1$-$C_{18}$-alkyl-O—$C_1$-$C_{18}$-alkyl-C(═O)—, —C(═O)—$C_1$-$C_{18}$-alkyl-S—$C_1$-$C_{18}$-alkyl-C(═O)—, —C(═O)—$C_1$-$C_{18}$-alkyl-$NR^6$—$C_1$-$C_{18}$-alkyl-C(═O)—, —C(═O)-aryl-C(═O)—, —C(═O)-heteroaryl-C(═O)—;
wherein the alkylene, alkenylene, and alkynyl enemoieties are optionally substituted by —CN, —$CF_3$, —$OCF_3$, —$OR^6$, or —$NR^6R^7$ and the arylene and heteroarylene moieties are optionally substituted by halogen, —C(O)$OR^6$, —C(O)H, $OCOR^6$, —$SO_2$, —CN, —$CF_3$, —$OCF_3$, —$NO_2$, —$OR^6$, —$NR^6R^7$, $C_1$-$C_{18}$-alkyl, or $C_1$-$C_{18}$-alkanoyl;
$R^6$ and $R^7$ are independently H, $C_1$-$C_4$-alkyl;
C is a fragment consisting of 1 to 5 neutral α- or β-amino acids
D is a fragment comprising 1 to 20 positively charged groups independently selected from amino or guanidine groups; and
X is —OH, —$NH_2$ or a diamino group, or a salt thereof with a pharmaceutically acceptable acid or base, or any optical isomer or mixture of optical isomers, including a racemic mixture, or any tautomeric forms.

In another embodiment A is a chemical structure selected from the group consisting of carboxylates, dithiocarboxylates, phenolates, thiophenolates, alkylthiolates, sulfonamides, imidazoles, triazoles, 4-cyano-1,2,3-triazoles, benzimidazoles, benzotriazoles, purines, thiazolidinediones, tetrazoles, 5-mercaptotetrazoles, rhodanines, N-hydroxyazoles, hydantoines, thiohydantoines, barbiturates, naphthoic acids and salicylic acids.

In another embodiment A is a chemical structure selected from the group consisting of benzotriazoles, 3-hydroxy 2-napthoic acids, salicylic acids, tetrazoles or thiazolidinediones In another embodiment A is one of the following structures:

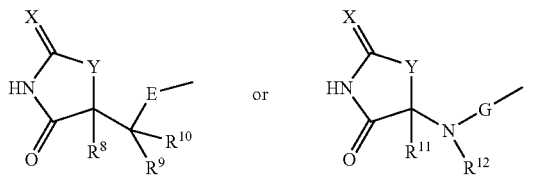

wherein

X is =O, =S or =NH

Y is —S—, —O— or —NH—

$R^8$ and $R^{11}$ are independently hydrogen or $C_1$-$C_6$-alkyl, $R^9$ is hydrogen or $C_1$-$C_6$-alkyl or aryl, $R^8$ and $R^9$ may optionally be combined to form a double bond, $R^{10}$ and $R^{12}$ are independently hydrogen, aryl, $C_1$-$C_6$-alkyl, or —C(O)NR$^{16}$R$^{17}$ E and G are independently $C_1$-$C_6$-alkylene, arylene, -aryl-$C_1$-$C_6$-alkyl, -aryl-$C_2$-$C_6$-alkenyl- or heteroarylene, wherein the alkylene or alkenylene is optionally substituted with one or more substituents independently selected from halogen, —CN, —CF$_3$, —OCF$_3$, aryl, —COOH and —NH$_2$, and the arylene or heteroarylene is optionally substituted with up to three substituents $R^{13}$, $R^{14}$ and $R^{15}$.

E and $R^{10}$ may be connected through one or two valence bonds, G and $R^{12}$ may be connected through one or two valence bonds;

$R^{13}$, $R^{14}$ and $R^{15}$ are independently selected from hydrogen, halogen, —CN, —CH$_2$CN, —CHF$_2$, —CF$_3$, —OCF$_3$, —OCHF$_2$, —OCH$_2$CF$_3$, —OCF$_2$CHF$_2$, —S(O)$_2$CF$_3$, —OS(O)$_2$CF$_3$, —SCF$_3$, —NO$_2$, —OR$^6$, —NR$^{16}$R$^{17}$, —SR$^{16}$, —NR$^{16}$S(O)$_2$R$^{17}$, —S(O)$_2$NR$^{16}$R$^{17}$, —S(O)NR$^{16}$R$^{17}$, —S(O)R$^{16}$, —S(O)$_2$R$^{16}$, —OS(O)$_2$R$^{16}$, —C(O)NR$^{16}$R$^{17}$, —OC(O)NR$^{16}$R$^{17}$, —NR$^{16}$C(O)R$^{17}$, —CH$_2$C(O)NR$^{16}$R$^{17}$, —OC$_1$-C$_6$-alkyl-C(O)NR$^{16}$R$^{17}$, —CH$_2$OR$^{16}$, —CH$_2$OC(O)R$^{16}$, —CH$_2$NR$^{16}$R$^{17}$, —OC(O)R$^{16}$, —OC$_1$-C$_6$-alkyl-C(O)OR$^{16}$, —OC$_1$-C$_6$-alkyl-OR$^{16}$, —SC$_1$-C$_6$-alkyl-C(O)OR$^{16}$, —C$_2$-C$_6$-alkenyl-C(=O)OR$^{16}$, —NR$^{16}$—C(=O)—C$_1$-C$_6$-alkyl-C(=O)OR$^{16}$, —NR$^{16}$—C(=O)—C$_1$-C$_{16}$-alkenyl-C(=)OR$^{16}$, —C(=O)OR$^{16}$, or —C$_2$-C$_6$-alkenyl-C(=O)R$^{16}$, $C_1$-$C_6$-alkyl, $C_2$-$C_6$-alkenyl or $C_2$-$C_6$-alkynyl, which may optionally be substituted with one or more substituents selected from halogen, —CN, —CF$_3$, —OCF$_3$, —OR$^{16}$, and —NR$^{16}$R$^{17}$ aryl, aryloxy, aryloxycarbonyl, aroyl, arylsulfanyl, aryl-$C_1$-$C_6$-alkoxy, aryl-$C_1$-$C_6$-alkyl, aryl-$C_2$-$C_6$-alkenyl, aroyl-$C_2$-$C_6$-alkenyl, aryl-$C_2$-$C_6$-alkynyl, heteroaryl, heteroaryl-$C_1$-$C_6$-alkyl, heteroaryl-$C_2$-$C_6$-alkenyl or heteroaryl-$C_2$-$C_6$-alkynyl, of which the cyclic moieties optionally may be substituted with one or more substituents selected from halogen, —C(O)OR$^{16}$, —CH$_2$C(O)OR$^{16}$, —CH$_2$OR$^{16}$, —CN, —CF$_3$, —OCF$_3$, —NO$_2$, —OR$^{16}$, —NR$^{16}$R$^{17}$ and $C_1$-$C_6$-alkyl, $R^{16}$ and $R^{17}$ independently are hydrogen, OH, $C_1$-$C_6$-alkyl, aryl-$C_1$-$C_6$-alkyl or aryl, wherein the alkyl groups may optionally be substituted with one or more substituents selected from halogen, —CN, —CF$_3$, —OCF$_3$, —OC$_1$-C$_6$-alkyl, —C(O)OC$_1$-C$_6$-alkyl, —COOH and —NH$_2$, and the aryl groups may optionally be substituted by halogen, —C(O)OC$_1$-C$_6$-alkyl, —COOH, —CN, —CF$_3$, —OCF$_3$, —NO$_2$, —OH, —OC$_1$-C$_6$-alkyl, —NH$_2$, C(=O) or $C_1$-$C_6$-alkyl; $R^{16}$ and $R^{17}$ when attached to the same nitrogen atom may form a 3 to 8 membered heterocyclic ring with the said nitrogen atom, the heterocyclic ring optionally containing one or two further heteroatoms selected from nitrogen, oxygen and sulphur, and optionally containing one or two double bonds In another embodiment X is =O or =S In another embodiment X is =O In another embodiment X is =S In another embodiment Y is —O— or —S—

In another embodiment Y is —O—

In another embodiment Y is —S—

In another embodiment E is arylene optionally substituted with up to three substituents $R^{13}$, $R^{14}$ and $R^{15}$.

In another embodiment E is phenylene or naphtylene optionally substituted with up to three substituents $R^{13}$, $R^{14}$ and $R^{15}$.

In another embodiment E is heteroarylene optionally substituted with up to three substituents $R^{13}$, $R^{14}$ and $R^{15}$.

In another embodiment E is indolylene optionally substituted with up to three substituents $R^{13}$, $R^{14}$ and $R^{15}$.

In another embodiment $R^8$ is hydrogen.

In another embodiment $R^9$ is hydrogen.

In another embodiment $R^8$ and $R^9$ are combined to form a double bond.

In another embodiment $R^{10}$ is $C_1$-$C_6$-alkyl.

In another embodiment $R^{10}$ is methyl.

In another embodiment G is phenylene optionally substituted with up to three substituents $R^{13}$, $R^{14}$ and $R^{15}$.

In another embodiment $R^{11}$ is hydrogen.

In another embodiment $R^{12}$ is hydrogen.

In another embodiment $R^{13}$, $R^{14}$ and $R^{15}$ are independently selected from hydrogen, halogen, —NO$_2$, —OR$^6$, —NR$^{16}$R$^{17}$, —SR$^{16}$, —NR$^{16}$S(O)$_2$R$^{17}$, —S(O)$_2$NR$^{16}$R$^{17}$, —S(O)NR$^{16}$R$^{17}$, —S(O)R$^{16}$, —S(O)$_2$R$^{16}$, —OS(O)$_2$R$^{16}$, —NR$^{16}$C(O)R$^{17}$, —CH$_2$OR$^{16}$, —CH$_2$OC(O)R$^{16}$, —CH$_2$NR$^{16}$R$^{17}$, —OC$_1$-C$_6$-alkyl-C(O)OR$^{16}$, —OC$_1$-C$_6$-alkyl-C(O)NR$^{16}$R$^{17}$, —OC$_1$-C$_6$-alkyl-OR$^{16}$, —SC$_1$-C$_6$-alkyl-C(O)OR$^{16}$, —C$_2$-C$_6$-alkenyl-C(=O)OR$^{16}$, or —C$_2$-C$_6$-alkenyl-C(=O)R$^{16}$, $C_1$-$C_6$-alkyl, $C_2$-$C_6$-alkenyl or $C_2$-$C_6$-alkynyl, which may optionally be substituted with one or more substituents selected from halogen, —CN, —CF$_3$, —OCF$_3$, —OR$^{16}$, and —NR$^{16}$R$^{17}$ aryl, aryloxy, aroyl, arylsulfanyl, aryl-$C_1$-$C_6$-alkoxy, aryl-$C_1$-$C_6$-alkyl, aryl-$C_2$-$C_6$-alkenyl, aroyl-$C_2$-$C_6$-alkenyl, aryl-$C_2$-$C_6$-alkynyl, heteroaryl, heteroaryl-$C_1$-$C_6$-alkyl, of which the cyclic moieties optionally may be substituted with one or more substituents selected from halogen, —C(O)OR$^{16}$, —CH$_2$C(O)OR$^{16}$, —CH$_2$OR$^{16}$, —CN, —CF$_3$, —OCF$_3$, —NO$_2$, —OR$^{16}$, —NR$^{16}$R$^{17}$ and $C_1$-$C_6$-alkyl.

In another embodiment $R^{13}$, $R^{14}$ and $R^{15}$ are independently selected from hydrogen, halogen, —NO$_2$, —OR$^6$, —NR$^{16}$R$^{17}$, —SR$^{16}$, —S(O)$_2$R$^{16}$, —OS(O)$_2$R$^{16}$, —CH$_2$OC(O)R$^{16}$, —OC(O)R$^{16}$, —OC$_1$-C$_6$-alkyl-C(O)OR$^{16}$, —OC$_1$-C$_6$-alkyl- $OR^{16}$, $-SC_1-C_6$-alkyl-$C(O)R^{16}$, $-C(O)OR^{16}$, or $-C_2-C_6$-alkenyl-$C(=O)R^{16}$, $C_1-C_6$-alkyl or $C_1-C_6$-alkenyl which may optionally be substituted with one or more substituents selected from halogen, $-CN$, $-CF_3$, $-OCF_3$, $-OR^{16}$, and $-NR^{16}R^{17}$ aryl, aryloxy, aroyl, aryl-$C_1-C_6$-alkoxy, aryl-$C_1-C_6$-alkyl, heteroaryl, of which the cyclic moieties optionally may be substituted with one or more substituents selected from halogen, $-C(O)OR^{16}$, $-CH_2C(O)OR^{16}$, $-CH_2OR^{16}$, $-CN$, $-CF_3$, $-OCF_3$, $-NO_2$, $-OR^{16}$, $-NR^{16}R^{17}$ and $C_1-C_6$-alkyl.

In another embodiment $R^{13}$, $R^{14}$ and $R^{15}$ are independently selected from hydrogen, halogen, $-NO_2$, $-OR^6$, $-NR^{16}R^{17}$, $-SR^{16}$, $-S(O)_2R^{16}$, $-OS(O)_2R^{16}$, $-CH_2OC(O)R^{16}$, $-OC(O)R^{16}$, $-OC_1-C_6$-alkyl-$C(O)OR^{16}$, $-OC_1-C_6$-alkyl-$OR^{16}$, $-SC_1-C_6$-alkyl-$C(O)OR^{16}$, $-C(O)OR^{16}$, or $-C_2-C_6$-alkenyl-$C(=O)R^{16}$, $C_1-C_6$-alkyl or $C_1-C_6$-alkenyl which may optionally be substituted with one or more substituents selected from halogen, $-CF_3$, $-OR^{16}$, and $-NR^{16}R^{17}$ aryl, aryloxy, aroyl, aryl-$C_1-C_6$-alkoxy, aryl-$C_1-C_6$-alkyl, heteroaryl, of which the cyclic moieties optionally may be substituted with one or more substituents selected from halogen, $C(O)OR^{16}$, $-CN$, $-NO_2$, $-OR^{16}$, $-NR^{16}R^{17}$ and $C_1-C_6$-alkyl.

In another embodiment $R^{13}$, $R^{14}$ and $R^{15}$ are independently selected from hydrogen, halogen, $-OR^{16}$, $-OC_1-C_6$-alkyl-$C(O)OR^{16}$, or $-C(O)OR^{16}$, $C_1-C_6$-alkyl which may optionally be substituted with one or more substituents selected from halogen, $-OR^{16}$, and $-NR^{16}R^{17}$ aryl, aryloxy, aryl-$C_1-C_6$-alkoxy, of which the cyclic moieties optionally may be substituted with one or more substituents selected from halogen, $C(O)OR^{16}$, $OR^{16}$, and $C_1-C_6$-alkyl.

In another embodiment $R^{16}$ and $R^{17}$ independently are hydrogen, $C_1-C_6$-alkyl, or aryl, wherein the alkyl groups may optionally be substituted with one or more substituents selected from halogen, $-CF_3$, $-OCF_3$, $-OC_1-C_6$-alkyl, $-COOH$ and $-NH_2$, and the aryl groups may optionally be substituted by halogen, $-COOH$, $-CN$, $-CF_3$, $-OCF_3$, $-NO_2$, $-OH$, $-OC_1-C_6$-alkyl, $-NH_2$, $C(=O)$ or $C_1-C_6$-alkyl; $R^{16}$ and $R^{17}$ when attached to the same nitrogen atom may form a 3 to 8 membered heterocyclic ring with the said nitrogen atom, the heterocyclic ring optionally containing one or two further heteroatoms selected from nitrogen, oxygen and sulphur, and optionally containing one or two double bonds In another embodiment $R^{16}$ and $R^{17}$ independently are hydrogen, $C_1-C_6$-alkyl, or aryl, wherein the alkyl groups may optionally be substituted with one or more substituents selected from halogen, $-CF_3$, $-OC_1-C_6$-alkyl, $-COOH$ and $-NH_2$, and the aryl groups may optionally be substituted by halogen, $-COOH$, $-CN$, $-CF_3$, $-OCF_3$, $-OH$, $-NH_2$, or $C_1-C_6$-alkyl.

In another embodiment A is one of the following structures

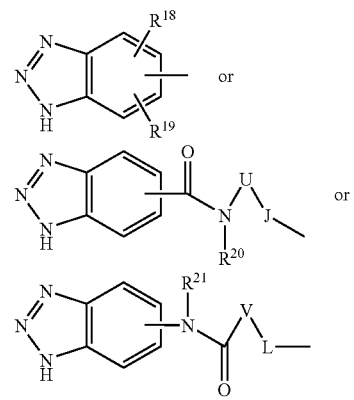

wherein $R^{20}$ is hydrogen or $C_1-C_6$-alkyl, $R^{21}$ is hydrogen or $C_1-C_6$-alkyl, U and V are a valence bond or $C_1-C_6$-alkylene optionally substituted with one or more hydroxy, $C_1-C_6$-alkyl, or aryl independently, J is $C_1-C_6$-alkylene, arylene or heteroarylene, wherein the arylene or heteroarylene is optionally substituted with up to three substituents $R^{22}$, $R^{23}$ and $R^{24}$, L is $C_1-C_6$-alkylene, arylene or heteroarylene, wherein the arylene or heteroarylene is optionally substituted with up to three substituents $R^{25}$, $R^{26}$ and $R^{27}$, $R^{18}$, $R^{19}$, $R^{22}$, $R^{23}$, $R^{24}$, $R^{25}$, $R^{26}$ and $R^{27}$ are independently selected from hydrogen, halogen, $-CN$, $-CH_2CN$, $-CHF_2$, $-CF_3$, $-OCF_3$, $-OCHF_2$, $-OCH_2CF_3$, $-OCF_2CHF_2$, $-S(O)_2CF_3$, $-SCF_3$, $-NO_2$, $-OR^{28}$, $-NR^{28}R^{29}$, $-SR^{28}$, $-NR^{28}S(O)_2R^{29}$, $-S(O)_2NR^{28}R^{29}$, $-S(O)NR^{28}R^{29}$, $-S(O)R^{28}$, $-S(O)_2R^{28}$, $-C(O)NR^{28}R^{29}$, $-OC(O)NR^{28}R^{29}$, $-NR^{28}C(O)R^{29}$, $-NR^{28}C(O)OR^{29}$, $-CH_2C(O)NR^{28}R^{29}$, $-OCH_2C(O)NR^{28}R^{29}$, $-CH_2OR^{28}$, $-CH_2NR^{28}R^{29}$, $-OC(O)R^{28}$, $-OC_1-C_6$-alkyl-$C(O)OR^{28}$, $-SC_1-C_6$-alkyl-$C(O)OR^{28}$, $-C_2-C_6$-alkenyl-$C(=O)OR^{28}$, $-NR^{28}-C(=O)-C_1-C_6$-alkyl-$C(=O)OR^{28}$, $-NR^{28}-C(=O)-C_1-C_6$-alkenyl-$C(=O)OR^{28}$, $-C(=O)NR^{28}-C_1-C_6$-alkyl-$C(=O)OR^{28}$, $-C_1-C_6$-alkyl-$C(=O)OR^{28}$, or $-C(O)OR^{28}$, $C_1-C_6$-alkyl, $C_2-C_6$-alkenyl or $C_2-C_6$-alkynyl, which may optionally be substituted with one or more substituents selected from halogen, $-CN$, $-CF_3$, $-OCF_3$, $-OR^{28}$, and $-NR^{28}R^{29}$ aryl, aryloxy, aryloxycarbonyl, aroyl, aryl-$C_1-C_6$-alkoxy, aryl-$C_1-C_6$-alkyl, aryl-$C_2-C_6$-alkenyl, aryl-$C_2-C_6$-alkynyl, heteroaryl, heteroaryl-$C_1-C_6$-alkyl, heteroaryl-$C_2-C_6$-alkenyl or heteroaryl-$C_2-C_6$-alkynyl, of which the cyclic moieties optionally may be substituted with one or more substituents selected from halogen, $-C(O)OR^{28}$, $-CN$, $-CF_3$, $-OCF_3$, $-NO_2$, $-OR^{28}$, $-NR^{28}R^{29}$ and $C_1-C_6$-alkyl, $R^{28}$ and $R^{29}$ independently are hydrogen, $C_1-C_6$-alkyl, aryl-$C_1-C_6$-alkyl or aryl, or $R^{28}$ and $R^{29}$ when attached to the same nitrogen atom together with the said nitrogen atom may form a 3 to 8 membered heterocyclic ring optionally containing one or two further heteroatoms selected from nitrogen, oxygen and sulphur, and optionally containing one or two double bonds In another embodiment U is a valence bond In another embodiment U is $C_1$-$C_6$-alkylene optionally substituted with one or more hydroxy, $C_1$-$C_6$-alkyl, or aryl In another embodiment J is arylene or heteroarylene, wherein the arylene or heteroarylene is optionally substituted with up to three substituents $R^{22}$, $R^{23}$ and $R^{24}$ In another embodiment J is arylene optionally substituted with up to three substituents $R^{22}$, $R^{23}$ and $R^{24}$ In another embodiment J is phenylene optionally substituted with up to three substituents $R^{22}$, $R^{23}$ and $R^{24}$ In another embodiment $R^{22}$, $R^{23}$ and $R^{24}$ are independently selected from hydrogen, halogen, —$CHF_2$, —$CF_3$, —$OCF_3$, —$OCHF_2$, —$OCH_2CF_3$, —$OCF_2CHF_2$, —$SCF_3$, —$NO_2$, —$OR^{28}$, —$NR^{28}R^{29}$, —$SR^{28}$, —$C(O)NR^{28}R^{29}$, —$OC(O)NR^{28}R^{29}$, —$NR^{28}C(O)R^{29}$, —$NR^{28}C(O)OR^{29}$, —$CH_2C(O)NR^{28}R^{29}$, —$OCH_2C(O)NR^{28}R^{29}$, —$CH_2OR^{28}$, —$CH_2NR^{28}R^{29}$, —$OC(O)R^{28}$, —$OC_1$-$C_6$-alkyl-$C(O)OR^{28}$, —$SC_1$-$C_6$-alkyl-$C(O)OR^{28}$, —$C_2$-$C_6$-alkenyl-$C(=O)OR^{28}$, —$NR^{28}$—$C(=O)$—$C_1$-$C_6$-alkyl-$C(=O)OR^{28}$, —$NR^{28}$—$C(=O)$—$C_1$-$C_6$-alkenyl-$C(=O)OR^{28}$—, —$C(=O)NR^{28}$—$C_1$-$C_6$-alkyl-$C(=O)OR^{28}$, $C_1$-$C_6$-alkyl-$C(=O)OR^{28}$, or —$C(O)OR^{28}$, $C_1$-$C_6$-alkyl, $C_2$-$C_6$-alkenyl or $C_2$-$C_6$-alkynyl, which may optionally be substituted with one or more substituents selected from halogen, —CN, —$CF_3$, —$OCF_3$, —$OR^{28}$, and —$NR^{28}R^{29}$ aryl, aryloxy, aryloxycarbonyl, aroyl, aryl-$C_1$-$C_6$-alkoxy, aryl-$C_1$-$C_6$-alkyl, aryl-$C_2$-$C_6$-alkenyl, aryl-$C_2$-$C_6$-alkynyl, heteroaryl, heteroaryl-$C_1$-$C_6$-alkyl, heteroaryl-$C_2$-$C_6$-alkenyl or heteroaryl-$C_2$-$C_6$-alkynyl, of which the cyclic moieties optionally may be substituted with one or more substituents selected from halogen, —$C(O)OR^{28}$, —CN, —$CF_3$, —$OCF_3$, —$NO_2$, —$OR^{28}$, —$NR^{28}R^{29}$ and $C_1$-$C_6$-alkyl In another embodiment $R^{22}$, $R^{23}$ and $R^{24}$ are independently selected from hydrogen, halogen, —$OCF_3$, —$OR^{28}$, —$NR^{28}R^{29}$, —$SR^{28}$, —$NR^{28}C(O)R^{29}$, —$NR^{28}C(O)OR^{29}$, —$OC(O)R^{28}$, —$OC_1$-$C_6$-alkyl-$C(O)OR^{28}$, —$SC_1$-$C_6$-alkyl-$C(O)OR^{28}$, —$C_2$-$C_6$-alkenyl-$C(=O)OR^{28}$, —$C(=O)NR^{28}$—$C_1$-$C_6$-alkyl-$C(=O)OR^{28}$, —$C_1$-$C_6$-alkyl-$C(=O)OR^{28}$, or —$C(O)OR^{28}$, $C_1$-$C_6$-alkyl optionally substituted with one or more substituents selected from halogen, —CN, —$CF_3$, —$OCF_3$, —$OR^{28}$, and —$NR^{28}R^{29}$ aryl, aryloxy, aroyl, aryl-$C_1$-$C_6$-alkoxy, aryl-$C_1$-$C_6$-alkyl, heteroaryl, heteroaryl-$C_1$-$C_6$-alkyl, of which the cyclic moieties optionally may be substituted with one or more substituents selected from halogen, —$C(O)OR^{28}$, —CN, —$CF_3$, —$OCF_3$, —$NO_2$, —$OR^{28}$, —$NR^{28}R^{29}$ and $C_1$-$C_6$-alkyl In another embodiment $R^{22}$, $R^{23}$ and $R^{24}$ are independently selected from hydrogen, halogen, —$OCF_3$, —$OR^{28}$, —$NR^{28}R^{29}$, —$SR^{28}$, —$NR^{28}C(O)R^{29}$, —$NR^{28}C(O)OR^{29}$, —$OC(O)R^{28}$, —$OC_1$-$C_6$-alkyl-$C(O)OR^{28}$, —$SC_1$-$C_6$-alkyl-$C(O)OR^{28}$, —$C_2$-$C_6$-alkenyl-$C(=O)OR^{28}$, —$C(=O)NR^{28}$—$C_1$-$C_6$-alkyl-$C(=O)OR^{28}$, —$C_1$-$C_6$-alkyl-$C(=O)OR^{28}$, or —$C(O)OR^{28}$, $C_1$-$C_6$-alkyl optionally substituted with one or more substituents selected from halogen, —CN, or —$CF_3$ aryl, aryloxy, aroyl, aryl-$C_1$-$C_6$-alkoxy, aryl-$C_1$-$C_6$-alkyl, heteroaryl, heteroaryl-$C_1$-$C_6$-alkyl, of which the cyclic moieties optionally may be substituted with one or more substituents selected from halogen, —C(O)OH, —CN, —$CF_3$, —$NO_2$, or $C_1$-$C_6$-alkyl In another embodiment $R^{20}$ is hydrogen or methyl In another embodiment $R^{20}$ is hydrogen In another embodiment $R^{28}$ is hydrogen, $C_1$-$C_6$-alkyl or aryl In another embodiment $R^{28}$ is hydrogen or $C_1$-$C_6$-alkyl In another embodiment $R^{29}$ is hydrogen or $C_1$-$C_6$-alkyl In another embodiment V is a valence bond In another embodiment V is $C_1$-$C_6$-alkylene optionally substituted with one or more hydroxy, $C_1$-$C_6$-alkyl, or aryl In another embodiment L is $C_1$-$C_6$-alkylene or arylene, wherein the arylene is optionally substituted with up to three substituents $R^{25}$, $R^{26}$ and $R^{27}$ In another embodiment L is $C_1$-$C_6$-alkyl In another embodiment L is phenylene optionally substituted with up to three substituents $R^{25}$, $R^{26}$ and $R^{27}$ In another embodiment $R^{25}$, $R^{26}$ and $R^{27}$ are independently selected from hydrogen, halogen, —$CHF_2$, —$CF_3$, —$OCF_3$, —$OCHF_2$, —$OCH_2CF_3$, —$OCF_2CHF_2$, —$SCF_3$, —$NO_2$, —$OR^{28}$, —$NR^{28}R^{29}$, —$SR^{28}$, —$C(O)NR^{28}R^{29}$, —$OC(O)NR^{28}R^{29}$, —$NR^{28}C(O)R^{29}$, —$NR^{28}C(O)OR^{29}$, —$CH_2C(O)NR^{28}R^{29}$, —$OCH_2C(O)NR^{28}R^{29}$, —$CH_2OR^{28}$, —$CH_2NR^{28}R^{29}$, —$OC(O)R^{28}$, —$OC_1$-$C_6$-alkyl-$C(O)OR^{28}$, —$SC_1$-$C_6$-alkyl-$C(O)OR^{28}$, —$C_2$-$C_6$-alkenyl-$C(=O)OR^{28}$, —$NR^{28}$—$C(=O)$—$C_1$-$C_6$-alkyl-$C(=O)OR^{28}$, —$NR^{28}$—$C(=O)$—$C_1$-$C_6$-alkenyl-$C(=O)OR^{28}$—, —$C(=O)NR^{28}$—$C_1$-$C_6$-alkyl-$C(=O)OR^{28}$, —$C_1$-$C_6$-alkyl-$C(=O)OR^{28}$, or —$C(O)OR^{28}$, $C_1$-$C_6$-alkyl, $C_2$-$C_6$-alkenyl or $C_2$-$C_6$-alkynyl, which may optionally be substituted with one or more substituents selected from halogen, —CN, —$CF_3$, —$OCF_3$, —$OR^{28}$, and —$NR^{28}R^{29}$ aryl, aryloxy, aryloxycarbonyl, aroyl, aryl-$C_1$-$C_6$-alkoxy, aryl-$C_1$-$C_6$-alkyl, aryl-$C_2$-$C_6$-alkenyl, aryl-$C_2$-$C_6$-alkynyl, heteroaryl, heteroaryl-$C_1$-$C_6$-alkyl, heteroaryl-$C_2$-$C_6$-alkenyl or heteroaryl-$C_2$-$C_6$-alkynyl, of which the cyclic moieties optionally may be substituted with one or more substituents selected from halogen, —$C(O)OR^{28}$, —CN, —$CF_3$, —$OCF_3$, —$NO_2$, —$OR^{28}$, —$NR^{28}R^{29}$ and $C_1$-$C_6$-alkyl In another embodiment $R^{25}$, $R^{26}$ and $R^{27}$ are independently selected from hydrogen, halogen, —$OCF_3$, —$OR^{28}$, —$NR^{28}R^{29}$, —$SR^{28}$, —$NR^{28}C(O)R^{29}$, —$NR^{28}C(O)OR^{29}$, —$OC(O)R^{28}$, —$OC_1$-$C_6$-alkyl-$C(O)R^{28}$, —$SC_1$-$C_6$-alkenyl-$C(O)OR^{28}$, $C_2$-$C_6$-alkenyl-$C(=O)OR^{28}$, —$C(=O)NR^{28}$—$C_1$-$C_6$-alkyl-$C(=O)OR^{28}$, —$C_1$-$C_6$-alkyl-$C(=O)OR^{28}$, or —$C(O)OR^{28}$, $C_1$-$C_6$-alkyl optionally substituted with one or more substituents selected from halogen, —CN, —$CF_3$, —$OCF_3$, —$OR^{28}$, and —$NR^{28}R^{29}$ aryl, aryloxy, aroyl, aryl-$C_1$-$C_6$-alkoxy, aryl-$C_1$-$C_6$-alkyl, heteroaryl, heteroaryl-$C_1$-$C_6$-alkyl, of which the cyclic moieties optionally may be substituted with one or more substituents selected from halogen, —$C(O)OR^{28}$, —CN, —$CF_3$, —$OCF_3$, —$NO_2$, —$OR^{28}$, —$NR^{28}R^{29}$ and $C_1$-$C_6$-alkyl In anther embodiment $R^{25}$, $R^{26}$ and $R^{27}$ are independently selected from hydrogen, halogen, —$OCF_3$, —$OR^{28}$, —$NR^{28}R^{29}$, —$SR^{28}$, —$NR^{28}C(O)R^{29}$, —$NR^{28}C(O)OR^{29}$, —$OC(O)R^{28}$, —$OC_1$-$C_6$-alkyl-$C(O)OR^{28}$, —$SC_1$-$C_6$-alkyl-$C(O)OR^{28}$, —$C_2$-$C_6$-alkenyl-$C(=O)OR^{28}$, —$C(=O)$ $NR^{28}$—$C_1$-$C_6$-alkyl-C(=O)$OR^{28}$, —$C_1$-$C_6$-alkyl-C(=O)$OR^{28}$, or —C(O)$OR^{28}$, $C_1$-$C_6$-alkyl optionally substituted with one or more substituents selected from halogen, —CN, or —$CF_3$ aryl, aryloxy, aroyl, aryl-$C_1$-$C_6$-alkoxy, aryl-$C_1$-$C_6$-alkyl, heteroaryl, heteroaryl-$C_1$-$C_6$-alkyl, of which the cyclic moieties optionally may be substituted with one or more substituents selected from halogen, —C(O)OH, —CN, —$CF_3$, —$NO_2$, or $C_1$-$C_6$-alkyl In another embodiment $R^{21}$ is hydrogen or methyl In another embodiment $R^{21}$ is hydrogen In another embodiment $R^{28}$ is Hydrogen, $C_1$-$C_6$-alkyl or aryl In another embodiment $R^{28}$ is Hydrogen or $C_1$-$C_6$-alkyl In another embodiment $R^{29}$ is Hydrogen or $C_1$-$C_6$-alkyl In another embodiment $R^{18}$ and $R^{19}$ are independently selected from hydrogen, halogen, —CN, —$CF_3$, —$OCF_3$, —$NO_2$, —$OR^{28}$, —$NR^{28}R^{29}$, —$SR^{28}$, —S(O)$R^{28}$, —$S(O)_2R^{28}$, —C(O)$NR^{28}R^{29}$, —$CH_2OR^{28}$, —OC(O)$R^{28}$, —$OC_1$-$C_6$-alkyl-C(O)$OR^{28}$, —$SC_1$-$C_6$-alkyl-C(O)$OR^{28}$, or —C(O)$OR^{28}$.

$C_1$-$C_6$-alkyl, $C_2$-$C_6$-alkenyl or $C_2$-$C_6$-alkynyl, which may optionally be substituted with one or more substituents selected from halogen, —CN, —$CF_3$, —$OCF_3$, —$OR^{28}$, and —$NR^{28}R^{29}$ aryl, aryloxy, aryl-$C_1$-$C_6$-alkoxy, aryl-$C_1$-$C_6$-alkyl, heteroaryl, heteroaryl-$C_1$-$C_6$-alkyl of which the cyclic moieties optionally may be substituted with one or more substituents selected from halogen, —C(O)$OR^{28}$, —CN, —$CF_3$, —$OCF_3$, —$NO_2$, —$OR^{28}$, —$NR^{28}R^{29}$ and $C_1$-$C_6$-alkyl In another embodiment $R^{18}$ and $R^{19}$ are independently selected from hydrogen, halogen, —CN, —$CF_3$, —$NO_2$, —$OR^{28}$, —$NR^{28}R^{29}$, or —C(O)$OR^{28}$ $C_1$-$C_6$-alkyl optionally substituted with one or more substituents selected from halogen, —CN, —$CF_3$, —$OCF_3$, —$OR^{28}$, and —$NR^{28}R^{29}$ aryl, aryloxy, aryl-$C_1$-$C_6$-alkyl, heteroaryl, of which the cyclic moieties optionally may be substituted with one or more substituents selected from halogen, —C(O)$OR^{28}$, —CN, —$CF_3$, —$OCF_3$, —$NO_2$, —$OR^{28}$, —$NR^{28}R^{29}$ and $C_1$-$C_6$-alkyl In another embodiment A is a compound of the form M-Q-T- wherein M is one of the following structures

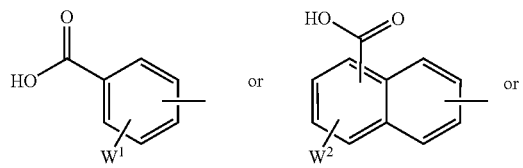

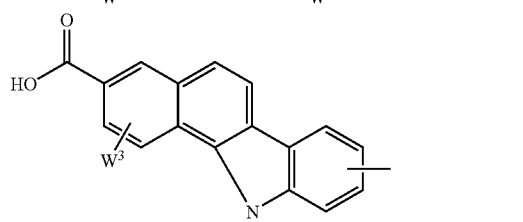

wherein $W^1$, $W^2$, and $W^3$ are independently OH, SH or $NH_2$ and the phenyl, naphthalene or benzocarbazole rings are optionally substituted by one or more $R^{34}$ independently Q is selected from the following:
a valence bond
—$CH_2N(R^{30})$— or —$SO_2N(R^{31})$—
A compound of the formula

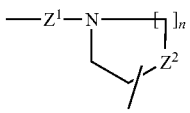

wherein $Z^1$ is $S(O)_2$ or $CH_2$, $Z^2$ is N, —O— or —S—, and n is 1 or 2;

T is

A valence bond $C_1$-$C_6$-alkylene, $C_2$-$C_6$-alkenylene or $C_2$-$C_6$-alkynylene, which may optionally be substituted with one or more substituents selected from halogen, —CN, —$CF_3$, —$OCF_3$, —$OR^{32}$, and —$NR^{32}R^{33}$ Arylene, -aryloxy-, -aryloxycarbonyl-, -aroyl-, -aryl-$C_1$-$C_6$-alkoxy-, -aryl-$C_1$-$C_6$-alkyl-, -aryl-$C_2$-$C_6$-alkenyl-, -aryl-$C_2$-$C_6$-alkynyl-, heteroarylene, -heteroaryl-$C_1$-$C_6$-alkyl-, -heteroaryl-$C_2$-$C_6$-alkenyl- or -heteroaryl-$C_2$-$C_6$-alkynyl-, wherein the cyclic moieties are optionally substituted by one or more substituents selected from halogen, —C(O)$OR^{32}$, —C(O)H, —CN, —$CF_3$, —$OCF_3$, —$NO_2$, —$OR^{32}R^{33}$, $C_1$-$C_6$-alkyl or $C_1$-$C_6$-alkanoyl, $R^{32}$ and $R^{33}$ independently are hydrogen, $C_1$-$C_6$-alkyl, aryl-$C_1$-$C_6$-alkyl or aryl, or $R^{32}$ and $R^{33}$ when attached to the same nitrogen atom together with the said nitrogen atom may form a 3 to 8 membered heterocyclic ring optionally containing one or two further heteroatoms selected from nitrogen, oxygen and sulphur, and optionally containing one or two double bonds, $R^{30}$ and $R^{31}$ are independently hydrogen, $C_1$-$C_6$-alkyl or $C_1$-$C_6$-alkanoyl.

$R^{34}$ is hydrogen, halogen, —CN, —$CH_2CN$, —$CHF_2$, —$CF_3$, —$OCF_3$, —$OCHF_2$, —$OCH_2CF_3$, —$OCF_2CHF_2$, —$S(O)_2CF_3$, —$SCF_3$, —$NO_2$, —$OR^{32}$, —C(O)$R^{32}$, —$NR^{32}R^{33}$, —$SR^{32}$, —$NR^{32}S(O)_2R^{33}$, —$S(O)_2NR^{32}R^{33}$, —$S(O)NR^{32}R^{33}$, —S(O)$R^{32}$, —$S(O)_2R^{32}$, —C(O)$NR^{32}R^{33}$, —OC(O)$NR^{32}R^{33}$, —$NR^{32}C(O)R^{33}$, —$CH_2C(O)NR^{32}R^{33}$, —$OCH_2C(O)NR^{32}R^{33}$, —$CH_2OR^{32}$, —$CH_2NR^{32}R^{33}$, —OC(O)$R^{32}$, —$OC_1$-$C_6$-alkyl-C(O)$OR^{32}$, —$SC_1$-$C_6$-alkyl-C(O)$OR^{32}$—$C_2$-$C_6$-alkenyl-C(=O)$OR^{32}$, —$NR^{32}$—C(=O)—$C_1$-$C_6$-alkyl-C(=O)$OR^{32}$, —$NR^{32}$—C(=O)—$C_1$-$C_6$-alkenyl-C(=O)$OR^{32}$—, $C_1$-$C_6$-alkyl, $C_1$-$C_6$-alkanoyl or —C(O)$OR^{32}$, In another embodiment M is one of the following structures

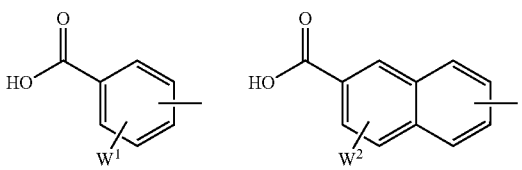

In another embodiment M is

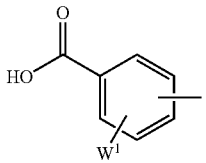

In another embodiment M is

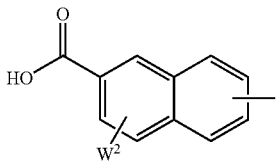

In another embodiment the salicylic acid moiety is of the formula

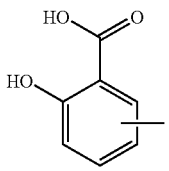

In another embodiment the napthoic acid moiety is of the formula

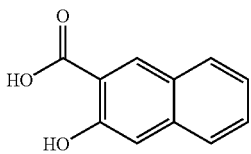

In another embodiment Q is a valence bond, —CH$_2$N(R$^{30}$)—, or —SO$_2$N(R$^{31}$)—

In another embodiment Q is a valence bond

In another embodiment T is

A valence bond

C$_1$-C$_6$-alkylene, C$_2$-C$_6$-alkenylene or C$_2$-C$_6$-alkynylene, which may optionally be substituted with one or more substituents selected from halogen, —CN, —CF$_3$, —OCF$_3$, —OR$^{32}$, and —NR$^{32}$R$^{33}$ Arylene, or heteroarylene, wherein the cyclic moieties are optionally substituted as defined in claim 70

In another embodiment T is

A valence bond

Arylene, or heteroarylene, wherein the cyclic moieties are optionally substituted as defined in claim 70

In another embodiment T is phenylene or naphthalene

In another embodiment the cyclic moiety in T is optionally substituted by halogen, —C(O)OR$^{32}$, —CN, —CF$_3$, —OR$^{32}$, —NR$^{32}$R$^{33}$, C$_1$-C$_6$-alkyl or C$_1$-C$_6$-alkanoyl In another embodiment the cyclic moiety in T is optionally substituted by halogen, —C(O)OR$^{32}$, —OR$^{32}$, —NR$^{32}$R$^{33}$, C$_1$-C$_6$-alkyl or C$_1$-C$_6$-alkanoyl In another embodiment the cyclic moiety in T is optionally substituted by halogen, —C(O)OR$^{32}$ or —OR$^{32}$ In another embodiment T is a valence bond In another embodiment R$^{30}$ and R$^{31}$ are independently hydrogen or C$_1$-C$_6$-alkyl In another embodiment R$^{34}$ is hydrogen, halogen, —CN, —CF$_3$, —OCF$_3$, —SCF$_3$, —NO$_2$, —OR$^{32}$, —C(O)R$^{32}$, —NR$^{32}$R$^{33}$, —SR$^{32}$, —C(O)NR$^{32}$R$^{33}$, —OC(O)NR$^{32}$R$^{33}$, —NR$^{32}$C(O)R$^{33}$, —OC(O)R$^{32}$, —OC$_1$-C$_6$-alkyl-C(O)OR$^{32}$, —SC$_1$-C$_6$-alkyl-C(O)OR$^{32}$ or —C(O)OR$^{32}$ In another embodiment R$^{34}$ is hydrogen, halogen, —CF$_3$, —NO$_2$, —OR$^{32}$, —NR$^{32}$R$^{33}$, —SR$^{32}$, —NR$^{32}$C(O)R$^{33}$, or —C(O)OR$^{32}$ In another embodiment R$^{34}$ is hydrogen, halogen, —CF$_3$, —NO$_2$, —OR$^{32}$, —NR$^{32}$R$^{33}$, or —NR$^{32}$C(O)R$^{33}$ In another embodiment R$^{34}$ is hydrogen, halogen, or —OR$^{32}$ In another embodiment R$^{32}$ and R$^{33}$ independently are hydrogen, C$_1$-C$_6$-alkyl, or aryl In another embodiment R$^{32}$ and R$^{33}$ independently are hydrogen or C$_1$-C$_6$-alkyl In another embodiment C consists of 1-5 neutral amino acids independently selected from the group consisting of Gly, Ala, Thr, and Ser In another embodiment C consists of 1-5 Gly In another embodiment G$^B$ is of the formula —B$^1$—B$^2$—C(O)—, —B$^1$—B$^2$—SO$_2$— or —B$^1$—B$^2$—CH$_2$—, wherein B$^1$ and B$^2$ are as defined above In another embodiment G$^B$ is of the formula —B$^1$—B$^2$—C(O)—, —B$^1$—B$^2$—SO$_2$— or —B$^1$—B$^2$—NH—, wherein B$^1$ and B$^2$ are as defined above In another embodiment G$^B$ is of the formula —B$^1$—B$^2$—C(O)—, —B$^1$—B$^2$—CH$_2$— or —B$^1$—B$^2$—NH—, wherein B$^1$ and B$^2$ are as defined above In another embodiment G$^B$ is of the formula —B$^1$—B$^2$—CH$_2$—, —B$^1$—B$^2$—SO$_2$— or —B$^1$—B$^2$—NH—, wherein B$^1$ and B$^2$ are as defined above In another embodiment G$^B$ is of the formula —B$^1$—B$^2$—C(O)— or —B$^1$—B$^2$—SO$_2$—, wherein B$^1$ and B$^2$ are as defined above In another embodiment G$^B$ is of the formula —B$^1$—B$^2$—C(O)— or —B$^1$—B$^2$—CH$_2$—, wherein B$^1$ and B$^2$ are as defined above In another embodiment G$^B$ is of the formula —B$^1$—B$^2$—C(O)— or —B$^1$—B$^2$—NH—, wherein B$^1$ and B$^2$ are as defined above In another embodiment G$^B$ is of the formula —B$^1$—B$^2$—CH$_2$— or —B$^1$—B$^2$—SO$_2$—, wherein B$^1$ and B$^2$ are as defined above In another embodiment G$^B$ is of the formula —B$^1$—B$^2$—NH— or —B$^1$—B$^2$—SO$_2$—, wherein B$^1$ and B$^2$ are as defined above In another embodiment G$^B$ is of the formula —B$^1$—B$^2$—CH$_2$— or —B$^1$—B$^2$—NH—, wherein B$^1$ and B$^2$ are as defined above In another embodiment G$^B$ is of the formula —B$^1$—B$^2$—C(O)—

In another embodiment G$^B$ is of the formula —B$^1$—B$^2$—CH$_2$—

In another embodiment G$^B$ is of the formula —B$^1$—B$^2$—SO$_2$—

In another embodiment G$^B$ is of the formula —B$^1$—B$^2$—NH—

In another embodiment B$^1$ is a valence bond, —O—, or —S—

In another embodiment B$^1$ is a valence bond, —O—, or —N(R$^6$)—

In another embodiment $B^1$ is a valence bond, —S—, or —N($R^6$)—

In another embodiment $B^1$ is —O—, —S— or —N($R^6$)—

In another embodiment $B^1$ is a valence bond or —O—

In another embodiment $B^1$ is a valence bond or —S—

In another embodiment $B^1$ is a valence bond or —N($R^6$)—

In another embodiment $B^1$ is —O— or —S—

In another embodiment $B^1$ is —O— or —N($R^6$)—

In another embodiment $B^1$ is —S— or —N($R^6$)—

In another embodiment $B^1$ is a valence bond

In another embodiment $B^1$ is —O—

In another embodiment $B^1$ is —S—

In another embodiment $B^1$ is —N($R^6$)—

In another embodiment $B^2$ is a valence bond, $C_1$-$C_{18}$-alkylene, $C_2$-$C_{18}$-alkenylene, $C_2$-$C_{18}$-alkynylene, arylene, heteroarylene, —$C_1$-$C_{18}$-alkyl-aryl-, —C(=O)—$C_1$-$C_{18}$-alkyl-C(=O)—, —C(=O)—$C_1$-$C_{18}$-alkyl-O—$C_1$-$C_{18}$-alkyl-C(=O)—, —C(=O)—$C_1$-$C_{18}$-alkyl-S—$C_1$-$C_{18}$-alkyl-C(=O)—, —C(=O)—$C_1$-$C_{18}$-alkyl-N$R^6$—$C_1$-$C_{18}$-alkyl-C(=O)—; and the alkylene and arylene moieties are optionally substituted as defined above In another embodiment $B^2$ is a valence bond, $C_1$-$C_{18}$-alkylene, $C_2$-$C_{18}$-alkenylene, $C_2$-$C_{18}$-alkynylene, arylene, heteroarylene, —$C_1$-$C_{18}$-alkyl-aryl-, —C(=O)—$C_1$-$C_{18}$-alkyl-C(=O)—, —C(=O)—$C_1$-$C_{18}$-alkyl-O—$C_1$-$C_{18}$-alkyl-C(=O)—, and the alkyl and aryl moieties are optionally substituted as defined above In another embodiment $B^2$ is a valence bond, $C_1$-$C_{18}$-alkylene, $C_2$-$C_{18}$-alkenylene, $C_2$-$C_{18}$-alkynylene, arylene, heteroarylene, —$C_1$-$C_{18}$-alkyl-aryl-, —C(=O)—$C_1$-$C_{18}$-alkyl-C(=O)—, and the alkylene and arylene moieties are optionally substituted as defined above In another embodiment $B^2$ is a valence bond, $C_1$-$C_{18}$-alkylene, arylene, heteroarylene, —$C_1$-$C_{18}$-alkyl-aryl-, —C(=O)—$C_1$-$C_{18}$-alkyl-C(=O)—, and the alkylene and arylene moieties are optionally substituted as defined above In another embodiment $B^2$ is a valence bond, $C_1$-$C_{18}$-alkylene, arylene, heteroarylene, —$C_1$-$C_{18}$-alkyl-aryl-, and the alkylene and arylene moieties are optionally substituted as defined above In another embodiment $B^2$ is a valence bond, $C_1$-$C_{18}$-alkylene, arylene, —$C_1$-$C_{18}$-alkyl-aryl-, and the alkylene and arylene moieties are optionally substituted as defined above In another embodiment $B^2$ is a valence bond or $C_1$-$C_{18}$-alkylene, and the alkylene moiety is optionally substituted as defined above In another embodiment D comprises 1 to 16 positively charged groups In another embodiment D comprises 1 to 12 positively charged groups In another embodiment D comprises 1 to 10 positively charged groups In another embodiment D is a fragment containing basic amino acids independently selected from the group consisting of Lys and Arg and D-isomers of these.

In another embodiment the basic amino acid is Arg

In another embodiment X is —OH or —$NH_2$

In another embodiment X is —$NH_2$

Also provided by the present invention is an R-state insulin hexamer comprising:

6 molecules of insulin, at least 2 zinc ions, and a zinc-binding ligand according to any one of the preceding claims.

In one embodiment the insulin forming the R-state insulin hexamer is selected from the group consisting of human insulin, an analogue thereof, a derivative thereof, and combinations of any of these In another embodiment the insulin is an analogue of human insulin selected from the group consisting of
i. An analogue wherein position B28 is Asp, Lys, Leu, Val, or Ala and position B29 is Lys or Pro; and
ii. des(B28-B30), des(B27) or des(B30) human insulin.

In another embodiment the insulin is an analogue of human insulin wherein position B28 is Asp or Lys, and position B29 is Lys or Pro.

In another embodiment the insulin is des(B30) human insulin.

In another embodiment the insulin is a derivative of human insulin having one or more lipophilic substituents.

In another embodiment the insulin derivative is selected from the group consisting of B29-$N^\epsilon$-myristoyl-des(B30) human insulin, B29-$N^\epsilon$-palmitoyl-des(B30) human insulin, B29-$N^\epsilon$-myristoyl human insulin, B29-$N^\epsilon$-palmitoyl human insulin, B28-$N^\epsilon$-myristoyl Lys$^{B28}$ Pro$^{B29}$ human insulin, B28-$N^\epsilon$-palmitoyl Lys$^{B28}$ Pro$^{B29}$ human insulin, B30-$N^\epsilon$-myristoyl-Thr$^{B29}$Lys$^{B30}$ human insulin, B30-$N^\epsilon$-palmitoyl-Thr$^{B29}$Lys$^{B30}$ human insulin, B29-$N^\epsilon$-(N-palmitoyl-$\gamma$-glutamyl)-des(B30) human insulin, B29-$N^\epsilon$-(N-lithocholyl-$\gamma$-glutamyl)-des(B30) human insulin, B29-$N^\epsilon$-($\omega$-carboxyheptadecanoyl)-des(B30) human insulin and B29-$N^\epsilon$-($\omega$-carboxyheptadecanoyl) human insulin.

In another embodiment the insulin derivative is B29-$N^\epsilon$-myristoyl-des(B30) human insulin.

In another embodiment the insulin hexamer of the invention further comprises at least 3 phenolic molecules.

In another embodiment the invention provides an insulin preparation comprising R-state insulin hexamers as defined above In another embodiment the invention provides a method of prolonging the action of an insulin preparation which comprises adding a zinc-binding ligand as defined above to the insulin preparation.

In another embodiment the invention provides an aqueous insulin preparation as defined above wherein the ratio between precipitated insulin and dissolved insulin is in the range from 99:1 to 1:99.

In another embodiment the ratio between precipitated insulin and dissolved insulin is in the range from 95:5 to 5:95

In another embodiment the ratio between precipitated insulin and dissolved insulin is in the range from 80:20 to 20:80

In another embodiment the ratio between precipitated insulin and dissolved insulin is in the range from 70:30 to 30:70.

In another embodiment the invention provides a zinc-binding ligand of the following general formula (III)

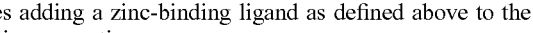

A-B-C-D-X  (III)

wherein:
A is a chemical group which reversibly binds to a His$^{B10}$ $Zn^{2+}$ site of an insulin hexamer;
B is a linker selected from
A valence bond
A chemical group $G^B$ of the formula —$B^1$—$B^2$—C(O)—, —$B^1$—$B^2$—$SO_2$—, —$B^1$—$B^2$—$CH_2$—, or —$B^1$—$B^2$—NH—; wherein $B^1$ is a valence bond, —O—, —S—, or —$NR^6$—,
$B^2$ is a valence bond, $C_1$-$C_{18}$-alkylene, $C_2$-$C_{18}$-alkenylene, $C_2$-$C_{18}$-alkynylene, arylene, heteroarylene, —$C_1$-$C_{18}$-alkyl-aryl-, —$C_2$-$C_{18}$-alkenyl-aryl-, —$C_2$-$C_{18}$-alkynyl-aryl-, —C(=O)—$C_1$-$C_{18}$-alkyl-C(=O)—, —C(=O)—$C_1$-$C_{18}$-alkenyl-C(=O)—, —C(=O)—$C_1$-$C_{18}$-alkyl-O—$C_1$-$C_{18}$-alkyl-C(=O)—, —C(=O)—$C_1$-$C_{18}$-alkyl-S—$C_1$-$C_{18}$-alkyl-C(=O)—, —C(=O)—$C_1$-$C_{18}$-alkyl-$NR^6$—

$C_1$-$C_{18}$-alkyl-C(=O), —C(=O)aryl-C(=O)—, —C(=O)-heteroaryl-C(=O)—;
wherein the alkylene, alkenylene, and alkynylene moieties are optionally substituted by —CN, —CF$_3$, —OCF$_3$, —OR$^6$, or —NR$^6$R$^7$ and the arylene and heteroarylene moieties are optionally substituted by halogen, —C(O)OR$^6$, —C(O)H, OCOR$^6$, —SO$_2$, —CN, —CF$_3$, —OCF$_3$, —NO$_2$, —OR$^6$, —NR$^6$R$^7$, $C_1$-$C_{18}$-alkyl, or $C_1$-$C_{18}$-alkanoyl;

R$^6$ and R$^7$ are independently H, $C_1$-$C_4$-alkyl;

C is a fragment consisting of 0 to 5 neutral amino acids, wherein the individual neutral amino acids are the same or different D is a fragment comprising 1 to 20 positively charged groups independently selected from amino or guanidino groups, wherein the individual positively charged groups are the same or different; and X is —OH, —NH$_2$ or a diamino group, or a salt thereof with a pharmaceutically acceptable acid or base, or any optical isomer or mixture of optical isomers, including a racemic mixture, or any tautomeric forms.

In another embodiment of the invention A is a chemical structure selected from the group consisting of carboxylates, dithiocarboxylates, phenolates, thiophenolates, alkylthiolates, sulfonamides, imidazoles, triazoles, 4-cyano-1,2,3-triazoles, benzimidazoles, benzotriazoles, purines, thiazolidinediones, tetrazoles, 5-mercaptotetrazoles, rhodanines, N-hydroxyazoles, hydantoines, thiohydantoines, barbiturates, naphthoic acids and salicylic acids.

In another embodiment of the invention A is a chemical structure selected from the group consisting of benzotriazoles, 3-hydroxy 2-napthoic acids, salicylic acids, tetrazoles, thiazolidinediones, 5-mercaptotetrazoles, or 4-cyano-1,2,3-triazoles.

In another embodiment of the invention A is

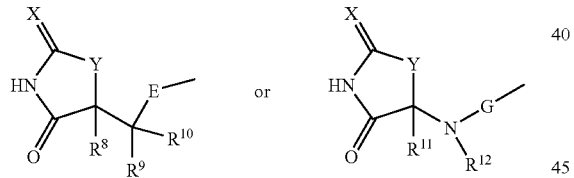

wherein
X is =O, =S or =NH
Y is —S—, —O— or —NH—
R$^8$ and R$^{11}$ are independently hydrogen or $C_1$-$C_6$-alkyl,
R$^9$ is hydrogen or $C_1$-$C_6$-alkyl or aryl, R$^8$ and R$^9$ may optionally be combined to form a double bond,
R$^{10}$ and R$^{12}$ are independently hydrogen, aryl, $C_1$-$C_6$-alkyl, or —C(O)NR$^{16}$R$^{17}$
E and G are independently $C_1$-$C_6$-alkylene, arylene, -aryl-$C_1$-$C_6$-alkyl-, -aryl-$C_2$-$C_6$-alkenyl- or heteroarylene, wherein the alkylene or alkenylene is optionally substituted with one or more substituents independently selected from halogen, —CN, —CF$_3$, —OCF$_3$, aryl, —COOH and —NH$_2$, and the arylene or heteroarylene is optionally substituted with up to four substituents R$^{13}$, R$^{14}$, R$^{15}$, and R$^{15A}$ E and R$^{10}$ may be connected through one or two valence bonds, G and R$^{12}$ may be connected through one or two valence bonds;

R$^{13}$, R$^{14}$, R$^{15}$ and R$^{15A}$ are independently selected from
hydrogen, halogen, —CN, —CH$_2$CN, —CHF$_2$, —CF$_3$, —OCF$_3$, —OCHF$_2$, —OCH$_2$CF$_3$, —OCF$_2$CHF$_2$, —S(O)$_2$CF$_3$, —OS(O)$_2$CF$_3$, —SCF$_3$, —NO$_2$, —OR$^{16}$, —NR$^{16}$R$^{17}$, —SR$^{16}$, —NR$^{16}$S(O)$_2$R$^{17}$, —S(O)$_2$NR$^{16}$R$^{17}$, —S(O)NR$^{16}$R$^{17}$, —S(O)R$^{16}$, —S(O)$_2$R$^{16}$, —OS(O)$_2$R$^{16}$, —C(O)NR$^{16}$R$^{17}$, —OC(O)NR$^{16}$R$^{17}$, —NR$^{16}$C(O)R$^{17}$, —CH$_2$C(O)NR$^{16}$R$^{17}$, —OC$_1$-C$_6$-alkyl-C(O)NR$^{16}$R$^{17}$, —CH$_2$OR$^{16}$, —CH$_2$OC(O)R$^{16}$, —CH$_2$NR$^{16}$R$^{17}$, —OC(O)R$^{16}$, —OC$_1$-C$_6$-alkyl-C(O)OR$^{16}$, —OC$_1$-C$_6$-alkyl-OR$^{16}$, —SC$_1$-C$_6$-alkyl-C(O)OR$^{16}$, —C$_2$-C$_6$-alkenyl-C(=O)OR$^{16}$, —NR$^{16}$—C(=O)—C$_1$-C$_6$-alkyl-C(=O)OR$^{16}$, —NR$^{16}$—C(=O)—C$_1$-C$_6$-alkenyl-C(=O)OR$^{16}$, —C(O)OR$^{16}$, or —C$_2$-C$_6$-alkenyl-C(=O)R$^{16}$, =O, or —C$_2$-C$_6$-alkenyl-C(=O)NR$^{16}$R$^{17}$, $C_1$-$C_6$-alkyl, $C_2$-$C_6$-alkenyl or $C_2$-$C_6$-alkynyl,
which may optionally be substituted with one or more substituents selected from halogen, —CN, —CF$_3$, —OCF$_3$, —OR$^{16}$, and —NR$^{16}$R$^{17}$ aryl, aryloxy, aryloxycarbonyl, aroyl, arylsulfanyl, aryl-$C_1$-$C_6$-alkoxy, aryl-$C_1$-$C_6$-alkyl, aryl-$C_2$-$C_6$-alkenyl, aroyl-$C_2$-$C_6$-alkenyl, aryl-$C_2$-$C_6$-alkynyl, heteroaryl, heteroaryl-$C_1$-$C_6$-alkyl, heteroaryl-$C_2$-$C_6$-alkenyl or heteroaryl-$C_2$-$C_6$-alkynyl, of which the cyclic moieties optionally may be substituted with one or more substituents selected from halogen, —C(O)OR$^{16}$, —CH$_2$C(O)O$^{16}$, —CH$_2$OR$^{16}$, —CN, —CF$_3$, —OCF$_3$, —NO$_2$, —OR$^{16}$, —NR$^{16}$R$^{17}$, S(O)$_2$R$^{16}$, aryl and $C_1$-$C_6$-alkyl, R$^{16}$ and R$^{17}$ independently are hydrogen, OH, $C_1$-$C_{20}$-alkyl, aryl-$C_1$-$C_6$-alkyl or aryl, wherein the alkyl groups may optionally be substituted with one or more substituents selected from halogen, —CN, —CF$_3$, —OCF$_3$, —OC$_1$-C$_6$-alkyl, —C(O)OC$_1$-C$_6$-alkyl, —COOH and —NH$_2$, and the aryl groups may optionally be substituted by halogen, —C(O)OC$_1$-C$_6$-alkyl, —COOH, —CN, —CF$_3$, —OCF$_3$, —NO$_2$, —OH, —OC$_1$-C$_6$-alkyl, —NH$_2$, C(=O) or $C_1$-$C_6$-alkyl; R$^{16}$ and R$^{17}$ when attached to the same nitrogen atom may form a 3 to 8 membered heterocyclic ring with the said nitrogen atom, the heterocyclic ring optionally containing one or two further heteroatoms selected from nitrogen, oxygen and sulphur, and optionally containing one or two double bonds In another embodiment of the invention X is =O or =S In another embodiment of the invention X is =O In another embodiment of the invention X is =S In another embodiment of the invention Y is —O— or —S—

In another embodiment of the invention Y is —O—

In another embodiment of the invention Y is —S—

In another embodiment of the invention E is arylene optionally substituted with up to four substituents, R$^{13}$, R$^{14}$, R$^{15}$, and R$^{15A}$.

In another embodiment of the invention E is phenylene or naphtylene optionally substituted with up to four substituents, R$^{13}$, R$^{14}$, R$^{15}$, and R$^{15A}$.

In another embodiment of the invention E is

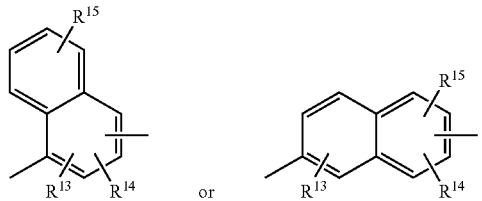

In another embodiment of the invention E is

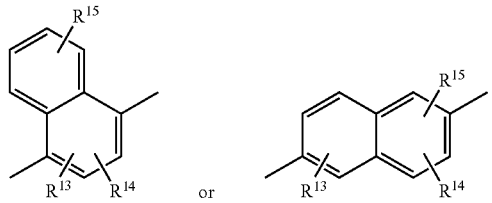

In another embodiment of the invention E is phenylene

In another embodiment of the invention E is heteroarylene optionally substituted with up to four substituents, $R^{13}$, $R^{14}$, $R^{15}$, and $R^{15A}$.

In another embodiment of the invention E is benzofuranylidene optionally substituted with up to four substituents $R^{13}$, $R^{14}$, $R^{15}$, and $R^{15A}$.

In another embodiment of the invention E is

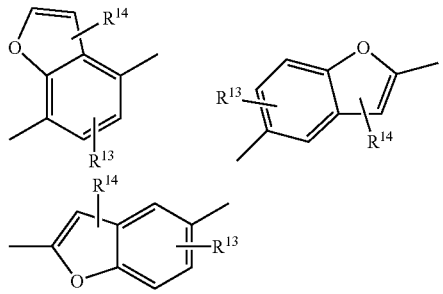

In another embodiment of the invention E is carbazolylidene optionally substituted with up to four substituents $R^{13}$, $R^{14}$, $R^{15}$, and $R^{15A}$.

In another embodiment of the invention E is

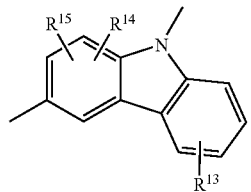

In another embodiment of the invention E is quinolylidene optionally substituted with up to four substituents $R^{13}$, $R^{14}$, $R^{15}$, and $R^{15A}$.

In another embodiment of the invention E is

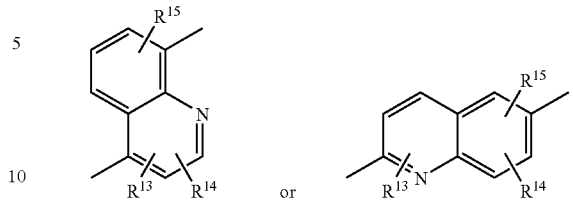

In another embodiment of the invention E is indolylene optionally substituted with up to four substituents $R^{13}$, $R^{14}$, $R^{15}$, and $R^{15A}$.

In another embodiment of the invention E is

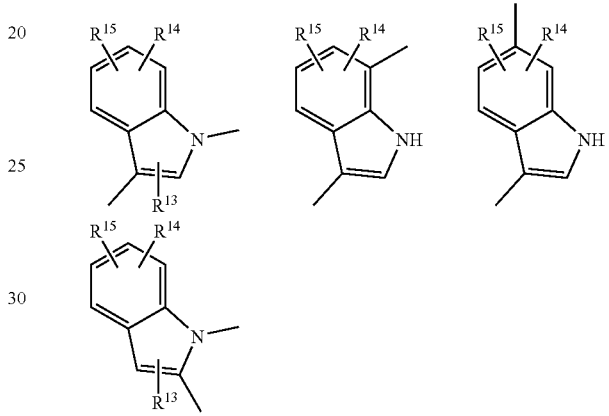

In another embodiment of the invention $R^8$ is Hydrogen.

In another embodiment of the invention $R^9$ is Hydrogen.

In another embodiment of the invention $R^8$ and $R^9$ are combined to form a double bond.

In another embodiment of the invention $R^{10}$ is $C_1$-$C_6$-alkyl.

In another embodiment of the invention $R^{10}$ is methyl.

In another embodiment of the invention G is phenylene optionally substituted with up to four substituents, $R^{13}$, $R^{14}$, $R^{15}$, and $R^{15A}$.

In another embodiment of the invention $R^{11}$ is Hydrogen.

In another embodiment of the invention $R^{12}$ is Hydrogen.

In another embodiment of the invention $R^{13}$, $R^{14}$, $R^{15}$ and $R^{15A}$ are independently selected from hydrogen, halogen —$NO_2$, —$OR^6$, —$NR^{16}R^{17}$, —$SR^{16}$, —$NR^{16}S(O)_2R^{17}$, —$S(O)_2NR^{16}R^{17}$, —$S(O)NR^{16}R^{17}$, —$S(O)R^{16}$, —$S(O)_2R^{16}$, —$OS(O)_2R^{16}$, —$NR^{16}C(O)R^{17}$, —$CH_2OR^{16}$, —$CH_2OC(O)R^{16}$, —$CH_2NR^{16}R^{17}$, —$OC(O)R^{16}$, —$OC_1$-$C_6$-alkyl-$C(O)OR^{16}$, —$OC_1$-$C_6$-alkyl-$C(O)NR^{16}R^{17}$, —$OC_1$-$C_6$-alkyl-$OR^{16}$, —$SC_1$-$C_6$-alkyl-$C(O)OR^{16}$, —$C_2$-$C_6$-alkenyl-$C(=O)OR^{16}$, —$C(O)OR^{16}$, or —$C_2$-$C_6$-alkenyl-$C(=O)R^{16}$, $C_1$-$C_6$-alkyl, $C_2$-$C_6$-alkenyl or $C_2$-$C_6$-alkynyl, which may optionally be substituted with one or more substituents selected from halogen, —CN, —$CF_3$, —$OCF_3$, —$OR^{16}$, and —$NR^{16}R^{17}$ aryl, aryloxy, aroyl, arylsulfanyl, aryl-$C_1$-$C_6$-alkoxy, aryl-$C_1$-$C_6$-alkyl, aryl-$C_2$-$C_6$-alkenyl, aroyl-$C_2$-$C_6$-alkenyl, aryl-$C_2$-$C_6$-alkynyl, heteroaryl, heteroaryl-$C_1$-$C_6$-alkyl, of which the cyclic moieties optionally may be substituted with one or more substituents selected from halogen, —C(O)OR$^{16}$, —CH$_2$C(O)OR$^{16}$, —CH$_2$OR$^{16}$, —CN, —CF$_3$, —OCF$_3$, —NO$_2$, —OR$^{16}$, —NR$^{16}$R$^{17}$ and C$_1$-C$_6$-alkyl.

In another embodiment of the invention R$^{13}$, R$^{14}$, R$^{15}$ and R$^{15A}$ are independently selected from

- hydrogen, halogen, —NO$_2$, —OR$^6$, —NR$^{16}$R$^{17}$, —S$^{16}$, —S(O)$_2$R$^{16}$, —OS(O)$_2$R$^{16}$, —CH$_2$OC(O)R$^{16}$, —OC(O)$^{16}$, —OC$_1$-C$_6$-alkyl-C(O)OR$^{16}$, —OC$_1$-C$_6$-alkyl-OR$^{16}$, —SC$_1$-C$_6$-alkyl-C(O)OR$^{16}$, —C(O)OR$^{16}$, or —C$_2$-C$_6$-alkenyl-C(=O)R$^{16}$,
- C$_1$-C$_6$-alkyl or C$_1$-C$_6$-alkenyl which may optionally be substituted with one or more substituents selected from halogen, —CN, —CF$_3$, —OCF$_3$, —OR$^{16}$, and —NR$^{16}$R$^{17}$
- aryl, aryloxy, aroyl, aryl-C$_1$-C$_6$-alkoxy, aryl-C$_1$-C$_6$-alkyl, heteroaryl,
- of which the cyclic moieties optionally may be substituted with one or more substituents selected from halogen, —C(O)OR$^{16}$, —CH$_2$C(O)OR$^{16}$, —CH$_2$OR$^{16}$, —CN, —CF$_3$, —OCF$_3$, —NO$_2$, —OR$^{16}$, —NR$^{16}$R$^{17}$ and C$_1$-C$_6$-alkyl.

In another embodiment of the invention R$^{13}$, R$^{14}$, R$^{15}$ and R$^{15A}$ are independently selected from

- hydrogen, halogen, —NO$_2$, —OR$^6$, —NR$^{16}$R$^{17}$, —SR$^{16}$, —S(O)$_2$R$^{16}$, —OS(O)$_2$R$^{16}$, —CH$_2$OC(O)R$^{16}$, —OC(O)R$^{16}$, —OC$_1$-C$_6$-alkyl-C(O)OR$^{16}$, —OC$_1$-C$_6$-alkyl-OR$^{16}$, —SC$_1$-C$_6$-alkyl-C(O)OR$^{16}$, —C(O)OR$^{16}$, or —C$_2$-C$_6$-alkenyl-C(=O)R$^{18}$,
- C$_1$-C$_6$-alkyl or C$_1$-C$_6$-alkenyl which may optionally be substituted with one or more substituents selected from halogen, —CF$_3$, —OR$^{16}$, and —NR$^{16}$R$^{17}$
- aryl, aryloxy, aroyl, aryl-C$_1$-C$_6$-alkoxy, aryl-C$_1$-C$_6$-alkyl, heteroaryl
- of which the cyclic moieties optionally may be substituted with one or more substituents selected from halogen, C(O)OR$^{16}$, —CN, —NO$_2$, —OR$^{16}$, —NR$^{16}$R$^{17}$ and C$_1$-C$_6$-alkyl.

In another embodiment of the invention R$^{13}$, R$^{14}$, R$^{15}$ and R$^{15A}$ are independently selected from

- hydrogen, halogen, —OR$^6$, —OC$_1$-C$_6$-alkyl-C(O)OR$^{16}$, or —C(O)OR$^{16}$,
- C$_1$-C$_6$-alkyl which may optionally be substituted with one or more substituents selected from halogen, —OR$^{16}$, and —NR$^{16}$R$^{17}$
- aryl, aryloxy, aryl-C$_1$-C$_6$-alkoxy,
- of which the cyclic moieties optionally may be substituted with one or more substituents selected from halogen, C(O)OR$^{16}$, OR$^{16}$, and C$_1$-C$_6$-alkyl.

In another embodiment of the invention R$^{16}$ and R$^{17}$ independently are hydrogen, C$_1$-C$_{20}$-alkyl, or aryl, wherein the alkyl groups may optionally be substituted with one or more substituents selected from halogen, —CF$_3$, —OCF$_3$, —OC$_1$-C$_6$-alkyl, —COOH and —NH$_2$, and the aryl groups may optionally be substituted by halogen, —COOH, —CN, —CF$_3$, —OCF$_3$, —NO$_2$, —OH, —OC$_1$-C$_6$-alkyl, —NH$_2$, C(=O) or C$_1$-C$_6$-alkyl; R$^{16}$ and R$^{17}$ when attached to the same nitrogen atom may form a 3 to 8 membered heterocyclic ring with the said nitrogen atom, the heterocyclic ring optionally containing one or two further heteroatoms selected from nitrogen, oxygen and sulphur, and optionally containing one or two double bonds In another embodiment of the invention R$^{16}$ and R$^{17}$ independently are hydrogen, C$_1$-C$_{20}$-alkyl, or aryl, wherein the alkyl groups may optionally be substituted with one or more substituents selected from halogen, —CF$_3$, —OC$_1$-C$_6$-alkyl, —COOH and —NH$_2$, and the aryl groups may optionally be substituted by halogen, —COOH, —CN, —CF$_3$, —OCF$_3$, —OH, —NH$_2$, or C$_1$-C$_6$-alkyl.

In another embodiment of the invention A is

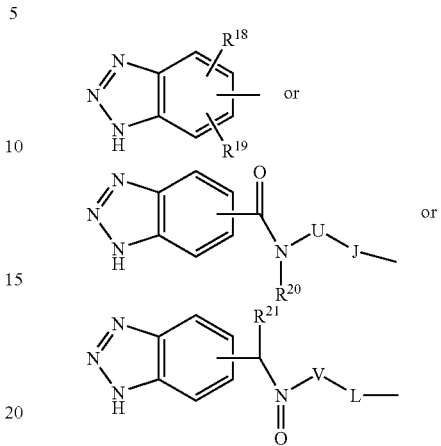

wherein

R$^{20}$ is hydrogen or C$_1$-C$_6$-alkyl,

R$^{21}$ is hydrogen or C$_1$-C$_6$-alkyl,

U and V are a valence bond or C$_1$-C$_6$-alkylene optionally substituted with one or more hydroxy, C$_1$-C$_6$-alkyl, or aryl independently, J is C$_1$-C$_6$-alkylene, arylene or heteroarylene, wherein the arylene or heteroarylene is optionally substituted with up to three substituents R$^{22}$, R$^{23}$ and R$^{24}$, L is C$_1$-C$_6$-alkylene, arylene or heteroarylene, wherein the arylene or heteroarylene is optionally substituted with up to three substituents R$^{25}$, R$^{26}$ and R$^{27}$, R$^{18}$, R$^{19}$, R$^{22}$, R$^{23}$R$^{24}$, R$^{25}$, R$^{26}$ and R$^{27}$ are independently selected from hydrogen, halogen, —CN, —CH$_2$CN, —CHF$_2$, —CF$_3$, —OCF$_3$, —OCHF$_2$, —OCH$_2$CF$_3$, —OCF$_2$CHF$_2$, —S(O)$_2$CF$_3$, —SCF$_3$, —NO$_2$, —OR$^{28}$, —NR$^{28}$R$^{29}$, —SR$^{28}$, —NR$^{28}$S(O)$_2$R$^{29}$, —S(O)$_2$NR$^{28}$R$^{29}$, —S(O)NR$^{28}$R$^{29}$, —S(O)R$^{28}$, —S(O)$_2$R$^{28}$, —C(O)NR$^{28}$R$^{29}$, —OC(O)NR$^{28}$R$^{29}$, —NR$^{28}$C(O)R$^{29}$, —NR$^{28}$C(O)R$^{29}$, —CH$_2$C(O)NR$^{28}$R$^{29}$, —OCH$_2$C(O)NR$^{28}$R$^{29}$, —CH$_2$OR$^{28}$, —CH$_2$NR$^{28}$R$^{29}$, —OC(O)R$^{28}$, —OC$_1$-C$_6$-alkyl-C(O)OR$^{28}$, —SC$_1$-C$_6$-alkyl-C(O)OR$^{28}$, —C$_2$-C$_6$-alkenyl-C(=O)OR$^{28}$, —NR$^{28}$—C(=O)—C$_1$-C$_6$-alkyl-C(=O)OR$^{28}$, —NR$^{28}$—C(=O)—C$_1$-C$_6$-alkenyl-C(=O)OR$^{28}$, —C(=O)NR$^{28}$—C$_1$-C$_6$-alkyl-C(=O)OR$^{28}$, —C$_1$-C$_6$-alkyl-C(=O)OR$^{28}$, or —C(O)OR$^{28}$, C$_1$-C$_6$-alkyl, C$_2$-C$_6$-alkenyl or C$_2$-C$_6$-alkynyl, which may optionally be substituted with one or more substituents selected from halogen, —CN, —CF$_3$, —OCF$_3$, —OR$^{28}$, and —NR$^{28}$R$^{29}$ aryl, aryloxy, aryloxycarbonyl, aroyl, aryl-C$_1$-C$_6$-alkoxy, aryl-C$_1$-C$_6$-alkyl, aryl-C$_2$-C$_6$-alkenyl, aryl-C$_2$-C$_6$-alkynyl, heteroaryl, heteroaryl-C$_1$-C$_6$-alkyl, heteroaryl-C$_2$-C$_6$-alkenyl or heteroaryl-C$_2$-C$_6$-alkynyl, of which the cyclic moieties optionally may be substituted with one or more substituents selected from halogen, —C(O)OR$^{28}$, —CN, —CF$_3$, —OCF$_3$, —NO$_2$, —OR$^{28}$, —NR$^{28}$R$^{29}$ and C$_1$-C$_6$-alkyl, R$^{28}$ and R$^{29}$ independently are hydrogen, C$_1$-C$_6$-alkyl, aryl-C$_1$-C$_6$-alkyl or aryl, or R$^{28}$ and R$^{29}$ when attached to the same nitrogen atom together with the said nitrogen atom may form a 3 to 8 membered heterocyclic ring optionally containing one or two further heteroatoms selected from nitrogen, oxygen and sulphur, and optionally containing one or two double bonds In another embodiment of the invention U is a valence bond In another embodiment of the invention U is $C_1$-$C_6$-alkylene optionally substituted with one or more hydroxy, $C_1$-$C_6$-alkyl, or aryl In another embodiment of the invention J is arylene or heteroarylene, wherein the arylene or heteroarylene is optionally substituted with up to three substituents $R^{22}$, $R^{23}$ and $R^{24}$ In another embodiment of the invention J is arylene optionally substituted with up to three substituents $R^{22}$, $R^{23}$ and $R^{24}$ In another embodiment of the invention J is phenylene optionally substituted with up to three substituents $R^{22}$, $R^{23}$ and $R^{24}$ In another embodiment of the invention J is

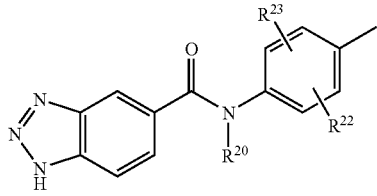

In another embodiment of the invention $R^{22}$, $R^{23}$ and $R^{24}$ are independently selected from hydrogen, halogen, —$CHF_2$, —$CF_3$, —$OCF_3$, —$OCHF_2$, —$OCH_2CF_3$, —$OCF_2CHF_2$, —$SCF_3$, —$NO_2$, —$OR^{28}$, —$NR^{28}R^{29}$, —$SR^{28}$ —$C(O)NR^{28}R^{29}$, —$OC(O)NR^{28}R^{29}$, —$NR^{28}C(O)R^{29}$, —$NR^{28}C(O)OR^{29}$, —$CH_2C(O)NR^{28}R^{29}$, —$OCH_2C(O)NR^{28}R^{29}$, —$CH_2OR^{28}$, —$CH_2NR^{28}R^{29}$, —$OC(O)R^{28}$, —$OC_1$-$C_6$-alkyl-$C(O)OR^{28}$, —$SC_1$-$C_6$-alkyl-$C(O)OR^{28}$, —$C_2$-$C_6$-alkenyl-$C(=O)OR^{28}$, —$NR^{28}$—$C(=O)$—$C_1$-$C_6$-alkyl-$C(=O)OR^{28}$, —$NR^{28}$—$C(=O)$—$C_1$-$C_6$-alkenyl-$C(=O)OR^{28}$—, —$C(=O)NR^{28}$—$C_1$-$C_6$-alkyl-$C(=O)OR^{28}$, —$C_1$-$C_6$-alkyl-$C(=O)OR^{28}$, or —$C(O)OR^{28}$, $C_1$-$C_6$-alkyl, $C_2$-$C_6$-alkenyl or $C_2$-$C_6$-alkynyl, which may optionally be substituted with one or more substituents selected from halogen, —CN, —$CF_3$, —$OCF_3$, —$OR^{28}$, and —$NR^{28}R^{29}$ aryl, aryloxy, aryloxycarbonyl, aroyl, aryl-$C_1$-$C_6$-alkoxy, aryl-$C_1$-$C_6$-alkyl, aryl-$C_2$-$C_6$-alkenyl, aryl-$C_2$-$C_6$-alkynyl, heteroaryl, heteroaryl-$C_1$-$C_6$-alkyl, heteroaryl-$C_2$-$C_6$-alkenyl or heteroaryl-$C_2$-$C_6$-alkynyl, of which the cyclic moieties optionally may be substituted with one or more substituents selected from halogen, —$C(O)OR^{28}$, —CN, —$CF_3$, —$OCF_3$, —$NO_2$, —$OR^{28}$, —$NR^{28}R^{29}$ and $C_1$-$C_6$-alkyl In another embodiment of the invention $R^{22}$, $R^{23}$ and $R^{24}$ are independently selected from hydrogen, halogen, —$OCF_3$, —$OR^{28}$, —$NR^{28}R^{29}$, —$SR^{28}$, —$NR^{28}C(O)R^{29}$, —$NR^{28}C(O)OR^{29}$, —$OC(O)R^{28}$, —$OC_1$-$C_6$-alkyl-$C(O)OR^{28}$, —$SC_1$-$C_6$-alkyl-$C(O)OR^{28}$, —$C_2$-$C_6$-alkenyl-$C(=O)OR^{28}$, —$C(=O)NR^{28}$—$C_1$-$C_6$-alkyl-$C(=O)OR^{28}$, —$C_1$-$C_6$-alkyl-$C(=O)OR^{28}$, or —$C(O)OR^{28}$, $C_1$-$C_6$-alkyl optionally substituted with one or more substituents selected from halogen, —CN, —$CF_3$, —$OCF_3$, —$OR^{28}$, and —$NR^{28}R^{29}$ aryl, aryloxy, aroyl, aryl-$C_1$-$C_6$-alkoxy, aryl-$C_1$-$C_6$-alkyl, heteroaryl, heteroaryl-$C_1$-$C_6$-alkyl, of which the cyclic moieties optionally may be substituted with one or more substituents selected from halogen, —$C(O)OR^{28}$, —CN, —$CF_3$, —$OCF_3$, —$NO_2$, —$OR^{28}$, —$NR^{28}R^{29}$ and $C_1$-$C_6$-alkyl In another embodiment of the invention $R^{22}$, $R^{23}$ and $R^{24}$ are independently selected from hydrogen, halogen, —$OCF_3$, —$OR^{28}$, —$NR^{28}R^{29}$, —$SR^{28}$, —$NR^{28}C(O)R^{29}$, —$NR^{28}C(O)OR^{29}$, —$OC(O)R^{28}$, —$OC_1$-$C_6$-alkyl-$C(O)OR^{28}$, —$SC_1$-$C_6$-alkyl-$C(O)OR^{28}$, —$C_2$-$C_6$-alkenyl-$C(=O)OR^{28}$, —$C(=O)NR^{28}$—$C_1$-$C_6$-alkyl-$C(=O)OR^{28}$, —$C_1$-$C_6$-alkyl-$C(=O)OR^{28}$, or —$C(O)OR^{28}$, $C_1$-$C_6$-alkyl optionally substituted with one or more substituents selected from halogen, —CN, or —$CF_3$ aryl, aryloxy, aroyl, aryl-$C_1$-$C_6$-alkoxy, aryl-$C_1$-$C_6$-alkyl, heteroaryl, heteroaryl-$C_1$-$C_6$-alkyl, of which the cyclic moieties optionally may be substituted with one or more substituents selected from halogen, —$C(O)OH$, —CN, —$CF_3$, —$NO_2$, or $C_1$-$C_6$-alkyl In another embodiment of the invention $R^{20}$ is hydrogen or methyl In another embodiment of the invention $R^{20}$ is hydrogen In another embodiment of the invention $R^{28}$ is Hydrogen, $C_1$-$C_6$-alkyl or aryl In another embodiment of the invention $R^{28}$ is Hydrogen or $C_1$-$C_6$-alkyl In another embodiment of the invention $R^{29}$ is Hydrogen or $C_1$-$C_6$-alkyl In another embodiment of the invention V is a valence bond In another embodiment of the invention V is $C_1$-$C_6$-alkylene optionally substituted with one or more hydroxy, $C_1$-$C_6$-alkyl, or aryl In another embodiment of the invention L is $C_1$-$C_6$-alkylene or arylene, wherein the arylene is optionally substituted with up to three substituents $R^{25}$, $R^{26}$ and $R^{27}$ In another embodiment of the invention L is $C_1$-$C_6$-alkylene In another embodiment of the invention L is phenylene optionally substituted with up to three substituents $R^{25}$, $R^{26}$ and $R^{27}$ In another embodiment of the invention $R^{25}$, $R^{26}$ and $R^{27}$ are independently selected from hydrogen, halogen, —$CHF_2$, —$CF_3$, —$OCF_3$, —$OCHF_2$, —$OCH_2CF_3$, —$OCF_2CHF_2$, —$SCF_3$, —$NO_2$, —$OR^{28}$, —$NR^{28}R^{29}$, —$SR^{28}$, —$C(O)NR^{28}R^{29}$, —$OC(O)NR^{28}R^{29}$, —$NR^{28}C(O)R^{29}$, —$NR^{28}C(O)OR^{29}$, —$CH_2C(O)NR^{28}R^{29}$, —$OCH_2C(O)NR^{28}R^{29}$, —$CH_2OR^{28}$, —$CH_2NR^{28}R^{29}$, —$OC(O)R^{28}$, —$OC_1$-$C_6$-alkyl-$C(O)OR^{28}$, —$SC_1$-$C_6$-alkyl-$C(O)OR^{28}$, —$C_2$-$C_6$-alkenyl-$C(=O)OR^{28}$, —$NR^{28}$—$C(=O)$—$C_1$-$C_6$-alkyl-$C(=O)OR^{28}$, —$NR^{28}$—$C(=)$—$C_1$-$C_6$-alkenyl-$C(=O)OR^{28}$—, —$C(=O)NR^{28}$—$C_1$-$C_6$-alkyl-$C(=O)OR^{28}$, —$C_1$-$C_6$-alkyl-$C(=O)OR^{28}$, or —$C(O)OR^{28}$, $C_1$-$C_6$-alkyl, $C_2$-$C_6$-alkenyl or $C_2$-$C_6$-alkynyl, which may optionally be substituted with one or more substituents selected from halogen, —CN, —$CF_3$, —$OCF_3$, —$OR^{28}$, and —$NR^{28}R^{29}$ aryl, aryloxy, aryloxycarbonyl, aroyl, aryl-$C_1$-$C_6$-alkoxy, aryl-$C_1$-$C_6$-alkyl, aryl-$C_2$-$C_6$-alkenyl, aryl-$C_2$-$C_6$-alkynyl, heteroaryl, heteroaryl-$C_1$-$C_6$-alkyl, heteroaryl-$C_2$-$C_6$-alkenyl or heteroaryl-$C_2$-$C_6$-alkynyl, of which the cyclic moieties optionally may be substituted with one or more substituents selected from halogen, —$C(O)OR^{28}$, —CN, —$CF_3$, —$OCF_3$, —$NO_2$, —$OR^{28}$, —$NR^{28}R^{29}$ and $C_1$-$C_6$-alkyl In another embodiment of the invention $R^{25}$, $R^{26}$ and $R^{27}$ are independently selected from hydrogen, halogen, —$OCF_3$, —$OR^{28}$, —$NR^{28}R^{29}$, —$SR^{28}$, —$NR^{28}C(O)R^{29}$, —$NR^{28}C(O)OR^{29}$, —$OC(O)R^{28}$, —$OC_1$-$C_6$-alkyl-$C(O)OR^{28}$, —$SC_1$-$C_6$-alkyl-$C(O)OR^{28}$, —$C_2$-$C_6$-alkenyl-$C(=O)OR^{28}$, —$C(=O)NR^{28}$—$C_1$-$C_6$-alkyl-$C(=O)OR^{28}$, —$C_1$-$C_6$-alkyl-$C(=O)OR^{28}$, or —$C(O)OR^{28}$, $C_1$-$C_6$-alkyl optionally substituted with one or more substituents selected from halogen, —CN, —$CF_3$, —$OCF_3$, —$OR^{28}$, and —$NR^{28}R^{29}$ aryl, aryloxy, aroyl, aryl-$C_1$-$C_6$-alkoxy, aryl-$C_1$-$C_6$-alkyl, heteroaryl, heteroaryl-$C_1$-$C_6$-alkyl, of which the cyclic moieties optionally may be substituted with one or more substituents selected from halogen, —$C(O)OR^{28}$, —CN, —$CF_3$, —$OCF_3$, —$NO_2$, —$OR^{28}$, —$NR^{28}R^{29}$ and $C_1$-$C_6$-alkyl In another embodiment of the invention $R^{25}$, $R^{26}$ and $R^{27}$ are independently selected from hydrogen, halogen, —$OCF_3$, —$OR^{28}$, —$NR^{28}R^{29}$, —$SR^{28}$, —$NR^{28}C(O)R^{29}$, —$NR^{28}C(O)OR^{29}$, —$OC(O)R^{28}$, —$OC_1$-$C_6$-alkyl-$C(O)OR^{28}$, —$SC_1$-$C_6$-alkyl-$C(O)OR^{28}$, —$C_2$-$C_6$-alkenyl-$C(=O)OR^{28}$, —$C(=O)NR^{28}$—$C_1$-$C_6$-alkyl-$C(=O)OR^{28}$, —$C_1$-$C_6$-alkyl-$C(=O)OR^{28}$, or —$C(O)OR^{28}$, $C_1$-$C_6$-alkyl optionally substituted with one or more substituents selected from halogen, —CN, or —$CF_3$ aryl, aryloxy, aroyl, aryl-$C_1$-$C_6$-alkoxy, aryl-$C_1$-$C_6$-alkyl, heteroaryl, heteroaryl-$C_1$-$C_6$-alkyl, of which the cyclic moieties optionally may be substituted with one or more substituents selected from halogen, —C(O)OH, —CN, —$CF_3$, —$NO_2$, or $C_1$-$C_6$-alkyl In another embodiment of the invention $R^{21}$ is hydrogen or methyl In another embodiment of the invention $R^{21}$ is hydrogen In another embodiment of the invention $R^{28}$ is Hydrogen, $C_1$-$C_6$-alkyl or aryl In another embodiment of the invention $R^{28}$ is Hydrogen or $C_1$-$C_6$-alkyl In another embodiment of the invention $R^{29}$ is Hydrogen or $C_1$-$C_6$-alkyl In another embodiment of the invention $R^{18}$ and $R^{19}$ are independently selected from hydrogen, halogen, —CN, —$CF_3$, —$OCF_3$, —$NO_2$, —$OR^{28}$, —$NR^{28}R^{29}$, —$SR^{28}$, —$S(O)R^{28}$, —$S(O)_2R^{28}$, —$C(O)NR^{28}R^{29}$, —$CH_2OR^{28}$, —$OC(O)R^{28}$, —$OC_1$-$C_6$-alkyl-$C(O)OR^{28}$, —$SC_1$-$C_6$-alkyl-$C(O)OR^{28}$, or —$C(O)OR^{28}$, $C_1$-$C_6$-alkyl, $C_2$-$C_6$-alkenyl or $C_2$-$C_6$-alkynyl, which may optionally be substituted with one or more substituents selected from halogen, —CN, —$CF_3$, —$OCF_3$, —$OR^{28}$, and —$NR^{28}R^{29}$ aryl, aryloxy, aryl-$C_1$-$C_6$-alkoxy, aryl-$C_1$-$C_6$-alkyl, heteroaryl, heteroaryl-$C_1$-$C_6$-alkyl of which the cyclic moieties optionally may be substituted with one or more substituents selected from halogen, —$C(O)OR^{28}$, —CN, —$CF_3$, —$OCF_3$, —$NO_2$, —$OR^{28}$, —$NR^{28}R^{29}$ and $C_1$-$C_6$-alkyl In another embodiment of the invention $R^{18}$ and $R^{19}$ are independently selected from hydrogen, halogen, —CN, —$CF_3$, —$NO_2$, —$OR^{28}$, —$NR^{28}R^{29}$, or —$C(O)OR^{28}$, $C_1$-$C_6$-alkyl optionally substituted with one or more substituents selected from halogen, —CN, —$CF_3$, —$OCF_3$, —$OR^{28}$, and —$NR^{28}R^{29}$ aryl, aryloxy, aryl-$C_1$-$C_6$-alkyl, heteroaryl, of which the cyclic moieties optionally may be substituted with one or more substituents selected from halogen, —$C(O)OR^{28}$, —CN, —$CF_3$, —$OCF_3$, —$NO_2$, —$OR^{28}$, —$NR^{28}R^{29}$ and $C_1$-$C_6$-alkyl In another embodiment of the invention A is

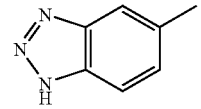

In another embodiment of the invention A is of the form M-Q-T-
wherein M is

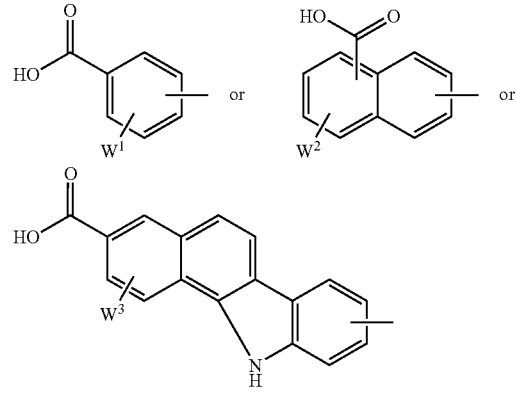

wherein $W^1$, $W^2$, and $W^3$ are independently OH, SH or $NH_2$ and the phenyl, naphthalene or benzocarbazole rings are optionally substituted by one or more $R^{34}$ independently Q is selected from the following:
a valence bond
—$CH_2N(R^{30})$— or —$SO_2N(R^{31})$—
A compound of the formula

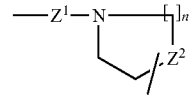

wherein $Z^1$ is $S(O)_2$ or $CH_2$, $Z^2$ is N, —O— or —S—, and n is 1 or 2;

T is $C_1$-$C_6$-alkylene, $C_2$-$C_6$-alkenylene or $C_2$-$C_6$-alkynylene, which may optionally be substituted with; one or more substituents selected from halogen, —CN, —$CF_3$, —$OCF_3$, —$OR^{32}$, and —$NR^{32}R^{33}$ Arylene, arylene-oxy, -aryl-oxycarbonyl-, -aroyl-, -aryl-$C_1$-$C_6$-alkoxy-, -aryl-$C_1$-$C_6$-alkyl-, -aryl-$C_2$-$C_6$-alkenyl-, -aryl-$C_2$-$C_6$-alkynyl-, heteroarylene, -heteroaryl-$C_1$-$C_6$-alkyl-, -heteroaryl-$C_2$-$C_6$-alkenyl- or -heteroaryl-$C_2$-$C_6$-alkynyl-, wherein the cyclic moieties are optionally substituted by one or more substituents selected from halogen, —$C(O)OR^{32}$, —C(O)H, —CN, —$CF_3$, —$OCF_3$, —$NO_2$, —$OR^{32}$, —$NR^{32}R^{33}$, $C_1$-$C_6$-alkyl or $C_1$-$C_6$-alkanoyl, A valence bond $R^{32}$ and $R^{33}$ independently are hydrogen, $C_1$-$C_6$-alkyl, aryl-$C_1$-$C_6$-alkyl or aryl, or $R^{32}$ and $R^{33}$ when attached to the same nitrogen atom together with the said nitrogen atom may form a 3 to 8 membered heterocyclic ring optionally containing one or two further heteroatoms selected from nitrogen, oxygen and sulphur, and optionally containing one or two double bonds, $R^{30}$ and $R^{31}$ are independently hydrogen, $C_1$-$C_6$-alkyl or $C_1$-$C_6$-alkanoyl.

$R^{34}$ is hydrogen, halogen, —CN, —$CH_2CN$, —$CHF_2$, —$CF_3$, —$OCF_3$, —$OCHF_2$, —$OCH_2CF_3$, —$OCF_2CHF_2$, —$S(O)_2CF_3$, —$SCF_3$, —$NO_2$, —$OR^{32}$, —$C(O)R^{32}$, —$NR^{32}R^{33}$, —$SR^{32}$, —$NR^{32}S(O)_2R^{33}$, —$S(O)_2NR^{32}R^{33}$, —$S(O)NR^{32}R^{33}$, —$S(O)R^{32}$, —$S(O)_2R^{32}$, —$C(O)NR^{32}R^{33}$, —$OC(O)NR^{32}R^{33}$, —$NR^{32}C(O)R^{33}$, —$CH_2C(O)NR^{32}R^{33}$, —$OCH_2C(O)NR^{32}R^{33}$, —$CH_2OR^{32}$, —$CH_2NR^{32}R^{33}$, —$OC(O)R^{32}$, —$OC_1$-$C_6$-alkyl-$C(O)OR^{32}$, —$SC_1$-$C_6$-alkyl-$C(O)OR^{32}$—$C_2$-$C_6$-alkenyl-$C(=O)OR^{32}$, —$NR^{32}$—$C(=O)$—$C_1$-$C_6$-alkyl-$C(=O)OR^{32}$, —$NR^{32}$—$C(=O)$—$C_1$-$C_6$-alkenyl-$C(=O)OR^{32}$—, $C_1$-$C_6$-alkyl, $C_1$-$C_6$-alkanoyl or —$C(O)OR^{32}$, In another embodiment of the invention M is

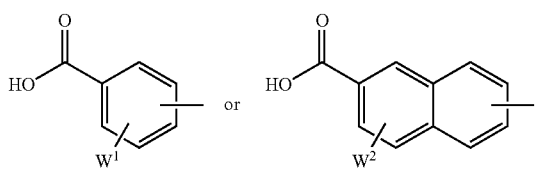

In another embodiment of the invention M is

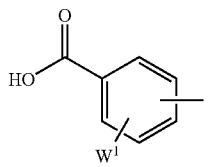

In another embodiment of the invention M is

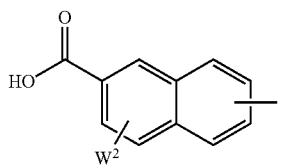

In another embodiment of the invention M is

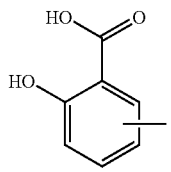

In another embodiment of the invention M is

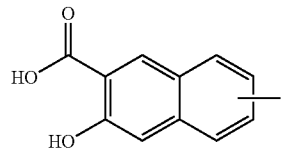

In another embodiment of the invention Q is a valence bond, —$CH_2N(R^{30})$—, or —$SO_2N(R^{31})$—

In another embodiment of the invention Q is a valence bond

In another embodiment of the invention T is

A valence bond $C_1$-$C_6$-alkylene, $C_2$-$C_6$-alkenylene or $C_2$-$C_6$-alkynylene, which may optionally be substituted with one or more substituents selected from halogen, —CN, —$CF_3$, —$OCF_3$, —$OR^{32}$, and —$NR^{32}R^{33}$ Arylene, or heteroarylene, wherein the cyclic moieties are optionally substituted as defined in claim 70

In another embodiment of the invention T is

A valence bond

Arylene, or heteroarylene, wherein the cyclic moieties are optionally substituted as defined in claim 70

In another embodiment of the invention T is phenylene or naphthalene

In another embodiment of the invention the cyclic moiety in T is optionally substituted by halogen, —$C(O)OR^{32}$, —CN, —$CF_3$, —$OR^{32}$, —$NR^{32}R^{33}$, $C_1$-$C_6$-alkyl or $C_1$-$C_6$-alkanoyl In another embodiment of the invention the cyclic moiety in T is optionally substituted by halogen, —$C(O)OR^{32}$, —$OR^{32}$, —$NR^{32}R^{33}$, $C_1$-$C_6$-alkyl or $C_1$-$C_6$-alkanoyl In another embodiment of the invention the cyclic moiety in T is optionally substituted by halogen, —$C(O)OR^{32}$ or —$OR^{32}$ In another embodiment of the invention T is a valence bond In another embodiment of the invention $R^{30}$ and $R^{31}$ are independently hydrogen or $C_1$-$C_6$-alkyl In another embodiment of the invention $R^{34}$ is hydrogen, halogen, —CN, —$CF_3$, —$OCF_3$, —$SCF_3$, —$NO_2$, —$OR^{32}$, —$C(O)R^{32}$, —$NR^{32}R^{33}$, —$SR^{32}$, —$C(O)NR^{32}R^{33}$, —$OC(O)NR^{32}R^{33}$, —$NR^{32}C(O)R^{33}$, —$OC(O)R^{32}$, —$OC_1$-$C_6$-alkyl-$C(O)OR^{32}$, —$SC_1$-$C_6$-alkyl-$C(O)OR^{32}$ or —$C(O)OR^{32}$ In another embodiment of the invention $R^{34}$ is hydrogen, halogen, —$CF_3$, —$NO_2$, —$OR^{32}$, —$NR^{32}R^{33}$, —$SR^{32}$, —$NR^{32}C(O)R^{33}$, or —$C(O)OR^{32}$ In another embodiment of the invention $R^{34}$ is hydrogen, halogen, —$CF_3$, —$NO_2$, —$OR^{32}$, —$NR^{32}R^{33}$, or —$NR^{32}C(O)R^{33}$ In another embodiment of the invention $R^{34}$ is hydrogen, halogen, or —$OR^{32}$ In another embodiment of the invention $R^{32}$ and $R^{33}$ independently are hydrogen, $C_1$-$C_6$-alkyl, or aryl In another embodiment of the invention $R^{32}$ and $R^{33}$ independently are hydrogen or $C_1$-$C_6$-alkyl In another embodiment of the invention A is

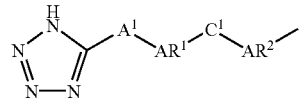

wherein $A^1$ is a valence bond, $C_1$-$C_6$-alkylene, —NH—C(=O)-$A^2$—, —$C_1$-$C_6$-alkyl-S—, —$C_1$-$C_6$-alkyl-O—, —C(=O)—, or —C(=O)—NH—, wherein any $C_1$-$C_6$-alkyl moiety is optionally substituted by $R^{1A}$;

$A^2$ is a valence bond, $C_1$-$C_6$-alkylene, $C_1$-$C_6$-alkenylene, or —$C_1$-$C_6$-alkyl-O—;

$R^{1A}$ is $C_1$-$C_6$-alkyl, aryl, wherein the alkyl or aryl moieties are optionally substituted by one or more halogen, cyano, nitro, amino;

$AR^1$ is a valence bond, arylene or heteroarylene, wherein the aryl or heteroaryl moieties are optionally substituted by one or more $R^{1B}$ independently $R^{1B}$ is selected from hydrogen, halogen, —CN, —$CH_2CN$, —$CHF_2$, —$CF_3$, —$OCF_3$, —$OCHF_2$, —$OCH_2CF_3$, —$OCF_2CHF_2$, —$S(O)_2CF_3$, —$OS(O)_2CF_3$, —$SCF_3$, —$NO_2$, —$OR^{1C}$, —$NR^{1C}R^{1D}$, —$SR^{1C}$, —$NR^{1C}S(O)_2R^{1D}$, —$S(O)_2NR^{1C}R^{1D}$, —$S(O)NR^{1C}R^{1D}$, —$S(O)R^{1C}$, —$S(O)_2R^{1C}$, —$OS(O)_2R^{1C}$, —$C(O)NR^{1C}R^{1D}$, —$OC(O)NR^{1C}R^{1D}$, —$NR^{1C}C(O)R^{1D}$, —$CH_2C(O)NR^{1C}R^{1D}$, —$OC_1$-$C_6$-alkyl-$C(O)NR^{1C}R^{1D}$, —$CH_2OR^{1C}$, —$CH_2OC(O)R^{1C}$, —$CH_2NR^{1C}R^{1D}$, —$OC(O)R^{1C}$, —$OC_1$-$C_6$-alkyl-$C(O)OR^{1C}$, —$OC_1$-$C_6$-alkyl-$OR^{1C}$, —$S$—$C_1$-$C_6$-alkyl-$C(O)OR^{1C}$, —$C_2$-$C_6$-alkenyl-$C(=O)OR^{1C}$, —$NR^{1C}$—$C(=O)$—$C_1$-$C_6$-alkyl-$C(=O)OR^{1C}$, —$NR^{1C}$—$C(=O)$—$C_1$-$C_6$-alkenyl-$C(=O)OR^{1C}$, —$C_2$-$C_6$-alkenyl-$C(=O)R^{1C}$, =O, —NH—C(=O)—O—$C_1$-$C_6$-alkyl, or —NH—C(=O)—C(=O)—O—$C_1$-$C_6$-alkyl $C_1$-$C_6$-alkyl, $C_2$-$C_6$-alkenyl or $C_2$-$C_6$-alkynyl, which may optionally be substituted with one or more substituents selected from halogen, —CN, —$CF_3$, —$OCF_3$, —$OR^{1C}$, and —$NR^{1C}R^{1D}$ aryl, aryloxy, aryloxycarbonyl, arylsulfanyl, aryl-$C_1$-$C_6$-alkoxy, aryl-$C_1$-$C_6$-alkyl, aryl-$C_2$-$C_6$-alkenyl, aroyl-$C_2$-$C_6$-alkenyl, aryl-$C_2$-$C_6$-alkynyl, heteroaryl, heteroaryl-$C_1$-$C_6$-alkyl, heteroaryl-$C_2$-$C_6$-alkenyl or heteroaryl-$C_2$-$C_6$-alkynyl, of which the cyclic moieties optionally may be substituted with one or more substituents selected from halogen, —$C(O)OR^{1C}$, —$CH_2C(O)OR^{1C}$, —$CH_2OR^{1C}$, —CN, —$CF_3$, —$OCF_3$, —$NO_2$, —$OR^{1C}$, —$NR^{1C}R^{1D}$ and $C_1$-$C_6$-alkyl, $R^{1C}$ and $R^{1D}$ independently are hydrogen, —OH, $C_1$-$C_6$-alkyl, $C_1$-$C_6$-alkenyl, aryl-$C_1$-$C_6$-alkyl or aryl, wherein the alkyl moieties may optionally be substituted with one or more substituents selected from halogen, —CN, —$CF_3$, —$OCF_3$, —O—$C_1$-$C_6$-alkyl, —C(O)—O—$C_1$-$C_6$-alkyl, —COOH and —$NH_2$, and the aryl moieties may optionally be substituted by halogen, —$C(O)OC_1$-$C_6$-alkyl, —COOH, —CN, —$CF_3$, —$OCF_3$, —$NO_2$, —OH, —$OC_1$-$C_6$-alkyl, —$NH_2$, C(=O) or $C_1$-$C_6$-alkyl; $R^{1C}$ and $R^{1D}$ when attached to the same nitrogen atom may form a 3 to 8 membered heterocyclic ring with the said nitrogen atom, the heterocyclic ring optionally containing one or two further heteroatoms selected from nitrogen, oxygen and sulphur, and optionally containing one or two double bonds, $C^1$ is a valence bond, $C_1$-$C_6$-alkylene, —$C_1$-$C_6$-alkyl-O—, —$C_1$-$C_6$-alkyl-NH—, —NH—$C_1$-$C_6$-alkyl, —NH—C(=O)—, —C(=O)—NH—, —O—$C_1$-$C_6$-alkyl, —C(=O)—, or —$C_1$-$C_6$-alkyl-C(=O)—N($R^{1E}$) wherein the alkyl moieties are optionally substituted by one or more $R^{1F}$ independently $R^{1E}$ and $R^{1F}$ are independently selected from $C_1$-$C_6$-alkyl, aryl optionally substituted by one or more halogen, —COOH;

$AR^2$ is a valence bond $C_1$-$C_6$-alkylene, $C_2$-$C_6$-alkenylene, $C_2$-$C_6$-alkynylene wherein the alkyl, alkenyl and alkynyl moieties are optionally substituted by one or more $R^{2A}$ independently;

arylene, -aryloxy-, -aryloxy-carbonyl-, aryl-$C_1$-$C_6$-alkyl, -aroyl-, aryl-$C_1$-$C_6$-alkoxy-, aryl-$C_2$-$C_6$-alkenyl-, aryl-$C_2$-$C_6$-alkynyl-, heteroarylene, -heteroaryl-$C_1$-$C_6$-alkyl-, -heteroaryl-$C_2$-$C_6$-alkenyl-, -heteroaryl-$C_2$-$C_6$-alkynyl- wherein the aryl and heteroaryl moieties are optionally substituted by one or more $R^{2A}$ independently;

$R^{2A}$ is $C_1$-$C_6$-alkyl, $C_1$-$C_6$-alkoxy, aryl, aryloxy, aryl-$C_1$-$C_6$-alkoxy, —C(=O)—NH—$C_1$-$C_6$-alkyl-aryl, heteroaryl, heteroaryl-$C_1$-$C_6$-alkoxy, —$C_1$-$C_6$-alkyl-COOH, —O—$C_1$-$C_6$-alkyl-COOH, —$S(O)_2R^{2B}$, —$C_2$-$C_6$-alkenyl-COOH, —$OR^{2B}$, —$NO_2$, halogen, —COOH, —$CF_3$, —CN, —$N(R^{2B}R^{2C})$, wherein the aryl or heteroaryl moieties are optionally substituted by one or more $C_1$-$C_6$-alkyl, $C_1$-$C_6$-alkoxy, —$C_1$-$C_6$-alkyl-COOH, —$C_2$-$C_6$-alkenyl-COOH, —$OR^{2B}$, —$NO_2$, halogen, —COOH, —$CF_3$, —CN, or —$N(R^{2B}R^{2C})$ $R^{2B}$ and $R^{2C}$ are independently selected from hydrogen and $C_1$-$C_6$-alkyl In another embodiment of the invention $A^1$ is a valence bond, $C_1$-$C_6$-alkylene, —NH—C(=O)-$A^2$—, —$C_1$-$C_6$-alkyl-S—, —$C_1$-$C_6$-alkyl-O—, or —C(=O)—, wherein any $C_1$-$C_6$-alkyl moiety is optionally substituted by $R^{1A}$ In another embodiment of the invention $A^1$ is a valence bond, $C_1$-$C_6$-alkylene, —NH—C(=O)-$A^2$—, —$C_1$-$C_6$-alkyl-S—, or —$C_1$-$C_6$-alkyl-O, wherein any $C_1$-$C_6$-alkyl moiety is optionally substituted by $R^{1A}$ In another embodiment of the invention $A^1$ is a valence bond, $C_1$-$C_6$-alkylene, or —NH—C(=O)-$A^2$, wherein any $C_1$-$C_6$-alkyl moiety is optionally substituted by $R^{1A}$ In another embodiment of the invention $A^1$ is a valence bond or $C_1$-$C_6$-alkylene, wherein any $C_1$-$C_6$-alkyl moiety is optionally substituted by $R^{1A}$ In another embodiment of the invention $A^1$ is a valence bond In another embodiment of the invention $A^2$ is a valence bond or —$C_1$-$C_6$-alkyl-O—

In another embodiment of the invention $A^2$ is a valence bond

In another embodiment of the invention $AR^1$ is arylene or heteroarylene, wherein the aryl or heteroaryl moieties are optionally substituted by one or more $R^{1B}$ independently In another embodiment of the invention $AR^1$ is selected from the group of compounds consisting of phenylene, biphenylylene, naphthylene, anthracenylene, phenanthrenylene, fluorenylene, indenylene, azulenylene, furylene, thienylene, pyrrolylene, oxazolylene, thiazolylene, imidazolylene, isoxazolylene, isothiazolylene, 1,2,3-triazolylene, 1,2,4-triazolylene, pyranylene, pyridylene, pyridazinylene, pyrimidinylene, pyrazinylene, 1,2,3-triazinylene, 1,2,4-triazinylene, 1,3,5-triazinylene, 1,2,3-oxadiazolylene, 1,2,4-oxadiazolylene, 1,2,5-oxadiazolylene, 1,3,4-oxadiazolylene, 1,2,3-thiadiazolylene, 1,2,4-thiadiazolylene, 1,2,5-thiadiazolylene, 1,3,4-thiadiazolylene, tetrazolylene, thiadiazinylene, indolylene, isoindolylene, benzofurylene, benzothienylene, indazolylene, benzimidazolylene, benzthiazolylene, benzisothiazolylene, benzoxazolylene, benzisoxazolylene, purinylene, quinazolinylene, quinolizinylene, quinolinylene, isoquinolinylene, quinoxalinylene, naphthyridinylene, pteridinylene, carbazolylene, azepinylene, diazepinylene, or acridinylene, optionally substituted by one or more $R^{1B}$ independently In another embodiment of the invention $AR^1$ is selected from phenylene, biphenylylene, naphthylene, pyridinylene, fyrylene, indolylene, or carbazolylene, optionally substituted by one or more $R^{1B}$ independently In another embodiment of the invention $AR^1$ is selected from the group of compounds consisting of phenylene, indolylene, or carbazolylene, optionally substituted by one or more $R_{1B}$ independently In another embodiment of the invention $AR^1$ is phenylene optionally substituted by one or more $R^{1B}$ independently In another embodiment of the invention $AR^1$ is indolylene In another embodiment of the invention $AR^1$ is carbazolylene In another embodiment of the invention $AR^1$ is

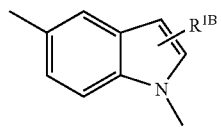

In another embodiment of the invention $AR^1$ is

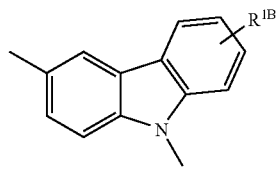

In another embodiment of the invention $R^{1B}$ is selected from
hydrogen, halogen, —CN, —$CF_3$, —$OCF_3$, —$NO_2$, —$OR^{1C}$, —$NR^{1C}R^{1D}$, —$SR^{1C}$, —$S(O)_2R^{1C}$, —$NR^{1C}C(=O)R^{1D}$, —$OC_1$-$C_6$-alkyl-C(O)$NR^{1C}R^{1D}$, —$C_2$-$C_6$-alkenyl-C(=O)$OR^{1C}$, —C(O)$OR^{1C}$, =O, —NH—C(=O)—O—$C_1$-$C_6$-alkyl, or —NH—C(=O)—C(=O)—O—$C_1$-$C_6$-alkyl
$C_1$-$C_6$-alkyl or $C_2$-$C_6$-alkenyl
which may optionally be substituted with one or more substituents selected from halogen, —CN, —$CF_3$, —$OCF_3$, —$OR^{1C}$, and —$NR^{1C}R^{1D}$
aryl, aryloxy, aryl-$C_1$-$C_6$-alkoxy, aryl-$C_1$-$C_6$-alkyl, aryl-$C_2$-$C_6$-alkenyl, heteroaryl, heteroaryl-$C_1$-$C_6$-alkyl, or heteroaryl-$C_2$-$C_6$-alkenyl
of which the cyclic moieties optionally may be substituted with one or more substituents selected from halogen, —C(O)$OR^{1C}$, —CN, —$CF_3$, —$OCF_3$, —$NO_2$, —$OR^{1C}$, —$NR^{1C}R^{1D}$ and $C_1$-$C_6$-alkyl In another embodiment of the invention $R^{1B}$ is selected from
hydrogen, halogen, —$CF_3$, —$NO_2$, —$OR^{1C}$, —$NR^{1C}R^{1D}$, —C(O)$OR^{1C}$, =O, —NH—C(=O)—O—$C_1$-$C_6$-alkyl, or —NH—C(=O)—C(=O)—O—$C_1$-$C_6$-alkyl
$C_1$-$C_6$-alkyl In another embodiment of the invention $R^{1C}$ and $R^{1D}$ independently are hydrogen, $C_1$-$C_6$-alkyl, or aryl, wherein the aryl moieties may optionally be substituted by halogen or —COOH In another embodiment of the invention $R^{1C}$ and $R^{1D}$ independently are hydrogen, methyl, ethyl, or phenyl, wherein the phenyl moieties may optionally be substituted by halogen or —COOH In another embodiment of the invention $C^1$ is a valence bond, $C_1$-$C_6$-alkylene, —$C_1$-$C_6$-alkyl-O—, —$C_1$-$C_6$-alkyl-NH—, —NH—$C_1$-$C_6$-alkyl, —NH—C(=O)—, —C(=O)—NH—, —O—$C_1$-$C_6$-alkyl, —C(=O)—, or —$C_1$-$C_6$-alkyl-C(=O)—N($R^{1E}$)— wherein the alkyl moieties are optionally substituted by one or more $R^{1F}$ independently In another embodiment of the invention $C^1$ is a valence bond, —$CH_2$—, —$CH_2$—$CH_2$—, —$CH_2$—O—, —$CH_2$—$CH_2$—O—, —$CH_2$—NH—, —$CH_2$—$CH_2$—NH—, —NH—$CH_2$—, —NH—$CH_2$—$CH_2$—, —NH—C(=O)—, —C(=O)—NH—, —O—$CH_2$—, —O—$CH_2$—$CH_2$—, or —C(=O)—

In another embodiment of the invention $R^{1E}$ and $R^{1F}$ are independently selected from $C_1$-$C_6$-alkyl In another embodiment of the invention $AR^2$ is
a valence bond
$C_1$-$C_6$-alkylene, wherein the alkyl is optionally substituted by one or more $R^{2A}$ independently
arylene, aryl-$C_1$-$C_6$-alkyl, heteroarylene, wherein the aryl and heteroaryl moieties are optionally substituted by one or more $R^{2A}$ independently In another embodiment of the invention $AR^2$ is
a valence bond
$C_1$-$C_6$-alkylene, wherein the alkyl is optionally substituted by one or more $R^{2A}$ independently
phenyl, phenyl-$C_1$-$C_6$-alkyl, wherein the phenyl moieties are optionally substituted by one or more $R^{2A}$ independently In another embodiment of the invention $R^{2A}$ is $C_1$-$C_6$-alkyl, $C_1$-$C_6$-alkoxy, aryl, aryloxy, heteroaryl, —$C_1$-$C_6$-alkyl-COOH, —O—$C_1$-$C_6$-alkyl-COOH, —$S(O)_2R^{2B}$, —$C_2$-$C_6$-alkenyl-COOH, —$OR^{2B}$, —$NO_2$, halogen, —COOH, —$CF_3$, —CN, —$N(R^{2B}R^{2C})$, wherein the aryl or heteroaryl moieties are optionally substituted by one or more $C_1$-$C_6$-alkyl, $C_1$-$C_6$-alkoxy, —$C_1$-$C_6$-alkyl-COOH, —$C_2$-$C_6$-alkenyl-COOH, —$OR^{2B}$, —$NO_2$, halogen, —COOH, —$CF_3$, —CN, or —$N(R^{2B}R^{2C})$ In another embodiment of the invention $R^{2A}$ is $C_1$-$C_6$-alkyl, $C_1$-$C_6$-alkoxy, aryl, —$OR^{2B}$, —$NO_2$, halogen, —COOH, —$CF_3$, —CN, —$N(R^{2B}R^{2C})$, wherein the aryl is optionally substituted by one or more $C_1$-$C_6$-alkyl, $C_1$-$C_6$-alkoxy, —$OR^{2B}$, —$NO_2$, halogen, —COOH, —$CF_3$, —CN, or —$N(R^{2B}R^{2C})$ In another embodiment of the invention $R^{2A}$ is $C_1$-$C_6$-alkyl, $C_1$-$C_6$-alkoxy, aryl, halogen, —$CF_3$, wherein the aryl is optionally substituted by one or more $C_1$-$C_6$-alkyl, halogen, —COOH, —$CF_3$, or —CN In another embodiment of the invention $R^{2A}$ is $C_1$-$C_6$-alkyl, $C_1$-$C_6$-alkoxy, phenyl, halogen, —COOH, —$CF_3$, or —CN In another embodiment of the invention A is

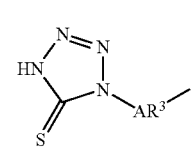

wherein $AR^3$ is $C_1$-$C_6$-alkylene, arylene, heteroarylene, -aryl-$C_{1-6}$-alkyl- or -aryl-$C_{2-6}$-alkenyl-, wherein the alkylene or alkenylene is optionally substituted with one or more substituents independently selected from halogen, —CN, —CF$_3$, —OCF$_3$, aryl, —COOH and —NH$_2$, and the arylene or heteroarylene is optionally substituted with one or more R$^{3A}$ independently R$^{3A}$ is independently selected from
hydrogen, halogen, —CN, —CH$_2$CN, —CHF$_2$, —CF$_3$, —OCF$_3$, —OCHF$_2$, —OCH$_2$CF$_3$, —OCF$_2$CHF$_2$, —S(O)$_2$CF$_3$, —OS(O)$_2$CF$_3$, —SCF$_3$, —NO$_2$, —OR$^{3B}$, —NR$^{3B}$R$^{3C}$, —SR$^{3B}$, —NR$^{3B}$S(O)$_2$R$^{3C}$, —S(O)$_2$NR$^{3B}$R$^{4C}$, —S(O)NR$^{3B}$R$^{3C}$, —S(O)R$^{3B}$, —S(O)$_2$R$^{3B}$, —OS(O)$_2$R$^{3B}$, —C(O)NR$^{3B}$R$^{3C}$, —OC(O)NR$^{3B}$R$^{3C}$, —NR$^{3B}$C(O)R$^{3C}$, —CH$_2$C(O)NR$^{3C}$R$^{3B}$, —OC$_1$-C$_6$-alkyl-C(O)NR$^{3B}$R$^{3C}$, —CH$_2$OR$^{3B}$, —CH$_2$OC(O)R$^{3B}$, —CH$_2$NR$^{3B}$R$^{3C}$, —OC(O)R$^{3B}$, —OC$_1$-C$_6$-alkyl-C(O)OR$^{3B}$, —OC$_1$-C$_6$-alkyl-OR$^{3B}$, —SC$_1$-C$_6$-alkyl-C(O)OR$^{3B}$, —C$_2$-C$_6$-alkenyl-C(=O)OR$^{3B}$, —NR$^{3B}$—C(=O)—C$_1$-C$_6$-alkyl-C(=O)OR$^{3B}$, —NR$^{3B}$—C(=O)—C$_1$-C$_6$-alkenyl-C(=O)OR$^{3B}$, —C(O)OR$^{3B}$, or —C$_2$-C$_6$-alkenyl-C(=O)R$^{3B}$, C$_1$-C$_6$-alkyl, C$_2$-C$_6$-alkenyl or C$_2$-C$_6$-alkynyl,
which may optionally be substituted with one or more substituents selected from halogen, —CN, —CF$_3$, —OCF$_3$, —OR$^{3B}$, and —NR$^{3B}$R$^{3C}$ aryl, aryloxy, aryloxycarbonyl, aroyl, arylsulfanyl, aryl-C$_1$-C$_6$-alkoxy, aryl-C$_1$-C$_6$-alkyl, aryl-C$_2$-C$_6$-alkenyl, aroyl-C$_2$-C$_6$-alkenyl, aryl-C$_2$-C$_6$-alkynyl, heteroaryl, heteroaryl-C$_1$-C$_6$-alkyl, heteroaryl-C$_2$-C$_6$-alkenyl or heteroaryl-C$_2$-C$_6$-alkynyl, of which the cyclic moieties optionally may be substituted with one or more substituents selected from halogen, —C(O)OR$^{3B}$, —CH$_2$C(O)OR$^{3B}$, —CH$_2$OR$^{3B}$, —CN, —CF$_3$, —OCF$_3$, —NO$_2$, —OR$^{3B}$, —NR$^{3B}$R$^{3C}$ and C$_1$-C$_6$-alkyl, R$^{3B}$ and R$^{3C}$ are independently hydrogen, OH, CF$_3$, C$_1$-C$_2$-alkyl, aryl-C$_1$-C$_6$-alkyl, —C(=O)—C$_1$-C$_6$-alkyl or aryl, wherein the alkyl groups may optionally be substituted with one or more substituents selected from halogen, —CN, —CF$_3$, —OCF$_3$, —OC$_1$-C$_6$-alkyl, —C(O)OC$_1$-C$_6$-alkyl, —C(=O)—R$^{3D}$, —COOH and —NH$_2$, and the aryl groups may optionally be substituted by halogen, —C(O)OC$_1$-C$_6$-alkyl, —COOH, —CN, —CF$_3$, —OCF$_3$, —NO$_2$, —OH, —OC$_1$-C$_6$-alkyl, —NH$_2$, C(=O) or C$_1$-C$_6$-alkyl; R$^{3B}$ and R$^{3C}$ when attached to the same nitrogen atom may form a 3 to 8 membered heterocyclic ring with the said nitrogen atom, the heterocyclic ring optionally containing one or two further heteroatoms selected from nitrogen, oxygen and sulphur, and optionally containing one or two double bonds R$^{3D}$ is C$_1$-C$_6$-alkyl, aryl optionally substituted with one or more halogen, or heteroaryl optionally substituted with one or more C$_1$-C$_6$-alkyl.

In another embodiment of the invention AR$^3$ is arylene, heteroarylene, or aryl-C$_{1-6}$-alkyl, wherein the alkyl is optionally substituted with one or more substituents independently selected from —CN, —CF$_3$, —OCF$_3$, aryl, —COOH and —NH$_2$, and the arylene or heteroarylene is optionally substituted with one or more R$^{3A}$ independently In another embodiment of the invention AR$^3$ is arylene optionally substituted with one or more R$^{3A}$ independently In another embodiment of the invention AR$^3$ is phenylene, naphthalene or anthranylene optionally substituted with one or more R$^{3A}$ independently In another embodiment of the invention AR$^3$ is phenylene optionally substituted with one or more R$^{3A}$ independently In another embodiment of the invention R$^{3A}$ is independently selected from
halogen, —CN, —CF$_3$, —NO$_2$, —OR$^{3B}$, —NR$^{3B}$R$^{3C}$, —SR$^{3B}$, —OC$_1$-C$_6$-alkyl-C(O)OR$^{3B}$ or —C(O)OR$^{3B}$ C$_1$-C$_6$-alkyl optionally substituted with one or more substituents selected from halogen, —CN, —CF$_3$, —OCF$_3$, —OR$^{3B}$, and —NR$^{3B}$R$^{3C}$ aryl, aryl-C$_1$-C$_6$-alkyl, heteroaryl, or heteroaryl-C$_1$-C$_6$-alkyl of which the cyclic moieties optionally may be substituted with one or more substituents selected from halogen, —C(O)OR$^{3B}$, —CN, —CF$_3$, —OCF$_3$, —NO$_2$, —OR$^{3B}$, —NR$^{3B}$R$^{3C}$ and C$_1$-C$_6$-alkyl In another embodiment of the invention R$^{3A}$ is independently selected from halogen, —OR$^{3B}$, —NR$^{3B}$R$^{3C}$, —C(O)OR$^{3B}$, —OC$_1$-C$_6$-alkyl-C(O)OR$^{3B}$, or C$_1$-C$_6$-alkyl In another embodiment of the invention R$^{3B}$ and R$^{3C}$ are independently hydrogen, CF$_3$, C$_1$-C$_{12}$-alkyl, or —C(=O)—C$_1$-C$_6$-alkyl; R$^{3B}$ and R$^{3C}$ when attached to the same nitrogen atom may form a 3 to 8 membered heterocyclic ring with the said nitrogen atom In another embodiment of the invention A is

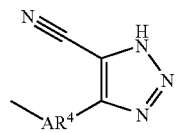

wherein AR$^4$ is C$_1$-C$_6$-alkylene, arylene, heteroarylene, -aryl-C$_{1-6}$-alkyl- or -aryl-C$_{2-6}$-alkenyl, wherein the alkylene or alkenylene is optionally substituted with one or more substituents independently selected from halogen, —CN, —CF$_3$, —OCF$_3$, aryl, —COOH and —NH$_2$, and the arylene or heteroarylene is optionally substituted with one or more R$^{4A}$ independently R$^{4A}$ is independently selected from
hydrogen, halogen, —CN, —CH$_2$CN, —CHF$_2$, —CF$_3$, —OCF$_3$, —OCHF$_2$, —OCH$_2$CF$_3$, —OCF$_2$CHF$_2$, —S(O)$_2$CF$_3$, —OS(O)$_2$CF$_3$, —SCF$_3$, —NO$_2$, —OR$^{4B}$, —NR$^{4B}$R$^{4C}$, —SR$^{4B}$, —NR$^{4B}$S(O)$_2$R$^{4C}$, —S(O)$_2$NR$^{4B}$R$^{4C}$, —S(O)NR$^{4B}$R$^{4C}$, —S(O)R$^{4B}$, —S(O)R$^{4B}$, —OS(O)$_2$R$^{4B}$, —C(O)NR$^{4B}$R$^{4C}$, —OC(O)NR$^{4B}$R$^{4C}$, —NR$^{4B}$C(O)R$^{4C}$, —CH$_2$C(O)NR$^{4B}$R$^{4C}$, —OC$_1$-C$_6$-alkyl-C(O)NR$^{4B}$R$^{4C}$, —CH$_2$OR$^{4B}$, —CH$_2$OC(O)R$^{4B}$, —CH$_2$NR$^{4B}$R$^{4C}$, —OC(O)R$^{4B}$, —OC$_1$-C$_6$-alkyl-C(O)O$^{4B}$, —OC$_1$-C$_6$-alkyl-OR$^{4B}$, —SC$_1$-C$_6$-alkyl-C(O)OR$^{4B}$, —C$_2$-C$_6$-alkenyl-C(=O)OR$^{4B}$, —NR$^{4B}$—C(=O)—C$_1$-C$_6$-alkyl-C(=O)OR$^{4B}$, —NR$^{4B}$—C(=O)—C$_1$-C$_6$-alkenyl-C(=O)OR$^{4B}$, —C(O)OR$^{4B}$, or —C$_2$-C$_6$-alkenyl-C(=O)R$^{4B}$, C$_1$-C$_6$-alkyl, C$_2$-C$_6$-alkenyl or C$_2$-C$_6$-alkynyl,
which may optionally be substituted with one or more substituents selected from halogen, —CN, —CF$_3$, —OCF$_3$, —OR$^{4B}$, and —NR$^{4B}$R$^{4C}$ aryl, aryloxy, aryloxycarbonyl, aroyl, arylsulfanyl, aryl-C$_1$-C$_6$-alkoxy, aryl-C$_1$-C$_6$-alkyl, aryl-C$_2$-C$_6$-alkenyl, aroyl-C$_2$-C$_6$-alkenyl, aryl-C$_2$-C$_6$-alkynyl, heteroaryl, heteroaryl-C$_1$-C$_6$-alkyl, heteroaryl-C$_2$-C$_6$-alkenyl or heteroaryl-C$_2$-C$_6$-alkynyl, of which the cyclic moieties optionally may be substituted with one or more substituents selected from halogen, —C(O)OR$^{4B}$, —CH$_2$C(O)OR$^{4B}$, —CH$_2$OR$^{4B}$, —CN, —CF$_3$, —OCF$_3$, —NO$_2$, —OR$^{4B}$, —NR$^{4B}$R$^{4C}$ and C$_1$-C$_6$-alkyl, $R^{4B}$ and $R^{4C}$ are independently hydrogen, OH, $CF_3$, $C_1$-$C_{12}$-alkyl, aryl-$C_1$-$C_6$-alkyl, —C(=O)—$R^{4D}$, or aryl, wherein the alkyl groups may optionally be substituted with one or more substituents selected from halogen, —CN, —$CF_3$, —$OCF_3$, —$OC_1$-$C_6$-alkyl, —C(O)$OC_1$-$C_6$-alkyl, —COOH and —$NH_2$, and the aryl groups may optionally be substituted by halogen, —C(O)$OC_1$-$C_6$-alkyl, —COOH, —CN, —$CF_3$, —$OCF_3$, —$NO_2$, —OH, —$OC_1$-$C_6$-alkyl, —$NH_2$, C(=O) or $C_1$-$C_6$-alkyl; $R^{4B}$ and $R^{4C}$ when attached to the same nitrogen atom may form a 3 to 8 membered heterocyclic ring with the said nitrogen atom, the heterocyclic ring optionally containing one or two further heteroatoms selected from nitrogen, oxygen and sulphur, and optionally containing one or two double bonds $R^{4D}$ is $C_1$-$C_6$-alkyl, aryl optionally substituted with one or more halogen, or heteroaryl optionally substituted with one or more $C_1$-$C_6$-alkyl.

In another embodiment of the invention $AR^4$ is arylene, heteroarylene or aryl-$C_{1-6}$-alkyl-, wherein the alkyl is optionally substituted with one or more substituents independently selected from halogen, —CN, —$CF_3$, —$OCF_3$, aryl, —COOH and —$NH_2$, and the arylene or heteroaryl is optionally substituted with one or more $R^{4A}$ independently In another embodiment of the invention $AR^4$ is arylene or heteroarylene optionally substituted with one or more $R^{4A}$ independently In another embodiment of the invention $AR^4$ is phenylene, naphtylene, anthrylene, thienylene, pyridylene, or benzodioxylene optionally substituted with one or more $R^{4A}$ independently In another embodiment of the invention $AR^4$ is phenylene optionally substituted with one or more $R^{4A}$ independently In another embodiment of the invention $R^{4A}$ is independently selected from hydrogen, halogen, —$CF_3$, —$OR^{4B}$, —$NR^{4B}R^{4C}$, $C_1$-$C_6$-alkyl, aryl-$C_2$-$C_6$-alkenyl or aryl optionally substituted with one or more substituents selected from halogen, —$CF_3$, or —$OR^{4B}$ In another embodiment of the invention $R^{4B}$ and $R^{4C}$ are independently hydrogen, $CF_3$, $C_1$-$C_{12}$-alkyl, —C(=O)—$R^{4D}$, or aryl In another embodiment of the invention $R^{4D}$ is $C_1$-$C_6$-alkyl, phenyl optionally substituted with one or more halogen, or a heteroaryl selected from isoxazole and thiadiazole optionally substituted with one or more $C_1$-$C_6$-alkyl In another embodiment of the invention C consists of 0 to 5 neutral amino acids independently selected from the group consisting of Abz, Gly, Ala, Thr, and Ser In another embodiment of the invention C consists of 0 to 5 Gly In another embodiment of the invention C consists of 0 Gly
In another embodiment of the invention C consists of 1 Gly
In another embodiment of the invention C consists of 2 Gly
In another embodiment of the invention C consists of 3 Gly
In another embodiment of the invention C consists of 4 Gly
In another embodiment of the invention C consists of 5 Gly In another embodiment of the invention $G^B$ is of the formula —$B^1$—$B^2$—C(O)—, —$B^1$—$B^2$—$SO_2$— or —$B^1$—$B^2$—$CH_2$—, wherein $B^1$ and $B^2$ are as defined in claim 1

In another embodiment of the invention $G^B$ is of the formula —$B^1$—$B^2$—C(O)—, —$B^1$—$B^2$—$SO_2$— or —$B^1$—$B^2$—NH—, wherein $B^1$ and $B^2$ are as defined in claim 1

In another embodiment of the invention $G^B$ is of the formula —$B^1$—$B^2$—C(O)—, —$B^1$—$B^2$—$CH_2$, or —$B^1$—$B^2$—NH—, wherein $B^1$ and $B^2$ are as defined in claim 1

In another embodiment of the invention $G^B$ is of the formula —$B^1$—$B^2$—$CH_2$—, —$B^1$—$B^2$—$SO_2$— or —$B^1$—$B^2$—NH—, wherein $B^1$ and $B^2$ are as defined in claim 1

In another embodiment of the invention $G^B$ is of the formula —$B^1$—$B^2$—C(O)— or —$B^1$—$B^2$—$SO_2$—, wherein $B^1$ and $B^2$ are as defined in claim 1

In another embodiment of the invention $G^B$ is of the formula —$B^1$—$B^2$—C(O)— or —$B^1$—$B^2$—$CH_2$—, wherein $B^1$ and $B^2$ are as defined in claim 1

In another embodiment of the invention $G^B$ is of the formula —$B^1$—$B^2$—C(O)— or —$B^1$—$B^2$—NH—, wherein $B^1$ and $B^2$ are as defined in claim 1

In another embodiment of the invention $G^B$ is of the formula —$B^1$—$B^2$—$CH_2$— or —$B^1$—$B^2$—$SO_2$—, wherein $B^1$ and $B^2$ are as defined in claim 1

In another embodiment of the invention $G^B$ is of the formula —$B^1$—$B^2$—NH— or —$B^1$—$B^2$—$SO_2$—, wherein $B^1$ and $B^2$ are as defined in claim 1

In another embodiment of the invention $G^B$ is of the formula —$B^1$—$B^2$—$CH_2$— or —$B^1$—$B^2$—NH—, wherein $B^1$ and $B^2$ are as defined in claim 1

In another embodiment of the invention $G^B$ is of the formula —$B^1$—$B^2$—C(O)—

In another embodiment of the invention $G^B$ is of the formula —$B^1$—$B^2$—$CH_2$—

In another embodiment of the invention $G^B$ is of the formula —$B^1$—$B^2$—$SO_2$—

In another embodiment of the invention $G^B$ is of the formula —$B^1$—$B^2$—NH—

In another embodiment of the invention $B^1$ is a valence bond, —O—, or —S—

In another embodiment of the invention $B^1$ is a valence bond, —O—, or —N($R^6$)—

In another embodiment of the invention $B^1$ is a valence bond, —S—, or —N($R^6$)—

In another embodiment of the invention $B^1$ is —O—, —S— or —N($R_6$)—

In another embodiment of the invention $B^1$ is a valence bond —O—

In another embodiment of the invention $B^1$ is a valence bond or —S—

In another embodiment of the invention $B^1$ is a valence bond or —N($R^6$)—

In another embodiment of the invention $B^1$ is —O— or —S—

In another embodiment of the invention $B^1$ is —O— or —N($R^6$)—

In another embodiment of the invention $B^1$ is —S— or —N($R^6$)—

In another embodiment of the invention $B^1$ is a valence bond

In another embodiment of the invention $B^1$ is —O—
In another embodiment of the invention $B^1$ is —S—
In another embodiment of the invention $B^1$ is —N($R^6$)—

In another embodiment of the invention $B^2$ is a valence bond, $C_1$-$C_{18}$-alkylene, $C_2$-$C_{18}$-alkenylene, $C_2$-$C_{18}$-alkynylene, arylene, heteroarylene, —$C_1$-$C_{18}$-alkyl-aryl-, —C(=O)—$C_1$-$C_{18}$-alkyl-C(=O)—, —C(=O)—$C_1$-$C_{18}$-alkyl-O—$C_1$-$C_{18}$-alkyl-C(=O)—, —C(=O)—$C_1$-$C_{18}$-alkyl-S—$C_1$-$C_{18}$—C(=O)—, —C(=O)—$C_1$-$C_{18}$-alkyl-$NR^6$—$C_1$-$C_{18}$-alkyl-C(=O)—; and the alkylene and arylene moieties are optionally substituted as defined in claim 1

In another embodiment of the invention $B^2$ is a valence bond, $C_1$-$C_{18}$-alkylene, $C_2$-$C_{18}$-alkenylene, $C_2$-$C_{18}$-alkynylene, arylene, heteroarylene, —$C_1$-$C_{18}$-alkyl-aryl-, —C(=O)—$C_1$-$C_{18}$-alkyl-C(=O)—, —C(=O)—$C_1$-$C_{18}$- alkyl-O—C$_1$-C$_{18}$-alkyl-C(=O)—, and the alkylene and arylene moieties are optionally substituted as defined in claim 1

In another embodiment of the invention B$^2$ is a valence bond, C$_1$-C$_{18}$-alkylene, C$_2$-C$_{18}$-alkenylene, C$_2$-C$_{18}$-alkynylene, arylene, heteroarylene, —C$_1$-C$_{18}$-alkyl-aryl-, —C(=O)—C$_1$-C$_{18}$-alkyl-C(=O)—, and the alkylene and arylene moieties are optionally substituted as defined in claim 1

In another embodiment of the invention B$^2$ is a valence bond, C$_1$-C$_{18}$-alkylene, arylene, heteroarylene, —C$_1$-C$_{18}$-alkyl-aryl-, —C(=O)—C$_1$-C$_{18}$-alkyl-C(=O)—, and the alkylene and arylene moieties are optionally substituted as defined in claim 1

In another embodiment of the invention B$^2$ is a valence bond, C$_1$-C$_{18}$-alkylene, arylene, heteroarylene, —C$_1$-C$_{18}$-alkyl-aryl-, and the alkylene and arylene moieties are optionally substituted as defined in claim 1

In another embodiment of the invention B$^2$ is a valence bond, C$_1$-C$_{18}$-alkylene, arylene, —C$_1$-C$_{18}$-alkyl-aryl-, and the alkylene and arylene moieties are optionally substituted as defined in claim 1

In another embodiment of the invention B$^2$ is a valence bond or —C$_1$-C$_{18}$-alkylene, and the alkylene moieties are optionally substituted as defined in claim 1

In another embodiment of the invention D comprises 1 to 16 positively charged groups In another embodiment of the invention D comprises 1 to 12 positively charged groups In another embodiment of the invention D comprises 1 to 10 positively charged groups In another embodiment of the invention D is a fragment containing basic amino acids independently selected from the group consisting of Lys and Arg and D-isomers of these.

In another embodiment of the invention the basic amino acid is Arg

In another embodiment of the invention X is —OH or —NH$_2$

In another embodiment of the invention X is —NH$_2$

The invention furthermore provides an R-state insulin hexamer comprising:
  6 molecules of insulin, at least 2 zinc ions, and a zinc-binding ligand as defined above In another embodiment of the invention the insulin is selected from the group consisting of human insulin, an analogue thereof, a derivative thereof, and combinations of any of these In another embodiment of the invention the insulin is an analogue of human insulin selected from the group consisting of
  iii. An analogue wherein position B28 is Asp, Lys, Leu, Val, or Ala and position B29 is Lys or Pro; and
  iv. des(B28-B30), des(B27) or des(B30) human insulin.

In another embodiment of the invention the insulin is an analogue of human insulin wherein position B28 is Asp or Lys, and position B29 is Lys or Pro.

In another embodiment of the invention the insulin is des (B30) human insulin.

In another embodiment of the invention the insulin is a derivative of human insulin having one or more lipophilic substituents.

In another embodiment of the invention the insulin derivative is selected from the group consisting of B29-N$^\epsilon$-myristoyl-des(B30) human insulin, B29-N$^\epsilon$-palmitoyl-des(B30) human insulin, B29-N$^\epsilon$-myristoyl human insulin, B29-N$^\epsilon$-palmitoyl human insulin, B28-N$^\epsilon$-myristoyl Lys$^{B28}$ Pro$^{B29}$ human insulin, B28-N$^\epsilon$-palmitoyl Lys$^{B28}$ Pro$^{B29}$ human insulin, B30-N$^\epsilon$-myristoyl-Thr$^{B29}$Lys$^{B30}$ human insulin, B30-N$^\epsilon$-palmitoyl-Thr$^{B29}$Lys$^{B30}$ human insulin, B29-N$^\epsilon$-(N-palmitoyl-γ-glutamyl)-des(B30) human insulin, B29-N$^\epsilon$-(N-lithocholyl-γ-glutamyl)-des(B30) human insulin, B29-N$^\epsilon$-(ω-carboxyheptadecanoyl)-des(B30) human insulin and B29-N$^\epsilon$-(ω-carboxyheptadecanoyl) human insulin.

In another embodiment of the invention the insulin derivative is B29-N$^\epsilon$-myristoyl-des(B30) human insulin.

In another embodiment of the invention the insulin hexamer as defined above further comprises at least 3 phenolic molecules.

The invention furthermore provides an aqueous insulin preparation comprising R-state insulin hexamers as defined above The invention furthermore provides a method of prolonging the action of an insulin preparation which comprises adding a zinc-binding ligand as defined above to the insulin preparation.

In another embodiment of the invention the ratio between precipitated insulin and dissolved insulin is in the range from 99:1 to 1:99.

In another embodiment of the invention the ratio between precipitated insulin and dissolved insulin is in the range from 95:5 to 5:95

In another embodiment of the invention the ratio between precipitated insulin and dissolved insulin is in the range from 80:20 to 20:80

In another embodiment of the invention the ratio between precipitated insulin and dissolved insulin is in the range from 70:30 to 30:70

The invention furthermore provides a method of preparing a zinc-binding ligand as defined above comprising the steps of
  Identifying starter compounds that are able to displace a ligand from the R-state His$^{B10}$-Zn$^{2+}$ site
  optionally attaching a fragment consisting of 0 to 5 neutral α- or β-amino acids
  attaching a fragment comprising 1 to 20 positively charged groups independently selected from amino or guanidino groups The compounds of the present invention may be chiral, and it is intended that any enantiomers, as separated, pure or partially purified enantiomers or racemic mixtures thereof are included within the scope of the invention.

Furthermore, when a double bond or a fully or partially saturated ring system or more than one centre of asymmetry or a bond with restricted rotatability is present in the molecule diastereomers may be formed. It is intended that any diastereomers, as separated, pure or partially purified diastereomers or mixtures thereof are included within the scope of the invention.

Furthermore, some of the compounds of the present invention may exist in different tautomeric forms and it is intended that any tautomeric forms, which the compounds are able to form, are included within the scope of the present invention.

The present invention also encompasses pharmaceutically acceptable salts of the present compounds. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulphuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, picric, pyruvic, succinic, methanesulfonic, ethanesulfonic, tartaric, ascorbic, pamoic, ethanedisulfonic, gluconic, citraconic, aspartic, stearic, palmitic, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methyl-, dimethyl-, trimethyl-, ethyl-, hydroxyethyl-, diethyl-, n-butyl-, sec-butyl-, tert-butyl-, tetramethylammonium salts and the like.

Also intended as pharmaceutically acceptable acid addition salts are the hydrates, which the present compounds, are able to form.

Furthermore, the pharmaceutically acceptable salts comprise basic amino acid salts such as lysine, arginine and ornithine.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds of the present invention may form solvates with standard low molecular weight solvents using methods well known to the person skilled in the art. Such solvates are also contemplated as being within the scope of the present invention.

Pharmaceutical Compositions

The present invention also relates to a pharmaceutical composition for the treatment of diabetes in a patient in need of such a treatment comprising an R-state hexamer of insulin according to the invention together with a pharmaceutically acceptable carrier.

In one embodiment of the invention the insulin preparation comprises 60 to 3000 nmol/ml of insulin.

In another embodiment of the invention the insulin preparation comprises 240 to 1200 nmol/ml of insulin.

In another embodiment of the invention the insulin preparation comprises about 600 nmol/ml of insulin.

Zinc ions may be present in an amount corresponding to 10 to 40 µg Zn/100 U insulin, more preferably 10 to 26 µg Zn/100 U insulin.

Insulin formulations of the invention are usually administered from multi-dose containers where a preservative effect is desired. Since phenolic preservatives also stabilize the R-state hexamer the formulations may contain up to 50 mM of phenolic molecules. The phenolic molecules in the insulin formulation may be selected from the group consisting of phenol, m-cresol, chloro-cresol, thymol, 7-hydroxyindole or any mixture thereof.

In one embodiment of the invention 0.5 to 4.0 mg/ml of phenolic compound may be employed.

In another embodiment of the invention 0.6 to 4.0 mg/ml of m-cresol may be employed.

In another embodiment of the invention 0.5 to 4.0 mg/ml of phenol may be employed.

In another embodiment of the invention 1.4 to 4.0 mg/ml of phenol may be employed.

In another embodiment of the invention 0.5 to 4.0 mg/ml of a mixture of m-cresol or phenol may be employed.

In another embodiment of the invention 1.4 to 4.0 mg/ml of a mixture of m-cresol or phenol may be employed.

The pharmaceutical preparation may further comprises a buffer substance, such as a TRIS, phosphate, glycine or glycylglycine (or another zwitterionic substance) buffer, an isotonicity agent, such as NaCl, glycerol, mannitol and/or lactose. Chloride would be used at moderate concentrations (e.g. up to 50 mM) to avoid competition with the zinc-site ligands of the present invention.

The action of insulin may further be slowed down in vivo by the addition of physiologically acceptable agents that increase the viscosity of the pharmaceutical preparation. Thus, the pharmaceutical preparation according to the invention may furthermore comprise an agent which increases the viscosity, such as polyethylene glycol, polypropylene glycol, copolymers thereof, dextrans and/or polylactides.

In a particular embodiment the insulin preparation of the invention comprises between 0.001% by weight and 1% by weight of anon-ionic surfactant, for example tween 20 or Polox 188.

A nonionic detergent can be added to stabilise insulin against fibrillation during storage and handling.

The insulin preparation of the present invention may have a pH value in the range of 3.5 to 8.5, more preferably 7.4 to 7.9.

EXAMPLES

The following examples and general procedures refer to intermediate compounds and final products identified in the specification and in the synthesis schemes. The preparation of the compounds of the present invention is described in detail using the following examples, but the chemical reactions described are disclosed in terms of their general applicability to the preparation of compounds of the invention. Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, that is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may easily be prepared from known starting materials. All temperatures are set forth in degrees Celsius and unless otherwise indicated, all parts and percentages are by weight when referring to yields and all parts are by volume when referring to solvents and eluents.

HPLC-MS (Method A)
  The following instrumentation was used:
  Hewlett Packard series 1100 G1312A Bin Pump
  Hewlett Packard series 1100 Column compartment
  Hewlett Packard series 1100 G13 15A DAD diode array detector
  Hewlett Packard series 1100 MSD
  The instrument was controlled by HP Chemstation software.
  The HPLC pump was connected to two eluent reservoirs containing:
  A: 0.01% in water
  B: 0.01% TFA in acetonitrile
  The analysis was performed at 40° C. by injecting an appropriate volume of the sample (preferably 1 µL) onto the column, which was eluted with a gradient of acetonitrile.

The HPLC conditions, detector settings and mass spectrometer settings used are given in the following table.

| Column | Waters Xterra MS C-18 × 3 mm id |
|---|---|
| Gradient | 10%-100% acetonitrile lineary during 7.5 min at 1.0 mL/min |
| Detection | UV: 210 nm (analog output from DAD) |
| MS | Ionisation mode: API-ES |
|  | Scan 100-1000 amu step 0.1 amu |

HPLC-MS (Method B)

The following instrumentation was used:
Sciex API 100 Single quadropole mass spectrometer
Perkin Elmer Series 200 Quard pump
Perkin Elmer Series 200 autosampler
Applied Biosystems 785A UV detector
Sedex 55 evaporative light scattering detector
A Valco column switch with a Valco actuator controlled by timed events from the pump.

The Sciex Sample control software running on a Macintosh PowerPC 7200 Computer was used for the instrument control and data acquisition.

The HPLC pump was connected to four eluent reservoirs containing:
A: acetonitrile
B: water
C: 0.5% TFA in water
D: 0.02 M ammonium acetate The requirements for samples are that they contain approximately 500 μg/mL of the compound to be analysed in an acceptable solvent such as methanol, ethanol, acetonitrile, THF, water and mixtures thereof. (High concentrations of strongly eluting solvents will interfere with the chromatography at low acetonitrile concentrations.)

The analysis was performed at room temperature by injecting 20 μL of the sample solution on the column, which was eluted with a gradient of acetonitrile in either 0.05% TFA or 0.002 M ammonium acetate. Depending on the analysis method varying elution conditions were used.

The eluate from the column was passed through a flow splitting T-connector, which passed approximately 20 μL/min through approx. 1 m. 75μ fused silica capillary to the API interface of API 100 spectrometer.

The remaining 1.48 mL/min was passed through the UV detector and to the ELS detector.

During the LC-analysis the detection data were acquired concurrently from the mass spectrometer, the UV detector and the ELS detector.

The LC conditions, detector settings and mass spectrometer settings used for the different methods are given in the following table.

| Column | YMC ODS-A 120 Å s - 5μ 3 mm × 50 mm id | | |
|---|---|---|---|
| Gradient | 5%-90% acetonitrile in 0.05% TFA linearly during 7.5 min at 1.5 mL/min | | |
| Detection | UV: 214 nm | ELS: 40° C. | |
| MS | Experiment: Start: 100 amu | Stop: 800 amu | Step: 0.2 amu |
|  | Dwell: 0.571 msec | | |
|  | Method: Scan 284 times = 9.5 min | | |

HPLC-MS (Method C)

The Following Instrumentation is Used:
Hewlett Packard series 1100 G1312A Bin Pump
Hewlett Packard series 1100 Column compartment
Hewlett Packard series 1100 G1315A DAD diode array detector
Hewlett Packard series 1100 MSD
Sedere 75 Evaporative Light Scattering detector
The instrument is controlled by HP Chemstation software.
The HPLC pump is connected to two eluent reservoirs containing:

| A | 0.01% TFA in water |
|---|---|
| B | 0.01% TFA in acetonitrile |

The analysis is performed at 40° C. by injecting an appropriate volume of the sample (preferably 1 μl) onto the column which is eluted with a gradient of acetonitrile.

The HPLC conditions, detector settings and mass spectrometer settings used are given in the following table.

| Column | Waters Xterra MS C-18 × 3 mm id 5 μm |
|---|---|
| Gradient | 50%-100% acetonitrile linear during 7.5 min at 1.5 ml/min |
| Detection | 210 nm (analogue output from DAD) |
|  | ELS (analogue output from ELS) |
| MS | ionisation mode API-ES |
|  | Scan 100-1000 amu step 0.1 amu |

After the DAD the flow is divided yielding approximately 1 ml/min to the ELS and 0.5 ml/min to the MS.

HPLC-MS (Method D)

The following instrumentation was used:
Sciex API 150 Single Quadropole mass spectrometer
Hewlett Packard Series 1100 G1312A Bin pump
Gilson 215 micro injector
Hewlett Packard Series 1100 G1315A DAD diode array detector
Sedex 55 evaporative light scattering detector
A Valco column switch with a Valco actuator controlled by timed events from the pump.

The Sciex Sample control software running on a Macintosh Power G3 Computer was used for the instrument control and data acquisition.

The HPLC pump was connected to two eluent reservoirs containing:
A: Acetonitrile containing 0.05% TFA
B: Water containing 0.05% TFA The requirements for the samples are that they contain approximately 500 μg/ml of the compound to be analysed in an acceptable solvent such as methanol, ethanol, acetonitrile, THF, water and mixtures thereof. (High concentrations of strongly eluting solvents will interfere with the chromatography at low acetonitrile concentrations.)

The analysis was performed at room temperature by injecting 20 μl of the sample solution on the column, which was eluted with a gradient of acetonitrile in 0.05% TFA The eluate from the column was passed through a flow splitting T-connector, which passed approximately 20 μl/min through approx. 1 m 75μ fused silica capillary to the API interface of API 150 spectrometer.

The remaining 1.48 ml/min was passed through the UV detector and to the ELS detector. During the LC-analysis the detection data were acquired concurrently from the mass spectrometer, the UV detector and the ELS detector.

The LC conditions, detector settings and mass spectrometer settings used for the different methods are given in the following table.

| Column | Waters X-terra C18 5μ 3 mm × 50 mm id | | |
|---|---|---|---|
| Gradient | 5%-90% acetonitrile in 0.05% TFA linearly during 7.5 min at 1.5 ml/min | | |
| Detection | UV: 214 nm | ELS: 40° C. | |
| MS | Experiment: Start: 100 amu | Stop: 800 amu | Step: 0.2 amu |
| | Dwell: 0.571 msec | | |
| | Method: Scan 284 times = 9.5 min | | |

EXAMPLES

Example 1

1H-Benzotriazole

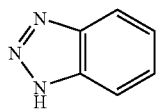

Example 2

5,6-Dimethyl-1H-benzotriazole

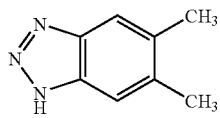

Example 3

1H-Benzotriazole-5-carboxylic acid

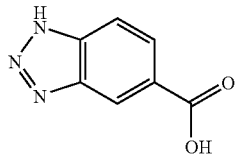

Example 4

4-Nitro-1H-benzotriazole

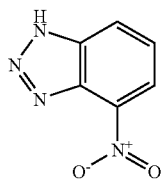

Example 5

5-Amino-1H-benzotriazole

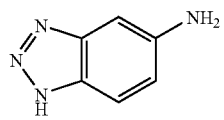

Example 6

5-Chloro-1H-benzotriazole

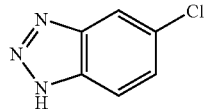

Example 7

5-Nitro-1H-benzotriazole

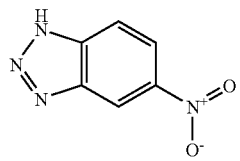

Example 8

4-[(1H-Benzotriazole-5-carbonyl)amino]benzoic acid

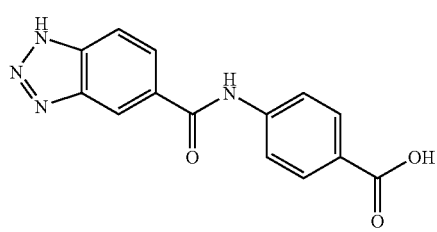

4-[(1H-Benzotriazole-5-carbonyl)amino]benzoic acid methyl ester (5.2 g, 17.6 mmol) was dissolved in THF (60 mL) and methanol (10 mL) was added followed by 1N sodium hydroxide (35 mL). The mixture was stirred at room temperature for 16 hours and then 1N hydrochloric acid (45 mL) was added. The mixture was added water (200 mL) and extracted with ethyl acetate (2×500 mL). The combined organic phases were evaporated in vacuo to afford 0.44 g of 4-[(1H-benzotriazole-5-carbonyl)amino]benzoic acid. By filtration of the aqueous phase a further crop of 4-[(1H-benzotriazole-5-carbonyl)amino]benzoic acid was isolated (0.52 g).

$^1$H-NMR (DMSO-$d_6$): δ 7.97 (4H, s), 8.03 (2H, m), 8.66 (1H, bs), 10.7 (1H, s), 12.6 (1H, bs); HPLC-MS (Method A): m/z: 283 (M+1); Rt=1.85 min.

General Procedure (A) for Preparation of Compounds of General Formula I₁:

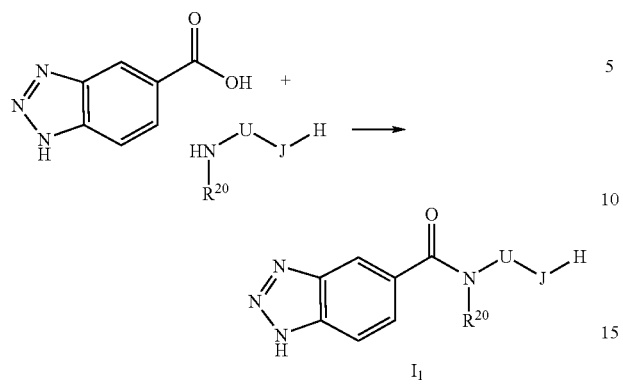

wherein U, J and $R^{20}$ are as defined above, and J is optionally containing up to three substituents, $R^{22}$, $R^{23}$ and $R^{24}$ as defined above.

The carboxylic acid of 1H-benzotriazole-5-carboxylic acid is activated, ie the OH functionality is converted into a leaving group L (selected from eg fluorine, chlorine, bromine, iodine, 1-imidazolyl, 1,2,4-triazolyl, 1-benzotriazolyloxy, 1-(4-aza benzotriazolyl)oxy, pentafluorophenoxy, N-succinyloxy 3,4-dihydro-4-oxo-3-(1,2,3-benzotriazinyl)oxy, benzotriazole 5-COO, or any other leaving group known to act as a leaving group in acylation reactions. The activated benzotriazole-5-carboxylic acid is then reacted with $R^2$—$(CH_2)_n$—B' in the presence of a base. The base can be either absent (i.e. $R^2$—$(CH_2)_n$—B' acts as a base) or triethylamine, N-ethyl-N,N-diisopropylamine, N-methylmorpholine, 2,6-lutidine, 2,2,6,6-tetramethylpiperidine, potassium carbonate, sodium carbonate, caesium carbonate or any other base known to be useful in acylation reactions. The reaction is performed in a solvent such as THF, dioxane, toluene, dichloromethane, DMF, NMP or a mixture of two or more of these. The reaction is performed between 0° C. and 80° C., preferably between 20° C. and 40° C. When the acylation is complete, the product is isolated by extraction, filtration, chromatography or other methods known to those skilled in the art.

The general procedure (A) is further illustrated in the following example:

Example 9

General Procedure (A)

1H-Benzotriazole-5-carboxylic acid phenylamide

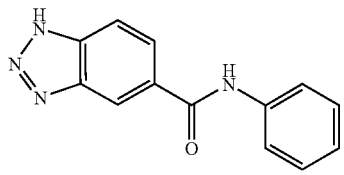

Benzotriazole-5-carboxylic acid (856 mg), HOAt (715 mg) and EDAC (1.00 g) were dissolved in DMF (17.5 mL) and the mixture was stirred at room temperature 1 hour. A 0.5 mL aliquot of this mixture was added to aniline (13.7 μL, 0.15 mmol) and the resulting mixture was vigorously shaken at room temperature for 16 hours. 1N hydrochloric acid (2 mL) and ethyl acetate (1 mL) were added and the mixture was vigorously shaken at room temperature for 2 hours. The organic phase was isolated and concentrated in vacuo to afford the title compound.

HPLC-MS (Method B): m/z: 239 (M+1); Rt=3.93 min.

The compounds in the following examples were similarly made. Optionally, the compounds may be isolated by filtration or by chromatography.

Example 10

General Procedure (A)

1H-Benzotriazole-5-carboxylic acid (4-methoxyphenyl)amide

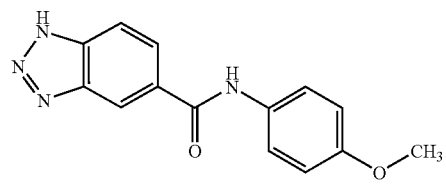

HPLC-MS (Method A): m/z: 269 (M+1) & 291 (M+23); Rt=2.41 min

HPLC-MS (Method B): m/z: 239 (M+1); Rt=3.93 min.

Example 11

General Procedure (A)

{4-[(1H-Benzotriazole-5-carbonyl)amino]phenyl}carbamic acid tert-butyl ester

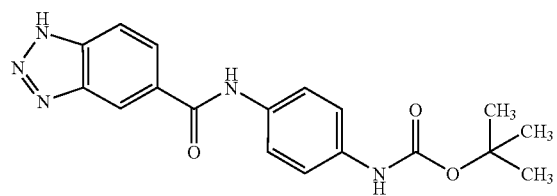

HPLC-MS (Method B): m/z: 354 (M+1); Rt=4.58 min.

Example 12

General Procedure (A)

1H-Benzotriazole-5-carboxylic acid (4-acetylaminophenyl)amide

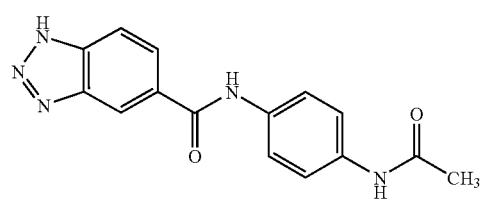

HPLC-MS (Method B): m/z: 296 (M+1); Rt=3.32 min.

Example 13

General Procedure (A)

1H-Benzotriazole-5-carboxylic acid (3-fluorophenyl)amide

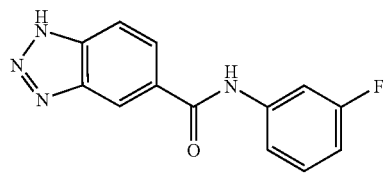

HPLC-MS (Method B): m/z: 257 (M+1); Rt=4.33 min.

Example 14

General Procedure (A)

1H-Benzotriazole-5-carboxylic acid (2-chlorophenyl)amide

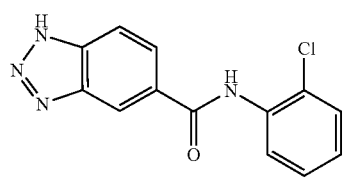

HPLC-MS (Method B): m/z: 273 (M+1); Rt=4.18 min.

Example 15

General Procedure (A)

4-[(1H-Benzotriazole-5-carbonyl)amino]benzoic acid methyl ester

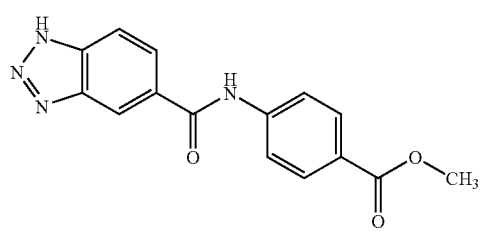

HPLC-MS (Method A): m/z: 297 (M+1); Rt: 2.60 min.
HPLC-MS (Method B): m/z: 297 (M+1); Rt=4.30 min.

Example 16

General Procedure (A)

1H-Benzotriazole-5-carboxylic acid (4-butylphenyl)amide

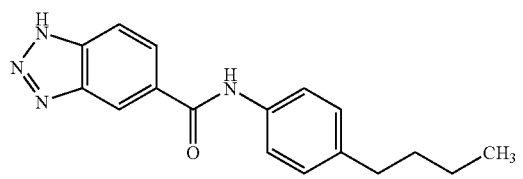

HPLC-MS (Method B): m/z: 295 (M+1); Rt=5.80 min.

Example 17

General Procedure (A)

1H-Benzotriazole-5-carboxylic acid (1-phenylethyl)amide

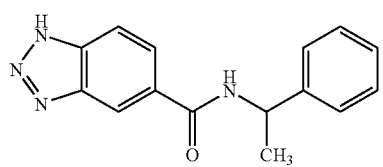

HPLC-MS (Method B): m/z: 267 (M+1); Rt=4.08 min.

Example 18

General Procedure (A)

1H-Benzotriazole-5-carboxylic acid benzylamide

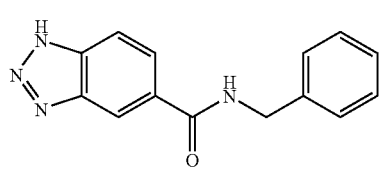

HPLC-MS (Method B): m/z: 253 (M+1); Rt=3.88 min.

Example 19

General Procedure (A)

1H-Benzotriazole-5-carboxylic acid 4-chlorobenzylamide

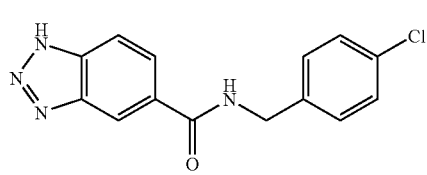

HPLC-MS (Method B): m/z: 287 (M+1); Rt=4.40 min.

Example 20

General Procedure (A)

1H-Benzotriazole-5-carboxylic acid 2-chlorobenzylamide

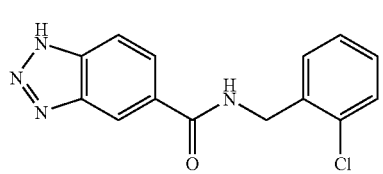

HPLC-MS (Method B): m/z: 287 (M+1); Rt=4.25 min.

Example 21

General Procedure (A)

1H-Benzotriazole-5-carboxylic acid 4-methoxybenzylamide

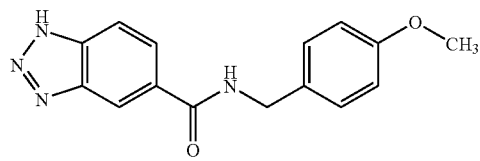

HPLC-MS (Method B): m/z: 283 (M+1); Rt=3.93 min.

Example 22

General Procedure (A)

1H-Benzotriazole-5-carboxylic acid 3-methoxybenzylamide

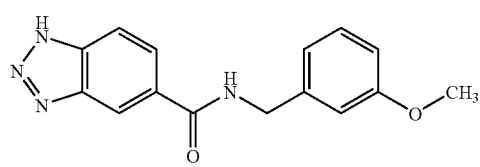

HPLC-MS (Method B): m/z: 283 (M+1); Rt=3.97 min.

Example 23

General Procedure (A)

1H-Benzotriazole-5-carboxylic acid (1,2-diphenylethyl)amide

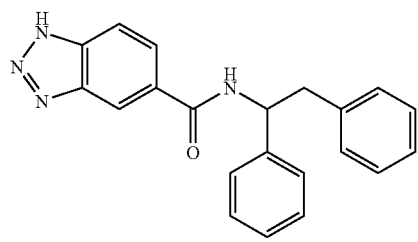

HPLC-MS (Method B): m/z: 343 (M+1); Rt=5.05 min.

Example 24

General Procedure (A)

1H-Benzotriazole-5-carboxylic acid 3-bromobenzylamide

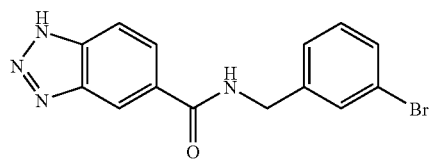

HPLC-MS (Method B): m/z: 331 (M+1); Rt=4.45 min.

Example 25

General Procedure (A)

4-{[(1H-Benzotriazole-5-carbonyl)amino]methyl}benzoic acid

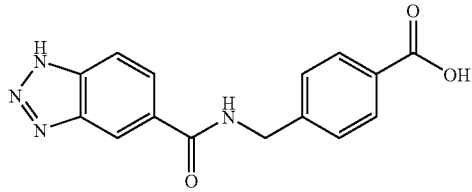

HPLC-MS (Method B): m/z: 297 (M+1); Rt=3.35 min.

Example 26

General Procedure (A)

1H-Benzotriazole-5-carboxylic acid phenethylamide

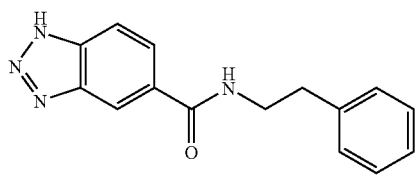

HPLC-MS (Method B): m/z: 267 (M+1); Rt=4.08 min.

Example 27

General Procedure (A)

1H-Benzotriazole-5-carboxylic acid [2-(4-chlorophenyl)ethyl]amide

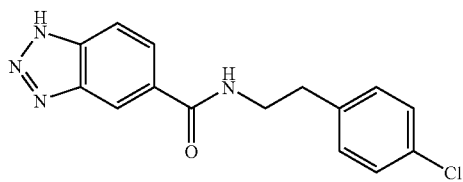

HPLC-MS (Method B): m/z: 301 (M+1); Rt=4.50 min.

Example 28

General Procedure (A)

1H-Benzotriazole-5-carboxylic acid [2-(4-methoxyphenyl)ethyl]amide

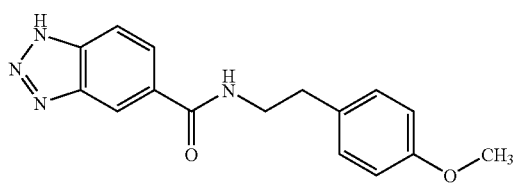

HPLC-MS (Method B): m/z: 297 (M+1); Rt=4.15 min.

Example 29

General Procedure (A)

1H-Benzotriazole-5-carboxylic acid
[2-(3-methoxyphenyl)ethyl]amide

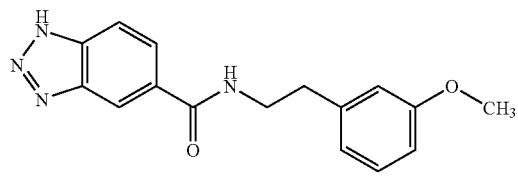

HPLC-MS (Method B): m/z: 297 (M+1); Rt=4.13 min.

Example 30

General Procedure (A)

1H-Benzotriazole-5-carboxylic acid
[2-(3-chlorophenyl)ethyl]amide

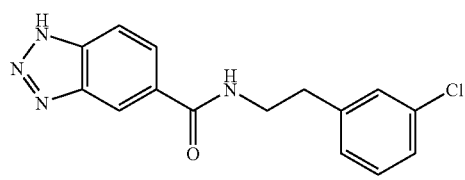

HPLC-MS (Method B): m/z: 301 (M+1); Rt=4.55 min.

Example 31

General Procedure (A)

1H-Benzotriazole-5-carboxylic acid
(2,2-diphenylethyl)amide

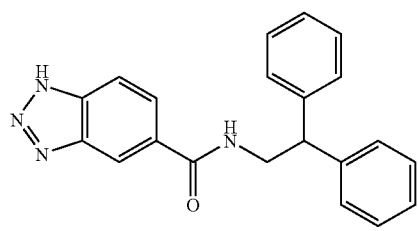

HPLC-MS (Method B): m/z: 343 (M+1); Rt=5.00 min.

Example 32

General Procedure (A)

1H-Benzotriazole-5-carboxylic acid
(3,4-dichlorophenyl)methylamide

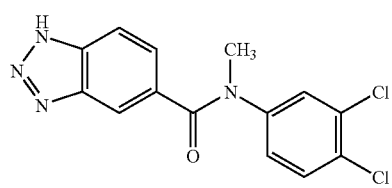

HPLC-MS (Method B): m/z: 321 (M+1); Rt=4.67 min.

Example 33

General Procedure (A)

1H-Benzotriazole-5-carboxylic acid
methylphenylamide

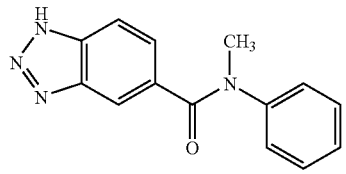

HPLC-MS (Method B): m/z: 253 (M+1); Rt=3.82 min.

Example 34

General Procedure (A)

1H-Benzotriazole-5-carboxylic acid
benzylmethylamide

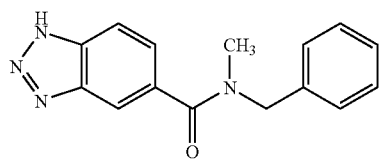

HPLC-MS (Method B): m/z: 267 (M+1); Rt=4.05 min.

Example 35

General Procedure (A)

1H-Benzotriazole-5-carboxylic acid
[2-(3-chloro-4-methoxyphenyl)ethyl]methyl-amide

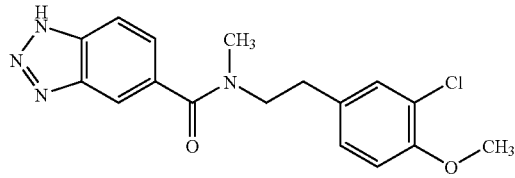

HPLC-MS (Method B): m/z: 345 (M+1); Rt=4.37 min.

Example 36

General Procedure (A)

1H-Benzotriazole-5-carboxylic acid
methylphenethylamide

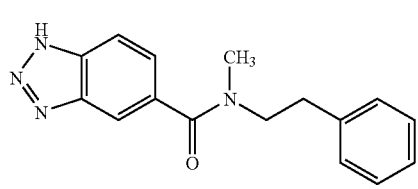

HPLC-MS (Method B): m/z 281 (M+1); Rt=4.15 min.

Example 37

General Procedure (A)

1H-Benzotriazole-5-carboxylic acid
[2-(3,4-dimethoxyphenyl)ethyl]methylamide

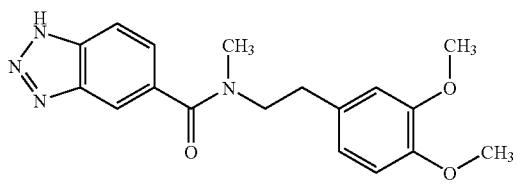

HPLC-MS (Method B): m/z: 341 (M+1); Rt=3.78 min;

Example 38

General Procedure (A)

1H-Benzotriazole-5-carboxylic acid
(2-hydroxy-2-phenylethyl)methylamide

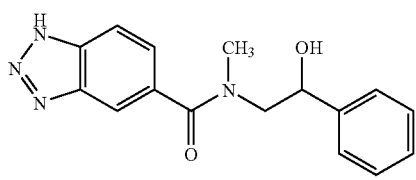

HPLC-MS (Method B): m/z: 297 (M+1); Rt=3.48 min.

Example 39

General Procedure (A)

1H-Benzotriazole-5-carboxylic acid
(3-bromophenyl)amide

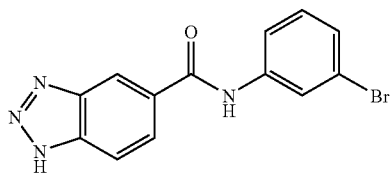

HPLC-MS (Method A): m/z: 317 (M+1); Rt=3.19 min.

Example 40

General Procedure (A)

1H-Benzotriazole-5-carboxylic acid
(4-bromophenyl)amide

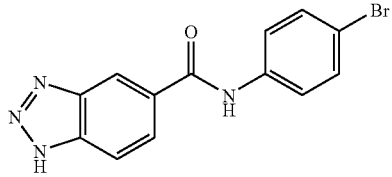

HPLC-MS (Method A): m/z: 317 (M+1); Rt=3.18 min.

Example 41

General Procedure (A)

{4-[(1H-Benzotriazole-5-carbonyl)amino]
benzoylamino}acetic acid

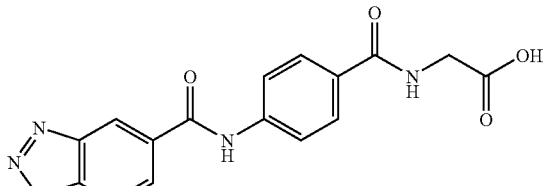

HPLC-MS (Method A): m/z: 340 (M+1); Rt=1.71 min.

Example 42

General Procedure (A)

{4-[(1H-Benzotriazole-5-carbonyl)amino]
phenyl}acetic acid

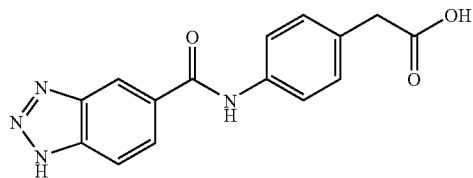

HPLC-MS (Method A): m/z: 297 (M+1); Rt=2.02 min.

Example 43

General Procedure (A)

3-{4-[(1H-Benzotriazole-5-carbonyl)amino]
phenyl}acrylic acid

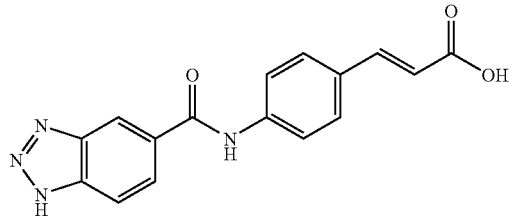

HPLC-MS (Method A): m/z: 309 (M+1); Rt=3.19 min.

Example 44

General Procedure (A)

{3-[(1H-Benzotriazole-5-carbonyl)amino]
phenyl}acetic acid

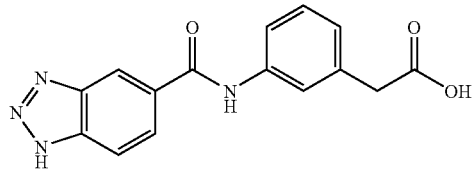

HPLC-MS (Method A): m/z: 297 (M+1); Rt=2.10 min.

Example 45

General Procedure (A)

2-{4-[(1H-Benzotriazole-5-carbonyl)amino]phenoxy}-2-methylpropionic acid

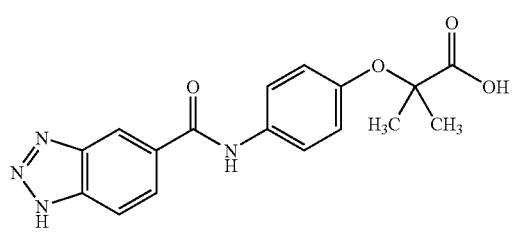

HPLC-MS (Method A): m/z: 341 (M+1); Rt=2.42 min.

Example 46

General Procedure (A)

3-{4-[(1H-Benzotriazole-5-carbonyl)amino]benzoylamino}propionic acid

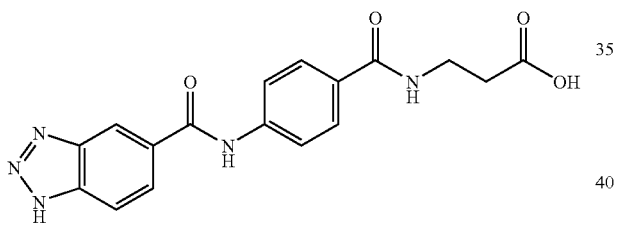

HPLC-MS (Method A): m/z: 354 (M+1); Rt=1.78 min.

Example 47

General Procedure (A)

3-{4-[(1H-Benzotriazole-5-carbonyl)amino]phenyl}propionic acid

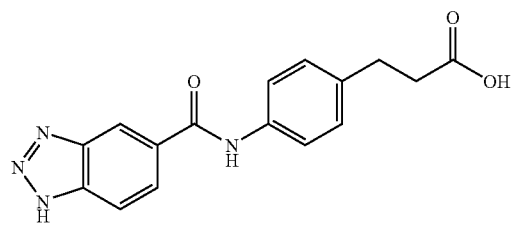

HPLC-MS (Method A): m/z: 311 (M+1); Rt=2.20 min.

Example 48

General Procedure (A)

1H-Benzotriazole-5-carboxylic acid (4-benzyloxyphenyl)amide

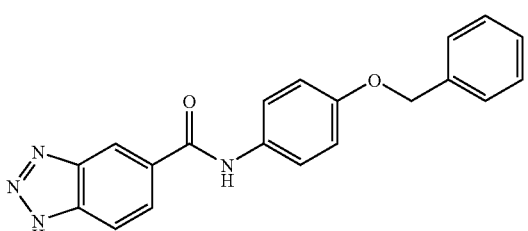

HPLC-MS (Method A): m/z: 345 (M+1); Rt=3.60 min.

Example 49

General Procedure (A)

1H-Benzotriazole-5-carboxylic acid (3-chloro-4-methoxyphenyl)amide

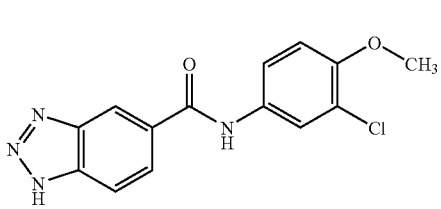

HPLC-MS (Method A): m/z: 303 (M+1); Rt=2.88 min.

Example 50

General Procedure (A)

1H-Benzotriazole-5-carboxylic acid (4-phenoxyphenyl)amide

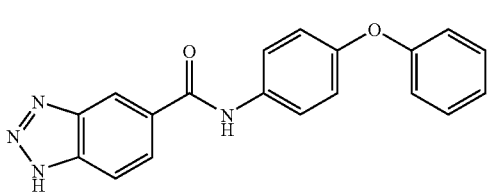

HPLC-MS (Method A): m/z: 331 (M+1); Rt=3.62 min.

Example 51

General Procedure (A)

1H-Benzotriazole-5-carboxylic acid (4-butoxyphenyl)amide

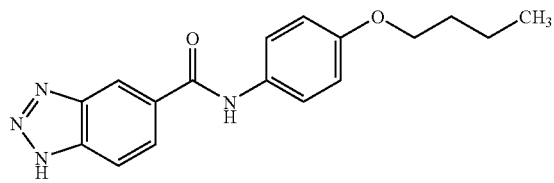

HPLC-MS (Method A): m/z: 311 (M+1); Rt=3.59 min.

Example 52

General Procedure (A)

1H-Benzotriazole-5-carboxylic acid (3-bromo-4-trifluoromethoxyphenyl)amide

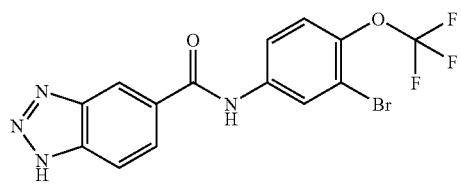

HPLC-MS (Method A): m/z: 402 (M+1); Rt=3.93 min.

Example 53

General Procedure (A)

1H-Benzotriazole-5-carboxylic acid (3,5-dichloro-4-hydroxyphenyl)amide

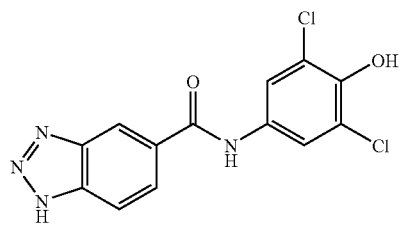

HPLC-MS (Method A): m/z: 323 (M+1); Rt=2.57 min.

Example 54

General Procedure (A)

4-{[(1H-Benzotriazole-5-carbonyl)amino]methyl}benzoic acid

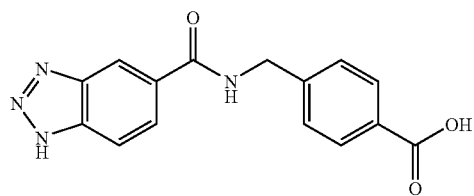

HPLC-MS (Method A): m/z: 297 (M+1); Rt=1.86 min.

Example 55

General Procedure (A)

{4-[(1H-Benzotriazole-5-carbonyl)amino]phenylsulfanyl}acetic acid

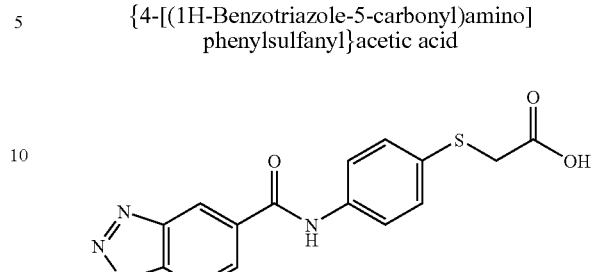

HPLC-MS (Method A): m/z: 329 (M+1); Rt=2.34 min.

Example 56

N-(1H-Benzotriazol-5-yl)acetamide

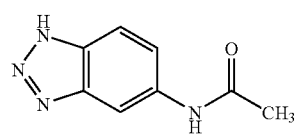

HPLC-MS (Method A): m/z: 177 (M+1); Rt=0.84 min.

Example 57

General Procedure (A)

1H-Benzotriazole-5-carboxylic acid 4-nitrobenzylamide

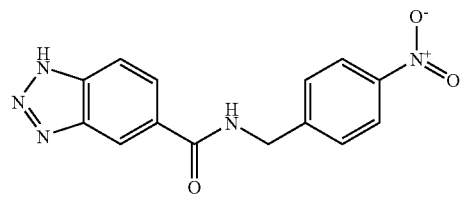

General Procedure (B) for Preparation of Compounds of General Formula $I_2$:

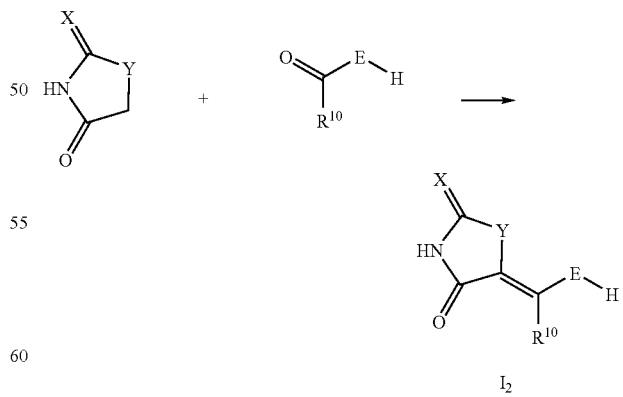

wherein X, Y, E and $R^{10}$ are as defined above and E is optionally containing up to four optional substituents, $R^{13}$, $R^{14}$, $R^{15}$, and $R^{15A}$ as defined above.

The chemistry is well known (eg Lohray et al., *J. Med. Chem.*, 1999, 42, 2569-81) and is generally performed by reacting a carbonyl compound (aldehyde or ketone) with the heterocyclic ring (eg thiazolidine-2,4-dione (X=O; Y=S), rhodanine (X=Y=S) and hydantoin (X=O; Y=NH) in the presence of a base, such as sodium acetate, potassium acetate, ammonium acetate, piperidinium benzoate or an amine (eg piperidine, triethylamine and the like) in a solvent (eg acetic acid, ethanol, methanol, DMSO, DMF, NMP, toluene, benzene) or in a mixture of two or more of these solvents. The reaction is performed at room temperature or at elevated temperature, most often at or near the boiling point of the mixture. Optionally, azeotropic removal of the formed water can be done.

This general procedure (B) is further illustrated in the following example:

Example 58

General Procedure (B)

5-(3-Phenoxybenzylidene)thiazolidine-2,4-dione

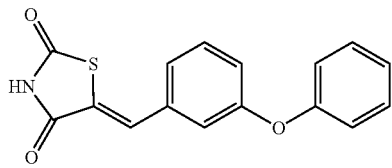

A solution of thiazolidine-2,4-dione (90%, 78 mg, 0.6 mmol) and ammonium acetate (92 mg, 1.2 mmol) in acetic acid (1 mL) was added to 3-phenoxybenzaldehyde (52 µL, 0.6 mmol) and the resulting mixture was shaken at 115° C. for 16 hours. After cooling, the mixture was concentrated in vacuo to afford the title compound.

HPLC-MS (Method A): m/z: 298 (M+1); Rt=4.54 min.

The compounds in the following examples were similarly prepared. Optionally, the compounds can be further purified by filtration and washing with water, ethanol and/or heptane instead of concentration in vacuo. Also optionally the compounds can be purified by washing with ethanol, water and/or heptane, or by chromatography, such as preparative HPLC.

Example 59

General Procedure (B)

5-(4-Dimethylaminobenzylidene)thiazolidine-2,4-dione

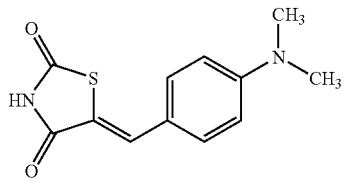

HPLC-MS (Method C): m/z: 249 (M+1); Rt=4.90 min

Example 60

General Procedure (B)

5-Naphthalen-1-ylmethylenethiazolidine-2,4-dione

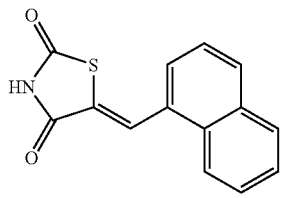

HPLC-MS (Method A): m/z: 256 (M+1); Rt=4.16 min.

Example 61

General Procedure (B)

5-Benzylidene-thiazolidine-2,4-dione

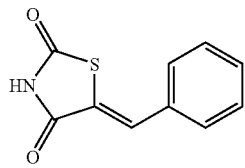

HPLC-MS (Method A): m/z: 206 (M+1); Rt=4.87 min.

Example 62

General Procedure (B)

5-(4-Methoxy-benzylidene)-thiazolidine-2,4-dione

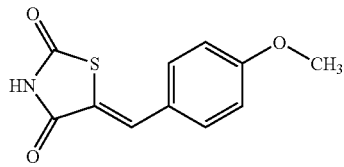

HPLC-MS (Method A): m/z: 263 (M+1); Rt=4.90 min.

Example 63

General Procedure (B)

5-(4-Chloro-benzylidene)-thiazolidine-2,4-dione

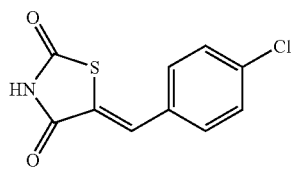

HPLC-MS (Method A): m/z: 240 (M+1); Rt=5.53 min.

Example 64

General Procedure (B)

5-(4-Nitro-benzylidene)-thiazolidine-2,4-dione

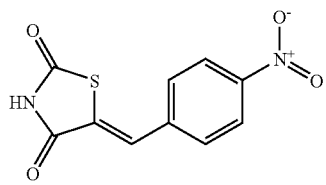

HPLC-MS (Method A): m/z: 251 (M+1); Rt=4.87 min.

Example 65

General Procedure (B)

5-(4-Hydroxy-3-methoxy-benzylidene)thiazolidine-2,4-dione

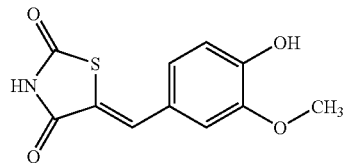

HPLC-MS (Method A): m/z: 252 (M+1); Rt=4.07 min.

Example 66

General Procedure (B)

5-(4-Methylsulfanyl-benzylidene)-thiazolidine-2,4-dione

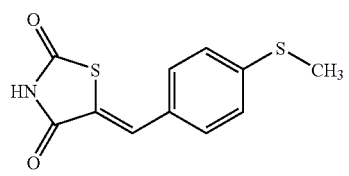

HPLC-MS (Method A): m/z: 252 (M+1); Rt=5.43 min.

Example 67

General Procedure (B)

5-(3-Fluoro-4-methoxy-benzylidene)-thiazolidine-2,4-dione

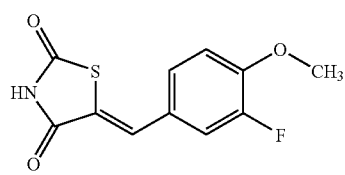

HPLC-MS (Method A): m/z: 354 (M+1); Rt=4.97 min.

Example 68

General Procedure (B)

5-(4-tert-Butylbenzylidene)thiazolidine-2,4-dione

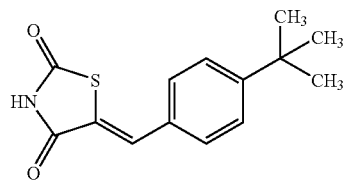

HPLC-MS (Method A): m/z: 262 (M+1); Rt=6.70 min.

Example 69

General Procedure (B)

N-[4-(2,4-Dioxothiazolidin-5-ylidenemethyl)phenyl]acetamide

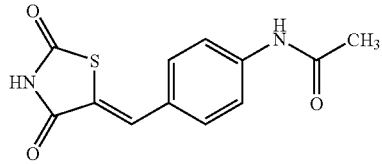

HPLC-MS (Method A): m/z: 263 (M+1); Rt=3.90 min.

Example 70

General Procedure (B)

5-Biphenyl-4-ylmethylene-thiazolidine-2,4-dione

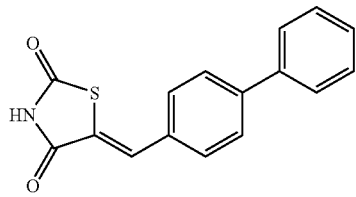

HPLC-MS (Method A): m/z: 282 (M+1); Rt=4.52 min.

Example 71

General Procedure (B)

5-(4-Phenoxy-benzylidene)-thiazolidine-2,4-dione

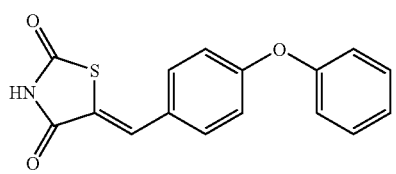

HPLC-MS (Method A): m/z: 298 (M+1); Rt=6.50 min.

Example 72

General Procedure (B)

5-(3-Benzyloxybenzylidene)thiazolidine-2,4-dione

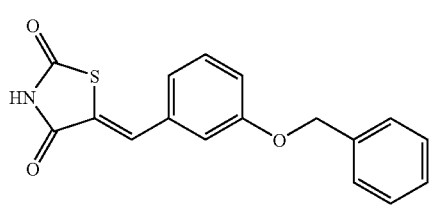

HPLC-MS (Method A): m/z: 312 (M+1); Rt=6.37 min.

Example 73

General Procedure (B)

5-(3-p-Tolyloxybenzylidene)thiazolidine-2,4-dione

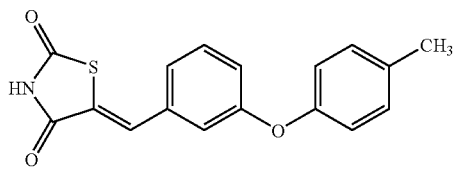

HPLC-MS (Method A): m/z: 312 (M+1); Rt=6.87 min.

Example 74

General Procedure (B)

5-Napthalen-2-ylmethylene-thiazolidine-2,4-dione

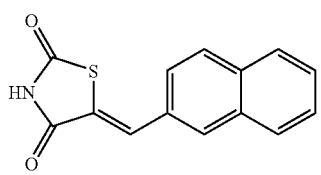

HPLC-MS (Method A): m/z: 256 (M+1); Rt=4.15 min.

Example 75

General Procedure (B)

5-Benzo[1,3]dioxol-5-ylmethylenethiazolidine-2,4-dione

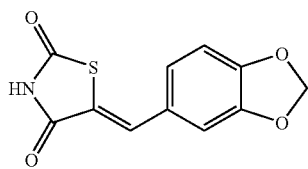

HPLC-MS (Method A): m/z: 250 (M+1), Rt=3.18 min.

Example 76

General Procedure (B)

5-(4-Chlorobenzylidene)-2-thioxothiazolidin-4-one

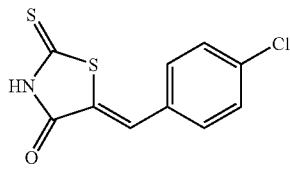

HPLC-MS (Method A): m/z: 256 (M+1); Rt=4.51 min.

Example 77

General Procedure (B)

5-(4-Dimethylaminobenzylidene)-2-thioxothiazolidin-4-one

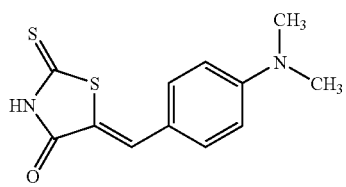

HPLC-MS (Method A): m/z: 265 (M+1); Rt=5.66 min.

Example 78

General Procedure (B)

5-(4-Nitrobenzylidene)-2-thioxothiazolidin-4-one

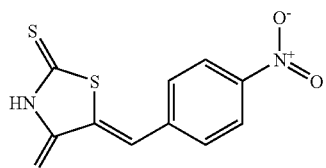

HPLC-MS (Method A): m/z: 267 (M+1); Rt=3.94 min.

Example 79

General Procedure (B)

5-(4-Methylsulfanylbenzylidene)-2-thioxothiazolidin-4-one

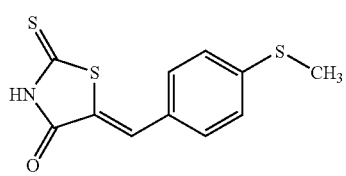

HPLC-MS (Method A): m/z: 268 (M+1); Rt=6.39 min.

Example 80

General Procedure (B)

5-(3-Fluoro-4-methoxybenzylidene)-2-thioxothiazolidin-4-one

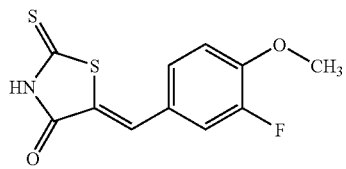

HPLC-MS (Method A): m/z: 270 (M+1); Rt=5.52 min.

Example 81

General Procedure (B)

5-Naphthalen-2-ylmethylene-2-thioxothiazolidin-4-one

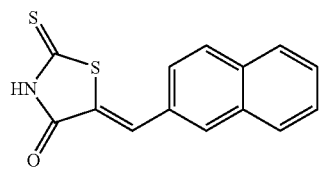

HPLC-MS (Method A): m/z: 272 (M+1); Rt=6.75 min.

Example 82

General Procedure (B)

5-(4-Diethylaminobenzylidene)-2-thioxothiazolidin-4-one

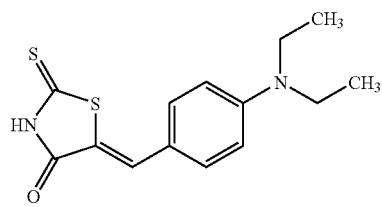

HPLC-MS (Method A): m/z: 293 (M+1); Rt=5.99 min.

Example 83

General Procedure (B)

5-Biphenyl-4-ylmethylene-2-thioxothiazolidin-4-one

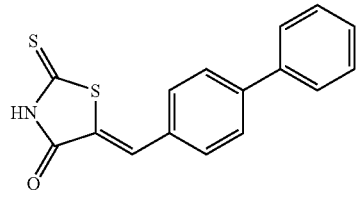

HPLC-MS (Method A): m/z: 298 (M+1); Rt=7.03 min.

Example 84

General Procedure (B)

5-(3-Phenoxybenzylidene)-2-thioxothiazolidin-4-one

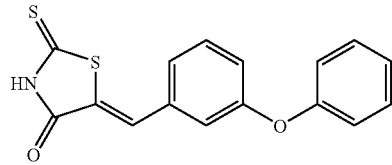

HPLC-MS (Method A): m/z: 314 (M+1); Rt=6.89 min.

Example 85

General Procedure (B)

5-(3-Benzyloxybenzylidene)-2-thioxothiazolidin-4-one

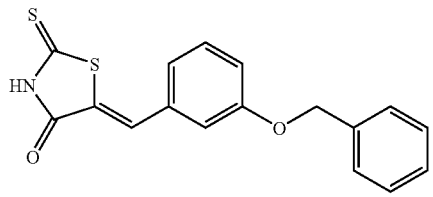

HPLC-MS (Method A): m/z: 328 (M+1); Rt=6.95 min.

Example 86

General Procedure (B)

5-(4-Benzyloxybenzylidene)-2-thioxothiazolidin-4-one

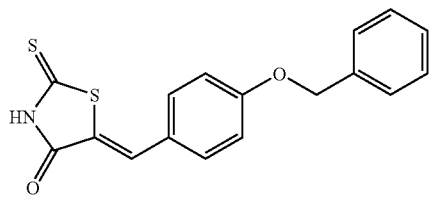

HPLC-MS (Method A): m/z: 328 (M+1); RT=6.89 min.

Example 87

General Procedure (B)

5-Naphthalen-1-ylmethylene-2-thioxothiazolidin-4-one

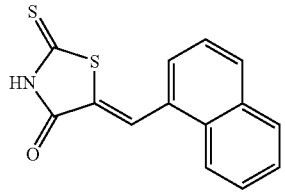

HPLC-MS (Method A): m/z: 272 (M+1); Rt=6.43 min.

Example 88

General Procedure (B)

5-(3-Methoxybenzyl)thiazolidine-2,4-dione

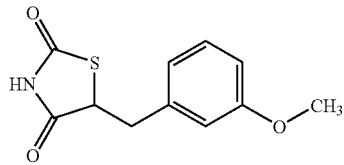

HPLC-MS (Method A): m/z: 236 (M+1); Rt=3.05 min.

Example 89

General Procedure (D)

4-[2-Chloro-4-(2,4-dioxothiazolidin-5-ylidenem-ethyl)phenoxy]butyric acid ethyl ester

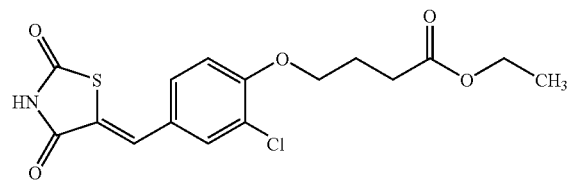

HPLC-MS (Method A): m/z: 392 (M+23), Rt=4.32 min.

Example 90

General Procedure (D)

4-[2-Bromo-4-(2,4-dioxothiazolidin-5-ylidenem-ethyl)-phenoxy]-butyric acid

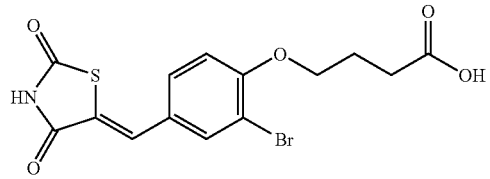

HPLC-MS (Method A): m/z: 410 (M+23); Rt=3.35 min.

Example 91

General Procedure (B)

5-(3-Bromobenzylidene)thiazolidine-2,4-dione

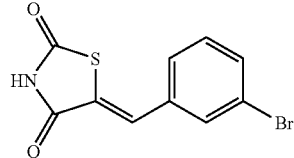

HPLC-MS (Method A): m/z: 285 (M+1); Rt=4.01 min.

Example 92

General Procedure (B)

5-(4-Bromobenzylidene)thiazolidine-2,4-dione

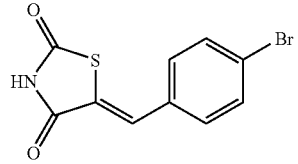

HPLC-MS (Method A): m/z: 285 (M+1); Rt=4.05 min.

Example 93

General Procedure (B)

5-(3-Chlorobenzylidene)thiazolidine-2,4-dione

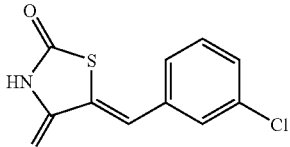

HPLC-MS (Method A): m/z: 240 (M+1); Rt=3.91 min.

Example 94

General Procedure (B)

5-Thiophen-2-ylmethylenethiazolidine-2,4-dione

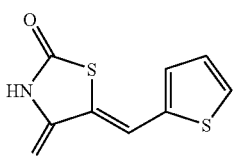

HPLC-MS (Method A): m/z: 212 (M+1); Rt=3.09 min.

Example 95

General Procedure (B)

5-(4-Bromothiophen-2-ylmethylene)thiazolidine-2,4-dione

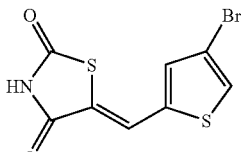

HPLC-MS (Method A): m/z: 291 (M+1); Rt=3.85 min.

Example 96

General Procedure (B)

5-(3,5-Dichlorobenzylidene)thiazolidine-2,4-dione

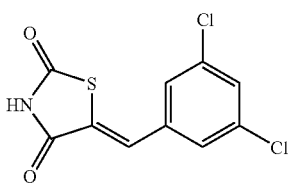

HPLC-MS (Method A): m/z: 274 (M+1); Rt=4.52 min.

Example 97

General Procedure (B)

5-(1-Methyl-1H-indol-3-ylmethylene)thiazolidine-2,4-dione

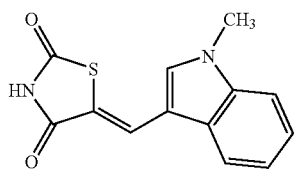

HPLC-MS (Method A): m/z: 259 (M+1); Rt=3.55 min.

Example 98

General Procedure (B)

5-(1H-Indol-3-ylmethylene)thiazolidine-2,4-dione

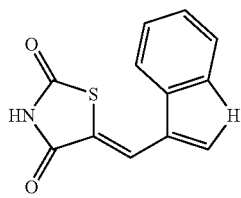

HPLC-MS (Method A): m/z: 245 (M+1); Rt=2.73 min.

Example 99

General Procedure (B)

5-Fluoren-9-ylidenethiazolidine-2,4-dione

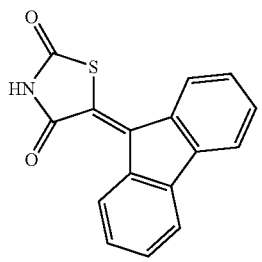

HPLC-MS (Method A): m/z: 280 (M+1); Rt=4.34 min.

Example 100

General Procedure (B)

5-(1-Phenylethylidene)thiazolidine-2,4-dione

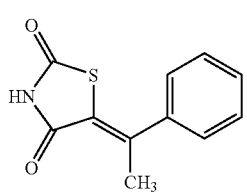

HPLC-MS (Method A): m/z: 220 (M+1); Rt=3.38 min.

Example 101

General Procedure (B)

5-[1-(4-Methoxyphenyl)-ethylidene]-thiazolidine-2,4-dione

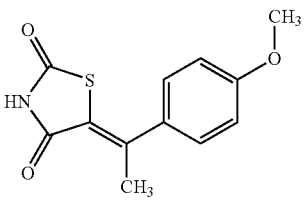

HPLC-MS (Method A): m/z: 250 (M+1); Rt=3.55 min.

Example 102

General Procedure (B)

5-(1-Naphthalen-2-yl-ethylidene)-thiazolidine-2,4-dione

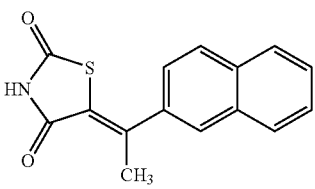

HPLC-MS (Method A): m/z: 270 (M+1); Rt=4.30 min.

Example 103

General Procedure (B)

5-[1-(4-Bromophenyl)-ethylidene]-thiazolidine-2,4-dione

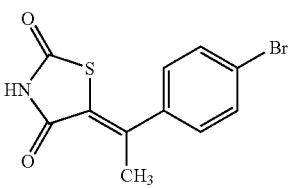

HPLC-MS (Method A): m/z: 300 (M+1); Rt=4.18 min.

Example 104

General Procedure (B)

5-(2,2-Diphenylethylidene)-thiazolidine-2,4-dione

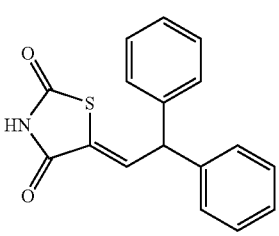

HPLC-MS (Method A): m/z: 296 (M+1); Rt=4.49 min.

Example 105

General Procedure (B)

5-[1-(3-Methoxyphenyl)-ethylidene]-thiazolidine-2,4-dione

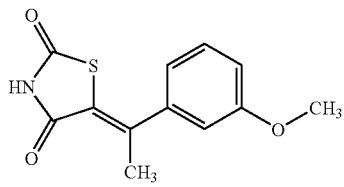

HPLC-MS (Method A): m/z: 250 (M+1); Rt=3.60 min.

Example 106

General Procedure (B)

5-[1-(6-Methoxynaphthalen-2-yl)-ethylidene]-thiazolidine-2,4-dione

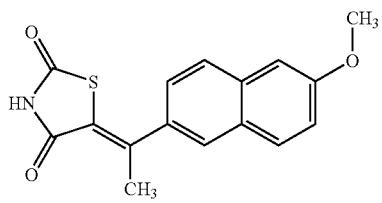

HPLC-MS (Method A): m/z: 300 (M+1); Rt=4.26 min.

Example 107

General Procedure (B)

5-[1-(4-Phenoxyphenyl)-ethylidene]-thiazolidine-2,4-dione

HPLC-MS (Method A): m/z: 312 (M+1); Rt=4.68 min.

Example 108

General Procedure (B)

5-[1-(3-Fluoro-4-methoxyphenyl)ethylidene]thiazolidine-2,4-dione

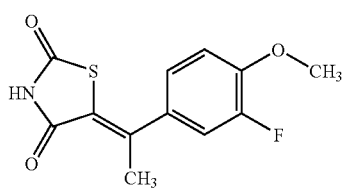

HPLC-MS (Method A): m/z: 268 (M+1); Rt=3.58 min.

Example 109

General Procedure (B)

5-[1-(3-Bromophenyl)-ethylidene]-thiazolidine-2,4-dione

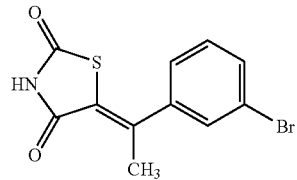

HPLC-MS (Method A): m/z: 300 (M+1); Rt=4.13 min.

Example 110

General Procedure (B)

5-Anthracen-9-ylmethylenethiazolidine-2,4-dione

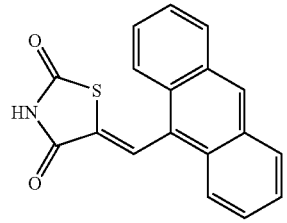

HPLC-MS (Method A): m/z: 306 (M+1); Rt=4.64 min.

Example 111

General Procedure (B)

5-(2-Methoxynaphthalen-1-ylmethylene)-thiazolidine-2,4-dione

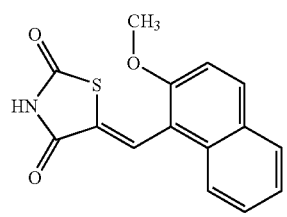

HPLC-MS (Method A): m/z: 286 (M+1); Rt=4.02 min.

Example 112

General Procedure (B)

5-(4-Methoxynaphthalen-1-ylmethylene)-thiazolidine-2,4-dione

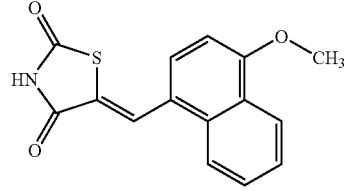

HPLC-MS (Method A): m/z: 286 (M+1); Rt=4.31 min.

Example 113

General Procedure (B)

5-(4-Dimethylaminonaphthalen-1-ylmethylene)-thiazolidine-2,4-dione

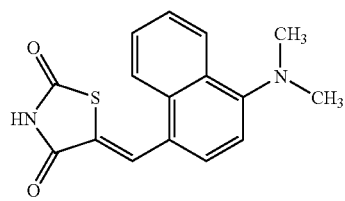

HPLC-MS (Method A): m/z: 299 (M+1); Rt=4.22 min.

Example 114

General Procedure (B)

5-(4-Methylnaphthalen-1-ylmethylene)-thiazolidine-2,4-dione

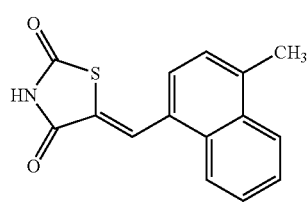

HPLC-MS (Method A): m/z: 270 (M+1); Rt=4.47 min.

Example 115

General Procedure (B)

5-Pyridin-2-ylmethylene-thiazolidine-2,4-dione

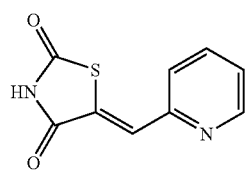

Example 116

5-Pyridin-2-ylmethyl-thiazolidine-2,4-dione

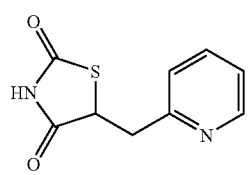

5-Pyridin-2-ylmethylene-thiazolidine-2,4-dione (5 g) in tetrahydrofuran (300 ml) was added 10% Pd/C (1 g) and the mixture was hydrogenated at ambient pressure for 16 hours. More 10% Pd/C (5 g) was added and the mixture was hydrogenated at 50 psi for 16 hours. After filtration and evaporation in vacuo, the residue was purified by column chromatography eluting with a mixture of ethyl acetate and heptane (1:1). This afforded the title compound (0.8 g, 16%) as a solid.

TLC: $R_f$=0.30 (SiO$_2$; EtOAc:heptane 1:1)

Example 117

General Procedure (B)

5-(1H-Imidazol-4-ylmethylene)-thiazolidine-2,4-dione

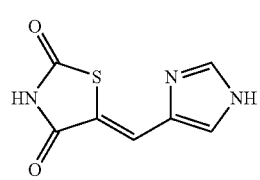

Example 118

General Procedure (B)

5-(4-Benzyloxy-benzylidene)-thiazolidine-2,4-dione

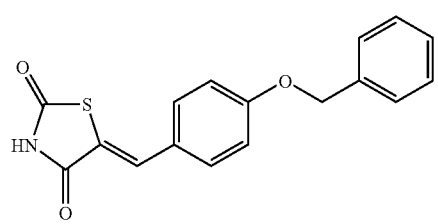

HPLC-MS (Method A): m/z: 6.43 min; 99% (2A)

Example 119

General Procedure (B)

5-[4-(4-Fluorobenzyloxy)benzylidene]-2-thioxothiazolidin-4-one

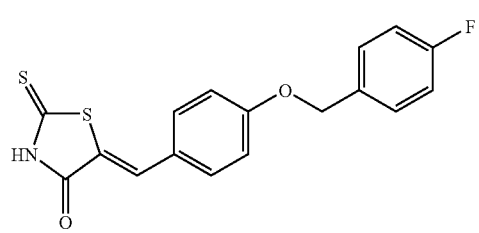

Example 120

General Procedure (B)

5-(4-Butoxybenzylidene)-2-thioxothiazolidin-4-one

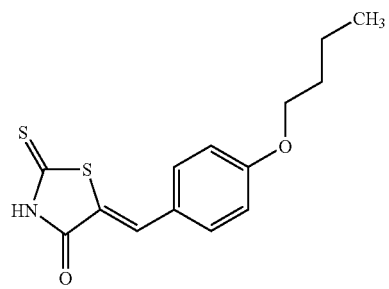

Example 121

General Procedure (B)

5-(3-Methoxybenzylidene)thiazolidine-2,4-dione

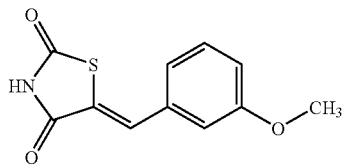

HPLC-MS (Method A): m/z: 236 (M+1); Rt=4.97 min

Example 122

General Procedure (B)

5-(3-Methoxybenzylidene)imidazolidine-2,4-dione

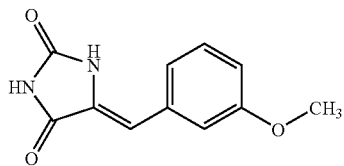

HPLC-MS (Method A): m/z: 219 (M+1); Rt=2.43 min.

Example 123

General Procedure (B)

5-(4-Methoxybenzylidene)imidazolidine-2,4-dione

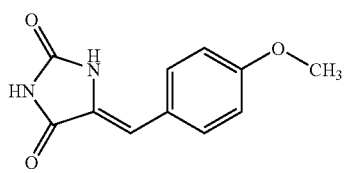

HPLC-MS (Method A): m/z: 219 (M+1); Rt=2.38 min.

Example 124

General Procedure (B)

5-(2,3-Dichlorobenzylidene)thiazolidine-2,4-dione

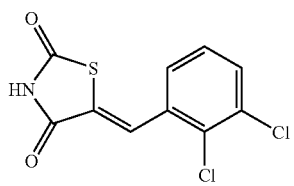

Example 125

General Procedure (B)

5-Benzofuran-7-ylmethylenethiazolidine-2,4-dione

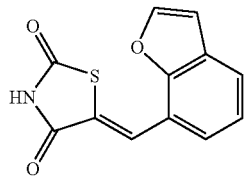

HPLC-MS (Method C): m/z: 247 (M+1); Rt=4.57 min.

Example 126

General Procedure (B)

5-Benzo[1,3]dioxol-4-ylmethylenethiazolidine-2,4-dione

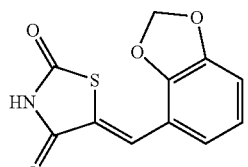

HPLC-MS (Method C): m/z: 250 (M+1); Rt=4.00 min.

Example 127

General Procedure (B)

5-(4-Methoxy-2,3-dimethylbenzylidene)thiazolidine-2,4-dione

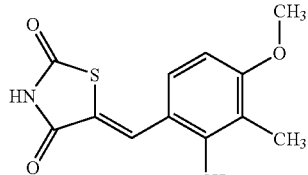

HPLC-MS (Method C): m/z: 264 (M+1); Rt=5.05 min.

Example 128

General Procedure (B)

5-(2-Benzyloxy-3-methoxybenzylidene)thiazolidine-2,4-dione

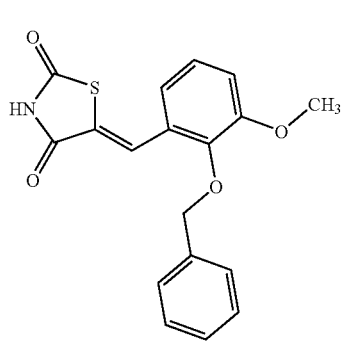

HPLC-MS (Method C): m/z: 342 (M+1); Rt=5.14 min.

Example 129

General Procedure (B)

5-(2-Hydroxybenzylidene)thiazolidine-2,4-dione

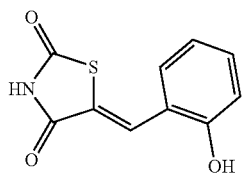

HPLC-MS (Method C): m/z: 222 (M+1); Rt=3.67 min.

Example 130

General Procedure (B)

5-(2,4-Dichlorobenzylidene)thiazolidine-2,4-dione

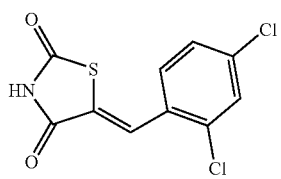

$^1$H-NMR (DMSO-$d_6$): 7.60 (2H, "s"), 7.78 (1H, s), 7.82 (1H, s).

Example 131

General Procedure (B)

5-(2-Chlorobenzylidene)thiazolidine-2,4-dione

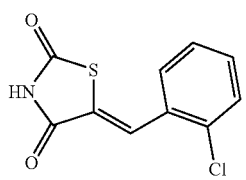

$^1$H-NMR (DMSO-$d_6$): 7.40 (1H, t), 7.46 (1H, t), 7.57 (1H, d), 7.62 (1H, d), 7.74 (1H, s).

Example 132

General Procedure (B)

5-(2-Bromobenzylidene)thiazolidine-2,4-dione

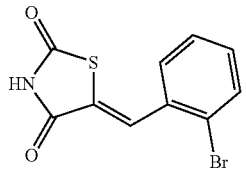

$^1$H-NMR (DMSO-$d_6$): 7.33 (1H, t), 7.52 (1H, t), 7.60 (1H, d), 7.71 (1H, s), 7.77 (1H, d).

Example 133

General Procedure (B)

5-(2,4-Dimethoxybenzylidene)thiazolidine-2,4-dione

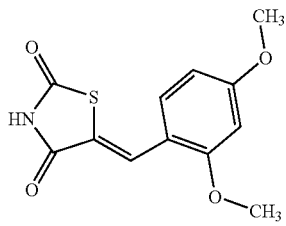

HPLC-MS (Method C): m/z: 266 (M+1) Rt=4.40 min.

Example 134

General Procedure (B)

5-(2-Methoxybenzylidene)thiazolidine-2,4-dione

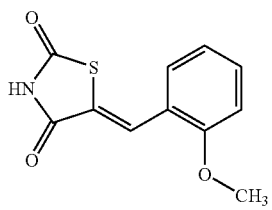

HPLC-MS (Method C): m/z: 236 (M+1); Rt=4.17 min.

Example 135

General Procedure (B)

5-(2,6-Difluorobenzylidene)thiazolidine-2,4-dione

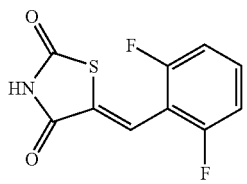

HPLC-MS (Method C): m/z: 242 (M+1); Rt=4.30 min.

Example 136

General Procedure (B)

5-(2,4-Dimethylbenzylidene)thiazolidine-2,4-dione

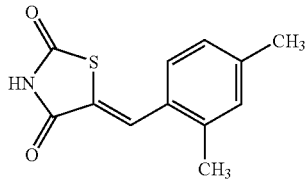

HPLC-MS (Method C): m/z: 234 (M+1); Rt=5.00 min.

Example 137

General Procedure (B)

5-(2,4,6-Trimethoxybenzylidene)thiazolidine-2,4-dione

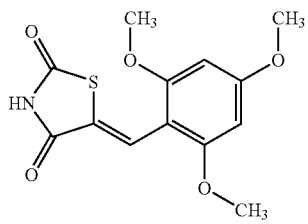

HPLC-MS (Method C): m/z: 296 (M+1); Rt=4.27 min.

Example 138

General Procedure (B)

5-(4-Hydroxy-2-methoxybenzylidene)thiazolidine-2,4-dione

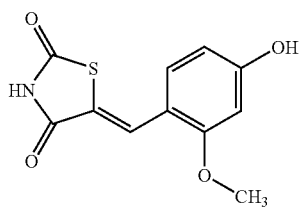

HPLC-MS (Method C): m/z: 252 (M+1); Rt=3.64 min.

Example 139

General Procedure (B)

5-(4-Hydroxynaphthalen-1-ylmethylene)thiazolidine-2,4-dione

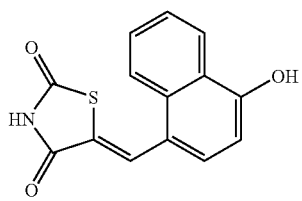

$^1$H-NMR (DMSO-$d_6$): δ=7.04 (1H, d), 7.57 (2H, m), 7.67 (1H, t), 8.11 (1H, d), 8.25 (1H, d), 8.39 (1H, s) 11.1 (1H, s), 12.5 (1H, bs). HPLC-MS (Method C): m/z: 272 (M+1); Rt=3.44 min.

Example 140

General Procedure (B)

5-(2-Trifluoromethoxybenzylidene)thiazolidine-2,4-dione

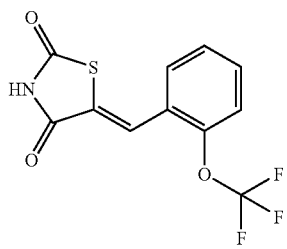

HPLC-MS (Method C): m/z: 290 (M+1); Rt=4.94 min.

Example 141

General Procedure (B)

5-Biphenyl-2-ylmethylenethiazolidine-2,4-dione

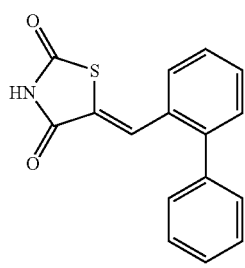

HPLC-MS (Method C): m/z: 282 (M+1); Rt=5.17 min.

Example 142

General Procedure (B)

5-(2-Benzyloxybenzylidene)thiazolidine-2,4-dione

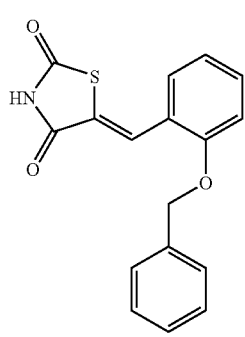

HPLC-MS (Method C): m/z: 312 (M+1); Rt=5.40 min.

Example 143

General Procedure (B)

5-Adamantan-2-ylidenethiazolidine-2,4-dione

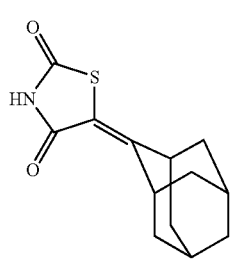

HPLC-MS (Method A): m/z: 250 (M+1); Rt=4.30 min.

General Procedure (C) for Preparation of Compounds of General Formula $I_2$:

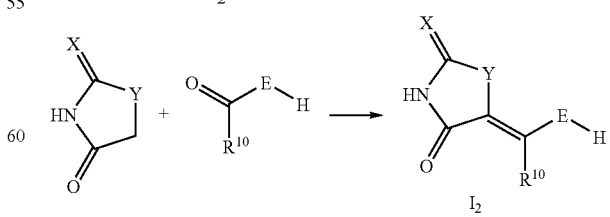

wherein X, Y, E, and $R^{10}$ are as defined above and E is optionally containing up to four optional substituents, $R^{13}$, $R^{14}$, $R^{15}$, and $R^{15A}$ as defined above.

This general procedure (C) is quite similar to general procedure (B) and is further illustrated in the following example:

Example 144

General Procedure (C)

5-(3,4-Dibromobenzylidene)thiazolidine-2,4-dione

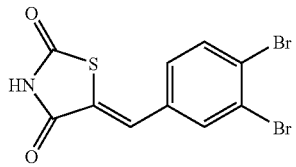

A mixture of thiazolidine-2,4-dione (90%, 65 mg, 0.5 mmol), 3,4-dibromobenzaldehyde (132 mg, 0.5 mmol), and piperidine (247 µL, 2.5 mmol) was shaken in acetic acid (2 mL) at 110° C. for 16 hours. After cooling, the mixture was concentrated to dryness in vacuo. The resulting crude product was shaken with water, centrifuged, and the supernatant was discarded. Subsequently the residue was shaken with ethanol, centrifuged, the supernatant was discarded and the residue was further evaporated to dryness to afford the title compound.

$^1$H NMR (Acetone-$d_6$): $\delta_H$ 7.99 (d, 1H), 7.90 (d, 1H), 7.70 (s, 1H), 7.54 (d, 1H); HPLC-MS (Method A): m/z: 364 (M+1); Rt=4.31 min.

The compounds in the following examples were similarly prepared. Optionally, the compounds can be further purified by filtration and washing with water instead of concentration in vacuo. Also optionally the compounds can be purified by washing with ethanol, water and/or heptane, or by preparative HPLC.

Example 145

General Procedure (C)

5-(4-Hydroxy-3-iodo-5-methoxybenzylidene)thiazolidine-2,4-dione

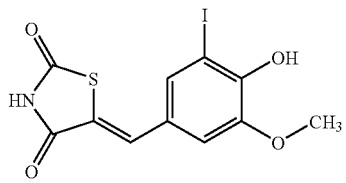

Mp=256° C.; $^1$H NMR (DMSO-$d_6$) δ=12.5 (s, broad, 1H), 10.5 (s, broad, 1H), 7.69 (s, 1H), 7.51 (d, 1H), 7.19 (d, 1H) 3.88 (s, 3H), $^{13}$C-NMR (DMSO-$d_6$) δ=168.0, 167.7, 149.0, 147.4, 133.0, 131.2, 126.7, 121.2, 113.5, 85.5, 56.5; HPLC-MS (Method A): m/z: 378 (M+1); Rt=3.21 min.

Example 146

General Procedure (C)

5-(4-Hydroxy-2,6-dimethylbenzylidene)thiazolidine-2,4-dione

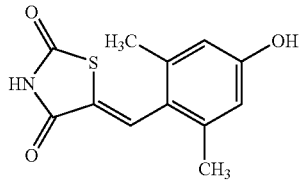

HPLC-MS (Method C): m/z 250 (M+1); Rt.=2.45 min.

Example 147

General Procedure (C)

4-[5-Bromo-6-(2,4-dioxothiazolidin-5-ylidenemethyl)-naphthalen-2-yloxymethyl]-benzoic acid

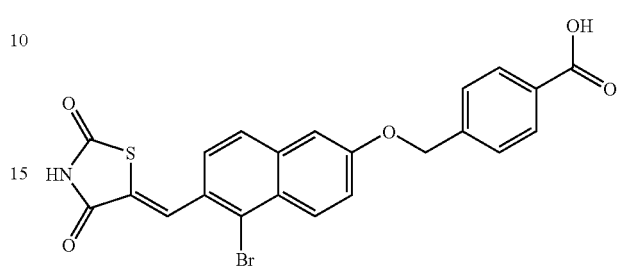

HPLC-MS (Method C): m/z: 506 (M+23); Rt.=4.27 min.

Example 148

General Procedure (C)

5-(4-Bromo-2,6-dichlorobenzylidene)thiazolidine-2,4-dione

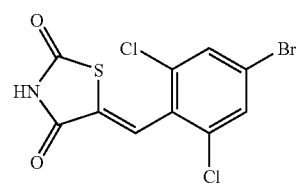

HPLC-MS (Method C): m/z: 354 (M+1); Rt.=4.36 min.

Example 149

General Procedure (C)

5-(6-Hydroxy-2-naphthylmethylene)thiazolidine-2,4-dione

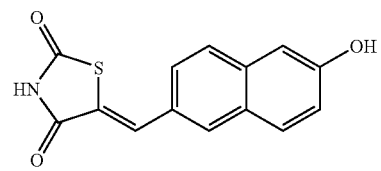

Mp 310-314° C., $^1$H NMR (DMSO-$d_6$): $\delta_H$=12.5 (s, broad, 1H), 8.06 (d, 1H), 7.90-7.78 (m, 2H), 7.86 (s, 1H), 7.58 (dd, 1H), 7.20 7.12 (m, 2H). $^{13}$C NMR (DMSO-$d_6$): $\delta_C$=166.2, 165.8, 155.4, 133.3, 130.1, 129.1, 128.6, 125.4, 125.3, 125.1, 124.3, 120.0, 117.8, 106.8; HPLC-MS (Method A): m/z: 272 (M+1); Rt=3.12 min.

Preparation of the Starting Material, 6-hydroxy-2-naphtalenecarbaldehyde

6-Cyano-2-naphthalenecarbaldehyde (1.0 g, 5.9 mmol) was dissolved in dry hexane (15 mL) under nitrogen. The solution was cooled to −60° C. and a solution of diisobutyl aluminium hydride (DIBAH) (15 mL, 1M in hexane) was added dropwise. After the addition, the solution was left at room temperature overnight. Saturated ammonium chloride solution (20 mL) was added and the mixture was stirred at room temperature for 20 min, subsequently aqueous $H_2SO_4$ (10% solution, 15 mL) was added followed by water until all salt was dissolved. The resulting solution was extracted with ethyl acetate (3×), the combined organic phases were dried with $MgSO_4$, evaporated to dryness to afford 0.89 g of 6-hydroxy-2-naphtalenecarbaldehyde.

Mp.: 153.5-156.5° C.; HPLC-MS (Method A): m/z: 173 (M+1); Rt=2.67 min; $^1$H NMR (DMSO-$d_6$): $\delta_H$=10.32 (s, 1H), 8.95 (d, 1H), 10.02 (s, 1H), 8.42 (s, broad, 1H), 8.01 (d, 1H), 7.82-7.78 (m, 2H), 7.23-7.18 (m, 2H).

Alternative Preparation of 6-hydroxy-2-naphtalenecarbaldehyde

To a stirred cooled mixture of 6-bromo-2-hydroxynaphthalene (25.3 g, 0.113 mol) in THF (600 mL) at −78° C. was added n-BuLi (2.5 M, 100 mL, 0.250 mol) dropwise. The mixture turned yellow and the temperature rose to −64° C. After ca 5 min a suspension appeared. After addition, the mixture was maintained at −78° C. After 20 minutes, a solution of DMF (28.9 mL, 0.373 mol) in THF (100 mL) was added over 20 minutes. After addition, the mixture was allowed to warm slowly to RT. After 1 hour, the mixture was poured in ice/water (200 mL). To the mixture citric acid was added to a pH of 5. The mixture was stirred for 0.5 hour. Ethyl acetate (200 mL) was added and the organic layer was separated and washed with brine (100 mL), dried over $Na_2SO_4$ and concentrated. To the residue was added heptane with 20% ethyl acetate (ca 50 mL) and the mixture was stirred for 1 hour. The mixture was filtered and the solid was washed with ethyl acetate and dried in vacuo to afford 16 g of the title compound.

Example 150

General Procedure (C)

5-(3-Iodo-4-methoxybenzylidene)thiazolidiene-2,4-dione

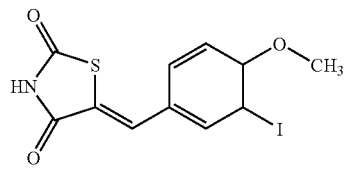

$^1$H NMR (DMSO-$d_6$): $\delta_H$ 12.55 (s, broad, 1H), 8.02 (d, 1H), 7.72 (s, 1H) 7.61 (d, 1H), 7.18 (d, 1H), 3.88 (s, 3H); $^{13}$C NMR (DMSO-$d_6$); $\delta_C$ 168.1, 167.7, 159.8, 141.5, 132.0, 130.8, 128.0, 122.1, 112.5, 87.5, 57.3. HPLC-MS (Method A): m/z: 362 (M+1); Rt=4.08 min.

Preparation of the Starting Material, 3-iodo-4-methoxybenzaldehyde

4-Methoxybenzaldehyde (0.5 g, 3.67 mmol) and silver trifluoroacetate (0.92 g, 4.19 mmol) were mixed in dichloromethane (25 mL). Iodine (1.19 g, 4.7 mmol) was added in small portions and the mixture was stirred overnight at room temperature under nitrogen. The mixture was subsequently filtered and the residue washed with DCM. The combined filtrates were treated with an aqueous sodium thiosulfate solution (1 M) until the colour disappeared. Subsequent extraction with dichloromethane (3×20 mL) followed by drying with $MgSO_4$ and evaporation in vacuo afforded 0.94 g of 3-iodo-4-methoxybenzaldehyde.

Mp 104-107° C.; HPLC-MS (Method A): m/z: 263 (M+1); Rt=3.56 min.; $^1$H NMR (CDCl$_3$): $\delta_H$=8.80 (s, 1H), 8.31 (d, 1H), 7.85 (dd, 1H) 6.92 (d, 1H), 3.99 (s, 3H).

Example 151

General Procedure (C)

5-(1-Bromonaphthalen-2-ylmethylene)thiazolidine-2,4-dione

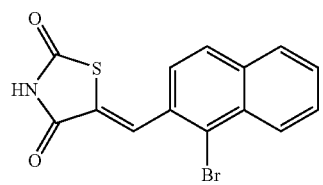

HPLC-MS (Method A): m/z:=336 (M+1); Rt=4.46 min.

Example 152

General Procedure (C)

1-[5-(2,4-Dioxothiazolidin-5-ylidenemethyl)thiazol-2-yl]piperidine-4-carboxylic acid ethyl ester

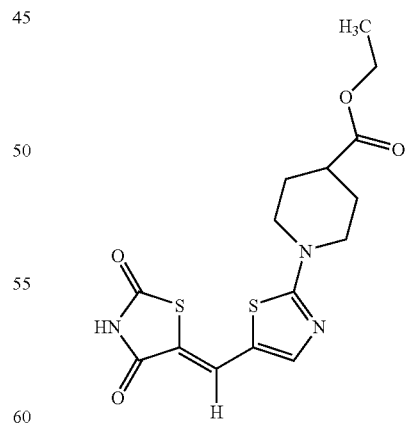

$^1$H NMR (DMSO-$d_6$): $\delta_H$=7.88 (s, 1H), 7.78 (s, 1H), 4.10 (q, 2H), 4.0-3.8 (m, 2H), 3.40-3.18 (m, 2H), 2.75-2.60 (m, 1H), 2.04-1.88 (m, 2H), 1.73-1.49 (m, 2H), 1.08 (t, 3H); HPLC-MS (Method A): m/z: 368 (M+1); Rt=3.41 min.

Example 153

General Procedure (C)

5-(2-Phenyl-[1,2,3]triazol-4-ylmethylene)thiazolidine-2,4-dione

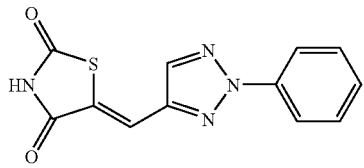

$^1$H NMR (DMSO-d$_6$): δ$_H$=12.6 (s, broad, 1H), 8.46 (s, 1H), 8.08 (dd, 2H), 7.82 (s, 1H), 7.70-7.45 (m, 3H). HPLC-MS (Method A): m/z: 273 (M+1); Rt=3.76 min.

Example 154

General Procedure (C)

5-(Quinolin-4-ylmethylene)thiazolidine-2,4-dione

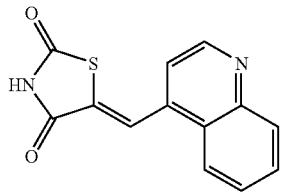

HPLC-MS (Method A): m/z: 257 (M+1); Rt=2.40 min.

Example 155

General Procedure (C)

5-(6-Methylpyridin-2-ylmethylene)thiazolidine-2,4-dione

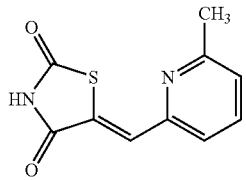

$^1$H NMR (DMSO-d$_6$): δ$_H$=12.35 (s, broad, 1H), 7.82 (t, 1H), 778 (s, 1H), 7.65 (d, 1H), 7.18 (d, 1H), 2.52 (s, 3H); HPLC-MS (Method A): m/z: 221 (M+1); Rt=3.03 min.

Example 156

General Procedure (C)

5-(2,4-dioxothiazolidin-5-ylidenemethyl)-furan-2-ylmethylacetate

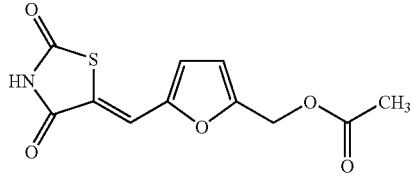

$^1$H NMR (DMSO-d$_6$): δ$_H$=12.46 (s, broad, 1H), 7.58 (s, 1H), 7.05 (d, 1H), 6.74 (s, 1H), 5.13 (s, 2H), 2.10 (s, 3H). HPLC-MS (Method A): m/z: 208 (M−CH$_3$COO); Rt=2.67 min.

Example 157

General Procedure (C)

5-(2,4-Dioxothiazolidin-5-ylidenemethyl)furan-2-sulfonic acid

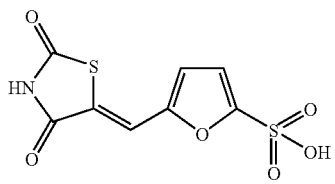

HPLC-MS (Method A): m/z: 276 (M+1); Rt=0.98 min.

Example 158

General Procedure (C)

5-(5-Benzyloxy-1H-pyrrolo[2,3-c]pyridin-3-ylmethylene)-thiazolidine-2,4-dione

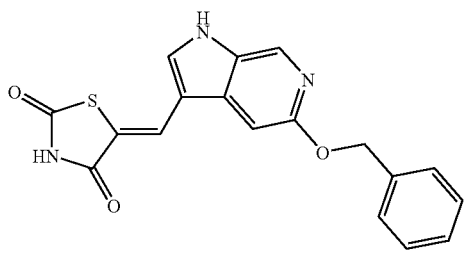

HPLC-MS (Method A): m/z: 352 (M+1); Rt=3.01 min.

Example 159

General Procedure (C)

5-(Quinolin-2-ylmethylene)thiazolidine-2,4-dione

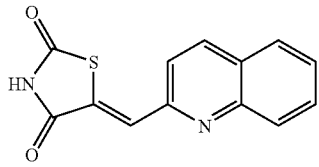

HPLC-MS (Method A): m/z: 257 (M+1); Rt=3.40 min.

Example 160

General Procedure (C)

5-(2,4-Dioxothiazolidin-5-ylidenemethyl)thiophene-2-carboxylic acid

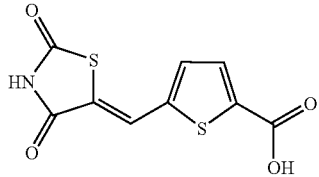

HPLC-MS (Method A): m/z: 256 (M+1); Rt=1.96 min.

Example 161

General Procedure (C)

5-(2-Phenyl-1H-imidazol-4-ylmethylene)thiazolidine-2,4-dione

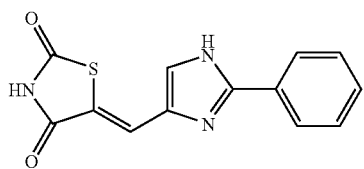

HPLC-MS (Method A): m/z: 272 (M+1); Rt=2.89 min.

Example 162

General Procedure (C)

5-(4-Imidazol-1-yl-benzylidene)thiazolidine-2,4-dione

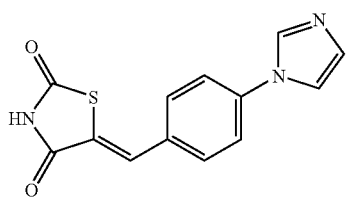

HPLC-MS (Method A): m/z: 272 (M+1); Rt=1.38 min.

Example 163

General Procedure (C)

5-(9-Ethyl-9H-carbazol-3-ylmethylene)thiazolidine-2,4-dione

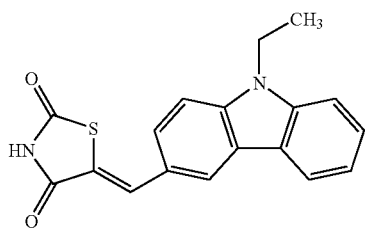

HPLC-MS (Method A): m/z: 323 (M+1); Rt=4.52 min.

Example 164

General Procedure (C)

5-(1,4-Dimethyl-9H-carbazol-3-ylmethylene)thiazolidine-2,4-dione

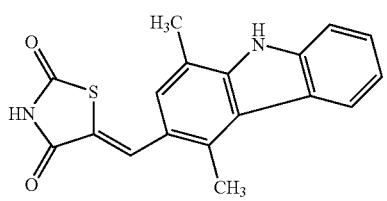

HPLC-MS (Method A): m/z: 323 (M+1); Rt=4.35 min.

Example 165

General Procedure (C)

5-(2-Methyl-1H-indol-3-ylmethylene)thiazolidine-2,4-dione

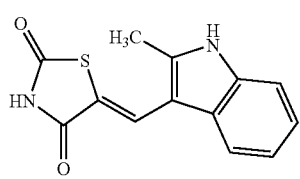

HPLC-MS (Method A): m/z: 259 (M+1); Rt=3.24 min.

Example 166

General Procedure (C)

5-(2-Ethylindol-3-ylmethylene)thiazolidine-2,4-dione

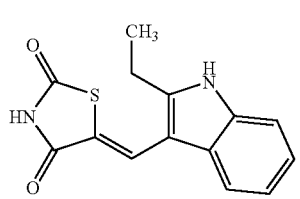

2-Methylindole (1.0 g, 7.6 mmol) dissolved in diethyl ether (100 mL) under nitrogen was treated with n-Butyl lithium (2 M in pentane, 22.8 mmol) and potassium tert-butoxide (15.2 mmol) with stirring at RT for 30 min. The temperature was lowered to −70 C. and methyl Iodide (15.2 mmol) was added and the resulting mixture was stirred at −70 for 2 h. Then 5 drops of water was added and the mixture allowed to warm up to RT. Subsequently, the mixture was poured into water (300 mL), pH was adjusted to 6 by means of 1N hydrochloric acid and the mixture was extracted with diethyl ether. The organic phase was dried with $Na_2SO_4$ and evaporated to dryness. The residue was purified by column chromatography on silica gel using heptane/ether (4/1) as eluent. This afforded 720 mg (69%) of 2-ethylindole.

$^1$H NMR (DMSO-$d_6$): δ=10.85 (1H, s); 7.39 (1H, d); 7.25 (1H, d); 6.98 (1H, t); 6.90 (1H, t); 6.10 (1H, s); 2.71 (2H, q); 1.28 (3H, t).

2-Ethylindole (0.5 g, 3.4 mmol) dissolved in DMF (2 mL) was added to a cold (0° C.) premixed (30 minutes) mixture of DMF (1.15 mL) and phosphorous oxychloride (0.64 g, 4.16 mmol). After addition of 2-ethylindole, the mixture was heated to 40° C. for 1 h, water (5 mL) was added and the pH adjusted to 5 by means of 1 N sodium hydroxide. The mixture was subsequently extracted with diethyl ether, the organic phase isolated, dried with $MgSO_4$ and evaporated to dryness affording 2-ethylindole-3-carbaldehyde (300 mg).

HPLC-MS (Method C): m/z: 174 (M+1); Rt.=2.47 min.

2-Ethylindole-3-carbaldehyde (170 mg) was treated with thiazolidine-2,4-dione using the general procedure (C) to afford the title compound (50 mg).

HPLC-MS (Method C): m/z: 273 (M+1); Rt.=3.26 min.

Example 167

General Procedure (C)

5-[2-(4-Bromophenylsulfanyl)-1-methyl-1H-indol-3-ylmethylene]thiazolidine-2,4-dione

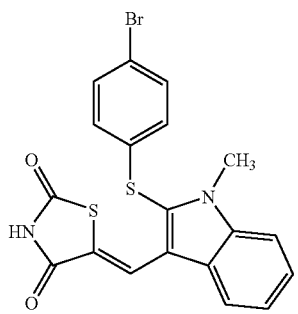

HPLC-MS (Method A): m/z: 447 (M+1); Rt=5.25 min.

Example 168

General Procedure (C)

5-[2-(2,4-Dichlorobenzyloxy)-naphthalen-1-ylmethylene]thiazolidine-2,4-dione

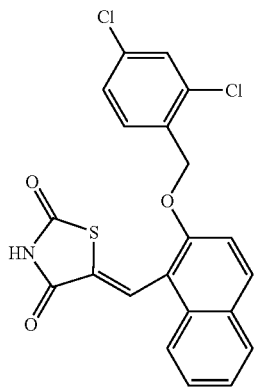

HPLC-MS (Method A): (anyone 1) m/z: 430 (M+1); Rt=5.47 min.

Example 169

General Procedure (C)

5-{4-[3-(4-Bromophenyl)-3-oxopropenyl]-benzylidene}thiazolidine-2,4-dione

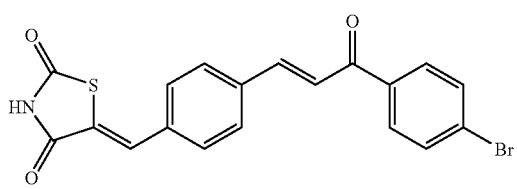

HPLC-MS (Method A): m/z: 416 (M+1); Rt=5.02 min.

Example 170

General Procedure (C)

5-(4-Pyridin-2-ylbenzylidene)thiazolidine-2,4-dione

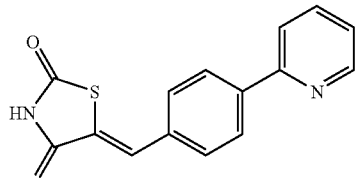

HPLC-MS (Method A): m/z: 283 (M+1), Rt=2.97 min.

Example 171

General Procedure (C)

5-(3,4-Bisbenzyloxybenzylidene)thiazolidine-2,4-dione

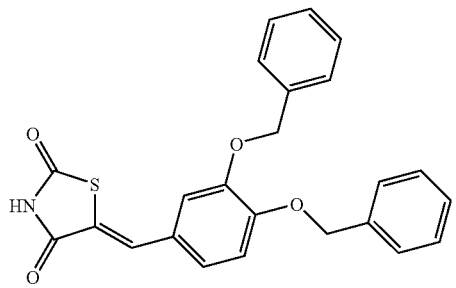

HPLC-MS (Method A): m/z: 418 (M+1); Rt=5.13 min.

Example 172

General Procedure (C)

5-[4-(4-Nitrobenzyloxy)-benzylidene]thiazolidine-2,4-dione

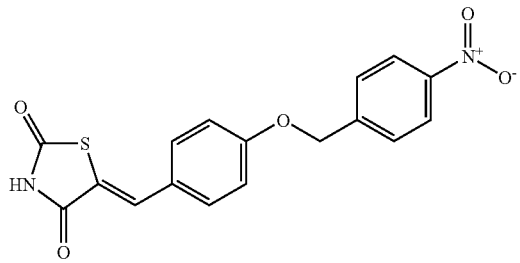

HPLC-MS (Method A): m/z: 357 (M+1); Rt=4.45 min.

Example 173

General Procedure (C)

5-(2-Phenyl-1H-indol-3-ylmethylene)thiazolidine-2,4-dione

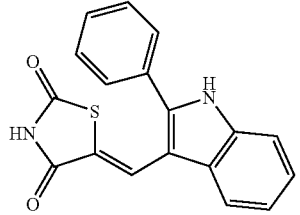

HPLC-MS (Method A): m/z: 321 (M+1); Rt=3.93 min.

Example 174

General Procedure (C)

5-(5-Benzyloxy-1H-indol-3-ylmethylene)thiazolidine-2,4-dione

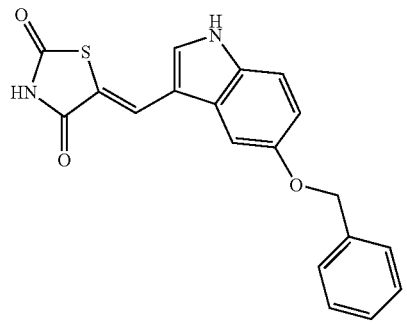

HPLC-MS (Method A): m/z: 351 (M+1); Rt=4.18 min.

Example 175

General Procedure (C)

5-(4-Hydroxybenzylidene)thiazolidine-2,4-dione

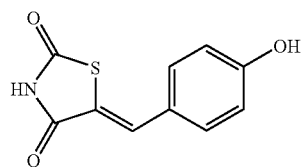

HPLC-MS (Method A); m/z: 222 (M+1); Rt=2.42 min.

Example 176

General Procedure (C)

5-(1-Methyl-1H-indol-2-ylmethylene)thiazolidine-2,4-dione

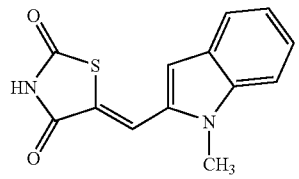

$^1$H NMR (DMSO-d$_6$): δ$_H$=12.60 (s, broad, 1H), 7.85 (s, 1H), 7.68 (dd, 1H), 7.55 (dd, 1H), 7.38 (dt, 1H), 7.11 (dt, 1H) 6.84 (s, 1H), 3.88 (s, 3H); HPLC-MS (Method A): m/z: 259 (M+1); Rt=4.00 min.

Example 177

General Procedure (C)

5-(5-Nitro-1H-indol-3-ylmethylene)thiazolidine-2,4-dione

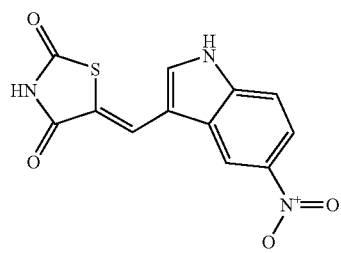

Mp 330-333° C., $^1$H NMR (DMSO-d$_6$): δ$_H$=12.62 (s, broad, 1H), 8.95 (d, 1H), 8.20 (s, 1H), 8.12 (dd, 1H), 7.98 (s, broad, 1H), 7.68 (d, 1H); HPLC-MS (Method A): m/z: 290 (M+1); Rt=3.18 min.

Example 178

General Procedure (C)

5-(6-Methoxynaphthalen-2-ylmethylene)thiazolidine-2,4-dione

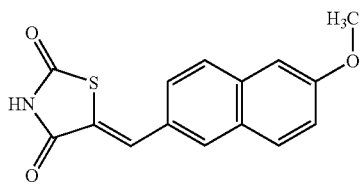

HPLC-MS (Method A): m/z: 286 (M+1); Rt=4.27 min.

Example 179

General Procedure (C)

5-(3-Bromo-4-methoxybenzylidene)thiazolidine-2,4-dione

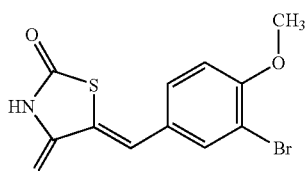

HPLC-MS (Method A): m/z: 314 (M+1), Rt=3.96 min.

Example 180

General Procedure (C)

3-{(2-Cyanoethyl)-[4-(2,4-dioxothiazolidin-5-ylidenemethyl)phenyl]amino}propionitrile

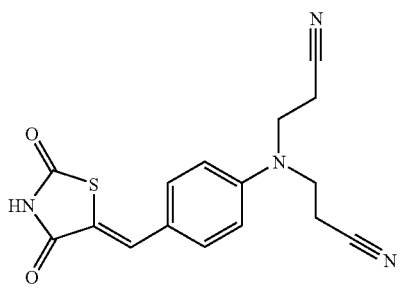

HPLC-MS (Method A): m/z: 327 (M+1); Rt=2.90 min.

Example 181

General Procedure (C)

3-(2,4-Dioxothiazolidin-5-ylidenemethyl)indole-6-carboxylic acid methyl ester

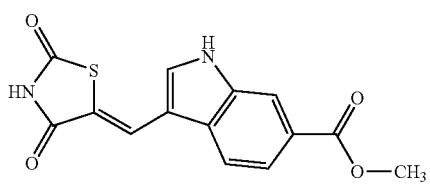

HPLC-MS (Method A): m/z: 303 (M+1); Rt=3.22-3.90 min.

Example 182

3-(2,4-Dioxothiazolidin-5-ylidenemethyl)indole-6-carboxylic acid pentyl ester

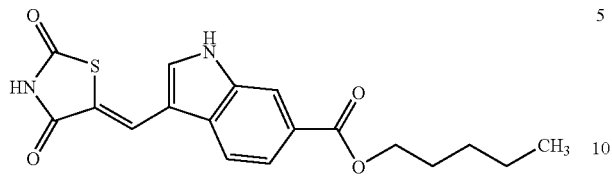

(3-(2,4-Dioxohiazolidin-5-ylidenemethyl)indole-6-carboxylic acid methyl ester (example 181, 59 mg; 0.195 mmol) was stirred in pentanol (20 mL) at 145° C. for 16 hours. The mixture was evaporated to dryness affording the title compound (69 mg).

HPLC-MS (Method C): m/z: 359 (M+1); Rt.=4.25 min.

Example 183

General Procedure (C)

3-(2,4-Dioxothiazolidin-5-ylidenemethyl)indole-7-carboxylic acid

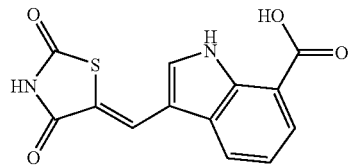

HPLC-MS (Method A): m/z: 289 (M+1); Rt=2.67 min.

Example 184

General Procedure (C)

5-(1-Benzylindol-3-ylmethylene)thiazolidine-2,4-dione

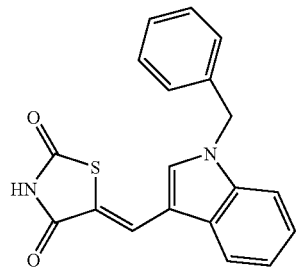

HPLC-MS (Method A): m/z: 335 (M+1); Rt=4.55 min.

Example 185

General Procedure (C)

5-(1-Benzenesulfonylindol-3-ylmethylene)thiazolidine-2,4-dione

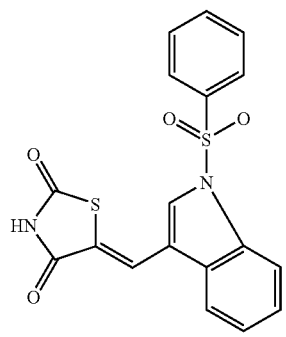

HPLC-MS (Method A): m/z:=385 (M+1); Rt=4.59 min.

Example 186

General Procedure (C)

5-(4-[1,2,3]Thiadiazol-4-ylbenzylidene)thiazolidine-2,4-dione

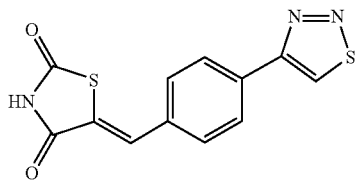

HPLC-MS (Method A): m/z: 290 (M+1); Rt=3.45 min.

Example 187

General Procedure (C)

5-[4-(4-Nitrobenzyloxy)-benzylidene]thiazolidine-2,4-dione

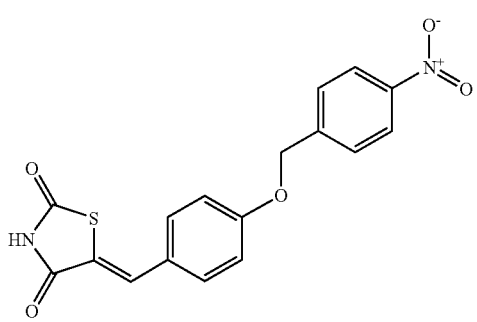

HPLC-MS (Method A): m/z: 357 (M+1); Rt=4.42 min.

Example 188

General Procedure (C)

3-(2,4-Dioxothiazolidin-5-ylidenemethyl)indole-1-carboxylic acid ethyl ester

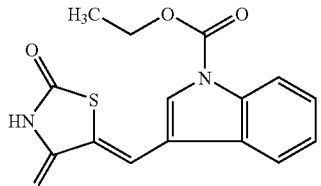

HPLC-MS (Method A): m/z: 317 (M+1); Rt=4.35 min.

Example 189

General Procedure (C)

5-[2-(4-Pentylbenzoyl)-benzofuran-5-ylmethylene]thiazolidine-2,4-dione

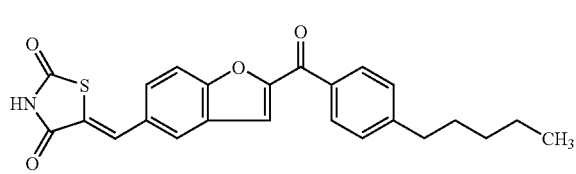

HPLC-MS (Method A): m/z: 420 (M+1); Rt=5.92 min.

Example 190

General Procedure (C)

5-[1-(2-Fluorobenzyl)-4-nitroindol-3-ylmethylene]thiazolidine-2,4-dione

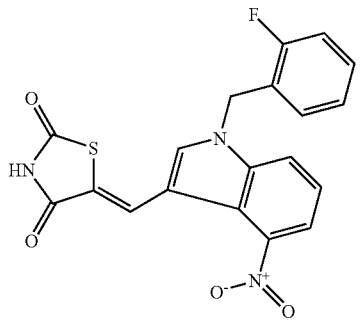

HPLC-MS (Method A): (Anyone 1) m/z: 398 (M+1); Rt=4.42 min.

Example 191

General Procedure (C)

5-(4-Benzyloxyindol-3-ylmethylene)thiazolidine-2,4-dione

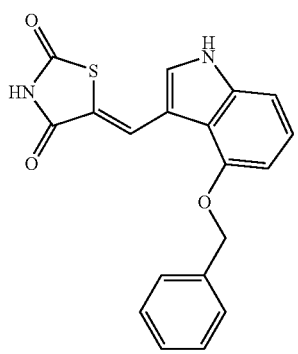

HPLC-MS (Method A): m/z: 351 (M+1); Rt=3.95 min.

Example 192

General Procedure (C)

5-(4-Isobutylbenzylidene)-thiazolidine-2,4-dione

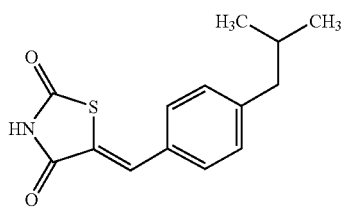

HPLC-MS (Method A): m/z: 262 (M+1); Rt=4.97 min.

Example 193

General Procedure (C)

Trifluoromethanesulfonic acid 4-(2,4-dioxothiazolidin-5-ylidenemethyl)naphthalen-1-yl ester

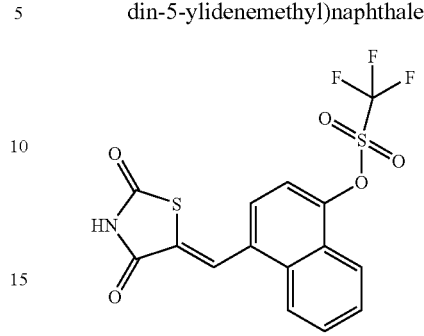

HPLC-MS (Method A): m/z: 404 (M+1); Rt=4.96 min.

Preparation of Starting Material:

4-Hydroxy-1-naphthaldehyde (10 g, 58 mmol) was dissolved in pyridin (50 ml) and the mixture was cooled to 0-5° C. With stirring, trifluoromethanesulfonic acid anhydride (11.7 ml, 70 mmol) was added drop-wise. After addition was complete, the mixture was allowed to warm up to room temperature, and diethyl ether (200 ml) was added. The mixture was washed with water (2×250 ml), hydrochloric acid (3N, 200 ml), and saturated aqueous sodium chloride (100 ml). After drying (MgSO4), filtration and concentration in vacuo, the residue was purified by column chromatography on silica gel eluting with a mixture of ethyl acetate and heptane (1:4). This afforded 8.35 g (47%) trifluoromethanesulfonic acid 4-formylnaphthalen-1-yl ester, mp 44-46.6° C.

Example 194

General Procedure (C)

5-(4-Nitroindol-3-ylmethylene)thiazolidine-2,4-dione

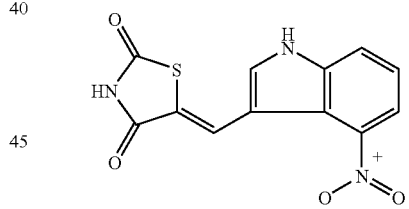

HPLC-MS (Method A): m/z: 290 (M+1); Rt=3.14 min.

Example 195

General Procedure (C)

5-(3,5-Dibromo-4-hydroxy-benzylidene)thiazolidine-2,4-dione

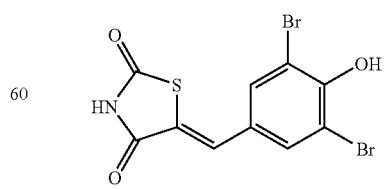

$^1$H NMR (DMSO-d$_6$): $\delta_H$=12.65 (broad, 1H), 10.85 (broad, 1H), 7.78 (s, 2H), 7.70 (s, 1H);

HPLC-MS (Method A): m/z: 380 (M+1); Rt=3.56 min.

Example 196

General Procedure (C)

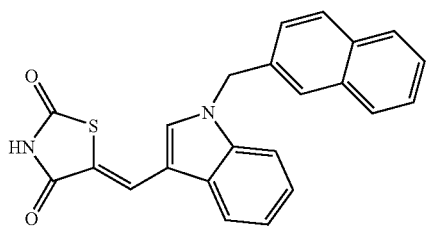

HPLC-MS (Method A): m/z: 385 (M+1); Rt=5.08 min.

General Procedure for Preparation of Starting Materials for Examples 196-199:

Indole-3-carbaldehyde (3.8 g, 26 mmol) was stirred with potassium hydroxide (1.7 g) in acetone (200 mL) at RT until a solution was obtained indicating full conversion to the indole potassium salt. Subsequently the solution was evaporated to dryness in vacuo. The residue was dissolved in acetone to give a solution containing 2.6 mmol/20 mL.

20 mL portions of this solution were mixed with equimolar amounts of arylmethylbromides in acetone (10 mL). The mixtures were stirred at RT for 4 days and subsequently evaporated to dryness and checked by HPLC-MS. The crude products, 1-benzylated indole-3-carbaldehydes, were used for the reaction with thiazolidine-2,4-dione using the general procedure C.

Example 197

General Procedure (C)

4-[3-(2,4-Dioxothiazolidin-5-ylidenemethyl)indol-1-ylmethyl]benzoic acid methyl ester

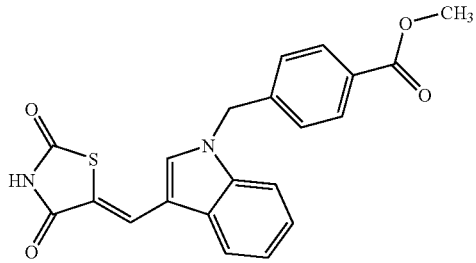

HPLC-MS (Method A): m/z: 393 (M+1); Rt=4.60 min.

Example 198

General Procedure (C)

5-[1-(9,10-Dioxo-9,10-dihydroanthracen-2-ylmethyl)-1H-indol-3-ylmethylene]thiazolidine-2,4-dione

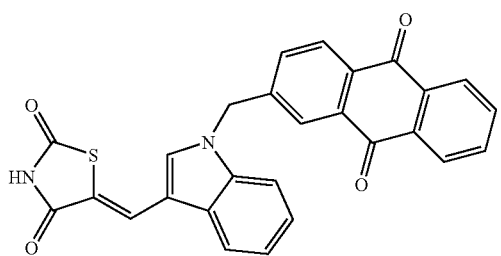

HPLC-MS (Method A): m/z: 465 (M+1); Rt=5.02 min.

Example 199

General Procedure (C)

4'-[3-(2,4-Dioxothiazolidin-5-ylidenemethyl)indol-1-ylmethyl]biphenyl-2-carbonitrile

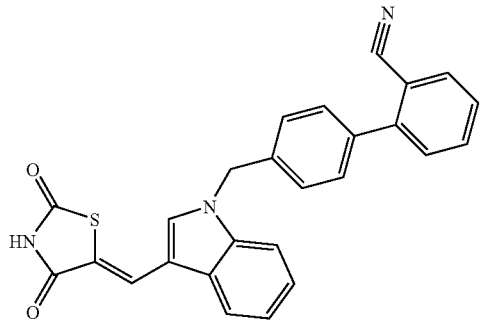

HPLC-MS (Method A): m/z: 458 (M+23); Rt=4.81 min.

Example 200

General Procedure (C)

3-[3-(2,4-Dioxothiazolidin-5-ylidenemethyl)-2-methylindol-1-ylmethyl]benzonitrile

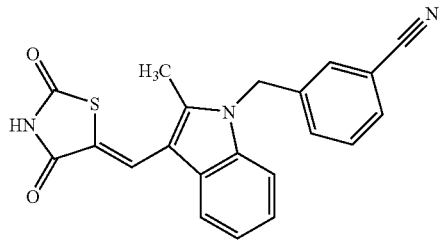

2-Methylindole-3-carbaldehyde (200 mg, 1.26 mmol) was added to a slurry of 3-bromomethylbenzenecarbonitrile (1.26 mmol) followed by sodium hydride, 60%, (1.26 mmol) in DMF (2 mL). The mixture was shaken for 16 hours, evaporated to dryness and washed with water and ethanol. The residue was treated with thiazolidine-2,4-dione following the general procedure C to afford the title compound (100 mg).

HPLC-MS (Method C): m/z: 374 (M+1); Rt.=3.95 min.

Example 201

General Procedure (C)

5-(1-Benzyl-2-methylindol-3-ylmethylene)thiazolidine-2,4-dione

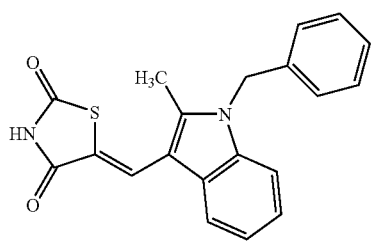

This compound was prepared in analogy with the compound described in example 200 from benzyl bromide and 2-methylindole-3-carbaldehyde, followed by reaction with thiazolidine-2,4-dione resulting in 50 mg of the title compound.

HPLC-MS (Method C): m/z: 349 (M+1); Rt.=4.19 min.

Example 202

4-[3-(2,4-Dioxothiazolidin-5-ylidenemethyl)-2-methylindol-1-ylmethyl]benzoic acid methyl ester

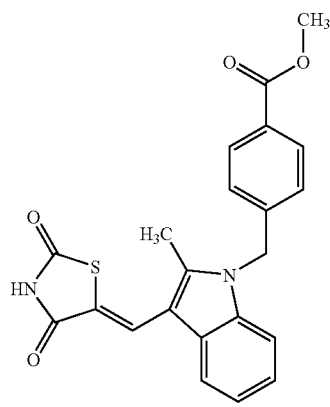

This compound was prepared in analogy with the compound described in example 200 from 4-(bromomethyl)benzoic acid methyl ester and 2-methylindole-3-carbaldehyde, followed by reaction with thiazolidine-2,4-dione.
HPLC-MS (Method C): m/z: 407 (M+1); Rt.=4.19 min.

Example 203

General Procedure (C)

5-(2-Chloro-1-methyl-1H-indol-3-ylmethylene)thiazolidine-2,4-dione

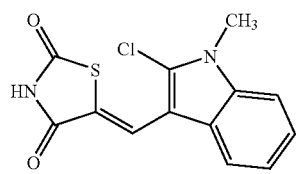

HPLC-MS (Method A): m/z: 293 (M+1); Rt=4.10 min.

Example 204

General Procedure (C)

5-(4-Hydroxy-3,5-diiodo-benzylidene)-thiazolidine-2,4-dione

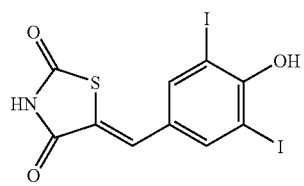

HPLC-MS (Method A): m/z: 474 (M+1); Rt=6.61 min.

Example 205

General Procedure (C)

5-(4-Hydroxy-3-iodobenzylidene)thiazolidine-2,4-dione

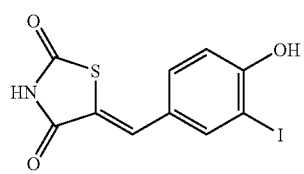

HPLC-MS (Method C): m/z: 348 (M+1); Rt.=3.13 min
$^1$H-NMR): (DMSO-d$_6$): 11.5 (1H, broad); 7.95 (1H, d); 7.65 (1H, s); 7.45 (1H, dd); 7.01 (1H, dd); 3.4 (1H, broad).

Example 206

General Procedure (C)

5-(2,3,6-Trichlorobenzylidene)thiazolidine-2,4-dione

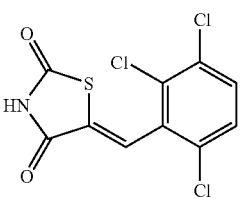

HPLC-MS (Method C): m/z: 309 (M+1); Rt.=4.07 min

Example 207

General Procedure (C)

5-(2,6-Dichlorobenzylidene)thiazolidine-2,4-dione

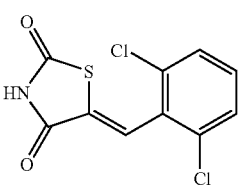

Mp. 152-154° C.
HPLC-MS (Method C): m/z: 274 (M+1), Rt.=3.70 min
$^1$H-NMR: (DMSO-d$_6$): 12.8 (1H, broad); 7.72 (1H, s); 7.60 (2H, d); 7.50 (1H, t).

Example 208

General Procedure (C)

5-[1-(2,6-Dichloro-4-trifluoromethylphenyl)-2,5-dimethyl-1H-pyrrol-3-ylmethylene]thiazolidine-2,4-dione

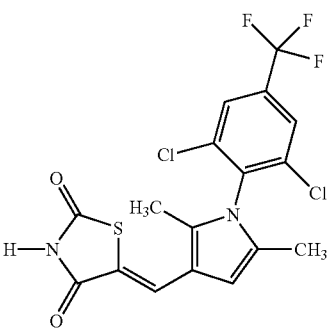

HPLC-MS (Method C): m/z: 436 (M+1); Rt.=4.81 min

Example 209

General Procedure (C)

5-[1-(3,5-Dichlorophenyl)-5-(4-methanesulfonylphenyl)-2-methyl-1H-pyrrol-3-ylmethylene]-thiazolidine-2,4-dione

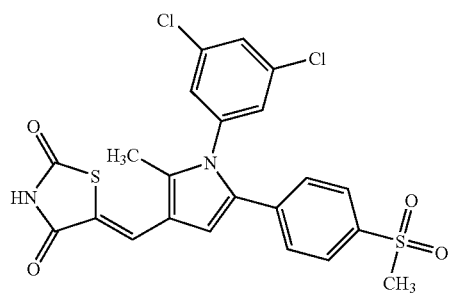

HPLC-MS (Method C): m/z: 508 (M+1); Rt.=4.31 min

Example 210

General Procedure (C)

5-[1-(2,5-Dimethoxyphenyl)-5-(4-methanesulfonylphenyl)-2-methyl-1H-pyrrol-3-ylmethylene]-thiazolidine-2,4-dione

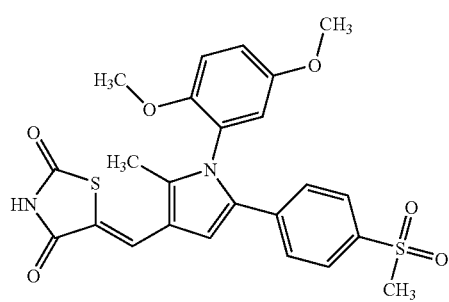

HPLC-MS (Method C): m/z: 499 (M+1); Rt.=3.70 min

Example 211

General Procedure (C)

4-[3-(2,4-Dioxothiazolidin-5-ylidenemethyl)-2,5-dimethylpyrrol-1-yl]benzoic acid

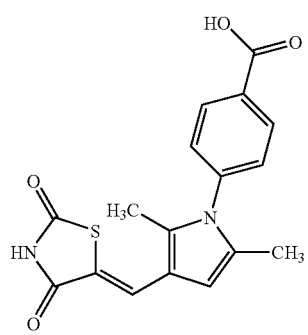

HPLC-MS (Method C): m/z: 342 (M+1); Rt.=3.19 min

Example 212

General Procedure (C)

5-(4-Hydroxy-2,6-dimethoxybenzylidene)thiazolidine-2,4-dione

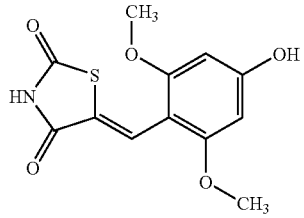

HPLC-MS (Method C): m/z: 282 (M+1); Rt.=2.56, mp=331-333° C.

Example 213

General Procedure (C)

5-(2,6-Dimethylbenzylidene)thiazolidine-2,4-dione

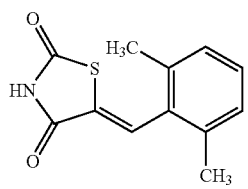

M.p: 104-105° C.
HPLC-MS (Method C): m/z: 234 (M+1); Rt.=3.58 min,

Example 214

General Procedure (C)

5-(2,6-Dimethoxybenzylidene)thiazolidine-2,4-dione

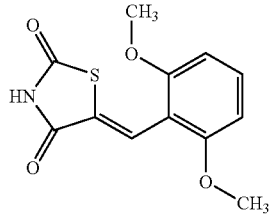

Mp: 241-242° C.
HPLC-MS (Method C): m/z: 266 (M+1); Rt.=3.25 min;

Example 215

General Procedure (C)

5-[4-(2-Fluoro-6-nitrobenzyloxy)-2,6-dimethoxybenzylidene]thiazolidine-2,4-dione

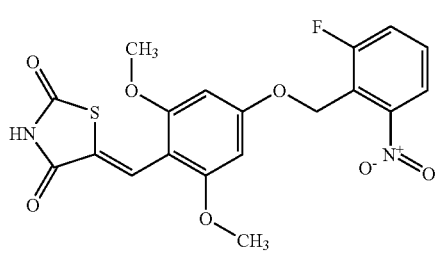

Mp: 255-256° C.
HPLC-MS (Method C): m/z: 435 (M+1), Rt=4.13 min,

Example 216

General Procedure (C)

5-Benzofuran-2-ylmethylenethiazolidine-2,4-dione

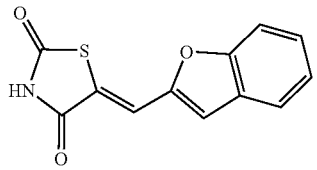

HPLC-MS (Method C): m/z: 246 (M+1); Rt.=3.65 min, mp=265-266° C.

Example 217

General Procedure (C)

5-[3-(4-Dimethylaminophenyl)allylidene]thiazolidine-2,4-dione

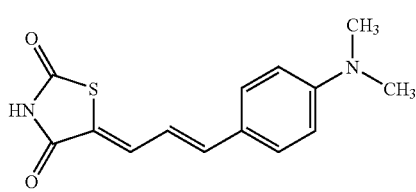

HPLC-MS (Method C): m/z: 276 (M+1); Rt.=3.63, mp=259-263° C.
$^1$H-NMR: (DMSO-$d_6$) δ=12.3 (1H, broad); 7.46 (2H, d); 7.39 (1H, d); 7.11 (1H, d); 6.69 (2H, d); 6.59 (1H, dd); 2.98 (3H, s).

Example 218

General Procedure (C)

5-(2-Methyl-3-phenylallylidene)thiazolidine-2,4-dione

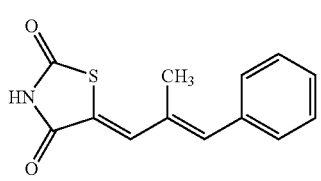

Mp: 203-210° C.
HPLC-MS (Method C): m/z: 246 (M+1); Rt=3.79 min.

Example 219

General Procedure (C)

5-(2-Chloro-3-phenylallylidene)thiazolidine-2,4-dione

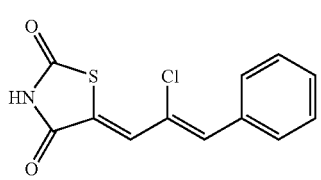

Mp: 251-254° C.
HPLC-MS (Method C): m/z: 266 (M+1; Rt=3.90 min

Example 220

General Procedure (C)

5-(2-Oxo-1,2-dihydroquinolin-3-ylmethylene)thiazolidine-2,4-dione

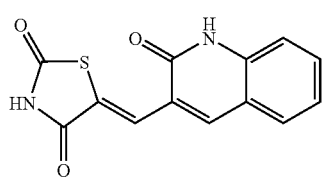

Mp: 338-347° C.
HPLC-MS (Method C): m/z: 273 (M+1); Rt.=2.59 min.

Example 221

General Procedure (C)

5-(2,4,6-Tribromo-3-hydroxybenzylidene)thiazolidine-2,4-dione

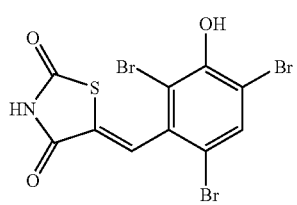

HPLC-MS (Method C): m/z: 459 (M+1); Rt.=3.65 min.

Example 222

General Procedure (C)

5-(5-Bromo-2-methylindol-3-ylmethylene)thiazolidine-2,4-dione

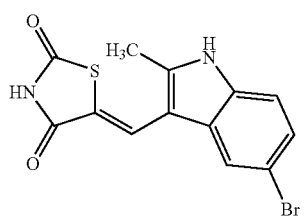

HPLC-MS (Method C): m/z: 339 (M+1); Rt=3.37 min.

Example 223

General Procedure (C)

5-(7-Bromo-2-methylindol-3-ylmethylene)thiazolidine-2,4-dione

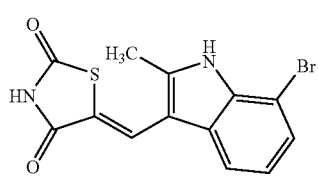

HPLC-MS (Method C): m/z: 319 (M+1); Rt=3.48 min.

Example 224

General Procedure (C)

5-(6-Bromoindol-3-ylmethylene)thiazolidine-2,4-dione

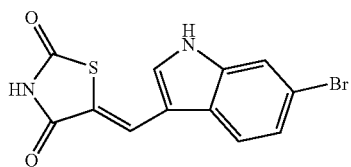

HPLC-MS (Method C): m/z: 325 (M+1); Rt=3.54 min.

Example 225

General Procedure (C)

5-(8-Methyl-2-oxo-1,2-dihydroquinolin-3-ylmethylene)thiazolidine-2,4-dione

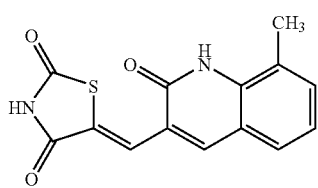

HPLC-MS (Method C): m/z: 287 (M+1); Rt=2.86 min.

Example 226

General Procedure (C)

5-(6-Methoxy-2-oxo-1,2-dihydroquinolin-3-ylmethylene)thiazolidine-2,4-dione

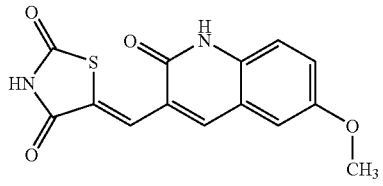

HPLC-MS (Method C): m/z: 303 (M+1); Rt=2.65 min.

Example 227

General Procedure (C)

5-Quinolin-3-ylmethylenethiazolidine-2,4-dione

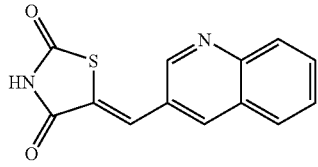

HPLC-MS (Method C): m/z: 257 (M+1); Rt=2.77 min.

Example 228

General Procedure (C)

5-(8-Hydroxyquinolin-2-ylmethylene)thiazolidine-2,4-dione

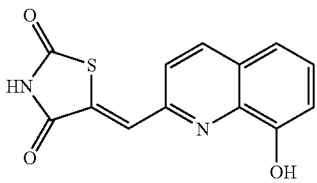

HPLC-MS (Method C): m/z: 273 (M+1); Rt=3.44 min.

Example 229

General Procedure (C)

5-Quinolin-8-ylmethylenethiazolidine-2,4-dione

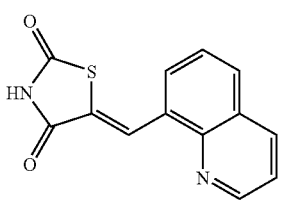

HPLC-MS (Method C): m/z: 257 (M+1); Rt=3.15 min.

Example 230

General Procedure (C)

5-(1-Bromo-6-methoxynaphthalen-2-ylmethylene)thiazolidine-2,4-dione

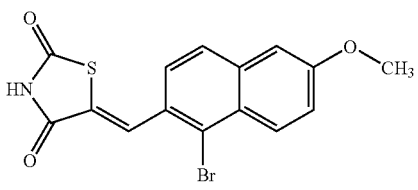

HPLC-MS (Method C): m/z: 366 (M+1); Rt=4.44 min.

Example 231

General Procedure (C)

5-(6-Methyl-2-oxo-1,2-dihydroquinolin-3-ylmethylene)thiazolidine-2,4-dione

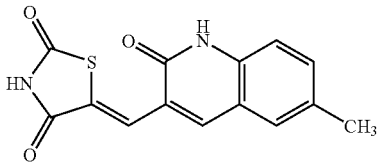

HPLC-MS (Method C): m/z: 287 (M+1); Rt.=2.89 min.

Example 232

General Procedure (D)

5-(2,6-Dichloro-4-dibenzylaminobenzylidene)thiazolidine-2,4-dione

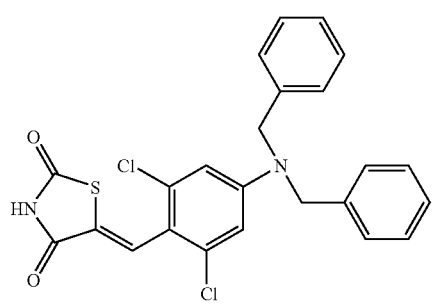

HPLC-MS (Method C): m/z: 469 (M+1); Rt=5.35 min.
Other preferred compounds include 3',5'-Dichloro-4'-(2,4-dioxothiazolidin-5-ylidenemethyl)biphenyl-4-carboxylic acid

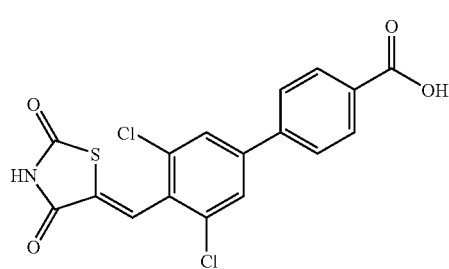

The following compounds are commercially available and may be prepared using general procedures (B) and/or (C).

Example 233

5-(5-Bromo-1H-indol-3-ylmethylene)thiazolidine-2,4-dione

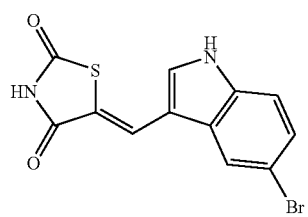

Example 234

5-Pyridin-4-ylmethylenethiazolidine-2,4-dione

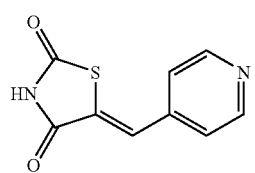

Example 235

5-(3-Bromo-4-methoxybenzylidene)thiazolidine-2,4-dione

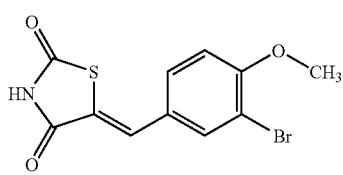

HPLC-MS (Method A):

Example 236

5-(3-Nitrobenzylidene)thiazolidine-2,4-dione

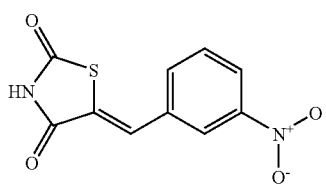

HPLC-MS (Method A):

Example 237

5-Cyclohexylidene-1,3-thiazolidine-2,4-dione

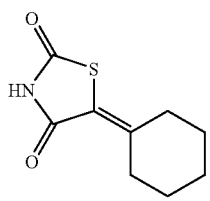

HPLC-MS (Method A):

Example 238

5-(3,4-Dihydroxybenzylidene)thiazolidine-2,4-dione

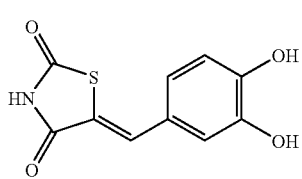

Example 239

5-(3-Ethoxy-4-hydroxybenzylidene)thiazolidine-2,4-dione

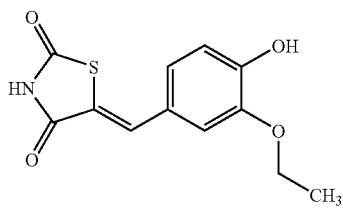

Example 240
5-(4-Hydroxy-3-methoxy-5-nitrobenzylidene)thiazolidine-2,4-dione
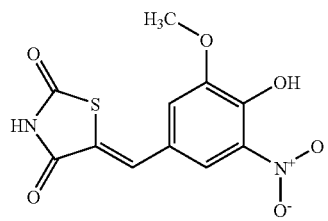
Example 241
5-(3-Ethoxy-4-hydroxybenzylidene)thiazolidine-2,4-dione
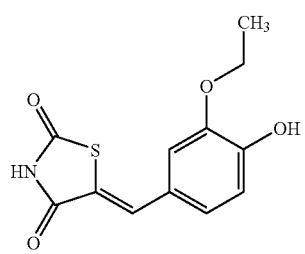
Example 242
5-(4-Hydroxy-3,5-dimethoxybenzylidene)thiazolidine-2,4-dione
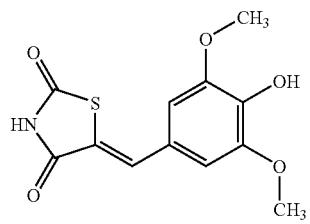
Example 243
5-(3-Bromo-5-ethoxy-4-hydroxybenzylidene)thiazolidine-2,4-dione
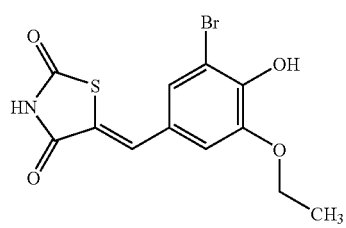
Example 244
5-(3-Ethoxy-4-hydroxy-5-nitrobenzylidene)thiazolidine-2,4-dione
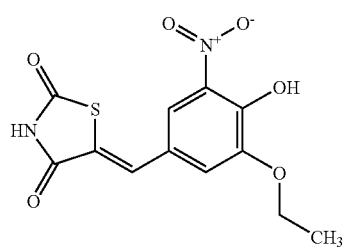
Example 245
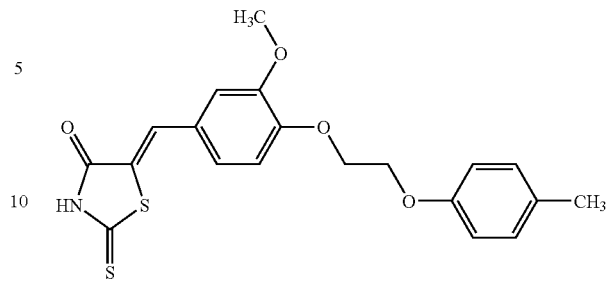
Example 246
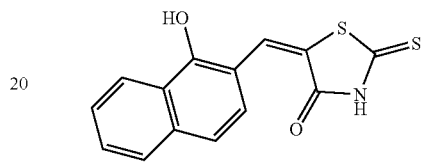
Example 247
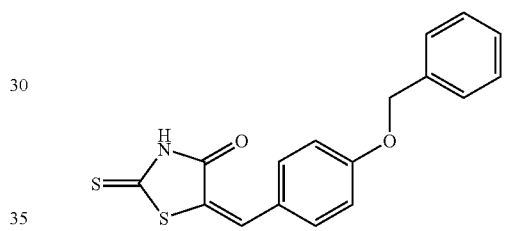
Example 248
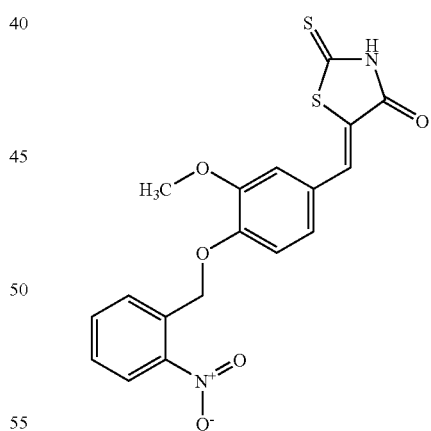
Example 249
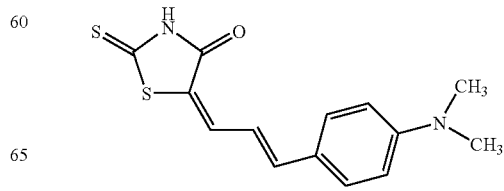

| 119 | 120 |
|---|---|
| Example 250 | Example 255 |
| 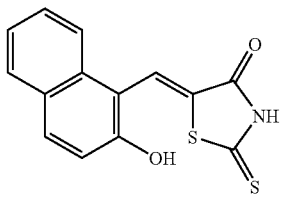 | 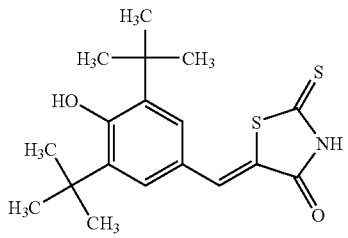 |
| Example 251 | Example 256 |
| 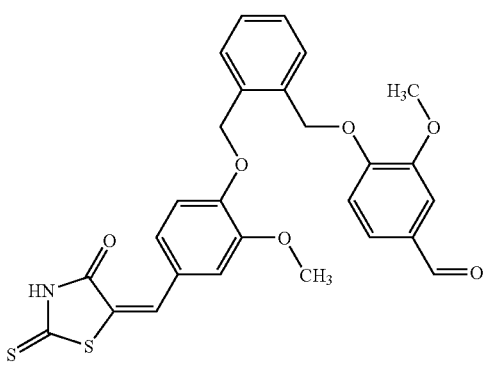 | 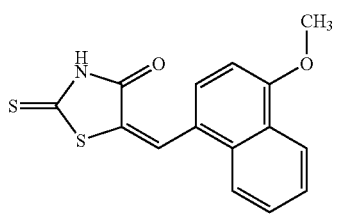 |
| Example 252 | Example 257 |
| | 5-(3-Hydroxy-5-methyl-phenylamino)-thiazolidine-2,4-dione |
| 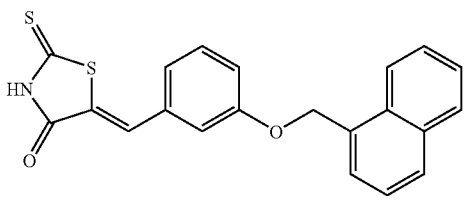 | 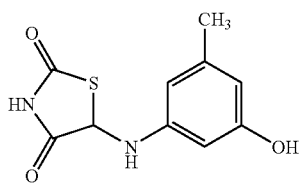 |
| Example 253 | Example 258 |
| 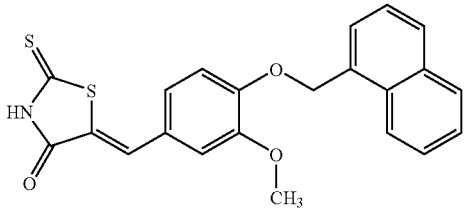 | 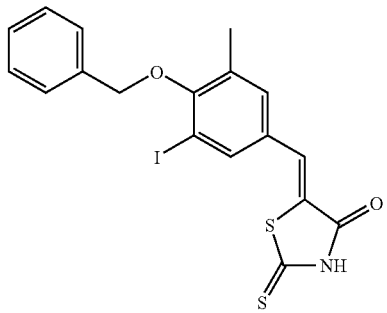 |
| Example 254 | Example 259 |
| 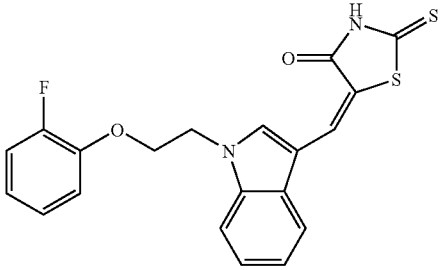 | 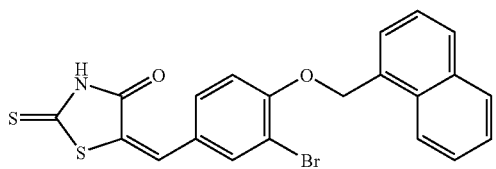 |

121
Example 260
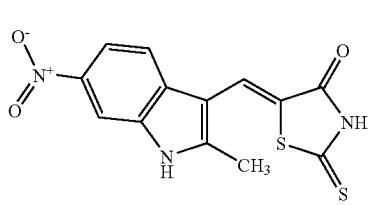
Example 261
Example 262
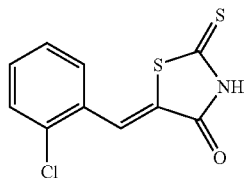
Example 263
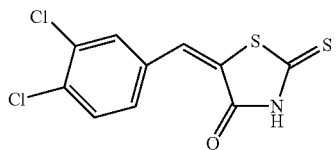
Example 264
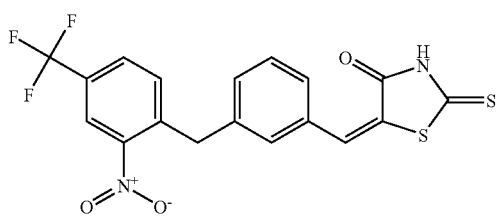
122
Example 265
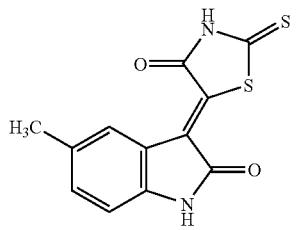
Example 266
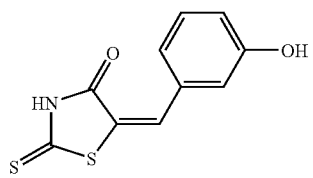
Example 267
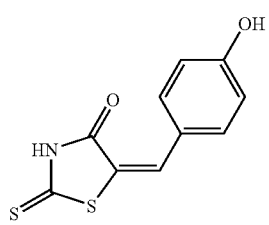
Example 268
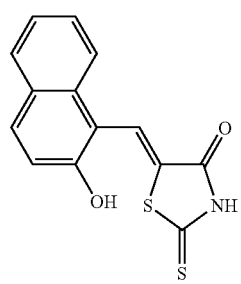
Example 269
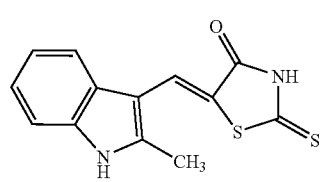

| 123 | 124 |
|---|---|
| Example 270 | Example 275 |
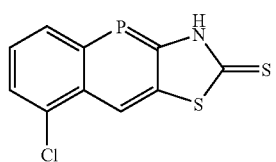
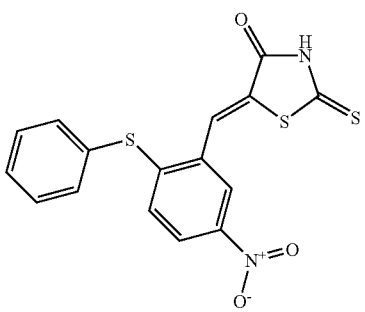
Example 271
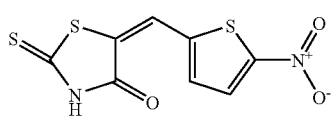
Example 276
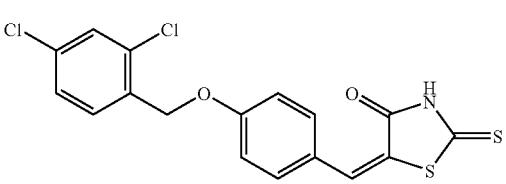
Example 272
Example 277
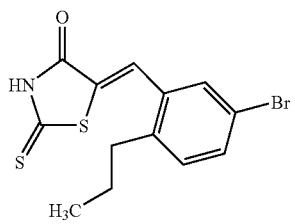
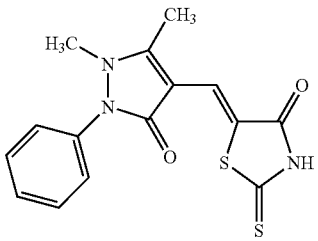
Example 273
Example 278
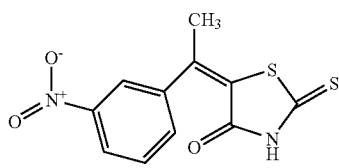
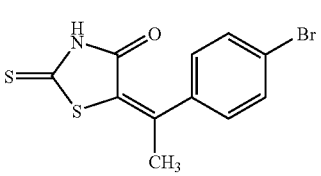
Example 274
Example 279
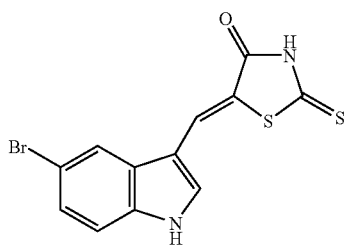
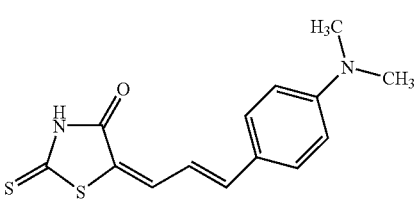

Example 280

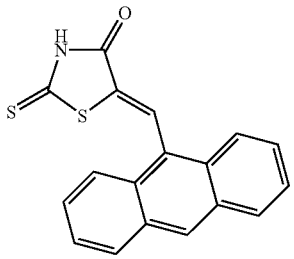

Example 281

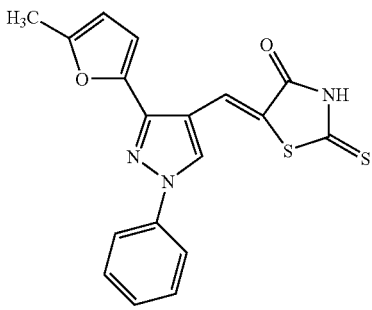

General Procedure (D) for Preparation of Compounds of General Formula $I_3$:

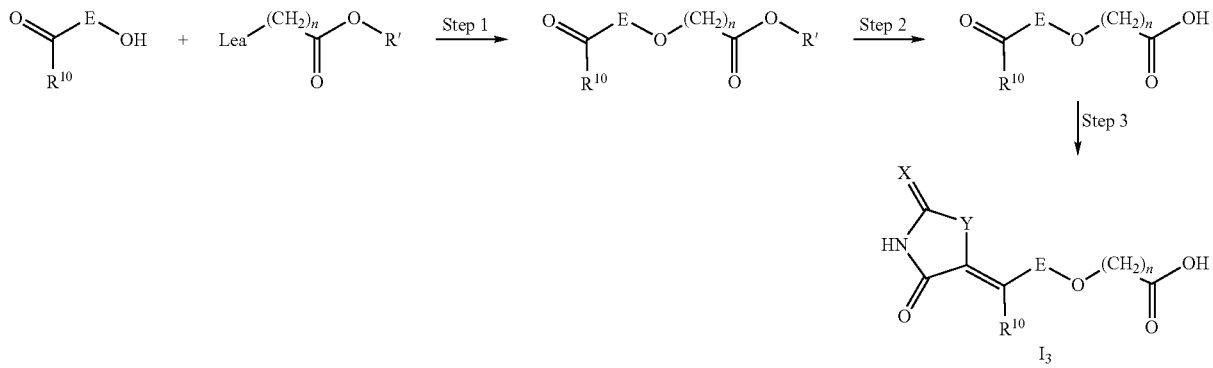

wherein X, Y, $R^{10}$ are as defined above,
n is 1 or 3-20,
E is arylene or heterarylene (including up to four optional substituents, $R^{13}$, $R^{14}$, $R^{15}$, and $R^{15A}$ as defined above),
R' is a standard carboxylic acid protecting group, such as $C_1$-$C_6$-alkyl or benzyl and Lea is a leaving group, such as chloro, bromo, iodo, methanesulfonyloxy, toluenesulfonyloxy or the like.

Step 1 is an alkylation of a phenol moiety. The reaction is preformed by reacting $R^{10}$—C(=O)-E-OH with an ω-bromo-alkane-carboxylic acid ester (or a synthetic equivalent) in the presence of a base such as sodium or potassium carbonate, sodium or potassium hydroxide, sodium hydride, sodium or potassium alkoxide in a solvent, such as DMF, NMP, DMSO, acetone, acetonitrile, ethyl acetate or isopropyl acetate. The reaction is performed at 20-160° C., usually at room temperature, but when the phenol moiety has one or more substituents heating to 50° C. or more can be beneficial, especially when the substituents are in the ortho position relatively to the phenol. This will readily be recognised by those skilled in the art.

Step 2 is a hydrolysis of the product from step 1.

Step 3 is similar to general procedure (B) and (C).

This general procedure (D) is further illustrated in the following examples:

Example 282

General Procedure (D)

4-[4-(2,4-Dioxothiazolidin-5-ylidenemethyl)phenoxy]butyric acid

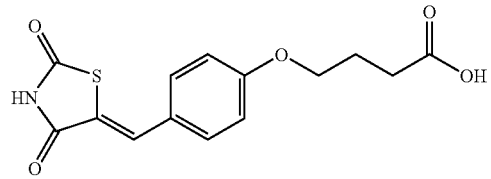

Step 1:

A mixture of 4-hydroxybenzaldehyde (9.21 g, 75 mmol), potassium carbonate (56 g, 410 mmol) and 4-bromobutyric acid ethyl ester (12.9 mL, 90 mmol) in N,N-dimethylformamide (250 mL) was stirred vigorously for 16 hours at room temperature. The mixture was filtered and concentrated in vacuo to afford 19.6 g (100%) of 4-(4-formylphenoxy)butyric acid ethyl ester as an oil. $^1$H-NMR (DMSO-$d_6$): δ 1.21 (3H, t), 2.05 (2H, p), 2.49 (2H, t), 4.12 (4H, m), 7.13 (2H, d), 7.87 (2H, d), 9.90 (1H, s). HPLC-MS (Method A): m/z=237 (M+1); $R_t$=3.46 min.

Step 2:

4-(4-Formylphenoxy)butyric acid ethyl ester (19.6 g, 75 mmol) was dissolved in methanol (250 mL) and 1N sodium hydroxide (100 mL) was added and the resulting mixture was stirred at room temperature for 16 hours. The organic solvent was evaporated in vacuo (40° C., 120 mBar) and the residue was acidified with 1N hydrochloric acid (110 mL). The mixture was filtered and washed with water and dried in vacuo to afford 14.3 g (91%) 4-(4-formylphenoxy)butyric acid as a solid. $^1$H-NMR (DMSO-$d_6$): δ 1.99 (2H, p), 2.42 (2H, t), 4.13 (2H, t), 7.14 (2H, d), 7.88 (2H, d), 9.90 (1H, s), 12.2 (1H, bs). HPLC-MS (Method A): m/z=209 (M+1); $R_t$=2.19 min.

Step 3:

Thiazolidine-2,4-dione (3.55 g, 27.6 mmol), 4-(4-formylphenoxy)butyric acid (5.74 g, 27.6 mmol), anhydrous sodium acetate (11.3 g, 138 mmol) and acetic acid (100 mL) was refluxed for 16 h. After cooling, the mixture was filtered and washed with acetic acid and water. Drying in vacuo afforded 2.74 g (32%) of 4-[4-(2,4-dioxothiazolidin-5-ylidenemethyl)phenoxy]butyric acid as a solid.

$^1$H-NMR (DMSO-$d_6$): δ 1.97 (2H, p), 2.40 (2H, t), 4.07 (2H, t), 7.08 (2H, d), 7.56 (2H, d), 7.77 (1H, s), 12.2 (1H, bs), 12.5 (1H, bs); HPLC-MS (Method A): m/z: 308 (M+1); Rt=2.89 min.

Example 283

General Procedure (D)

[3-(2,4-Dioxothiazolidin-5-ylidenemethyl)phenoxy] acetic acid

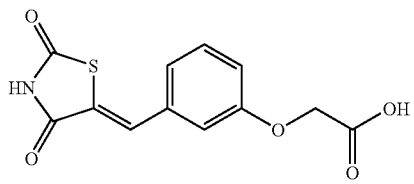

Step 3:

Thiazolidine-2,4-dione (3.9 g, 33 mmol), 3-formylphenoxyacetic acid (6.0 g, 33 mmol), anhydrous sodium acetate (13.6 g, 165 mmol) and acetic acid (100 mL) was refluxed for 16 h. After cooling, the mixture was filtered and washed with acetic acid and water. Drying in vacuo afforded 5.13 g (56%) of [3-(2,4-dioxothiazolidin-5-ylidenemethyl)phenoxy]acetic acid as a solid.

$^1$H-NMR (DMSO-$d_6$): δ 4.69 (2H, s), 6.95 (1H, dd), 7.09 (1H, t), 7.15 (1H, d), 7.39 (1H, t), 7.53 (1H, s); HPLC-MS (Method A): m/z=280 (M+1) (poor ionisation); $R_t$=2.49 min.

The compounds in the following examples were similarly prepared.

Example 284

General Procedure (D)

3-[4-(2,4-Dioxothiazolidin-5-ylidenemethyl)phenyl] acrylic acid

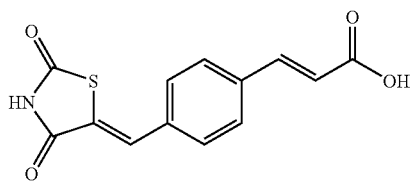

$^1$H-NMR (DMSO-$d_6$): δ 6.63 (1H, d), 7.59-7.64 (3H, m), 7.77 (1H, s), 7.83 (2H, m).

Example 285

General Procedure (D)

[4-(2,4-Dioxothiazolidin-5-ylidenemethyl)phenoxy] acetic acid

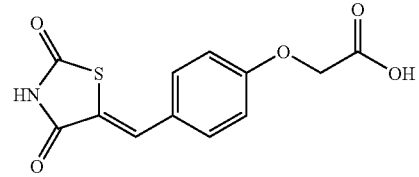

Triethylamine salt: $^1$H-NMR (DMSO-$d_6$): δ 4.27 (2H, s), 6.90 (2H, d), 7.26 (1H, s), 7.40 (2H, d).

Example 286

General Procedure (D)

4-(2,4-Dioxothiazolidin-5-ylidenemethyl)benzoic acid

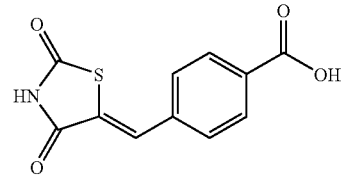

Example 287

General Procedure (D)

3-(2,4-Dioxothiazolidin-5-ylidenemethyl)benzoic acid

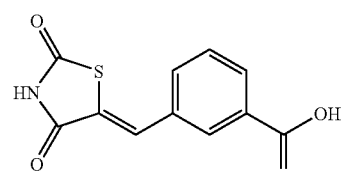

$^1$H-NMR (DMSO-$d_6$): δ 7.57 (1H, s), 7.60 (1H, t), 7.79 (1H, dt), 7.92 (1H, dt), 8.14 (1H, t).

Example 288

General Procedure (D)

4-[2-Chloro-4-(2,4-dioxothiazolidin-5-ylidenemethyl)phenoxy]butyric acid

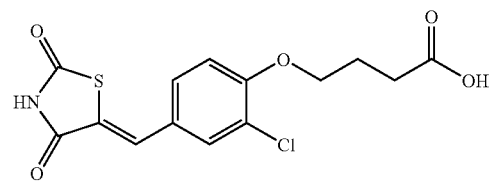

$^1$H-NMR (DMSO-$d_6$): δ 2.00 (2H, p), 2.45 (2H, t), 4.17 (2H, t), 7.31 (1H, d), 7.54 (1H, dd), 7.69 (1H, d), 7.74 (1H, s), 12.2 (1H, bs), 12.6 (1H, bs). HPLC-MS (Method A): m/z: 364 (M+23); Rt=3.19 min.

Example 289

General Procedure (D)

4-[2-Bromo-4-(2,4-dioxothiazolidin-5-ylidenemethyl)phenoxy]butyric acid

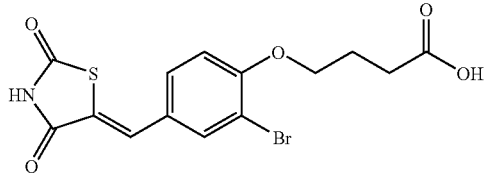

¹H-NMR (DMSO-d₆): δ 1.99 (2H, p), 2.46 (2H, t), 4.17 (2H, t), 7.28 (1H, d), 7.57 (1H, dd), 7.25 (1H, s), 7.85 (1H, d), 12.2 (1H, bs), 12.6 (1H, bs). HPLC-MS (Method A): m/z: 410 (M+23); Rt=3.35 min.

Example 290

General Procedure (D)

4-[2-Bromo-4-(4-oxo-2-thioxothiazolidin-5-ylidenemethyl)phenoxy]butyric acid

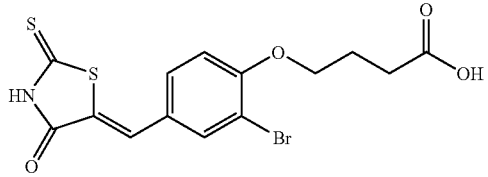

¹H-NMR (DMSO-d₆): δ 1.99 (2H, p), 2.45 (2H, t), 4.18 (2H, t), 7.28 (1H, d), 7.55 (1H, dd), 7.60 (1H, s), 7.86 (1H, d), 12.2 (1H, bs), 13.8 (1H, bs). HPLC-MS (Method A): m/z: 424 (M+23); Rt=3.84 min.
HPLC-MS (Method A): m/z: 424 (M+23); Rt=3.84 min

Example 291

General Procedure (D)

4-[4-(2,4-Dioxothiazolidin-5-ylidenemethyl)naphthalen-1-yloxy]butyric acid

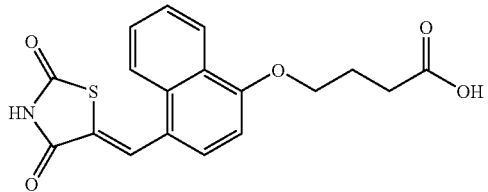

¹H-NMR (DMSO-d₆): δ 2.12 (2H, p), 2.5 (below DMSO), 4.28 (2H, t), 7.12 (1H, d), 7.6-7.7 (3H, m), 8.12 (1H, d), 8.31 (1H, d), 8.39 (1H, s), 12.2 (1H, bs, 12.6 (1H, bs). HPLC-MS (method A): m/z: 380 (M+23); Rt=3.76 min.

Example 292

General Procedure (D)

5-[4-(2,4-Dioxothiazolidin-5-ylidenemethyl)naphthalen-1-yloxy]pentanoic acid

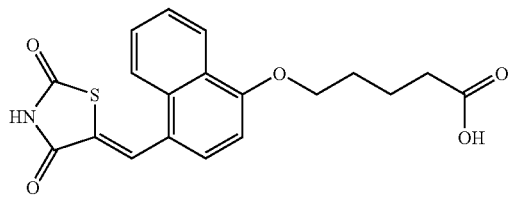

HPLC-MS (Method A): m/z: 394 (M+23); Rt=3.62 min.
¹H-NMR (DMSO-d₆): δ 1.78 (2H, m), 1.90 (2H, m), 2.38 (2H, t), 4.27 (2H, t), 7.16 (1H, d), 7.6-7.75 (3H, m), 8.13 (1H, d), 8.28 (1H, d), 8.39 (1H, s), 12.1 (1H, bs), 12.6 (1H, bs).

Example 293

5-[2-Bromo-4-(2,4-dioxothiazolidin-5-ylidenemethyl)naphthalen-1-yloxy]pentanoic acid

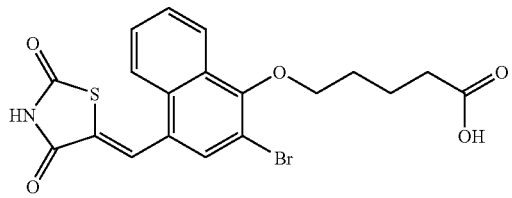

5-[4-(2,4-Dioxothiazolidin-5-ylidenemethyl)-naphthalen-1-yloxy]pentanoic acid (example 292, 185 mg, 0.5 mmol) was treated with an equimolar amount of bromine in acetic acid (10 mL). Stirring at RT for 14 days followed by evaporation to dryness afforded a mixture of the brominated compound and unchanged starting material. Purification by preparative HPLC on a C18 column using acetonitrile and water as eluent afforded 8 mg of the title compound.

HPLC-MS (Method C): m/z: 473 (M+23), Rt.=3.77 min

Example 294

4-[2-Bromo-4-(2,4-dioxothiazolidin-5-ylidenemethyl)naphthalen-1-yloxy]butyric acid

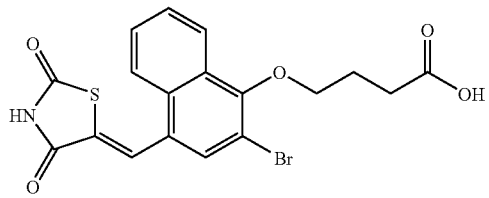

Starting with 4-[4-(2,4-dioxothiazolidin-5-ylidenemethyl)-naphthalen-1-yloxy]-butyric acid (example 291, 0.5 mmol) using the same method as in example 293 afforded 66 mg of the title compound.

HPLC-MS (Method C): m/z: 459 (M+23); Rt.=3.59 min.

Example 295

General Procedure (D)

[2-Bromo-4-(2,4-dioxothiazolidin-5-ylidenemethyl)phenoxy]acetic acid

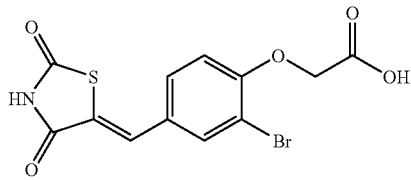

$^1$H-NMR (DMSO-$d_6$): δ 4.90 (2H, s), 7.12 (1H, d), 7.52 (1H, dd), 7.65 (1H, s) 7.84 (1H, d). HPLC-MS (Method A): m/z: not observed; Rt=2.89 min.

Example 296

General Procedure (D)

4-[3-(2,4-Dioxothiazolidin-5-ylidenemethyl)phenoxy]butyric acid

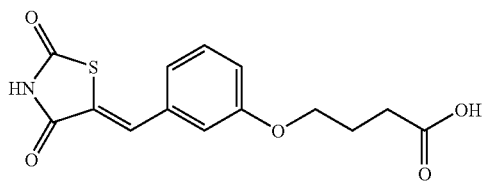

$^1$H-NMR (DMSO-$d_6$): δ 1.98 (2H, p), 2.42 (2H, t), 4.04 (2H, t), 7.05 (1H, dd), 7.15 (2H, m), 7.45 (1H, t), 7.77 (1H, s), 12.1 (1H, bs), 12.6 (1H, bs). HPLC-MS (Method A): m/z: 330 (M+23); Rt=3.05 min.

Example 297

General Procedure (D)

[4-(2,4-Dioxothiazolidin-5-ylidenemethyl)-3-methoxyphenoxy]acetic acid

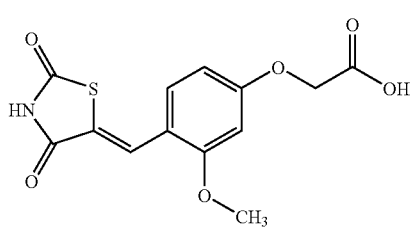

HPLC-MS (Method B): m/z: 310 (M+1); Rt=3.43 min.

Example 298

General Procedure (D)

[4-(2,4-Dioxothiazolidin-5-ylidenemethyl)naphthalen-1-yloxy]acetic acid

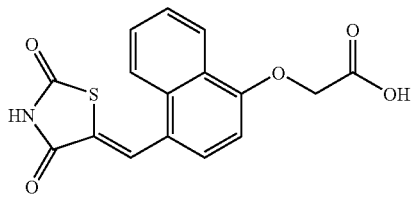

HPLC-MS (Method A): m/z: 330 (M+1); Rt=3.25 min.

Example 299

General Procedure (D)

8-(2,4-Dioxothiazolidin-5-ylidenemethyl)naphthalene-1-carboxylic acid

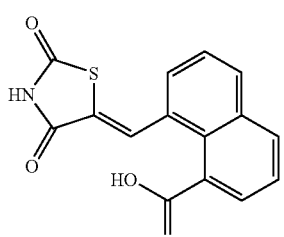

HPLC-MS (Method A): m/z: 299 (M+1); Rt=2.49 min.

Example 300

General Procedure (D)

[3-(2,4-Dioxothiazolidin-5-ylidenemethyl)indol-1-yl]acetic acid

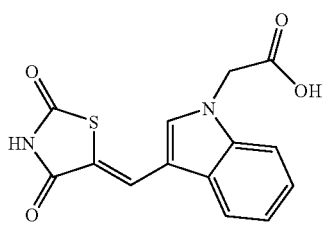

HPLC-MS (Method A): m/z: 303 (M+1); Rt=2.90 min.

Preparation of Starting Material:

3-Formylindol (10 g, 69 mmol) was dissolved in N,N-dimethylformamide (100 mL) and under an atmosphere of nitrogen and with external cooling, keeping the temperature below 15° C., sodium hydride (60% in mineral oil, 3.0 g, 76 mmol) was added in portions. Then a solution of ethyl bromoacetate (8.4 mL, 76 mmol) in N,N-dimethylformamide (15 mL) was added dropwise over 30 minutes and the resulting mixture was stirred at room temperature for 16 hours. The mixture was concentrated in vacuo and the residue was partitioned between water (300 mL) and ethyl acetate (2×150 mL). The combined organic extracts were washed with a saturated aqueous solution of ammonium chloride (100 mL), dried (MgSO$_4$) and concentrated in vacuo to afford 15.9 g (quant.) of (3-formylindol-1-yl)acetic acid ethyl ester as an oil.

$^1$H-NMR (CDCl$_3$): $\delta_H$=1.30 (3H, t), 4.23 (2H, q), 4.90 (2H, s), 7.3 (3H, m), 7.77 (1H, s), 8.32 (1H, d), 10.0 (1H, s).

(3-Formylindol-1-yl)acetic acid ethyl ester (15.9 g 69 mmol) was dissolved in 1,4-dioxane (100 mL) and 1N sodium hydroxide (10 mL) was added and the resulting mixture was stirred at room temperature for 4 days. Water (500 mL) was added and the mixture was washed with diethyl ether (150 mL). The aqueous phase was acidified with 5N hydrochloric acid and extracted with ethyl acetate (250+150 mL). The combined organic extracts were dried (MgSO$_4$) and concentrated in vacuo to afford 10.3 g (73%) of (3-formylindol-1-yl)acetic acid as a solid.

$^1$H-NMR (DMSO-d$_6$): $\delta_H$=5.20 (2H, s), 7.3 (2H, m), 7.55 (1H, d), 8.12 (1H, d), 8.30 (1H, s), 9.95 (1H, s), 13.3 (1H, bs).

Example 301

General Procedure (D)

3-[3-(2,4-Dioxothiazolidin-5-ylidenemethyl)indol-1-yl]propionic acid

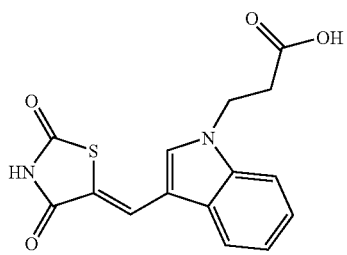

HPLC-MS (Method A): m/z: 317 (M+1); Rt=3.08 min.

Preparation of Starting Material:

A mixture of 3-formylindol (10 g, 69 mmol), ethyl 3-bromopropionate (10.5 mL, 83 mmol) and potassium carbonate (28.5 g, 207 mmol) and acetonitrile (100 mL) was stirred vigorously at refux temperature for 2 days. After cooling, the mixture was filtered and the filtrate was concentrated in vacuo to afford 17.5 g (quant.) of 3-(3-formylindol-1-yl)propionic acid ethyl ester as a solid.

$^1$H-NMR (DMSO-d$_6$): $\delta_H$=1.10 (3H, t), 2.94 (2H, t), 4.02 (2H, q), 4.55 (2H, t), 7.3 (2H, m), 7.67 (1H, d), 8.12 (1H, d), 8.30 (1H, s), 9.90 (1H, s).

3-(3-Formylindol-1-yl)propionic acid ethyl ester (17.5 g 69 mmol) was hydrolysed as described above to afford 12.5 g (83%) of 3-(3-formylindol-1-yl)propionic acid as a solid.

$^1$H-NMR (DMSO-d$_6$): $\delta_H$=2.87 (2H, t), 4.50 (2H, t), 7.3 (2H, m), 7.68 (1H, d), 8.12 (1H, d), 8.31 (1H, s), 9.95 (1H, s), 12.5 (1H, bs).

Example 302

General Procedure (D)

{5-[4-(2,4-Dioxothiazolidin-5-ylidenemethyl)benzylidene]-4-oxo-2-thioxothiazolidin-3-yl}acetic acid

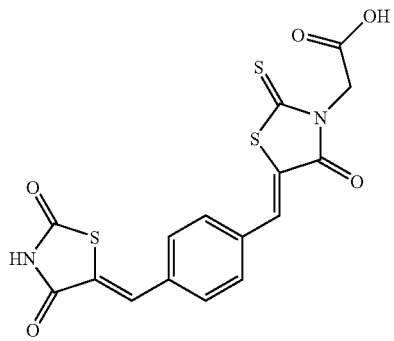

HPLC-MS (Method A): m/z: 429 (M+23); Rt=3.89 min.

Example 303

General Procedure (D)

6-(2,4-Dioxothiazolidin-5-ylidenemethyl)naphthalen-2-yloxyoctanoic acid

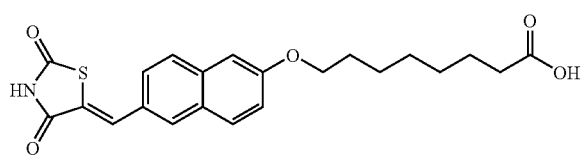

HPLC-MS (Method C): m/z: 436 (M+23); Rt.=4.36 min

The intermediate aldehyde for this compound was prepared by a slightly modified procedure: 6-Hydroxynaphthalene-2-carbaldehyde (1.0 g, 5.8 mmol) was dissolved in DMF (10 mL) and sodium hydride 60% (278 mg) was added and the mixture stirred at RT for 15 min. 8-Bromooctanoic acid (0.37 g, 1.7 mmol) was converted to the sodium salt by addition of sodium hydride 60% and added to an aliquot (2.5 mL) of the above naphtholate solution and the resulting mixture was stirred at RT for 16 hours. Aqueous acetic acid (10%) was added and the mixture was extracted 3 times with diethyl ether. The combined organic phases were dried with MgSO$_4$ and evaporated to dryness affording 300 mg of 8-(6-formylnaphthalen-2-yloxy)octanoic acid.

HPLC-MS (Method C): m/z 315 (M+1); Rt.=4.24 min.

Example 304

General Procedure (D)

12-[6-(2,4-Dioxothiazolidin-5-ylidenemethyl)naphthalen-2-yloxy]dodecanoic acid

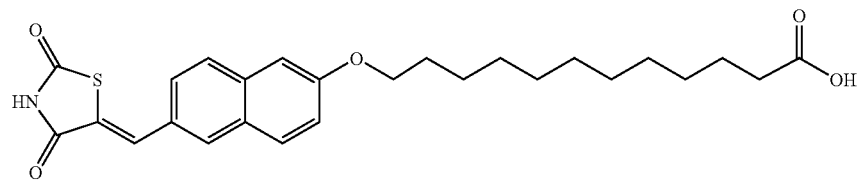

HPLC-MS (Method C): m/z: 492 (M+23); Rt.=5.3 min.
The intermediate aldehyde was prepared similarly as described in example 303.

Example 305

General Procedure (D)

11-[6-(2,4-Dioxothiazolidin-5-ylidenemethyl)naphthalen-2-yloxy]undecanoic acid

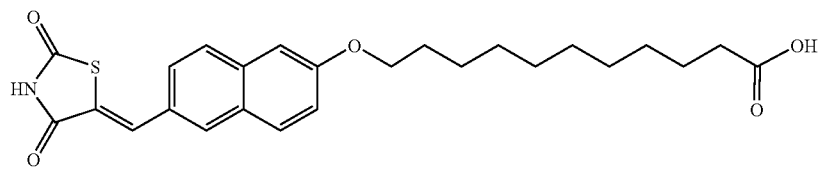

HPLC-MS (Method C): m/z: 478 (M+23); Rt.=5.17 min.
The intermediate aldehyde was prepared similarly as described in example 303.

Example 306

General Procedure (D)

15-[6-(2,4-Dioxothiazolidin-5-ylidenemethyl)naphthalen-2-yloxy]pentadecanoic acid

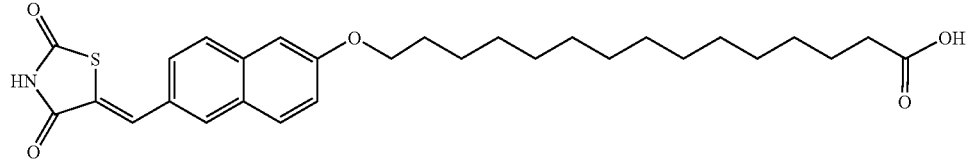

HPLC-MS (Method C): m/z: 534 (M+23); Rt.=6.07 min.
The intermediate aldehyde was prepared similarly as described in example 303.

Example 307

General Procedure (D)

6-[6-(2,4-Dioxothiazolidin-5-ylidenemethyl)naphthalen-2-yloxy]hexanoic acid

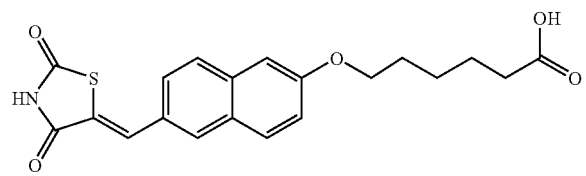

HPLC-MS (Method C): m/z: 408 (M+23); Rt.=3.71 min.

Example 308

General Procedure (D)

4-[6-(2,4-Dioxothiazolidin-5-ylidenemethyl)naphthalen-2-yloxy]butyric acid

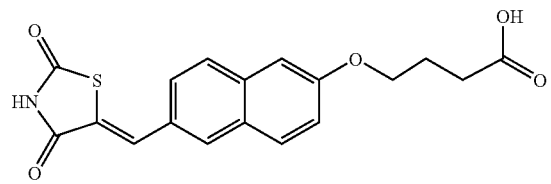

HPLC-MS (Method C): m/z: 380 (M+23); Rt.=3.23 min.

Example 309

General Procedure (D)

6-[6-(2,4-Dioxothiazolidin-5-ylidenemethyl)naphthalen-2-yloxy]hexanoic acid ethyl ester

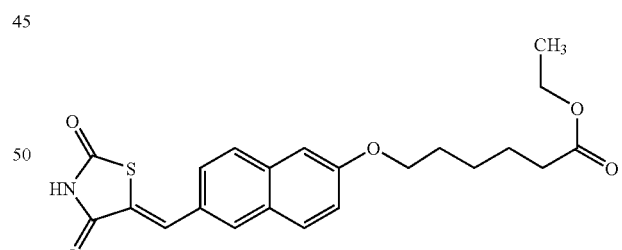

HPLC-MS (Method C): m/z: 436 (M+23); Rt.=4.64 min.

Example 310

General Procedure (D)

4-[6-(2,4-Dioxothiazolidin-5-ylidenemethyl)naphthalen-2-yloxy]butyric acid ethyl ester

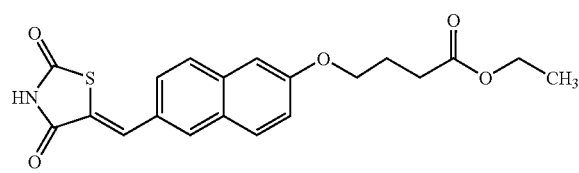

HPLC-MS (Method C): m/z: 408 (M+23); Rt.=4.28 min.

Example 311

N-(3-Aminopropyl)-4-[4-(2,4-dioxothiazolidin-5-ylidenemethyl)-naphthalen-1-yloxy]-butyramide

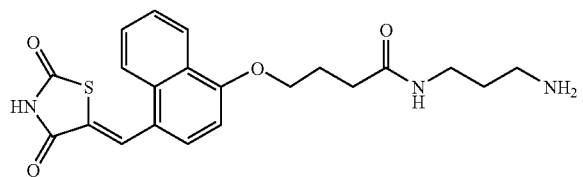

To a mixture of 4-[4-(2,4-dioxothiazolidin-5-ylidenemethyl)naphthalen-1-yloxy]butyric acid (example 291, 5.9 g, 16.5 mmol) and 1-hydroxybenzotriazole (3.35 g, 24.8 mmol) in DMF (60 mL) was added 1-ethyl-3-(3'-dimethylaminopropyl)carbodiimide hydrochloride (4.75 g, 24.8 mmol) and the resulting mixture was stirred at room temperature for 2 hours. N-(3-aminopropylcarbamic acid tert-butyl ester (3.45 g, 19.8 mmol) was added and the resulting mixture was stirred at room temperature for 16 hours. The mixture was concentrated in vacuo and ethyl acetate and dichloromethane were added to the residue. The mixture was filtered, washed with water and dried in vacuo to afford 4.98 g (59%) of (3-{4-[4-(2,4-dioxothiazolidin-5-ylidenemethyl)naphthalen-1-yloxy]butyrylamino}propyl)carbamic acid tert-butyl ester.

HPLC-MS (Method C): m/z: 515 (M+1); Rt=3.79 min.

(3-{4-[4-(2,4-Dioxothiazolidin-5-ylidenemethyl)naphthalen-1-yloxy]butyrylamino}-propyl)carbamic acid tert-butyl ester (4.9 g, 9.5 mmol) was added dichloromethane (50 mL) and trifluoroacetic acid (50 mL) and the resulting mixture was stirred at room temperature for 45 minutes. The mixture was concentrated in vacuo and co-evaporated with toluene. To the residue was added ethyl acetate (100 mL) and the mixture was filtered and dried in vacuo to afford the title compound as the trifluoroacetic acid salt.

HPLC-MS (Method C): m/z: 414 (M+1); Rt=2.27 min.

Preferred Compounds of the Invention Includes:

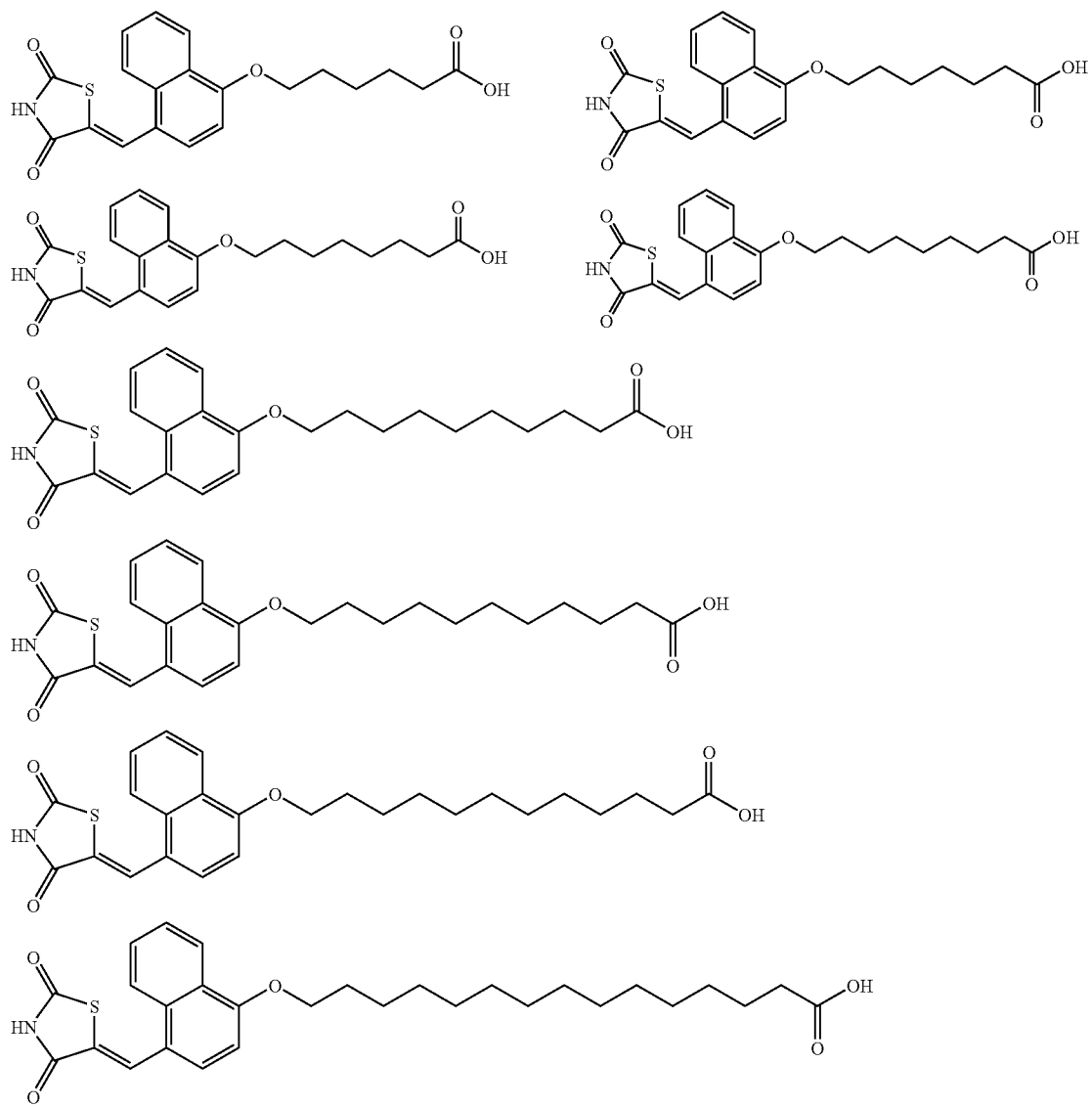

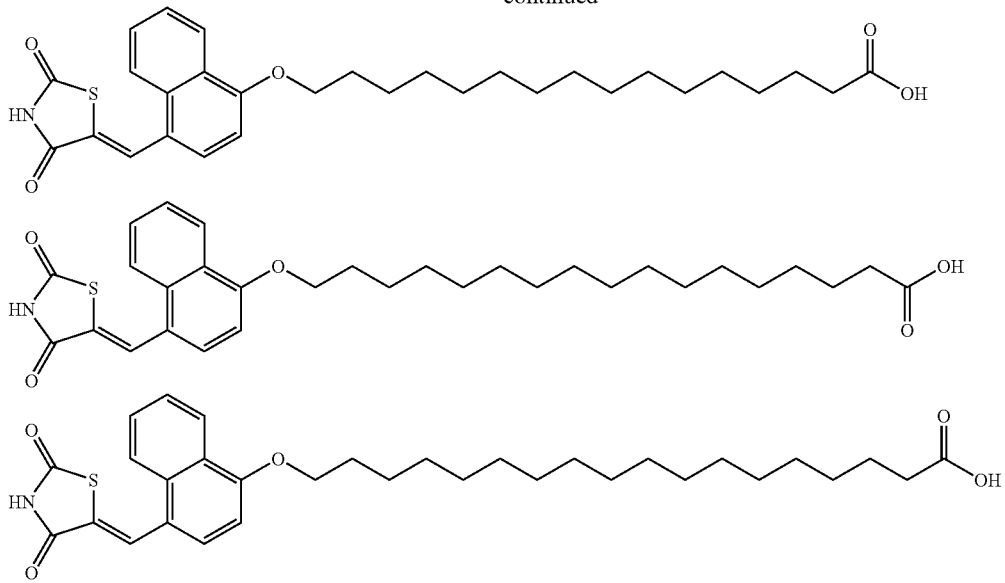
The following compounds are commercially available and may be prepared according to general procedure (D):
Example 312
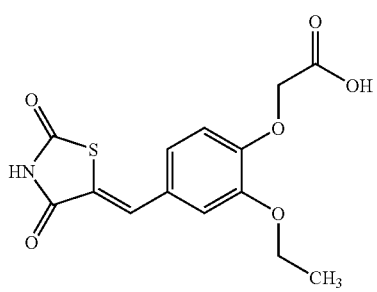
Example 313
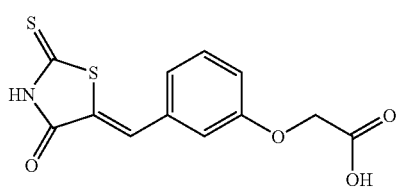
Example 314
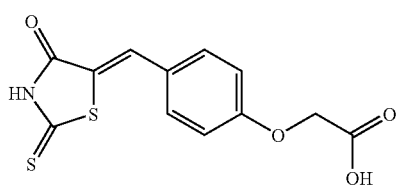
Example 315
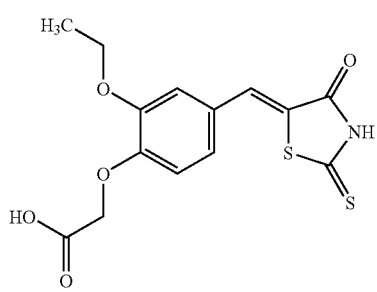
Example 316
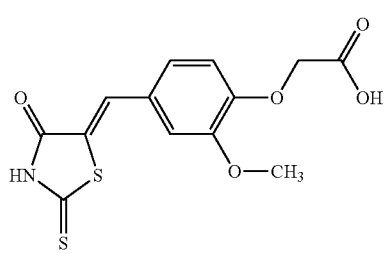
Example 317
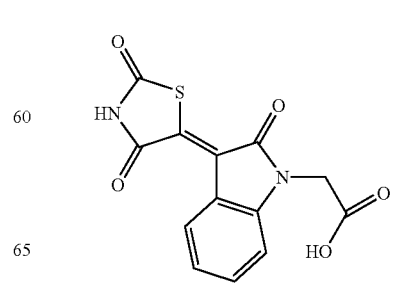

Example 318

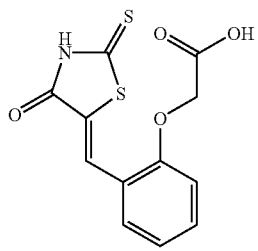

The following salicylic acid derivatives do all bind to the His B10 $Zn^{2+}$ site of the insulin hexamer:

Example 319

Salicylic Acid

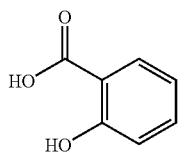

Example 320

Thiosalicylic Acid (or: 2-Mercaptobenzoic acid)

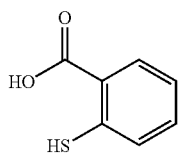

Example 321

2-Hydroxy-5-nitrobenzoic acid

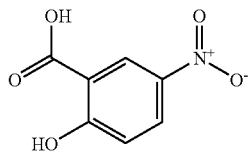

Example 322

3-Nitrosalicyclic acid

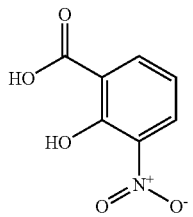

Example 323

5,5'-Methylenedisalicylic acid

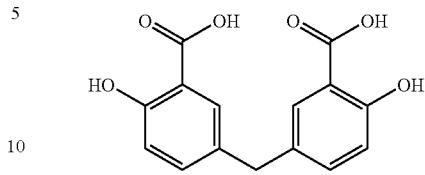

Example 324

2-Amino-5-trifluoromethylbenzoesyre

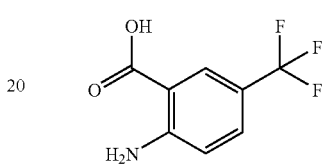

Example 325

2-Amino-4-chlorobenzoic acid

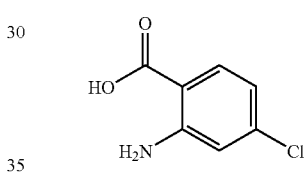

Example 326

2-Amino-5-methoxybenzoesyre

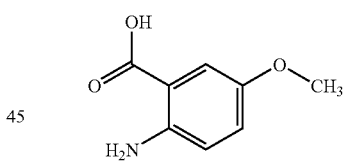

Example 327

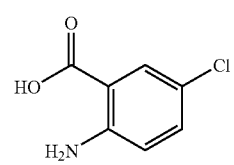

Example 328

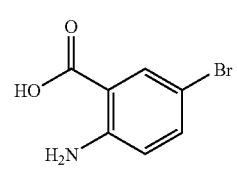

143
Example 329
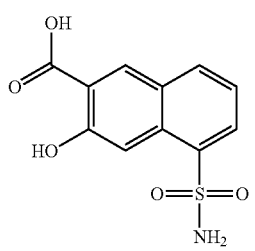
Example 330
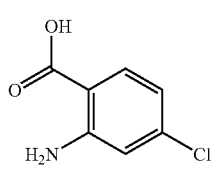
Example 331
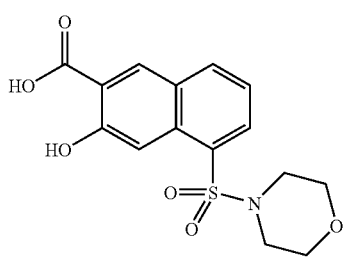
Example 332
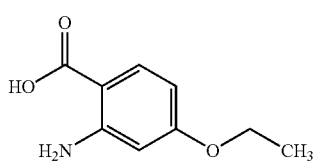
Example 333
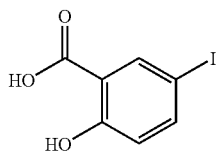
144
Example 334
5-Chlorosalicylic acid
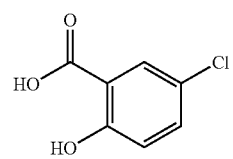
Example 335
1-Hydroxy-2-naphthoic acid
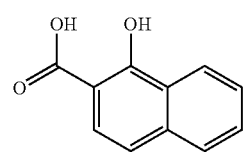
Example 336
3,5-Dihydroxy-2-naphthoic acid
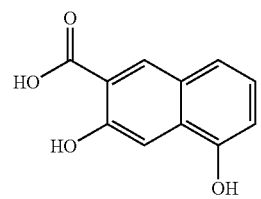
Example 337
3-Hydroxy-2-naphthoic acid
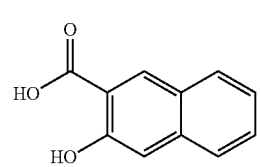
Example 338
3,7-Dihydroxy-2-naphthoic acid
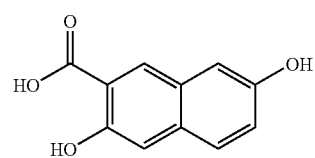

Example 339

2-Hydroxybenzo[a]carbazole-3-carboxylic acid

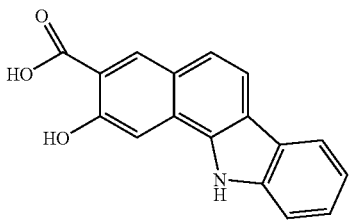

Example 340

7-Bromo-3-hydroxy-2-naphthoic acid

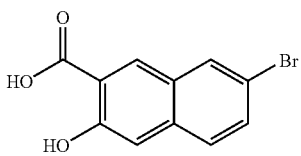

This compound was prepared according to Murphy et al., *J. Med. Chem.* 1990, 33, 171-8.
HPLC-MS (Method A): m/z: 267 (M+1), Rt:=3.78 min.

Example 341

1,6-Dibromo-2-hydroxynaphthalene-3-carboxylic acid

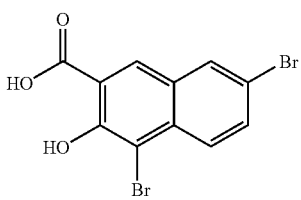

This compound was prepared according to Murphy et al., *J. Med. Chem.* 1990, 33, 171-8. HPLC-MS (Method A): m/z: 346 (M+1); Rt:=4.19 min.

Example 342

7-Formyl-3-hydroxynaphthalene-2-carboxylic acid

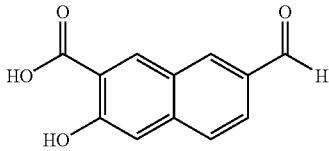

A solution of 7-bromo-3-hydroxynaphthalene-2-carboxylic acid (15.0 g, 56.2 mmol) (example 340) in tetrahydrofuran (100 mL) was added to a solution of lithium hydride (893 mg, 112 mmol) in tetrahydrofuran (350 mL). After 30 minutes stirring at room temperature, the resulting solution was heated to 50° C. for 2 minutes and then allowed to cool to ambient temperature over a period of 30 minutes. The mixture was cooled to −78° C., and butyllithium (1.6 M in hexanes, 53 mL, 85 mmol) was added over a period of 15 minutes. N,N-Dimethylformamide (8.7 mL, 8.2 g, 112 mmol) was added after 90 minutes additional stirring. The cooling was discontinued, and the reaction mixture was stirred at room temperature for 17 hours before it was poured into 1 N hydrochloric acid (aq.) (750 mL). The organic solvents were evaporated in vacuo, and the resulting precipitate was filtered off and rinsed with water (3×100 mL) to yield the crude product (16.2 g). Purification on silica gel (dichloromethane/methanol/acetic acid=90:9:1) furnished the title compound as a solid.

$^1$H-NMR (DMSO-$d_6$): δ 11.95 (1H, bs), 10.02 (1H, s), 8.61 (1H, s), 8.54 (1H, s), 7.80 (2H, bs), 7.24 (1H, s); HPLC-MS (Method (A)): m/z: 217 (M+1); Rt=2.49 min.

Example 343

3-Hydroxy-7-methoxy-2-naphthoic acid

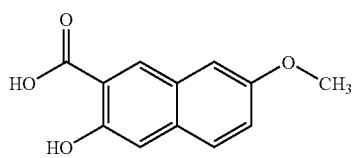

Example 344

4-Amino-2-hydroxybenzoic acid

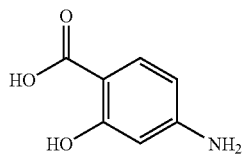

Example 345

5-Acetylamino-2-hydroxybenzoic acid

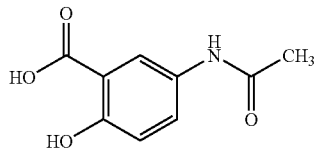

Example 346

2-Hydroxy-5-methoxybenzoic acid

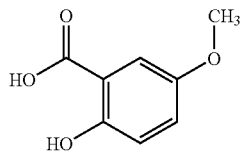

The following compounds were prepared as described below:

Example 347

4-Bromo-3-hydroxynaphthalene-2-carboxylic acid

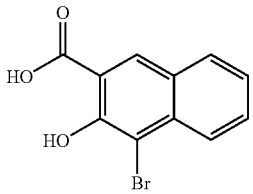

3-Hydroxynaphthalene-2-carboxylic acid (3.0 g, 15.9 mmol) was suspended in acetic acid (40 mL) and with vigorous stirring a solution of bromine (817 µL, 15.9 mmol) in acetic acid (10 mL) was added drop wise during 30 minutes. The suspension was stirred at room temperature for 1 hour, filtered and washed with water. Drying in vacuo afforded 3.74 g (88%) of 4-bromo-3-hydroxynaphthalene-2-carboxylic acid as a solid.

$^1$H-NMR (DMSO-$d_6$): δ 7.49 (1H, t), 7.75 (1H, t), 8.07 (2H, "t"), 8.64 (1H, s). The substitution pattern was confirmed by a COSY experiment, showing connectivities between the 3 (4 hydrogen) "triplets". HPLC-MS (Method A): m/z: 267 (M+1); Rt=3.73 min.

Example 348

3-Hydroxy-4-iodonaphthalene-2-carboxylic acid

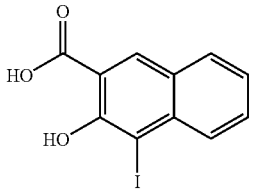

3-Hydroxynaphthalene-2-carboxylic acid (0.5 g, 2.7 mmol) was suspended in acetic acid (5 mL) and with stirring iodine monochloride (135 µL, 2.7 mml) was added. The suspension was stirred at room temperature for 1 hour, filtered and washed with water. Drying afforded 0.72 g (85%) of 4-iodo-3-hydroxynaphthalene-2-carboxylic acid as a solid.

$^1$H-NMR (DMSO-$d_6$): δ 7.47 (1H, t), 7.73 (1H, t), 7.98 (1H, d), 8.05 (1H, d), 8.66 (1H, s). HPLC-MS (Method A): m/z: 315 (M+1); Rt=3.94 min.

Example 349

2-Hydroxy-5-[(4-methoxyphenylamino)methyl]benzoic acid

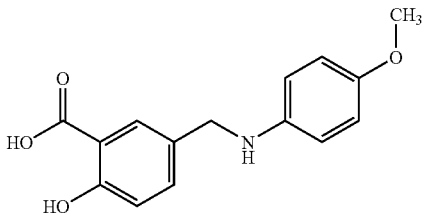

p-Anisidine (1.3 g, 10.6 mmol) was dissolved in methanol (20 mL) and 5-formylsalicylic acid (1.75 g, 10.6 mmol) was added and the resulting mixture was stirred at room temperature for 16 hours. The solid formed was isolated by filtration, re-dissolved in N-methyl pyrrolidone (20 mL) and methanol (2 mL). To the mixture was added sodium cyanoborohydride (1.2 g) and the mixture was heated to 70° C. for 3 hours. To the cooled mixture was added ethyl acetate (100 mL) and the mixture was extracted with water (100 mL) and saturated aqueous ammonium chloride (100 mL). The combined aqueous phases were concentrated in vacuo and a 2 g aliquot was purified by SepPac chromatography eluting with mixtures of aetonitrile and water containing 0.1% trifluoroacetic acid to afford the title compound.

HPLC-MS (Method A): m/z: 274 (M+1); Rt=1.77 min.

$^1$H-NMR (methanol-$d_4$): δ 3.82 (3H, s), 4.45 (2H, s), 6.96 (1H, d), 7.03 (2H, d), 7.23 (2H, d), 7.45 (1H, dd), 7.92 (1H, d).

Example 350

2-Hydroxy-5-(4-methoxyphenylsulfamoyl)benzoic acid

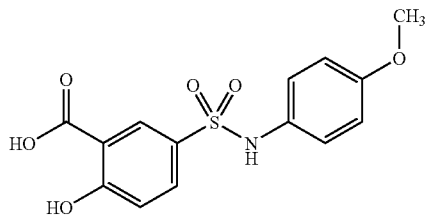

A solution of 5-chlrosulfonylsalicylic acid (0.96 g, 4.1 mmol) in dichloromethane (20 mL) and triethylamine (1.69 mL, 12.2 mmol) was added p-anisidine (0.49 g, 4.1 mmol) and the resulting mixture was stirred at room temperature for 16 hours. The mixture was added dichloromethane (50 mL) and was washed with water (2×100 mL). Drying (MgSO$_4$) of the organic phase and concentration in vacuo afforded 0.57 g crude product. Purification by column chromatography on silica gel eluting first with ethyl acetate:heptane (1:1) then with methanol afforded 0.1 g of the title compound.

HPLC-MS (Method A): m/z: 346 (M+23); Rt=2.89 min.

$^1$H-NMR (DMSO-$d_6$): δ 3.67 (3H, s), 6.62 (1H, d), 6.77 (2H, d), 6.96 (2H, d), 7.40 (1H, dd), 8.05 (1H, d), 9.6 (1H, bs).

General Procedure (E) for Preparation of Compounds of General Formula I$_4$:

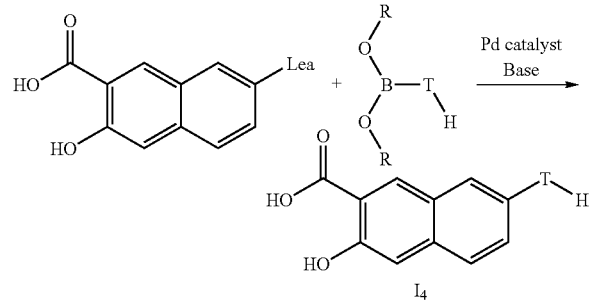

wherein Lea is a leaving group such as Cl, Br, I or OSO$_2$CF$_3$, R is hydrogen or C$_1$-C$_6$-alkyl, optionally the two R-groups may together form a 5-8 membered ring, a cyclic boronic acid ester, and T is as defined above.

An analogous chemical transformation has previously been described in the literature (Bumagin et al., *Tetrahedron*, 1997, 53, 14437-14450). The reaction is generally known as the Suzuki coupling reaction and is generally performed by reacting an aryl halide or triflate with an arylboronic acid or a heteroarylboronic acid in the presence of a palladium catalyst and a base such as sodium acetate, sodium carbonate or sodium hydroxide. The solvent can be water, acetone, DMF, NMP, HMPA, methanol, ethanol toluene or a mixture of two or more of these solvents. The reaction is performed at room temperature or at elevated temperature.

The general procedure (E) is further illustrated in the following example:

Example 351

General Procedure (E)

7-(4-Acetylphenyl)-3-hydroxynaphthalene-2-carboxylic acid

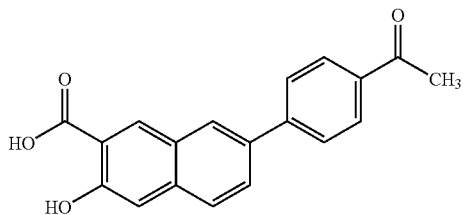

To 7-bromo-3-hydroxynaphthalene-2-carboxylic acid (100 mg, 0.37 mmol) (example 340) was added a solution of 4-acetylphenylboronic acid (92 mg, 0.56 mmol) in acetone (2.2 mL) followed by a solution of sodium carbonate (198 mg, 1.87 mmol) in water (3.3 mL). A suspension of palladium (II) acetate (4 mg, 0.02 mmol) in acetone (0.5 mL) was filtered and added to the above solution. The mixture was purged with $N_2$ and stirred vigorously for 24 hours at room temperature. The reaction mixture was poured into 1 N hydrochloric acid (aq.) (60 mL) and the precipitate was filtered off and rinsed with water (3×40 mL). The crude product was dissolved in acetone (25 mL) and dried with magnesium sulfate (1 h). Filtration followed by concentration furnished the title compound as a solid (92 mg). $^1$H-NMR (DMSO-$d_6$): δ 12.60 (1H, bs), 8.64 (1H, s), 8.42 (1H, s), 8.08 (2H, d), 7.97 (2H, d), 7.92 (2H, m), 7.33 (1H, s), 2.63 (3H, s); HPLC-MS (Method (A): m/z: 307 (M+1); Rt=3.84 min.

The compounds in the following examples were prepared in a similar fashion. Optionally, the compounds can be further purified by recrystallization from e.g. ethanol or by chromatography.

Example 352

General Procedure (E)

3-Hydroxy-7-(3-methoxyphenyl)naphthalene-2-carboxylic acid

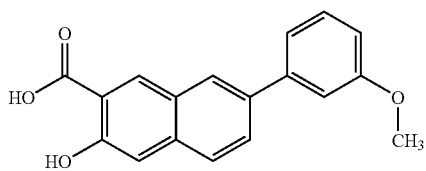

HPLC-MS (Method (A)): m/z: 295 (M+1); Rt=4.60 min.

Example 353

General Procedure (E)

3-Hydroxy-7-phenylnaphthalene-2-carboxylic acid

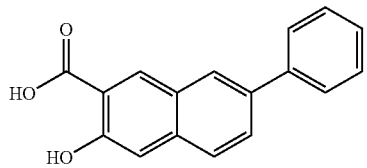

HPLC-MS (Method (A)): m/z: 265 (M+1); Rt=4.6 min.

Example 354

General Procedure (E)

3-Hydroxy-7-p-tolylnaphthalene-2-carboxylic acid

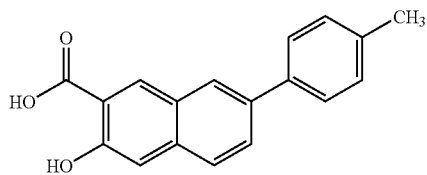

HPLC-MS (Method (A)): m/z: 279 (M+1); Rt=4.95 min.

Example 355

General Procedure (E)

7-(4-Formylphenyl)-3-hydroxynaphthalene-2-carboxylic acid

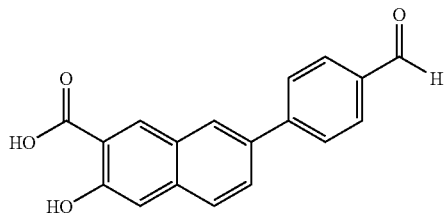

HPLC-MS (Method (A)): m/z: 293 (M+1); Rt=4.4 min.

Example 356

General Procedure (E)

6-Hydroxy-[1,2]binaphthalenyl-7-carboxylic acid

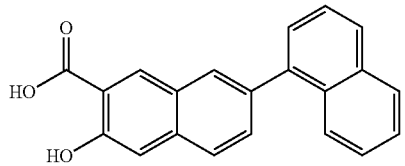

HPLC-MS (Method (A)): m/z: 315 (M+1); Rt=5.17 min.

Example 357

General Procedure (E)

7-(4-Carboxy-phenyl)-3-hydroxynaphthalene-2-carboxylic acid

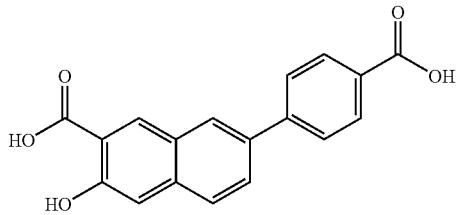

HPLC-MS (Method (A)): m/z: 309 (M+1); Rt=3.60 min.

Example 358

General Procedure (E)

7-Benzofuran-2-yl-3-hydroxynaphthalene-2-carboxylic acid

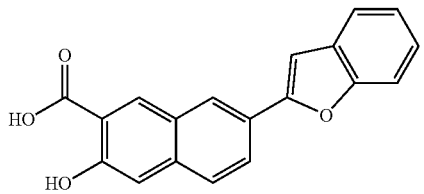

HPLC-MS (Method (A)): m/z: 305 (M+1); Rt=4.97 min.

Example 359

General Procedure (E)

3-Hydroxy-7-(4-methoxyphenyl)-naphthalene-2-carboxylic acid

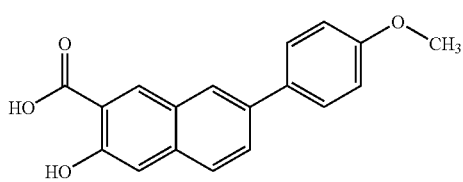

HPLC-MS (Method (A)): m/z: 295 (M+1); Rt=4.68 min.

Example 360

General Procedure (E)

7-(3-Ethoxyphenyl)-3-hydroxynaphthalene-2-carboxylic acid

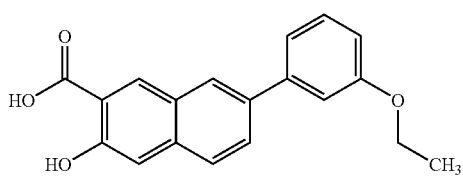

HPLC-MS (Method (A)): m/z: 309 (M+1); Rt=4.89 min.

Example 361

General Procedure (E)

7-Benzo[1,3]dioxol-5-yl-3-hydroxynaphthalene-2-carboxylic acid

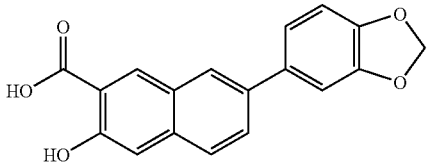

HPLC-MS (Method (A)): m/z: 309 (M+1); Rt=5.61 min.

Example 362

General Procedure (E)

7-Biphenyl-3-yl-3-hydroxynaphthalene-2-carboxylic acid

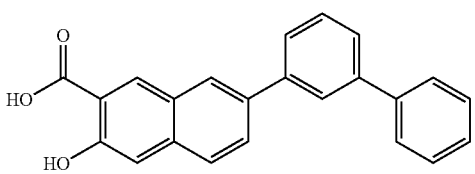

HPLC-MS (Method (A)): m/z: 341 (M+1); Rt=5.45 min.

General Procedure (F) for Preparation of Compounds of General Formula $I_5$:

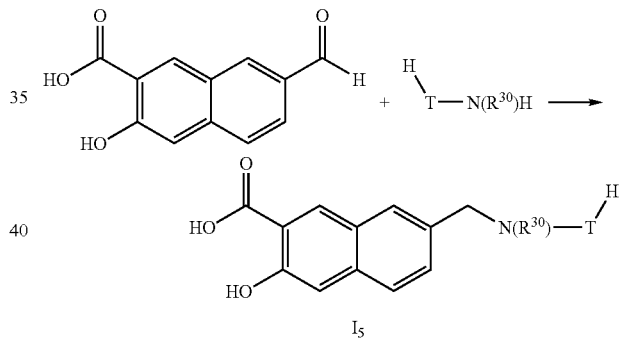

wherein $R^{30}$ is hydrogen or $C_1$-$C_6$-alkyl and T is as defined above

This general procedure (F) is further illustrated in the following example:

Example 363

General Procedure (F)

3-Hydroxy-7-[(4-(2-propyl)phenylamino)methyl]naphthalene-2-carboxylic acid

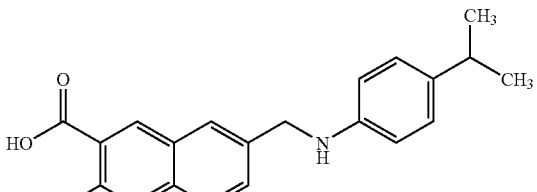

7-Formyl-3-hydroxynaphthalene-2-carboxylic acid (40 mg, 0.19 mmol) (example 342) was suspended in methanol (300 µL). Acetic acid (16 µL, 17 mg, 0.28 mmol) and 4-(2- propyl)aniline (40 μL, 40 mg, 0.30 mmol) were added consecutively, and the resulting mixture was stirred vigorously at room temperature for 2 hours. Sodium cyanoborohydride (1.0 M in tetrahydrofuran, 300 μL, 0.3 mmol) was added, and the stirring was continued for another 17 hours. The reaction mixture was poured into 6 N hydrochloric acid (aq.) (6 mL), and the precipitate was filtered off and rinsed with water (3×2 mL) to yield the title compound (40 mg) as its hydrochloride salt. No further purification was necessary.

$^1$H-NMR (DMSO-$d_6$): δ 10.95 (1H, bs), 8.45 (1H, s), 7.96 (1H, s), 7.78 (1H, d), 7.62 (1H, d), 7.32 (1H, s), 7.13 (2H, bd), 6.98 (2H, bd), 4.48 (2H, s), 2.79 (1H, sept), 1.14 (6H, d); HPLC-MS (Method (A)): m/z: 336 (M+1); Rt=3.92 min.

The compounds in the following examples were made using this general procedure (F).

Example 364

General Procedure (F)

7-{[(4-Bromophenyl)amino]methyl}-3-hydroxynaphthalene-2-carboxylic acid

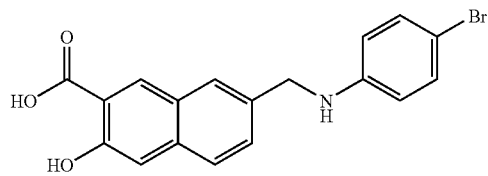

HPLC-MS (Method C): m/z: 372 (M+1); Rt=4.31 min.

Example 365

General Procedure (F)

7-{[(3,5-Dichlorophenyl)amino]methyl}-3-hydroxynaphthalene-2-carboxylic acid

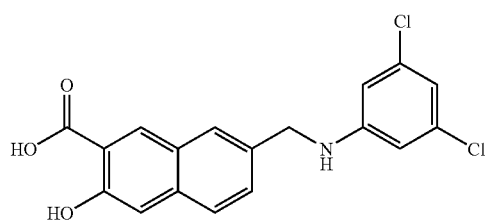

HPLC-MS (Method C): m/z: 362 (M+1); Rt=4.75 min.

Example 366

General Procedure (F)

7-{[(Benzothiazol-6-yl)amino]methyl}-3-hydroxynaphthalene-2-carboxylic acid

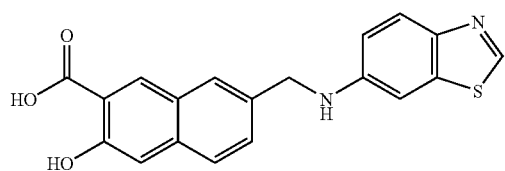

HPLC-MS (Method C): m/z 351 (M+1); Rt=3.43 min.

Example 367

General Procedure (F)

3-Hydroxy-7-{[(quinolin-6-yl)amino]methyl}naphthalene-2-carboxylic acid

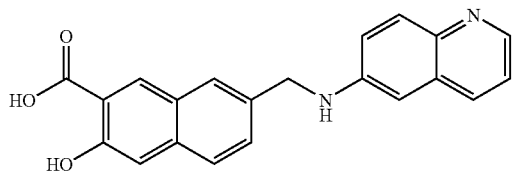

HPLC-MS (Method C): m/z: 345 (M+1); Rt=2.26 min.

Example 368

General Procedure (F)

3-Hydroxy-7-{[(4-methoxyphenyl)amino]methyl}naphthalene-2-carboxylic acid

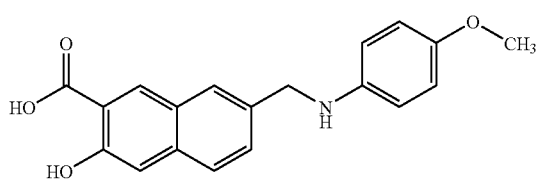

HPLC-MS (Method C): m/z: 324 (M+1); Rt=2.57 min.

Example 369

General Procedure (F)

7-{[(2,3-Dihydrobenzofuran-5-ylmethyl)amino]methyl}-3-hydroxynaphthalene-2-carboxylic acid

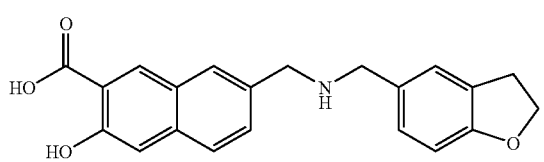

HPLC-MS (Method C): m/z: 350 (M+1); Rt=2.22 min.

Example 370

General Procedure (F)

7-{[(4-Chlorobenzyl)amino]methyl}-3-hydroxynaphthalene-2-carboxylic acid

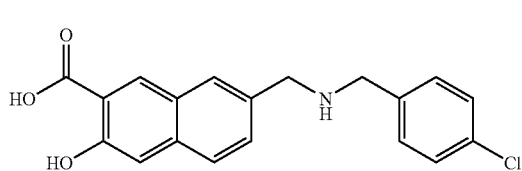

HPLC-MS (Method C): m/z: 342 (M+1); Rt=2.45 min.

Example 371

General Procedure (F)

3-Hydroxy-7-{[(naphthalen-1-ylmethyl)amino]methyl}naphthalene-2-carboxylic acid

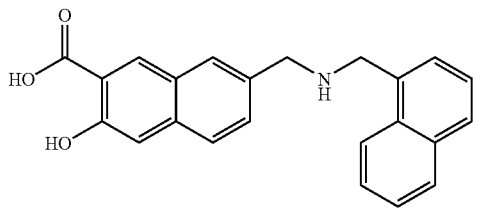

HPLC-MS (Method C): m/z: 357 (M+1); Rt=2.63 min.

Example 372

General Procedure (F)

7-{[(Biphenyl-2-ylmethyl)amino]methyl}-3-hydroxynaphthalene-2-carboxylic acid

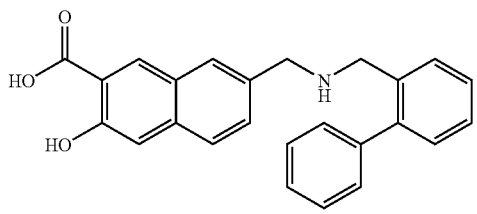

HPLC-MS (Method C): m/z: 384 (M+1); Rt=2.90 min.

Example 373

General Procedure (F)

3-Hydroxy-7-{[(4-phenoxybenzyl)amino]methyl}naphthalene-2-carboxylic acid

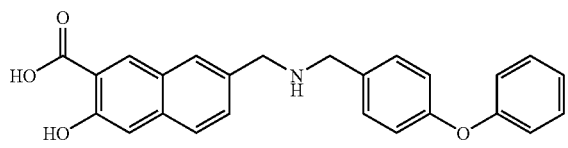

HPLC-MS (Method C): m/z: 400 (M+1); Rt=3.15 min.

Example 374

General Procedure (F)

3-Hydroxy-7-{[(4-methoxybenzyl)amino]methyl}naphthalene-2-carboxylic acid

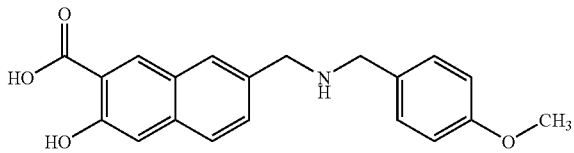

HPLC-MS (Method C): m/z: 338 (M+1); Rt=2.32 min.

General Procedure (G) for Preparation of Compounds of General Formula $I_6$:

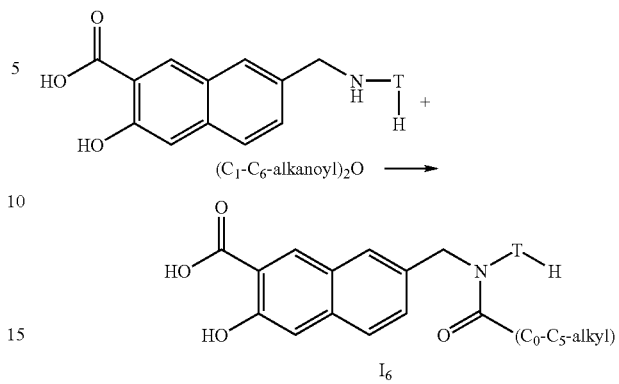

wherein T is as defined above and the moiety $(C_1-C_6\text{-alkanoyl})_2O$ is an anhydride.

The general procedure (G) is illustrated by the following example:

Example 375

General Procedure (G)

N-Acetyl-3-hydroxy-7-[(4-(2-propyl)phenylamino)methyl]naphthalene-2-carboxylic acid

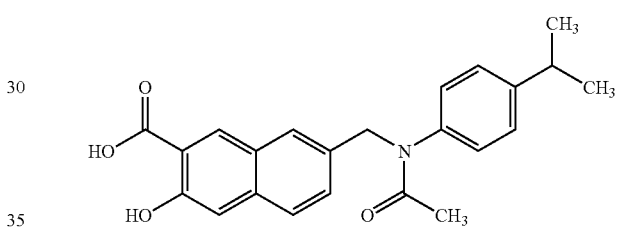

3-Hydroxy-7-[(4-(2-propyl)phenylamino)methyl]naphthalene-2-carboxylic acid (25 mg, 0.07 mmol) (example 363) was suspended in tetrahydrofuran (200 μL). A solution of sodium hydrogencarbonate (23 mg, 0.27 mmol) in water (200 μL) was added followed by acetic anhydride (14 μL, 15 mg, 0.15 mmol). The reaction mixture was stirred vigorously for 65 hours at room temperature before 6 N hydrochloric acid (4 mL) was added. The precipitate was filtered off and rinsed with water (3×1 mL) to yield the title compound (21 mg). No further purification was necessary.

$^1$H-NMR (DMSO-$d_6$): δ 10.96 (1H, bs), 8.48 (1H, s), 7.73 (1H, s), 7.72 (1H, d), 7.41 (1H, dd), 7.28 (1H, s), 7.23 (2H, d), 7.18 (2H, d), 4.96 (2H, s), 2.85 (1H, sept), 1.86 (3H, s), 1.15 (6H, d); HPLC-MS (Method (A)): m/z: 378 (M+1); Rt=3.90 min.

The compounds in the following examples were prepared in a similar fashion.

Example 376

General Procedure (G)

N-Acetyl-7-{[(4-bromophenyl)amino]methyl}-3-hydroxynaphthalene-2-carboxylic acid

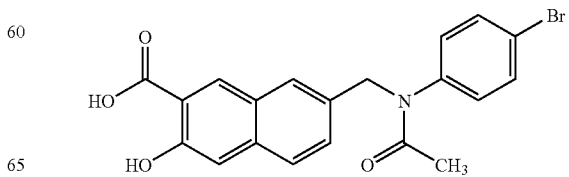

HPLC-MS (Method C): m/z: 414 (M+1); Rt=3.76 min.

Example 377

General Procedure (G)

N-Acetyl-7-{[(2,3-dihydrobenzofuran-5-ylmethyl)amino]methyl}-3-hydroxynaphthalene-2-carboxylic acid

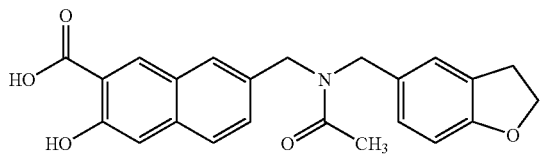

HPLC-MS (Method C): m/z: 392 (M+1); Rt=3.26 min.

Example 378

General Procedure (G)

N-Acetyl-7-{[(4-chlorobenzyl)amino]methyl}-3-hydroxynaphthalene-2-carboxylic acid

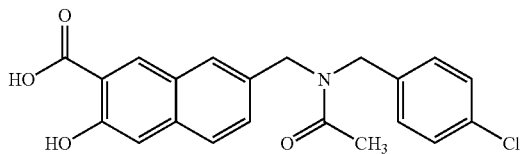

HPLC-MS (Method C): m/z: 384 (M+1); Rt=3.67 min.

Example 379

5-(3-(Naphthalen-2-yloxymethyl)-phenyl)-1H-tetrazole

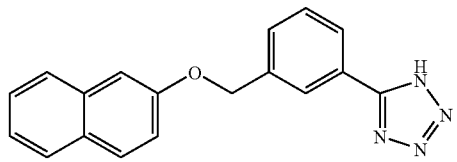

To a mixture of 2-naphthol (10 g, 0.07 mol) and potassium carbonate (10 g, 0.073 mol) in acetone (150 mL), alpha-bromo-m-tolunitril (13.6 g, 0.07 mol) was added in portions. The reaction mixture was stirred at reflux temperature for 2.5 hours. The cooled reaction mixture was filtered and evaporated in vacuo affording an oily residue (19 g) which was dissolved in diethyl ether (150 mL) and stirred with a mixture of active carbon and $MgSO_4$ for 16 hours. The mixture was filtered and evaporated in vacuo affording crude 18.0 g (100%) of 3-(naphthalen-2-yloxymethyl)benzonitrile as a solid.

12 g of the above benzonitrile was recrystallised from ethanol (150 mL) affording 8.3 g (69%) of 3-(naphthalen-2-yloxymethyl)-benzonitrile as a solid.

M.p. 60-61° C.

Calculated for $C_{18}H_{13}NO$: C, 83.37%; H, 5.05%; N, 5.40%. Found C, 83.51%; H, 5.03%; N, 5.38%.

To a mixture of sodium azide (1.46 g, 22.5 mmol) and ammonium chloride (1.28 g, 24.0 mmol) in dry dimethylformamide (20 mL) under an atmosphere of nitrogen, 3-(naphthalen-2-yloxymethyl)-benzonitrile (3.9 g, 15 mmol) was added and the reaction mixture was stirred at 125° C. for 4 hours. The cooled reaction mixture was poured on to ice water (300 mL) and acidified to pH=1 with 1 N hydrochloric acid. The precipitate was filtered off and washed with water, dried at 100° C. for 4 hours affording 4.2 g (93%) of the title compound.

M.p. 200-202° C.

Calculated for $C_{18}H_{14}N_4O$: C, 71.51%; H, 4.67%; N, 18.54%. Found C, 72.11%; H, 4.65%; N, 17.43%.

$^1$H NMR (400 MHz, DMSO-$d_6$) $\delta_H$ 5.36 (s, 2H), 7.29 (dd, 1H), 7.36 (dt, 1H), 7.47 (m, 2H), 7.66 (t, 1H), 7.74 (d, 1H), 7.84 (m, 3H), 8.02 (d, 1H), 8.22 (s, 1H).

Example 380

N-(3-(Tetrazol-5-yl)phenyl)-2-naphtoic acid amide

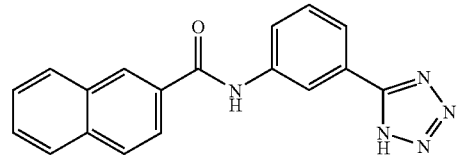

2-Naphtoic acid (10 g, 58 mmol) was dissolved in dichloromethane (100 mL) and N,N-dimethylformamide (0.2 mL) was added followed by thionyl chloride (5.1 ml, 70 mmol). The mixture was heated at reflux temperature for 2 hours. After cooling to room temperature, the mixture was added dropwise to a mixture of 3-aminobenzonitril (6.90 g, 58 mmol) and triethyl amine (10 mL) in dichloromethane (75 mL). The resulting mixture was stirred at room temperature for 30 minutes. Water (50 mL) was added and the volatiles was exaporated in vacuo. The resulting mixture was filtered and the filter cake was washed with water followed by heptane (2×25 mL). Drying in vacuo at 50° C. for 16 hours afforded 15.0 g (95%) of N-(3-cyanophenyl)-2-naphtoic acid amide.

M.p. 138-140° C.

The above naphthoic acid amide (10 g, 37 mmol) was dissolved in N,N-dimethylformamide (200 mL) and sodium azide (2.63 g, 40 mmol) and ammonium chloride (2.16 g, 40 mmol) were added and the mixture heated at 125° C. for 6 hours. Sodium azide (1.2 g) and ammonium chloride (0.98 g) were added and the mixture heated at 125° C. for 16 hours. After cooling, the mixture was poured into water (1.5 l) and stirred at room temperature for 30 minutes. The solid formed was filtered off, washed with water and dried in vacuo at 50° C. for 3 days affording 9.69 g (84%) of the title compound as a solid which could be further purified by treatment with ethanol at reflux temperature.

$^1$H NMR (200 MHz, DMSO-$d_6$): $\delta_H$ 7.58-7.70 (3H), 7.77 (d, 1H), 8.04-8.13 (m, 5H), 8.65 (d, 1H), 10.7 (s, 1H).

Calculated for $C_{18}H_{13}N_5O$, 0.75$H_2O$: C, 65.74%; H, 4.44%; N, 21.30%. Found: C, 65.58%; H, 4.50%; N, 21.05%.

Example 381

5-[3-(Biphenyl-4-yloxymethyl)phenyl]-1H-tetrazole

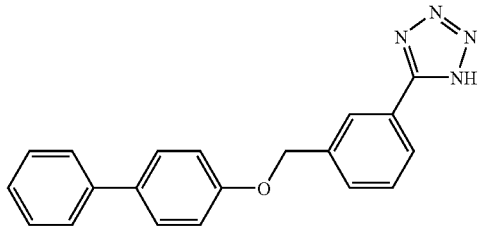

To a solution of 4-phenylphenol (10.0 g, 59 mmol) in dry N,N-dimethyl-formamide (45 mL) kept under an atmosphere of nitrogen, sodium hydride (2.82 g, 71 mmol, 60% dispersion in oil) was added in portions and the reaction mixture was stirred until gas evolution ceased. A solution of m-cyanobenzyl bromide (13 g, 65 mmol) in dry N,N-dimethylformamide (45 mL) was added dropwise and the reaction mixture was stirred at room temperature for 18 hours. The reaction mixture was poured on to ice water (150 mL). The precipitate was filtered of and washed with 50% ethanol (3×50 mL), ethanol (2×50 mL), diethyl ether (80 mL), and dried in vacuo at 50° C. for 18 hours affording crude 17.39 g of 3-(biphenyl-4-yloxymethyl)benzonitrile as a solid.

$^1$H NMR (200 MHz, CDCl$_3$) $\delta_H$ 5.14 (s, 2H), 7.05 (m, 2H), 7.30-7.78 (m, 11H).

To a mixture of sodium azide (2.96 g, 45.6 mmol) and ammonium chloride (2.44 g, 45.6 mmol) in dry N,N-dimethylformamide (100 mL) under an atmosphere of nitrogen, 3-(biphenyl-4-yloxymethyl)-benzonitrile (10.0 g, 35.0 mmol) was added and the reaction mixture was stirred at 125° C. for 18 hours. The cooled reaction mixture was poured on to a mixture of 1N hydrochloric acid (60 mL) and ice water (500 mL). The precipitate was filtered off and washed with water (3×100 mL), 50% ethanol (3×100 mL), ethanol (50 mL), diethyl ether (50 mL), ethanol (80 mL), and dried in vacuo at 50° C. for 18 hours affording 8.02 g (70%) of the title compound.

$^1$H NMR (200 MHz, DMSO-d$_6$) $\delta_H$ 5.31 (s, 2H), 7.19 (m, 2H), 7.34 (m, 1H), 7.47 (m, 2H), 7.69 (m, 6H), 8.05 (dt, 1H), 8.24 (s, 1H).

Example 382

5-(3-Phenoxymethyl)-phenyl)-tetrazole

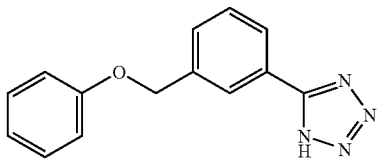

3-Bromomethylbenzonitrile (5.00 g, 25.5 mmol) was dissolved in N,N-dimethylformamide (50 mL), phenol (2.40 g, 25.5 mmol) and potassium carbonate (10.6 g, 77 mmol) were added. The mixture was stirred at room temperature for 16 hours. The mixture was poured into water (400 mL) and extracted with ethyl acetate (2×200 mL). The combined organic extracts were washed with water (2×100 mL), dried (MgSO$_4$) and evaporated in vacuo to afford 5.19 g (97%) 3-(phenoxymethyl)benzonitrile as an oil.

TLC: R$_f$=0.38 (Ethyl acetate/heptane=1:4)

The above benzonitrile (5.19 g, 24.8 mmol) was dissolved in N,N-dimethylformamide (100 mL) and sodium azide (1.93 g, 30 mmol) and ammonium chloride (1.59 g, 30 mmol) were added and the mixture was heated at 140° C. for 16 hours. After cooling, the mixture was poured into water (800 mL). The aqueous mixture was washed with ethyl acetate (200 mL). The pH of the aqueous phase was adjusted to 1 with 5 N hydrochloric acid and stirred at room temperature for 30 minutes. Filtration, washing with water and drying in vacuo at 50° C. afforded 2.06 g (33%) of the title compound as a solid.

$^1$H NMR (200 MHz, CDCl$_3$+DMSO-d$_6$) $\delta_H$ 5.05 (s, 2H), 6.88 (m, 3H), 7.21 (m, 2H), 7.51 (m, 2H), 7.96 (dt, 1H), 8.14 (s, 1H).

Example 383

5-[3-(Biphenyl-4-ylmethoxy)phenyl]-1H-tetrazole

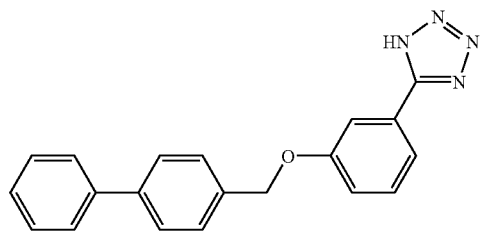

To a solution of 3-cyanophenol (5.0 g, 40.72 mmol) in dry N,N-dimethylformamide (100 mL) kept under an atmosphere of nitrogen, sodium hydride (2 g, 48.86 mmol, 60% dispersion in oil) was added in portions and the reaction mixture was stirred until gas evolution ceased. p-Phenylbenzyl chloride (9.26 g, 44.79 mmol) and potassium iodide (0.2 g, 1.21 mmol) were added and the reaction mixture was stirred at room temperature for 60 hours. The reaction mixture was poured on to a mixture of saturated sodium carbonate (100 mL) and ice water (300 mL). The precipitate was filtered of and washed with water (3×100 mL), n-hexane (2×80 mL) and dried in vacuo at 50° C. for 18 hours affording 11.34 g (98%) of 3-(biphenyl-4-ylmethoxy)-benzonitrile as a solid.

To a mixture of sodium azide (2.37 g, 36.45 mmol) and ammonium chloride (1.95 g, 36.45 mmol) in dry N,N-dimethylformamide (100 mL) under an atmosphere of nitrogen, 3-(biphenyl-4-ylmethoxy)benzonitrile (8.0 g, 28.04 mmol) was added and the reaction mixture was stirred at 125° C. for 18 hours. To the cooled reaction mixture water (100 mL) was added and the reaction mixture stirred for 0.75 hour. The precipitate was filtered off and washed with water, 96% ethanol (2×50 mL), and dried in vacuo at 50° C. for 18 hours affording 5.13 g (56%) of the title compound.

$^1$H NMR (200 MHz, DMSO-d$_6$) $\delta_H$ 5.29 (s, 2H), 7.31 (dd, 1H), 7.37-7.77 (m, 12H).

Example 384

5-[4-(Biphenyl-4-ylmethoxy)-3-methoxyphenyl]-1H-tetrazol

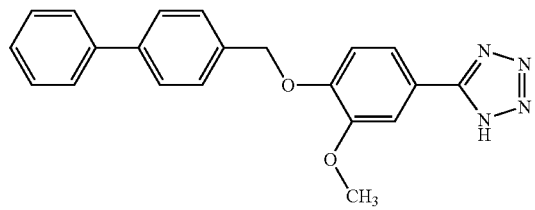

This compound was made similarly as described in example 383.

Example 385

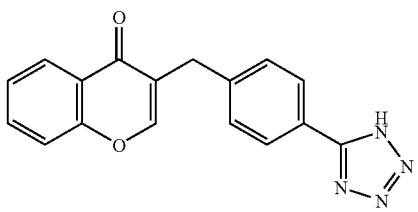

Example 386

5-(2-Naphtylmethyl)-1H-tetrazole

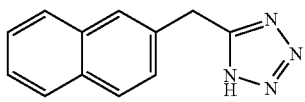

This compound was prepared similarly as described in example 379, step 2.

Example 387

5-(1-Naphtylmethyl)-1H-tetrazole

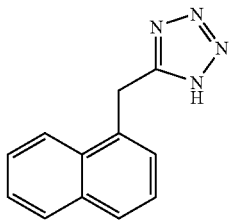

This compound was prepared similarly as described in example 379, step 2.

Example 388

5-[4-(Biphenyl-4-yloxymethyl)phenyl]-1H-tetrazole

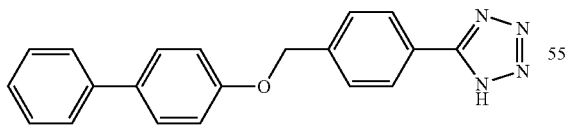

A solution of alpha-bromo-p-tolunitrile (5.00 g, 25.5 mmol), 4-phenylphenol (4.56 g, 26.8 mmol), and potassium carbonate (10.6 g, 76.5 mmol) in N,N-dimethylformamide (75 mL) was stirred vigorously for 16 hours at room temperature. Water (75 mL) was added and the mixture was stirred at room temperature for 1 hour. The precipitate was filtered off and washed with thoroughly with water. Drying in vacuo over night at 50° C. afforded 7.09 g (97%) of 4-(biphenyl-4-yloxymethyl)benzonitrile as a solid.

The above benzonitrile (3.00 g, 10.5 mmol) was dissolved in N,N-dimethylformamide (50 mL), and sodium azide (1.03 g, 15.8 mmol) and ammonium chloride (0.84 g, 15.8 mmol) were added and the mixture was stirred 16 hours at 125° C. The mixture was cooled to room temperature and water (50 mL) was added. The suspension was stirred overnight, filtered, washed with water and dried in vacuo at 50° C. for 3 days to give crude 3.07 g (89%) of the title compound. From the mother liquor crystals were collected and washed with water, dried by suction to give 0.18 g (5%) of the title compound as a solid.

$^1$H NMR (200 MHz, DMSO-d$_6$): $\delta_H$ 5.21 (s, 2H), 7.12 (d, 2H), 7.30 (t, 1H), 7.42 (t, 2H), 7.56-7.63 (m, 6H), 8.03 (d, 2H).

Calculated for C$_{20}$H$_{16}$N$_4$O, 2H$_2$O: C, 65.92%; H, 5.53%; N, 15.37%. Found: C, 65.65%; H, 5.01%; N, 14.92%.

Example 389

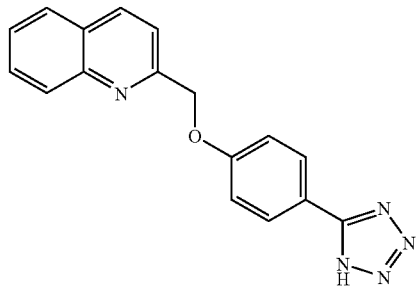

This compound was prepared similarly as described in example 383.

Example 390

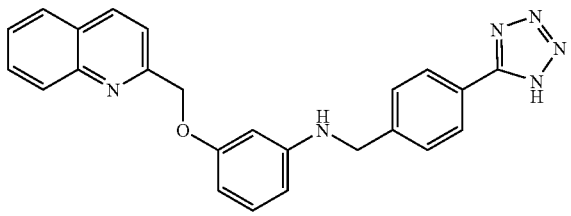

Example 391

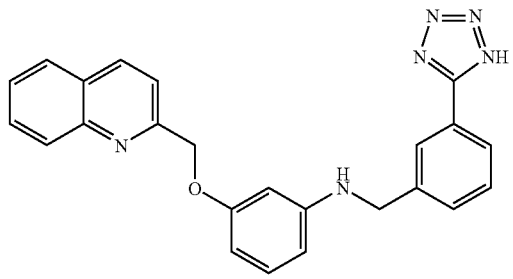

Example 392

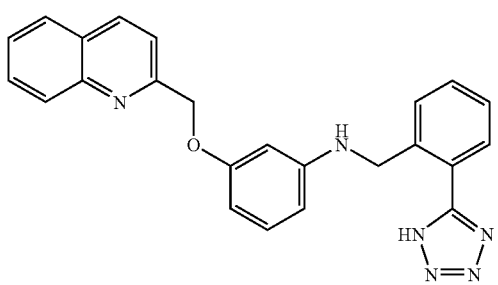

Example 393

5-(3-(Biphenyl-4-yloxymethyl)-benzyl)-1H-tetrazole

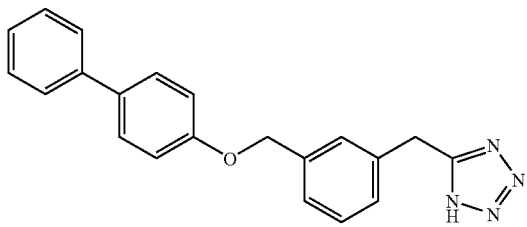

Example 394

5-(1-Naphthyl)-1H-tetrazole

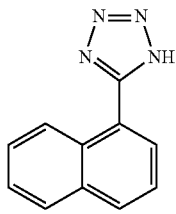

This compound was prepared similarly as described in example 379, step 2.

Example 395

5-[3-Methoxy-4-(4-methylsulfonylbenzyloxy)phenyl]-1H-tetrazole

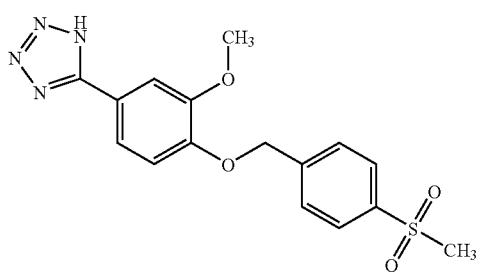

This compound was made similarly as described in example 383.

Example 396

5-(2-Naphthyl)-1H-tetrazole

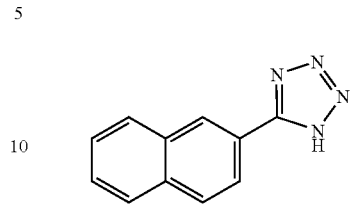

This compound was prepared similarly as described in example 379, step 2.

Example 397

2-Amino-N-(1H-tetrazol-5-yl)-benzamide

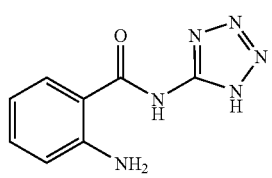

Example 398

5-(4-Hydroxy-3-methoxyphenyl)-1H-tetrazole

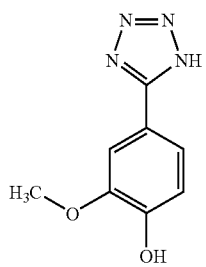

This compound was prepared similarly as described in example 379, step 2.

Example 399

4-(2H-Tetrazol-5-ylmethoxy)benzoic acid

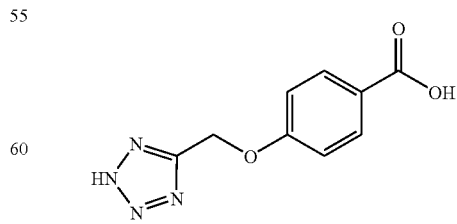

To a mixture of methyl 4-hydroxybenzoate (30.0 g, 0.20 mol), sodium iodide (30.0 g, 0.20 mol) and potassium carbonate (27.6 g, 0.20 mol) in acetone (2000 mL) was added chloroacetonitrile (14.9 g, 0.20 mol). The mixture was stirred at RT for 3 days. Water was added and the mixture was acidified with 1N hydrochloric acid and the mixture was extracted with diethyl ether. The combined organic layers were dried over $Na_2SO_4$ and concentrated in vacuo. The residue was dissolved in acetone and chloroacetonitrile (6.04 g, 0.08 mol), sodium iodide (12.0 g, 0.08 mol) and potassium carbonate (11.1 g, 0.08 mol) were added and the mixture was stirred for 16 hours at RT and at 60° C. More chloroacetonitrile was added until the conversion was 97%. Water was added and the mixture was acidified with 1N hydrochloric acid and the mixture was extracted with diethyl ether. The combined organic layers were dried over $Na_2SO_4$ and concentrated in vacuo to afford methyl 4-cyanomethyloxybenzoate in quantitative yield. This compound was used without further purification in the following step.

A mixture of methyl 4-cyanomethyloxybenzoate (53.5 g, 0.20 mol), sodium azide (16.9 g, 0.26 mol) and ammonium chloride (13.9 g, 0.26 mol) in DMF 1000 (mL) was refluxed overnight under $N_2$. After cooling, the mixture was concentrated in vacuo. The residue was suspended in cold water and extracted with ethyl acetate. The combined organic phases were washed with brine, dried over $Na_2SO_4$ and concentrated in vacuo, to afford methyl 4-(2H-tetrazol-5-ylmethoxy)benzoate. This compound was used as such in the following step.

Methyl 4-(2H-Tetrazol-5-ylmethoxy)-benzoate was refluxed in 3N sodium hydroxide. The reaction was followed by TLC (DCM:MeOH=9:1). The reaction mixture was cooled, acidified and the product filtered off. The impure product was washed with DCM, dissolved in MeOH, filtered and purified by column chromatography on silica gel (DCM:MeOH=9:1). The resulting product was recrystallised from DCM:MeOH=95:5. This was repeated until the product was pure. This afforded 13.82 g (30%) of the title compound.

$^1$H-NMR (DMSO-$d_6$): 4.70 (2H, s), 7.48 (2H, d), 7.73 (2H, d), 13 (1H, bs).

Example 400

4-(2H-Tetrazol-5-ylmethylsulfanyl)benzoic acid

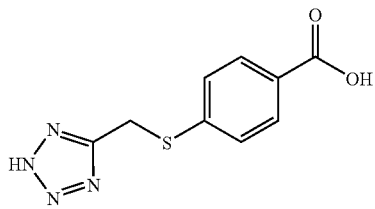

To a solution of sodium hydroxide (10.4 g, 0.26 mol) in degassed water (600 mL) was added 4-mercaptobenzoic acid (20.0 g, 0.13 mol). This solution was stirred for 30 minutes. To a solution of potassium carbonate (9.0 g, 65 mmol) in degassed water (400 mL) was added chloroacetonitrile (9.8 g, (0.13 mol) portion-wise. These two solutions were mixed and stirred for 48 hours at RT under $N_2$. The mixture was filtered and washed with heptane. The aqueous phase was acidified with 3N hydrochloric acid and the product was filtered off, washed with water and dried, affording 4-cyanomethylsulfanylbenzoic acid (27.2 g, 88%). This compound was used without further purification in the following step.

A mixture of 4-cyanomethylsulfanylbenzoic acid (27.2 g, 0.14 mol), sodium azide (11.8 g, 0.18 mol) and ammonium chloride (9.7 g, 0.18 mol) in DMF (1000 mL) was refluxed overnight under $N_2$. The mixture was concentrated in vacuo.

The residue was suspended in cold water and extracted with diethyl ether. The combined organic phases were washed with brine, dried over $Na_2SO_4$ and concentrated in vacuo. Water was added and the precipitate was filtered off. The aqueous layer was concentrated in vacuo, water was added and the precipitate filtered off. The combined impure products were purified by column chromatography using DCM:MeOH=9:1 as eluent, affording the title compound (5.2 g, 16%).

$^1$H-NMR (DMSO-$d_6$): 5.58 (2H, s), 7.15 (2H, d), 7.93 (2H, d), 12.7 (1H, bs).

Example 401

3-(2H-Tetrazol-5-yl)-9H-carbazole

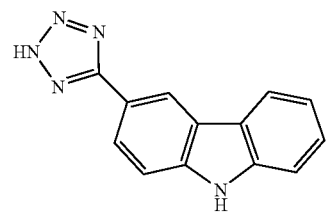

3-Bromo-9H-carbazole was prepared as described by Smith et al. in *Tetrahedron* 1992, 48, 7479-7488.

A solution of 3-bromo-9H-carbazole (23.08 g, 0.094 mol) and cuprous cyanide (9.33 g, 0.103 mol) in N-methyl-pyrrolidone (300 ml) was heated at 200° C. for 5 h. The cooled reaction mixture was poured on to water (600 ml) and the precipitate was filtered off and washed with ethyl acetate (3×50 ml). The filtrate was extracted with ethyl acetate (3×250 ml) and the combined ethyl acetate extracts were washed with water (150 ml), brine (150 ml), dried (MgSO$_4$) and concentrated in vacuo. The residue was crystallised from heptanes and recrystallised from acetonitrile (70 ml) affording 7.16 g (40%) of 3-cyano-9H-carbazole as a solid.

M.p. 180-181° C.

3-Cyano-9H-carbazole (5.77 g, 30 mmol) was dissolved in N,N-dimethylformamide (150 ml), and sodium azide (9.85 g, 152 mmol), ammonium chloride (8.04 g, 150 mmol) and lithium chloride (1.93 g, 46 mmol) were added and the mixture was stirred for 20 h at 125° C. To the reaction mixture was added an additional portion of sodium azide (9.85 g, 152 mmol) and ammonium chloride (8.04 g, 150 mmol) and the reaction mixture was stirred for an additional 24 h at 125° C. The cooled reaction mixture was poured on to water (500 ml). The suspension was stirred for 0.5 h, and the precipitate was filtered off and washed with water (3×200 ml) and dried in vacuo at 50° C. The dried crude product was suspended in diethyl ether (500 ml) and stirred for 2 h, filtered off and washed with diethyl ether (2×200 ml) and dried in vacuo at 50° C. affording 5.79 g (82%) of the title compound as a solid.

$^1$H-NMR (DMSO-$d_6$): δ 11.78 (1H, bs), 8.93 (1H, d), 8.23 (1H, d), 8.14 (1H, dd), 7.72 (1H, d), 7.60 (1H, d), 7.49 (1H, t), 7.28 (1H, t); HPLC-MS (Method C): m/z: 236 (M+1); Rt=2.77 min.

The following commercially available tetrazoles do all bind to the His B10 $Zn^{2+}$ site of the insulin hexamer:

Example 402
5-(3-Tolyl)-1H-tetrazole
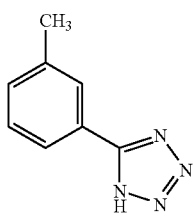
Example 403
5-(2-Bromophenyl)tetrazole
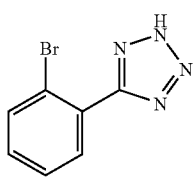
Example 404
5-(4-Ethoxalylamino-3-nitrophenyl)tetrazole
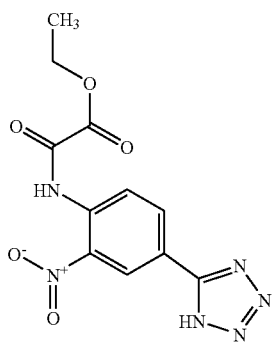
Example 405
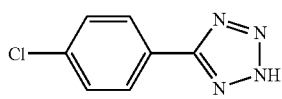
Example 406
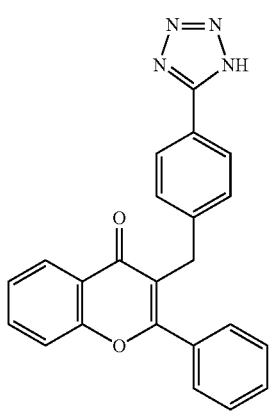
Example 407
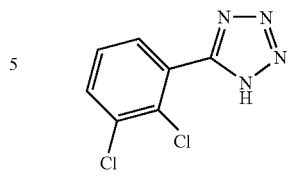
Example 408
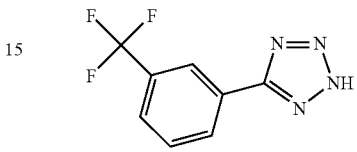
Example 409
Tetrazole
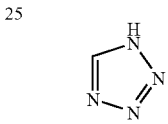
Example 410
5-Methyltetrazole
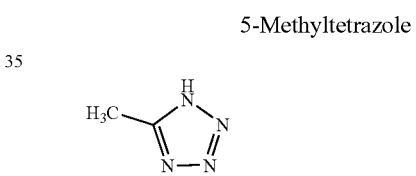
Example 411
5-Benzyl-2H-tetrazole
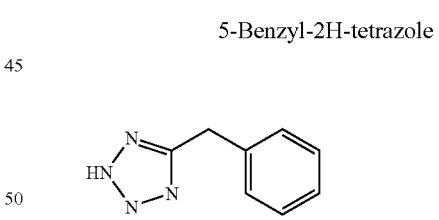
Example 412
4-(2H-Tetrazol-5-yl)benzoic acid
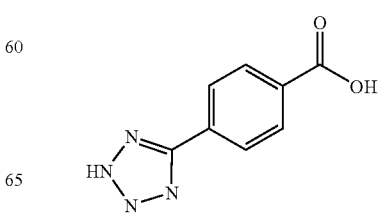

Example 413
5-Phenyl-2H-tetrazole
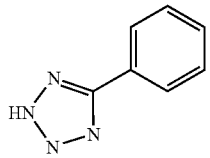
Example 414
5-(4-Chlorophenylsulfanylmethyl)-2H-tetrazole
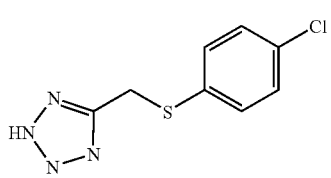
Example 415
5-(3-Benzyloxyphenyl)-2H-tetrazole
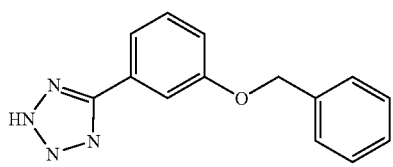
Example 416
2-Phenyl-6-(1H-tetrazol-5-yl)-chromen-4-one
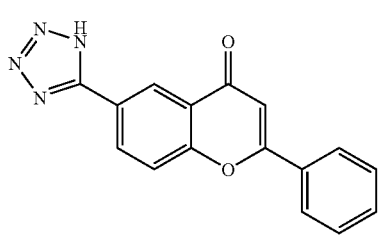
Example 417
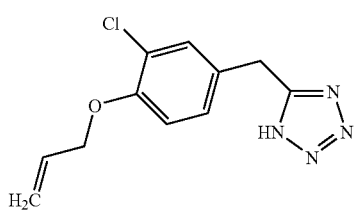
Example 418
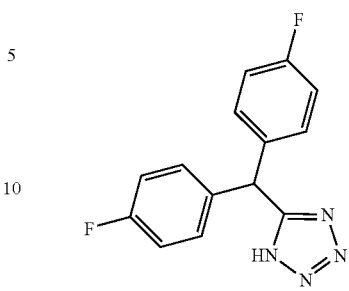
Example 419
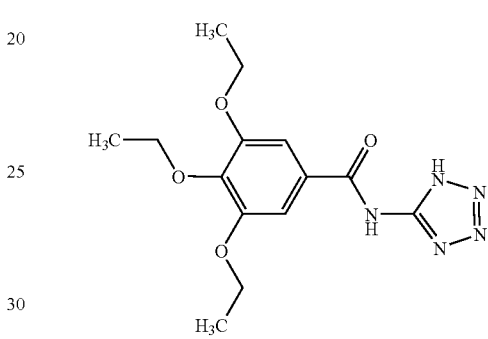
Example 420
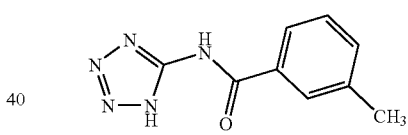
Example 421
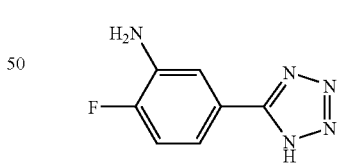
Example 422
5-(4-Bromo-phenyl)-1H-tetrazole
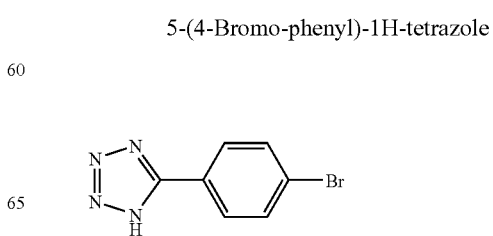

Example 423
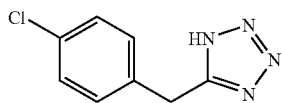
Example 424
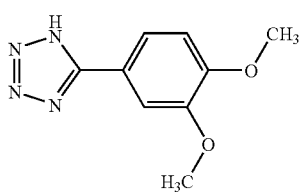
Example 425
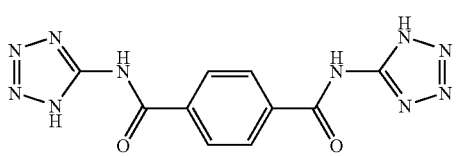
Example 426
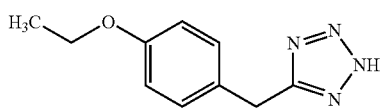
Example 427
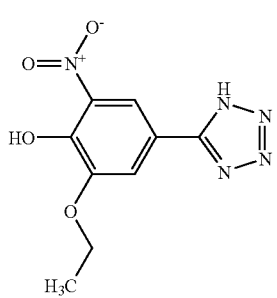
Example 428
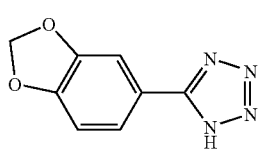
Example 429
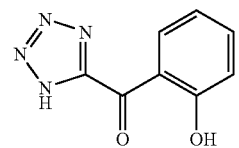
Example 430
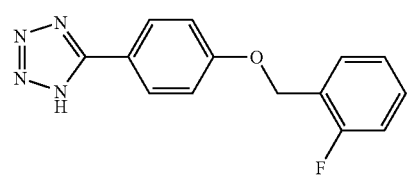
Example 431
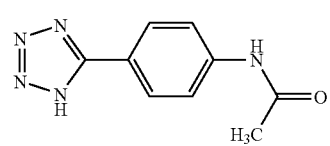
Example 432
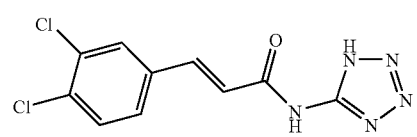
Example 433
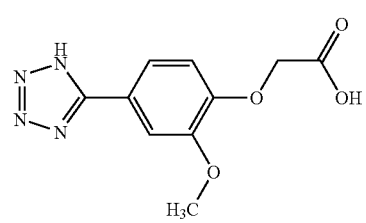
Example 434
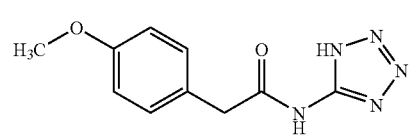

Example 435
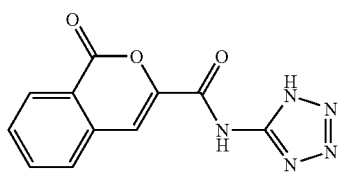
Example 436
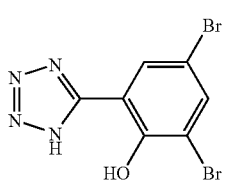
Example 437
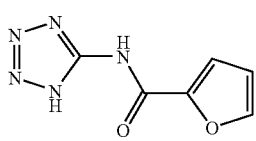
Example 438
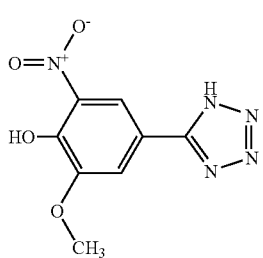
Example 439
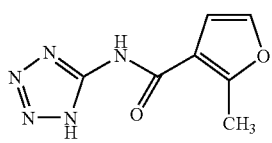
Example 440
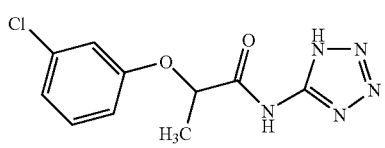
Example 441
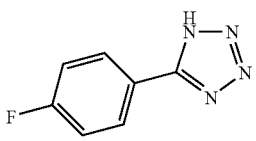
Example 442
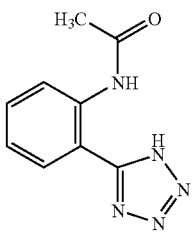
Example 443
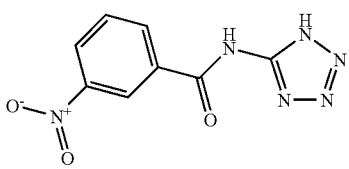
Example 444
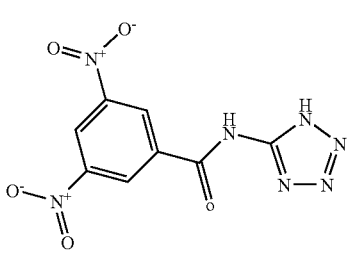
Example 445
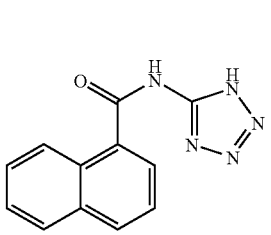
Example 446
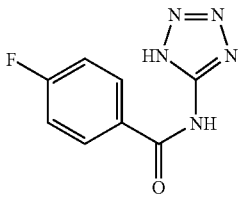

Example 447

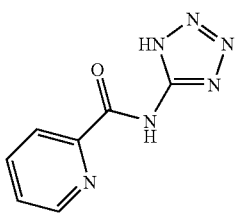

Example 448

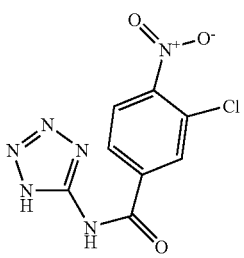

Example 449

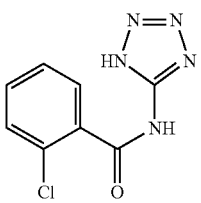

Example 450

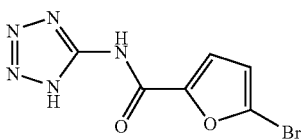

Example 451

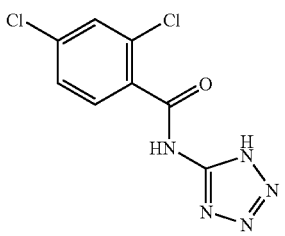

Example 452

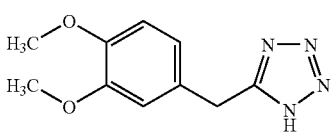

General Procedure (H) for Preparation of Compounds of General Formula $I_7$:

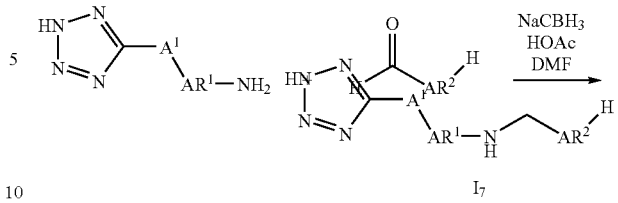

wherein $A^1$, $AR^1$, and $AR^2$ are as defined above.

The reaction is generally known as a reductive alkylation reaction and is generally performed by stirring an aldehyde with an amine at low pH (by addition of an acid, such as acetic acid or formic acid) in a solvent such as THF, DMF, NMP, methanol, ethanol, DMSO, dichloromethane, 1,2-dichloroethane, trimethyl orthoformate, triethyl orthoformate, or a mixture of two or more of these. As reducing agent sodium cyano borohydride or sodium triacetoxy borohydride may be used. The reaction is performed between 20° C. and 120° C., preferably at room temperature.

When the reductive alkylation is complete, the product is isolated by extraction, filtration, chromatography or other methods known to those skilled in the art.

The general procedure (H) is further illustrated in the following example 453:

Example 453

General Procedure (H)

Biphenyl-4-ylmethyl-[3-(2H-tetrazol-5-yl)phenyl]amine

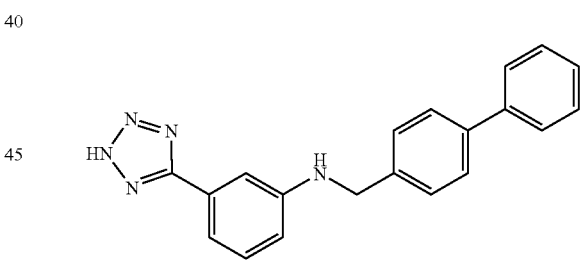

A solution of 5-(3-aminophenyl)-2H-tetrazole (example 589, 48 mg, 0.3 mmol) in DMF (250 μL) was mixed with a solution of 4-biphenylylcarbaldehyde (54 mg, 0.3 mmol) in DMF (250 μL) and acetic acid glacial (250 μL) was added to the mixture followed by a solution of sodium cyano borohydride (15 mg, 0.24 mmol) in methanol (250 μL). The resulting mixture was shaken at room temperature for 2 hours. Water (2 mL) was added to the mixture and the resulting mixture was shaken at room temperature for 16 hours. The mixture was centrifugated (6000 rpm, 10 minutes) and the supernatant was removed by a pipette. The residue was washed with water (3 mL), centrifugated (6000 rpm, 10 minutes) and the supernatant was removed by a pipette. The residue was dried in vacuo at 40° C. for 16 hours to afford the title compound as a solid.

HPLC-MS (Method C): m/z: 328 (M+1), 350 (M+23); Rt=4.09 min.

Example 454

General Procedure (H)

Benzyl-[3-(2H-tetrazol-5-yl)phenyl]amine

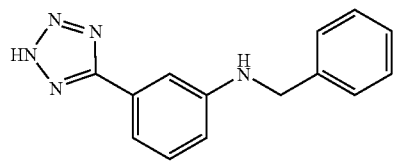

HPLC-MS (Method D): m/z: 252 (M+1); Rt=3.74 min.

Example 455

General Procedure (H)

(4-Methoxybenzyl)-[3-(2H-tetrazol-5-yl)phenyl]amine

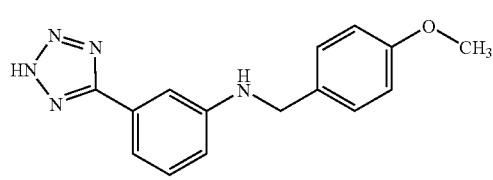

HPLC-MS (Method D): m/z: 282.2 (M+1); Rt=3.57 min.

Example 456

General Procedure (H)

4-{[3-(2H-Tetrazol-5-yl)phenylamino]methyl}phenol

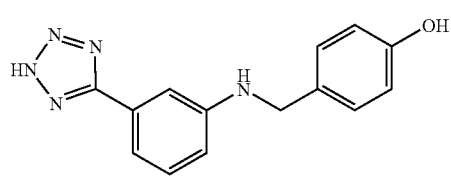

HPLC-MS (Method D): m/z: 268.4 (M+1); Rt=2.64 min.

Example 457

General Procedure (H)

(4-Nitrobenzyl)-[3-(2H-tetrazol-5-yl)phenyl]amine

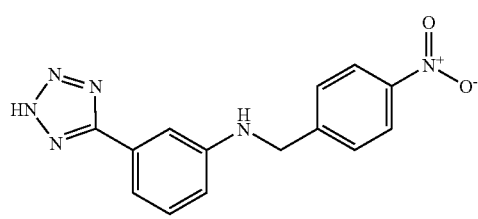

HPLC-MS (Method D): m/z: 297.4 (M+1); Rt=3.94 min.

Example 458

General Procedure (H)

(4-Chlorobenzyl)-[3-(2H-tetrazol-5-yl)phenyl]amine

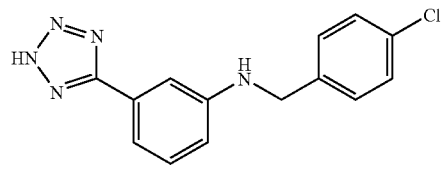

HPLC-MS (Method D): m/z: 287.2 (M+1); Rt=4.30 min.

Example 459

General Procedure (H)

(2-Chlorobenzyl)-[3-(2H-tetrazol-5-yl)phenyl]amine

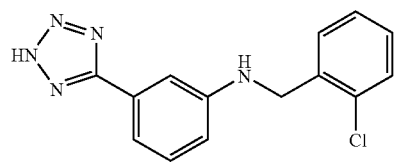

HPLC-MS (Method D): m/z: 286 (M+1); Rt=4.40 min.

Example 460

General Procedure (H)

(4-Bromobenzyl)-[3-(2H-tetrazol-5-yl)phenyl]amine

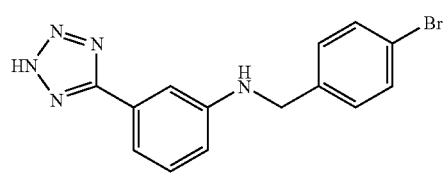

HPLC-MS (Method D): m/z: 332 (M+1); Rt=4.50 min.

Example 461

General Procedure (H)

(3-Benzyloxybenzyl)-[3-(2H-tetrazol-5-yl)phenyl]amine

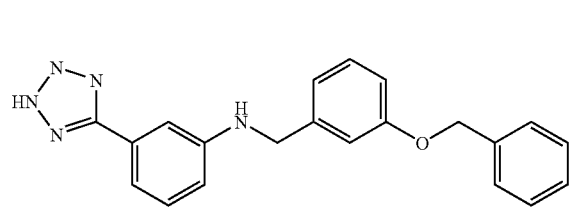

HPLC-MS (Method D): m/z: 358 (M+1); Rt=4.94 min.

Example 462

General Procedure (H)

Naphthalen-1-ylmethyl-[3-(2H-tetrazol-5-yl)phenyl]amine

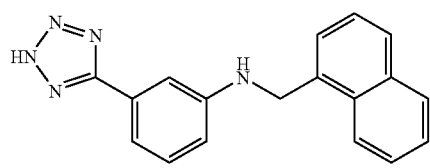

HPLC-MS (Method D): m/z: 302 (M+1); Rt=4.70 min.

Example 463

General Procedure (H)

Naphthalen-2-ylmethyl-[3-(2H-tetrazol-5-yl)phenyl]amine

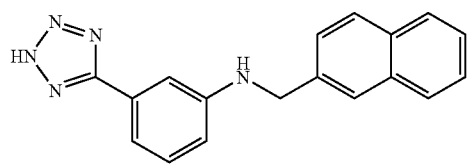

HPLC-MS (Method D): m/z: 302 (M+1); Rt=4.60 min.

Example 464

General Procedure (H)

4-{[3-(2H-Tetrazol-5-yl)phenylamino]methyl}benzoic acid

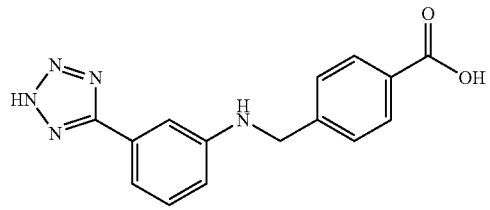

HPLC-MS (Method D): m/z: 296 (M+1); Rt=3.24 min.

Example 465

General Procedure (H)

[3-(2H-Tetrazol-5-yl)-phenyl]-[3-(3-trifluoromethyl-phenoxy)benzyl]amine

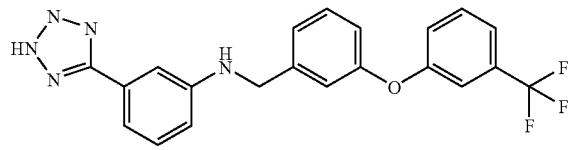

HPLC-MS (Method D): m/z: 412 (M+1); Rt=5.54 min.

Example 466

General Procedure (H)

(3-Phenoxybenzyl)-[3-(2H-tetrazol-5-yl)phenyl]amine

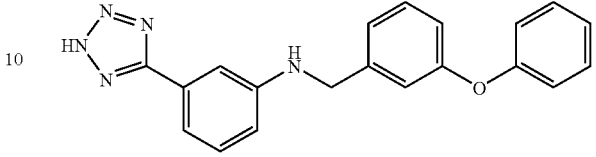

HPLC-MS (Method D): m/z: 344 (M+1); Rt=5.04 min.

Example 467

General Procedure (H)

(4-Phenoxy-benzyl)-[3-(2H-tetrazol-5-yl)phenyl]amine

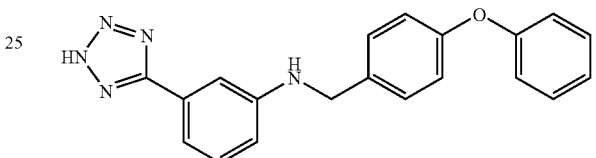

HPLC-MS (Method D): m/z: 344 (M+1); Rt=5.00 min.

Example 468

General Procedure (H)

(4-{[3-(2H-Tetrazol-5-yl)phenylamino]methyl}phenoxy)acetic acid

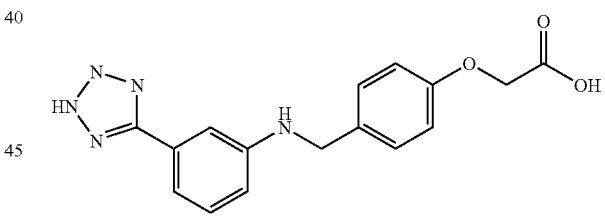

HPLC-MS (Method D): m/z: 326 (M+1); Rt=3.10 min.

Example 469

General Procedure (H)

(4-Benzyloxybenzyl)-[3-(2H-tetrazol-5-yl)phenyl]amine

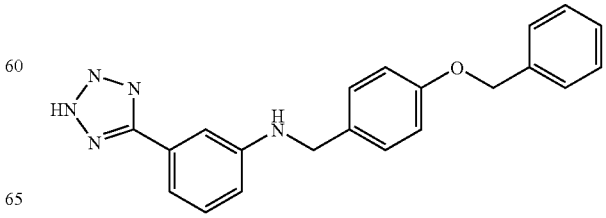

HPLC-MS (Method D): m/z: 358 (M+1); Rt=4.97 min.

Example 470

General Procedure (H)

3-(4-{[3-(2H-Tetrazol-5-yl)phenylamino]methyl}phenyl)acrylic acid

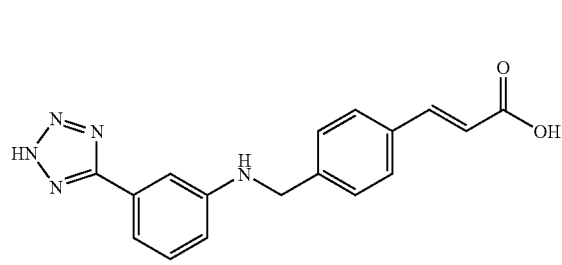

HPLC-MS (Method D): m/z: 322 (M+1); Rt=3.60 min.

Example 471

General Procedure (H)

Dimethyl-(4-{[3-(2H-tetrazol-5-yl)phenylamino]methyl}naphthalen-1-yl)amine

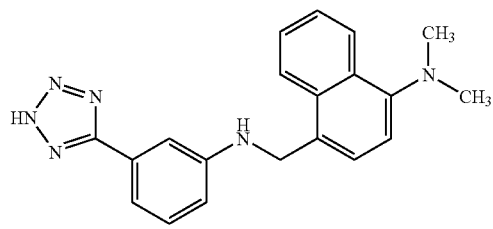

HPLC-MS (Method D): m/z: 345 (M+1); Rt=3.07 min.

Example 472

General Procedure (H)

(4'-Methoxybiphenyl-4-ylmethyl)-[3-(2H-tetrazol-5-yl)phenyl]amine

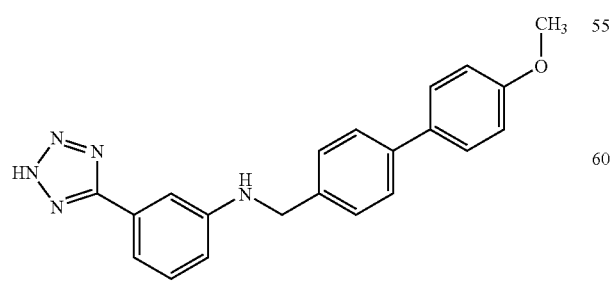

HPLC-MS (Method D): m/z: 358 (M+1); Rt=4.97 min.

Example 473

General Procedure (H)

(2'-Chlorobiphenyl-4-ylmethyl)-[3-(2H-tetrazol-5-yl)phenyl]amine

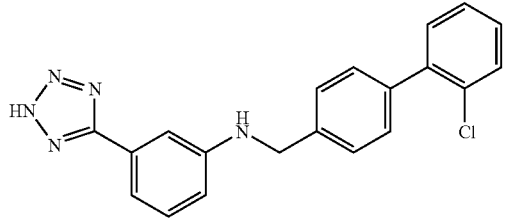

HPLC-MS (Method D): m/z: 362 (M+1); Rt=5.27 min.

Example 474

General Procedure (H)

Benzyl-[4-(2H-tetrazol-5-yl)phenyl]amine

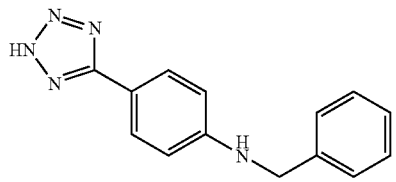

For preparation of starting material, see example 590.
HPLC-MS (Method D): m/z: 252 (M+1); Rt=3.97 min.

Example 475

General Procedure (H)

(4-Methoxybenzyl)-[4-(2H-tetrazol-5-yl)phenyl]amine

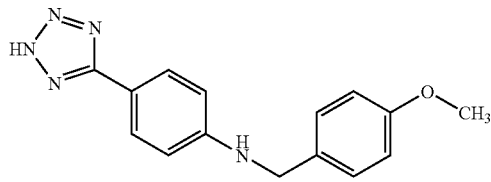

HPLC-MS (Method D): m/z: 282 (M+1); Rt=3.94 min.

Example 476

General Procedure (H)

4-{[4-(2H-Tetrazol-5-yl)phenylamino]methyl}phenol

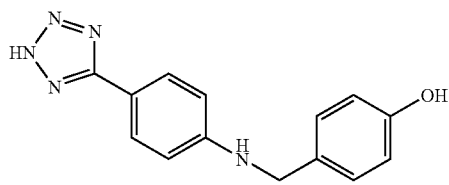

HPLC-MS (Method D): m/z: 268 (M+1); Rt=3.14 min.

Example 477

General Procedure (H)

(4-Nitrobenzyl)-[4-(2H-tetrazol-5-yl)phenyl]amine

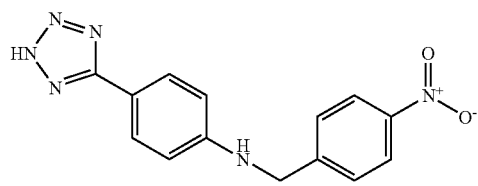

HPLC-MS (Method D): m/z: (M+1); Rt=3.94 min.

Example 478

General Procedure (H)

(4-Chlorobenzyl)-[4-(2H-tetrazol-5-yl)phenyl]amine

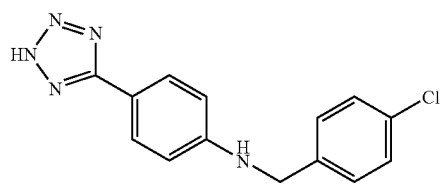

HPLC-MS (Method D): m/z: (M+1); Rt=4.47 min.

Example 479

General Procedure (H)

(2-Chlorobenzyl)-[4-(2H-tetrazol-5-yl)phenyl]amine

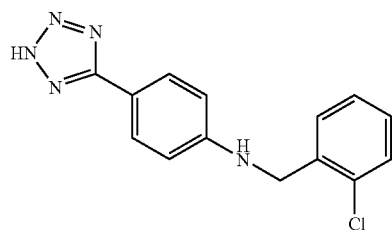

HPLC-MS (Method D): m/z: 286 (M+1); Rt=4.37 min.

Example 480

General Procedure (H)

(4-Bromobenzyl)-[4-(2H-tetrazol-5-yl)phenyl]amine

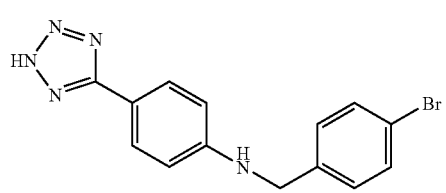

HPLC-MS (Method D): m/z: 331 (M+1); Rt=4.57 min.

Example 481

General Procedure (H)

(3-Benzyloxybenzyl)-[4-(2H-tetrazol-5-yl)phenyl]amine

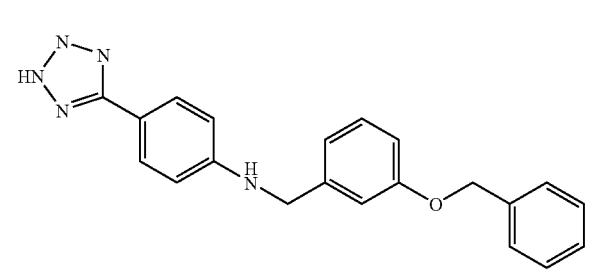

HPLC-MS (Method D): m/z: 358 (M+1); Rt=5.07 min.

Example 482

General Procedure (H)

Naphthalen-1-ylmethyl-[4-(2H-tetrazol-5-yl)phenyl]amine

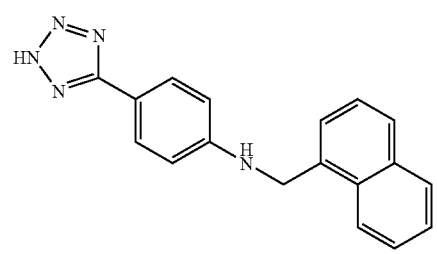

HPLC-MS (Method D): m/z: 302 (M+1); Rt=4.70 min.

Example 483

General Procedure (H)

Naphthalen-2-ylmethyl-[4-(2H-tetrazol-5-yl)phenyl]amine

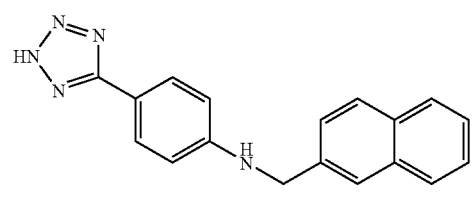

HPLC-MS (Method D): m/z: 302 (M+1); Rt=4.70 min.

Example 484

General Procedure (H)

Biphenyl-4-ylmethyl-[4-(2H-tetrazol-5-yl)phenyl]amine

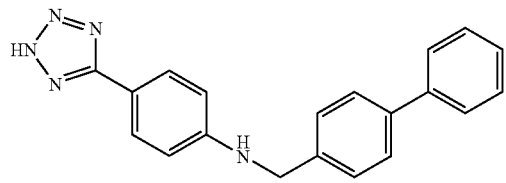

HPLC-MS (Method D): m/z: 328 (M+1); Rt=5.07 min.

Example 485

General Procedure (H)

4-{[4-(2H-Tetrazol-5-yl)phenylamino]methyl}benzoic acid

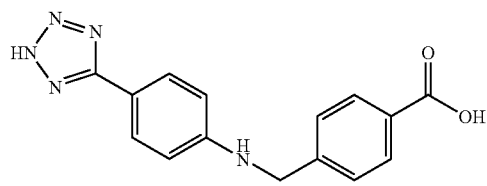

HPLC-MS (Method D): m/z: 296 (M+1); Rt=3.34 min.

Example 486

General Procedure (H)

[4-(2H-Tetrazol-5-yl)phenyl]-[3-(3-trifluoromethylphenoxy)benzyl]amine

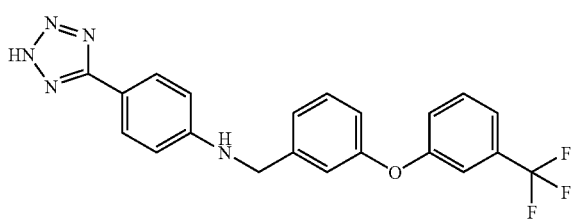

HPLC-MS (Method D): m/z: 412 (M+1); Rt=5.54 min.

Example 487

General Procedure (H)

(3-Phenoxybenzyl)-[4-(2H-tetrazol-5-yl)phenyl]amine

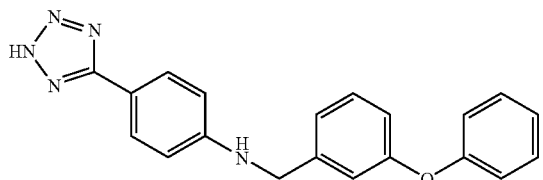

HPLC-MS (Method D): m/z: 344 (M+1); Rt=5.07 min.

Example 488

General Procedure (H)

(4-Phenoxybenzyl)-[4-(2H-tetrazol-5-yl)-phenyl]amine

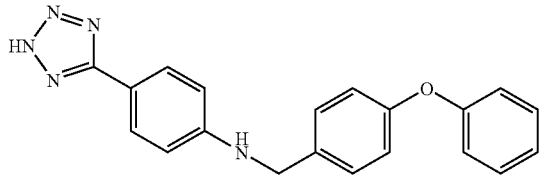

HPLC-MS (Method D): m/z: 344 (M+1); Rt=5.03 min.

Example 489

General Procedure (H)

3-{[4-(2H-Tetrazol-5-yl)phenylamino]methyl}benzoic acid

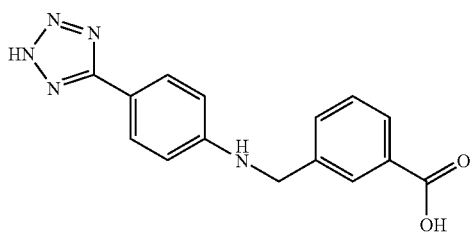

HPLC-MS (Method D): m/z: 286 (M+1); Rt=3.47 min.

Example 490

General Procedure (H)

(4-{[4-(2H-Tetrazol-5-yl)phenylamino]methyl}phenoxy)acetic acid

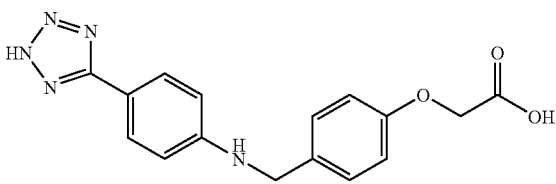

HPLC-MS (Method D): m/z: 326 (M+1); Rt=3.40 min.

Example 491

General Procedure (H)

(4-Benzyloxybenzyl)-[4-(2H-tetrazol-5-yl)phenyl]amine

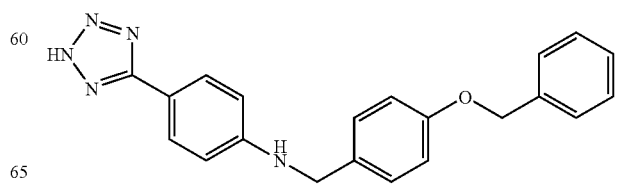

HPLC-MS (Method D): m/z: 358 (M+1); Rt=5.14 min.

Example 492

General Procedure (H)

3-(4-{[4-(2H-Tetrazol-5-yl)phenylamino]methyl}phenyl)acrylic acid

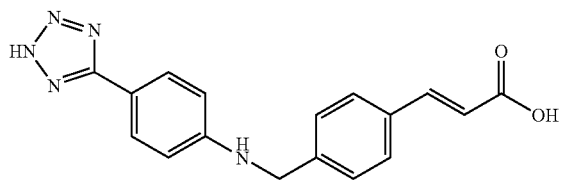

HPLC-MS (Method D): m/z: 322 (M+1); Rt=3.66 min.

Example 493

General Procedure (H)

Dimethyl-(4-{[4-(2H-tetrazol-5-yl)phenylamino]methyl}naphthalen-1-yl)amine

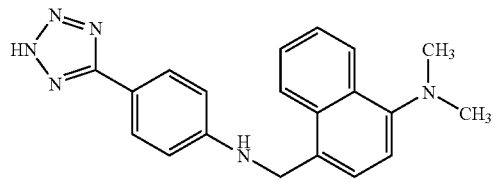

HPLC-MS (Method D): m/z: 345 (M+1); Rt=3.10 min.

Example 494

General Procedure (H)

(4'-Methoxybiphenyl-4-ylmethyl)-[4-(2H-tetrazol-5-yl)phenyl]amine

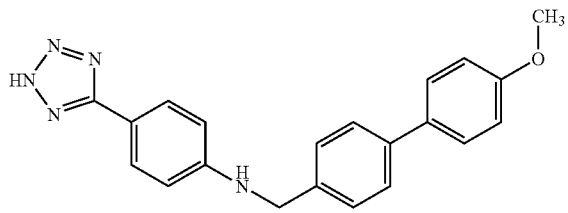

HPLC-MS (Method D): m/z: 358 (M+1); Rt=5.04 min.

Example 495

General Procedure (H)

(2'-Chlorobiphenyl-4-ylmethyl)-[4-(2H-tetrazol-5-yl)-phenyl]-amine

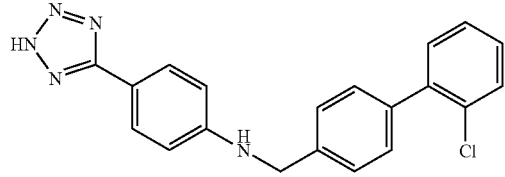

HPLC-MS (Method D): m/z: 362 (M+1); Rt=5.30 min.

General Procedure (I) for Preparation of Compounds of General Formula $I_8$:

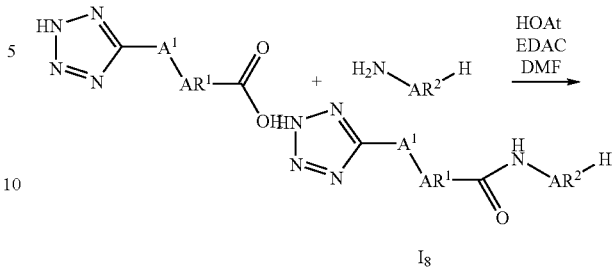

wherein $A^1$, $AR^1$, and $AR^2$ are as defined above.

This procedure is very similar to general procedure (A), the only difference being the carboxylic acid is containing a tetrazole moiety. When the acylation is complete, the product is isolated by extraction, filtration, chromatography or other methods known to those skilled in the art.

The general procedure (I) is further illustrated in the following example 496:

Example 496

General Procedure (I)

4-[4-(2H-Tetrazol-5-yl)benzoylamino]benzoic acid

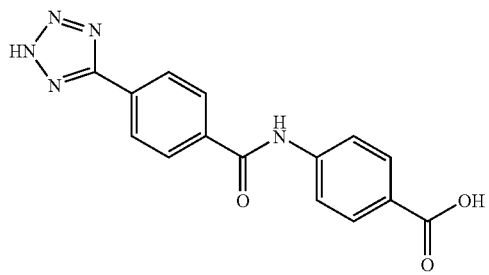

To a solution of 4-(2H-tetrazol-5-yl)benzoic acid (example 412, 4 mmol) and HOAt (4.2 mmol) in DMF (6 mL) was added 1-ethyl-3-(3'-dimethylaminopropyl)carbodiimide hydrochloride (4.2 mmol) and the resulting mixture was stirred at room temperature for 1 hour. An aliquot of this HOAt-ester solution (0.45 mL) was mixed with 0.25 mL of a solution of 4-aminobenzoic acid (1.2 mmol in 1 mL DMF). (Anilines as hydrochlorides can also be utilised, a slight excess of triethylamine was added to the hydrochloride suspension in DMF prior to mixing with the HOAt-ester.) The resulting mixture was shaken for 3 days at room temperature. 1N hydrochloric acid (2 mL) was added and the mixture was shaken for 16 hours at room temperature. The solid was isolated by centrifugation (alternatively by filtration or extraction) and was washed with water (3 mL). Drying in vacuo at 40° C. for 2 days afforded the title compound.

HPLC-MS (Method D): m/z: 310 (M+1); Rt=2.83 min.

Example 497

General Procedure (I)

3-[4-(2H-Tetrazol-5-yl)benzoylamino]benzoic acid

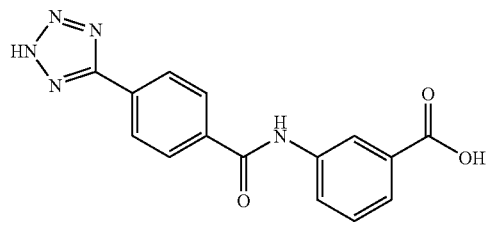

HPLC-MS (Method D): m/z: 310 (M+1); Rt=2.89 min.

Example 498

General Procedure (I)

3-{4-[4-(2H-Tetrazol-5-yl)benzoylamino]phenyl}acrylic acid

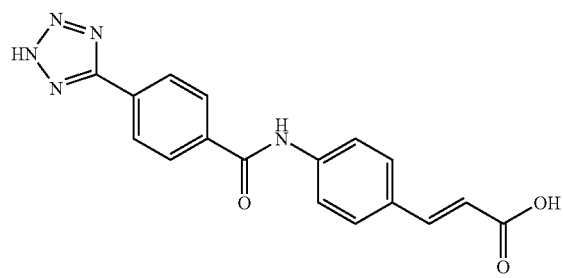

HPLC-MS (Method D): m/z: 336 (M+1); Rt=3.10 min.

Example 499

General Procedure (I)

3-{4-[4-(2H-Tetrazol-5-yl)benzoylamino]phenyl}propionic acid

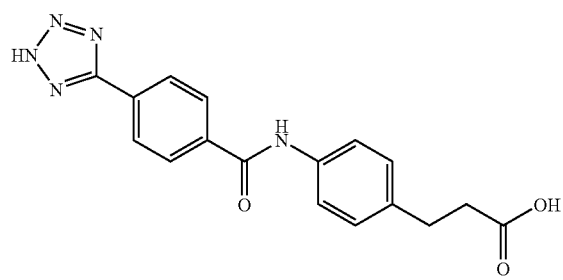

HPLC-MS (Method D): m/z: 338 (M+1); Rt=2.97 min.

Example 500

General Procedure (I)

3-Methoxy-4-[4-(2H-tetrazol-5-yl)benzoylamino]benzoic acid

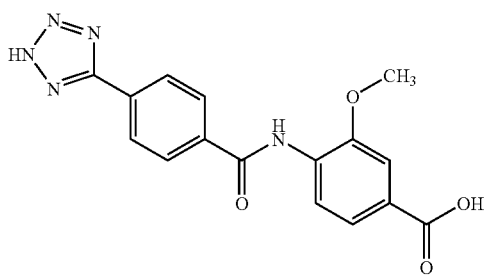

HPLC-MS (Method D): m/z: 340 (M+1); Rt=3.03 min.

Example 501

General Procedure (I)

N-(4-Benzyloxyphenyl)-4-(2H-tetrazol-5-yl)benzamide

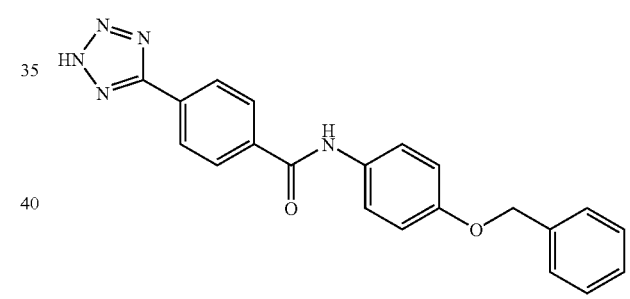

HPLC-MS (Method D): m/z: 372 (M+1); Rt=4.47 min.

Example 502

General Procedure (I)

N-(4-Phenoxyphenyl)-4-(2H-tetrazol-5-yl)benzamide

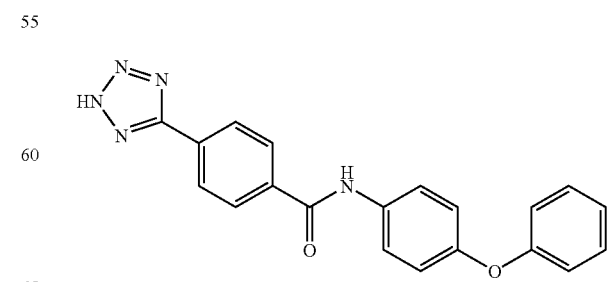

HPLC-MS (Method D): m/z: 358 (M+1); Rt=4.50 min.

Example 503

General Procedure (I)

N-(9H-Fluoren-2-yl)-4-(2H-tetrazol-5-yl)benzamide

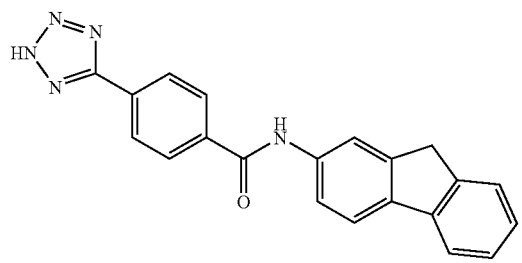

HPLC-MS (Method D): m/z: 354 (M+1); Rt=4.60 min.

Example 504

General Procedure (I)

N-(9-Ethyl-9H-carbazol-2-yl)-4-(2H-tetrazol-5-yl)benzamide

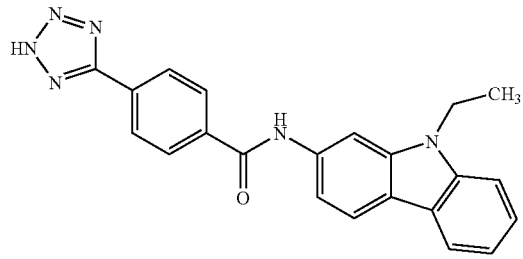

HPLC-MS (Method D): m/z: 383 (M+1); Rt=4.60 min.

Example 505

General Procedure (I)

N-Phenyl-4-(2H-tetrazol-5-yl)benzamide

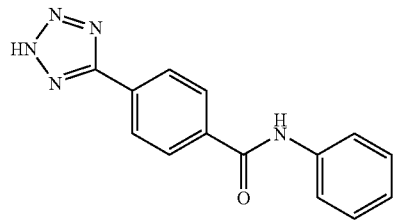

HPLC-MS (Method D): m/z: 266 (M+1); Rt=3.23 min.

Example 506

General Procedure (I)

4-[4-(2H-Tetrazol-5-ylmethoxy)benzoylamino]benzoic acid

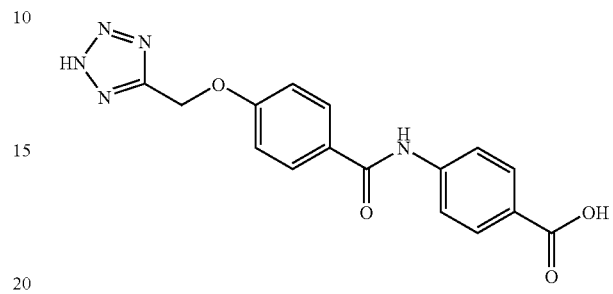

The starting material was prepared as described in example 399.

HPLC-MS (Method D): m/z: 340 (M+1); Rt=2.83 min.

Example 507

General Procedure (I)

3-[4-(2H-Tetrazol-5-ylmethoxy)benzoylamino]benzoic acid

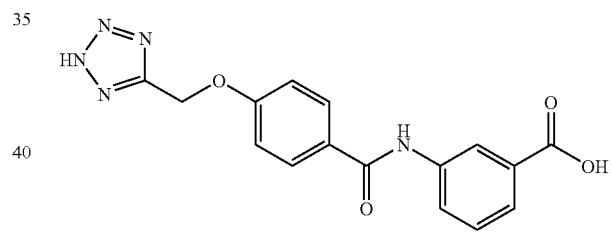

HPLC-MS (Method D): m/z: 340 (M+1); Rt=2.90 min.

Example 508

General Procedure (I)

3-{4-[4-(2H-Tetrazol-5-ylmethoxy)benzoylamino]phenyl}acrylic acid

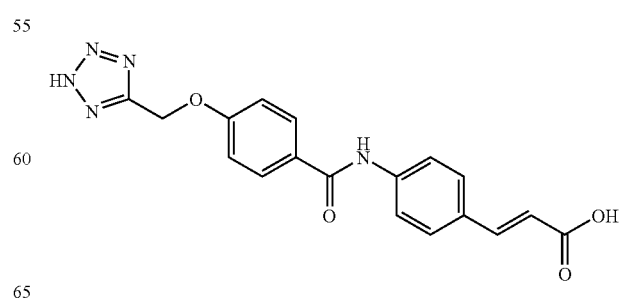

HPLC-MS (Method D): m/z: 366 (M+1); Rt=3.07 min.

Example 509

General Procedure (I)

3-{4-[4-(2H-Tetrazol-5-ylmethoxy)benzoylamino]phenyl}propionic acid

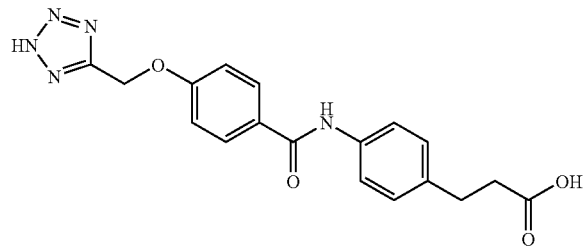

HPLC-MS (Method D): m/z: 368 (M+1); Rt=2.97 min.

Example 510

General Procedure (I)

3-Methoxy-4-[4-(2H-tetrazol-5-ylmethoxy)benzoylamino]benzoic acid

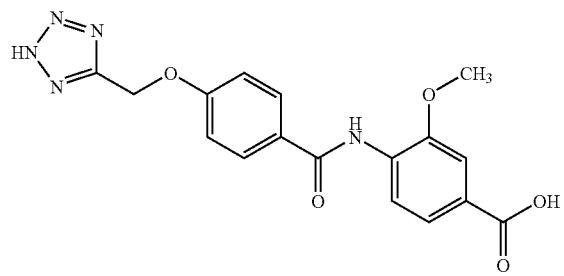

HPLC-MS (Method D): m/z: 370 (M+1); Rt=3.07 min.

Example 511

General Procedure (I)

N-(4-Benzyloxyphenyl)-4-(2H-tetrazol-5-ylmethoxy)benzamide

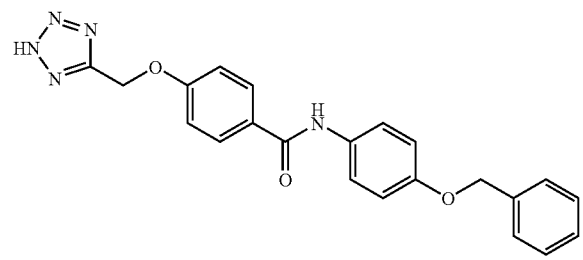

HPLC-MS (Method D): m/z: 402 (M+1); Rt=4.43 min.

Example 512

General Procedure (I)

N-(4-Phenoxyphenyl)-4-(2H-tetrazol-5-ylmethoxy)benzamide

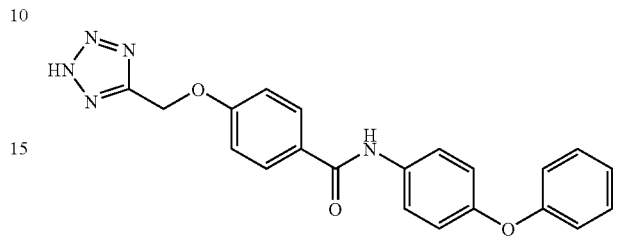

HPLC-MS (Method D): m/z: 388 (M+1); Rt=4.50 min.

Example 513

General Procedure (I)

N-(9H-Fluoren-2-yl)-4-(2H-tetrazol-5-ylmethoxy)benzamide

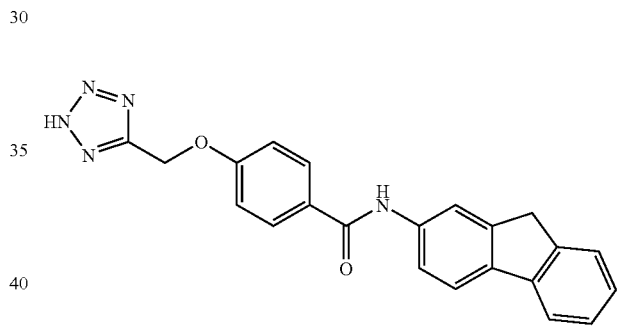

HPLC-MS (Method D): m/z: 384 (M+1); Rt=4.57 min.

Example 514

General Procedure (I)

N-(9-Ethyl-9H-carbazol-2-yl)-4-(2H-tetrazol-5-ylmethoxy)benzamide

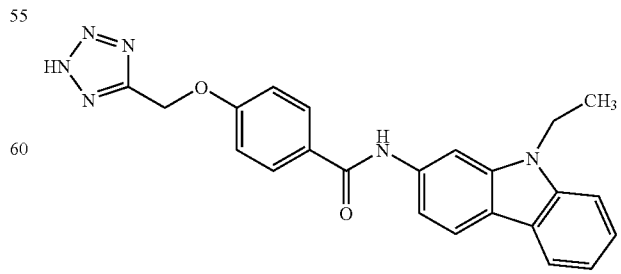

HPLC-MS (Method D): m/z: 413 (M+1); Rt=4.57 min.

Example 515

General Procedure (I)

N-Phenyl-4-(2H-tetrazol-5-ylmethoxy)benzamide

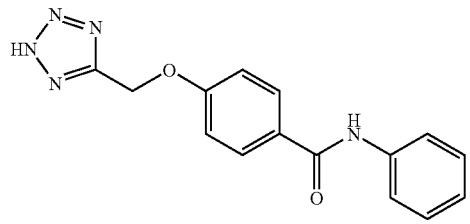

HPLC-MS (Method D): m/z: 296 (M+1); Rt=3.23 min.

Example 516

General Procedure (I)

4-[4-(2H-Tetrazol-5-ylmethylsulfanyl)benzoylamino]benzoic acid

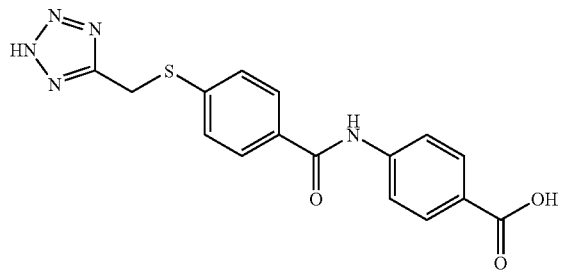

The starting material was prepared as described in example 400.

HPLC-MS (Method D): m/z: 356 (M+1); Rt=2.93 min.

Example 517

General Procedure (I)

3-[4-(2H-Tetrazol-5-ylmethylsulfanyl)benzoylamino]benzoic acid

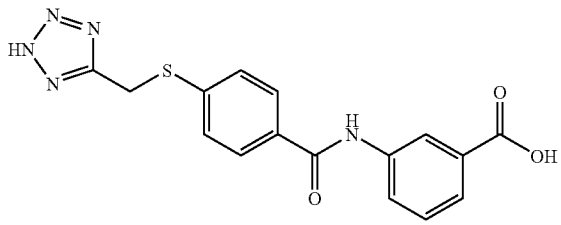

HPLC-MS (Method D): m/z: 356 (M+1); Rt=3.00 min.

Example 518

General Procedure (I)

3-{4-[4-(2H-Tetrazol-5-ylmethylsulfanyl)benzoylamino]phenyl}acrylic acid

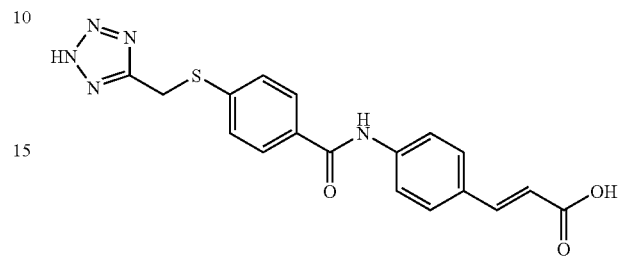

HPLC-MS (Method D): m/z: 382 (M+1); Rt=3.26 min.

Example 519

General Procedure (I)

3-{4-[4-(2H-Tetrazol-5-ylmethylsulfanyl)benzoylamino]phenyl}propionic acid

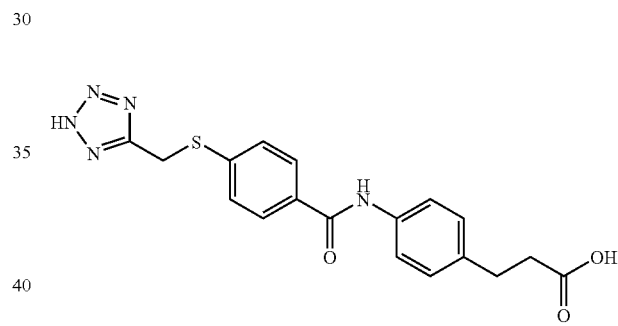

HPLC-MS (Method D): m/z: 384 (M+1); Rt=3.10 min.

Example 520

General Procedure (I)

3-Methoxy-4-[4-(2H-tetrazol-5-ylmethylsulfanyl)benzoylamino]benzoic acid

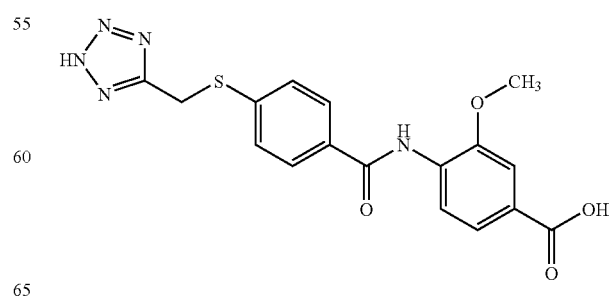

HPLC-MS (Method D): m/z: 386 (M+1); Rt=3.20 min.

Example 521

General Procedure (I)

N-(4-Benzyloxyphenyl)-4-(2H-tetrazol-5-ylmethyl-sulfanyl)benzamide

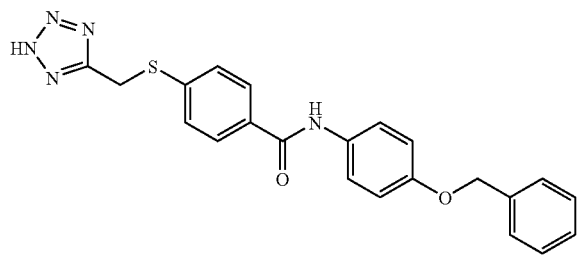

HPLC-MS (Method D): m/z: 418 (M+1); Rt=4.57 min.

Example 522

General Procedure (I)

N-(4-Phenoxyphenyl)-4-(2H-tetrazol-5-ylmethylsul-fanyl)benzamide

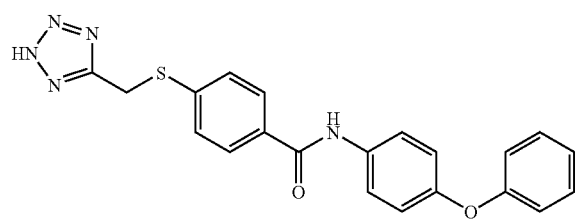

HPLC-MS (Method D): m/z: 404 (M+1); Rt=4.60 min.

Example 523

General Procedure (I)

N-(9H-Fluoren-2-yl)-4-(2H-tetrazol-5-ylmethylsul-fanyl)benzamide

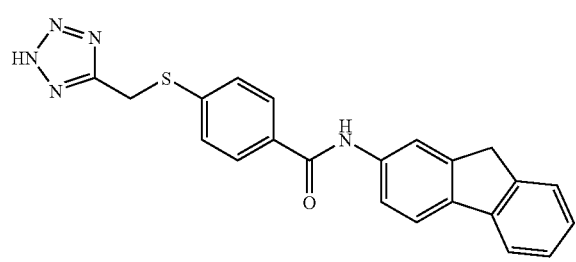

HPLC-MS (Method D): m/z: 400 (M+1); Rt=4.67 min.

Example 524

General Procedure (I)

N-(9-Ethyl-9H-carbazol-2-yl)-4-(2H-tetrazol-5-ylm-ethylsulfanyl)benzamide

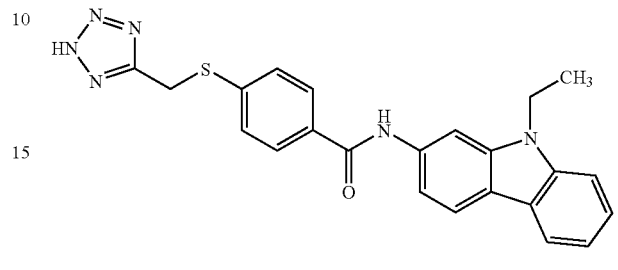

HPLC-MS (Method D): m/z: 429 (M+1); Rt=4.67 min.

Example 525

General Procedure (I)

N-Phenyl-4-(2H-tetrazol-5-ylmethylsulfanyl)benza-mide

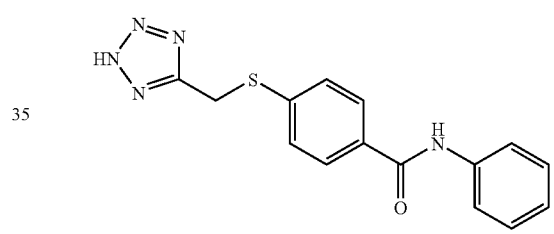

HPLC-MS (Method D): m/z: 312 (M+1); Rt=3.40 min.

General Procedure (J) for Solution Phase Preparation of Amides of General Formula $I_9$:

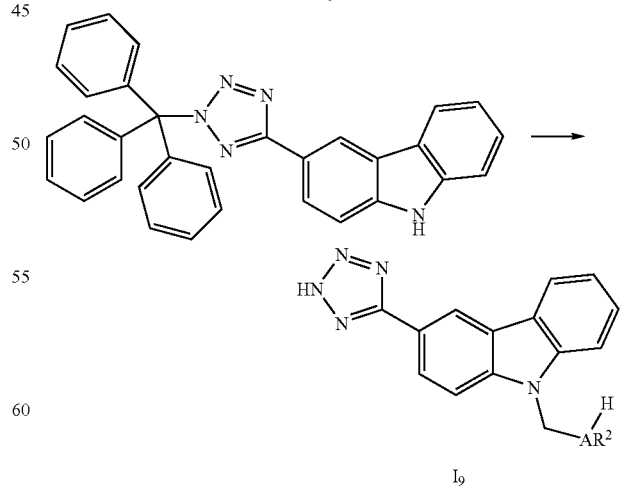

wherein AR2 is as defined above.

This general procedure (J) is further illustrated in the following example.

Example 526

General Procedure (J)

9-(3-Chlorobenzyl)-3-(2H-tetrazol-5-yl)-9H-carbazole

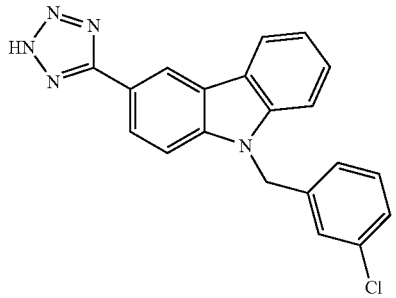

3-(2H-Tetrazol-5-yl)-9H-carbazole (example 401, 17 g, 72.26 mmol) was dissolved in N,N-dimethylformamide (150 mL). Triphenylmethyl chloride (21.153 g, 75.88 mmol) and triethylamine (20.14 mL, 14.62 g, 144.50 mmol) were added consecutively. The reaction mixture was stirred for 18 hours at room temperature, poured into water (1.5 L) and stirred for an additional 1 hour. The crude product was filtered off and dissolved in dichloromethane (500 mL). The organic phase was washed with water (2×250 mL) and dried with magnesium sulfate (1 h). Filtration followed by concentration yielded a solid which was triturated in heptanes (200 mL). Filtration furnished 3-[2-(triphenylmethyl)-2H-tetrazol-5-yl]-9H-carbazole (31.5 g) which was used without further purification.

$^1$H-NMR (CDCl$_3$): δ 8.87 (1H, d), 8.28 (1H, bs), 8.22 (1H, dd), 8.13 (1H, d), 7.49 (1H, d), 7.47-7.19 (18H, m); HPLC-MS (Method C): m/z: 243 (triphenylmethyl); Rt=5.72 min.

3-[2-(Triphenylmethyl)-2H-tetrazol-5-yl]-9H-carbazole (200 mg, 0.42 mmol) was dissolved in methyl sulfoxide (1.5 mL). Sodium hydride (34 mg, 60%, 0.85 mmol) was added, and the resulting suspension was stirred for 30 min at room temperature. 3-Chlorobenzyl chloride (85 µL, 108 mg, 0.67 mmol) was added, and the stirring was continued at 40° C. for 18 hours. The reaction mixture was cooled to ambient temperature and poured into 0.1 N hydrochloric acid (aq.) (15 mL) The precipitated solid was filtered off and washed with water (3×10 mL) to furnish 9-(3-chlorobenzyl)-3-[2-(triphenylmethyl)-2H-tetrazol-5-yl]-9H-carbazole, which was dissolved in a mixture of tetrahydrofuran and 6 N hydrochloric acid (aq.) (9:1) (10 mL) and stirred at room temperature for 18 hours. The reaction mixture was poured into water (100 mL). The solid was filtered off and rinsed with water (3×10 mL) and dichloromethane (3×10 mL) to yield the title compound (127 mg). No further purification was necessary.

$^1$H-NMR (DMSO-d$_6$): δ 8.89 (1H, d), 8.29 (1H, d), 8.12 (1H, dd), 7.90 (1H, d), 7.72 (1H, d), 7.53 (1H, t), 7.36-7.27 (4H, m), 7.08 (1H, bt), 5.78 (2H, s); HPLC-MS (Method B): m/z: 360 (M+1); Rt=5.07 min.

The compounds in the following examples were prepared in a similar fashion. Optionally, the compounds can be further purified by recrystallization from e.g. aqueous sodium hydroxide (1 N) or by chromatography.

Example 527

General Procedure (J)

9-(4-Chlorobenzyl)-3-(2H-tetrazol-5-yl)-9H-carbazole

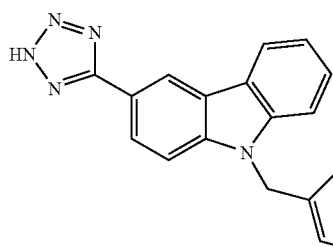

HPLC-MS (Method C): m/z: 360 (M+1); Rt=4.31 min.

Example 528

General Procedure (J)

9-(4-Methylbenzyl)-3-(2H-tetrazol-5-yl)-9H-carbazole

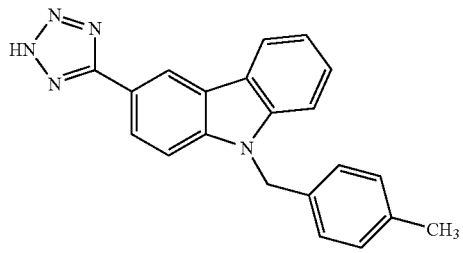

HPLC-MS (Method C): m/z: 340 (M+1); Rt=4.26 min.

Example 529

General Procedure (J)

3-(2H-Tetrazol-5-yl)-9-(4-trifluoromethylbenzyl)-9H-carbazole

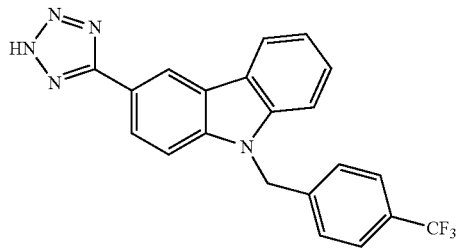

HPLC-MS (Method C): m/z: 394 (M+1); Rt=4.40 min.

Example 530

General Procedure (J)

9-(4-Benzyloxybenzyl)-3-(2H-tetrazol-5-yl)-9H-carbazole

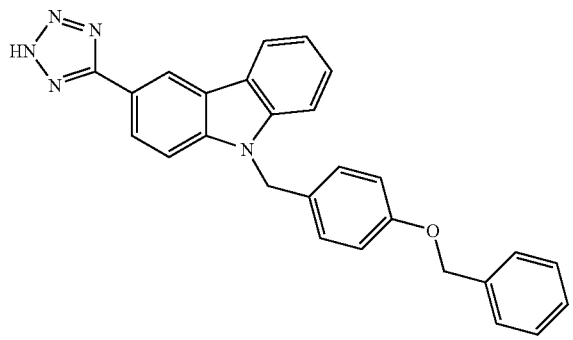

HPLC-MS (Method C): m/z: 432 (M+1); Rt=4.70 min.

Example 531

General Procedure (J)

9-(3-Methylbenzyl)-3-(2H-tetrazol-5-yl)-9H-carbazole

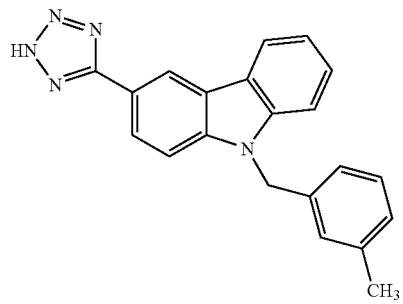

HPLC-MS (Method C): m/z: 340 (M+1); Rt=4.25 min.

Example 532

General Procedure (J)

9-Benzyl-3-(2H-tetrazol-5-yl)-9H-carbazole

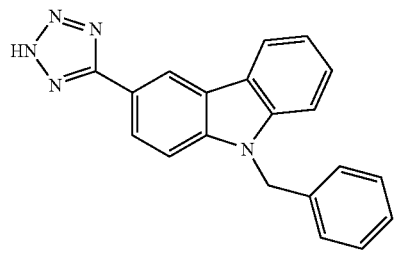

$^1$H-NMR (DMSO-$d_6$): δ 8.91 (1H, dd), 8.30 (1H, d), 8.13 (1H, dd), 7.90 (1H, d), 7.73 (1H, d), 7.53 (1H, t), 7.36-7.20 (6H, m), 5.77 (2H, s).

Example 533

General Procedure (J)

9-(4-Phenylbenzyl)-3-(2H-tetrazol-5-yl)-9H-carbazole

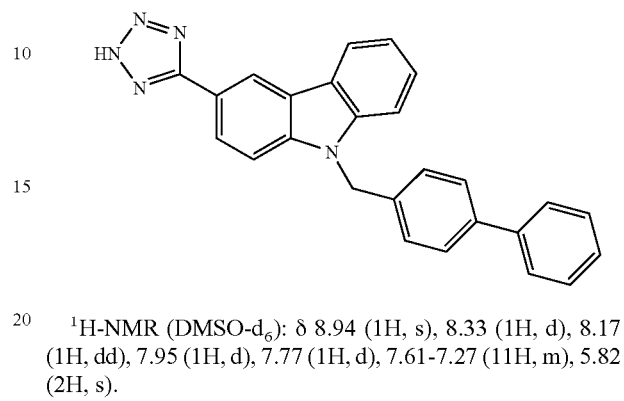

$^1$H-NMR (DMSO-$d_6$): δ 8.94 (1H, s), 8.33 (1H, d), 8.17 (1H, dd), 7.95 (1H, d), 7.77 (1H, d), 7.61-7.27 (11H, m), 5.82 (2H, s).

Example 534

General Procedure (J)

9-(3-Methoxybenzyl)-3-(2H-tetrazol-5-yl)-9H-carbazole

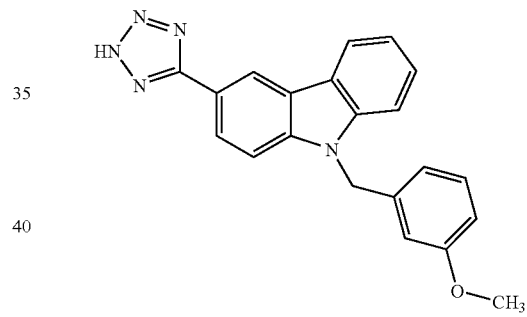

HPLC-MS (Method C): m/z: 356 (M+1); Rt=3.99 min.

Example 535

General Procedure (J)

9-(Naphthalen-2-ylmethyl)-3-(2H-tetrazol-5-yl)-9H-carbazole

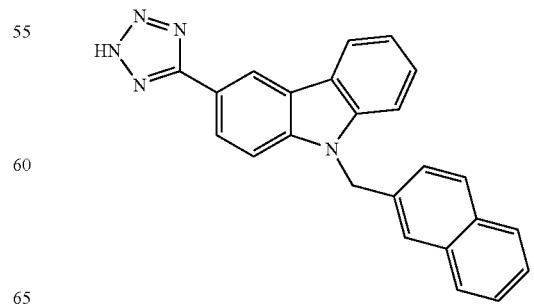

HPLC-MS (Method C): m/z: 376 (M+1); Rt=4.48 min.

Example 536

General Procedure (J)

9-(3-Bromobenzyl)-3-(2H-tetrazol-5-yl)-9H-carbazole

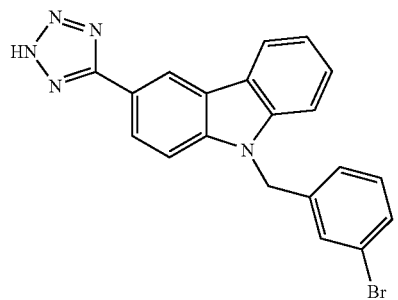

HPLC-MS (Method C): m/z: 404 (M+1); Rt=4.33 min.

Example 537

General Procedure (J)

9-(Biphenyl-2-ylmethyl)-3-(2H-tetrazol-5-yl)-9H-carbazole

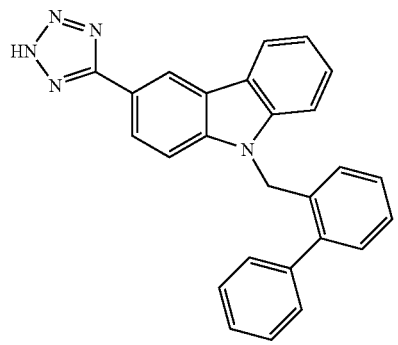

HPLC-MS (Method C): m/z: 402 (M+1); Rt=480 min.

Example 538

General Procedure (J)

3-(2H-Tetrazol-5-yl)-9-[4-(1,2,3-thiadiazol-4-yl)benzyl]-9H-carbazole

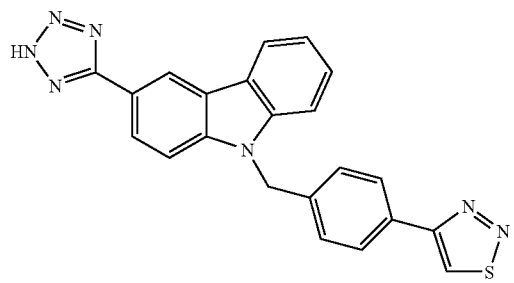

Example 539

General Procedure (J)

9-(2'-Cyanobiphenyl-4-ylmethyl)-3-(2H-tetrazol-5-yl)-9H-carbazole

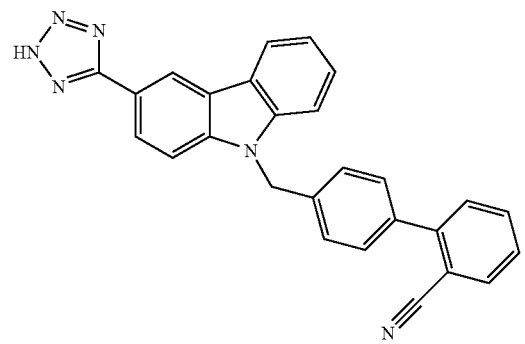

$^1$H-NMR (DMSO-$d_6$): δ 8.91 (1H, d), 8.31 (1H, d), 8.13 (1H, dd), 7.95 (1H, d), 7.92 (1H, d), 7.78 (1H, d), 7.75 (1H, dt), 7.60-7.47 (5H, m), 7.38-7.28 (3H, m), 5.86 (2H, s); HPLC-MS (Method C): m/z: 427 (M+1); Rt=4.38 min.

Example 540

General Procedure (J)

9-(4-Iodobenzyl)-3-(2H-tetrazol-5-yl)-9H-carbazole

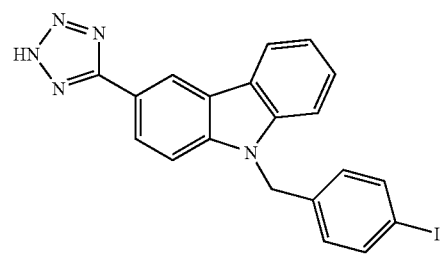

HPLC-MS (Method C): m/z: 452 (M+1); Rt=4.37 min.

Example 541

General Procedure (J)

9-(3,5-Bis(trifluoromethyl)benzyl)-3-(2H-tetrazol-5-yl)-9H-carbazole

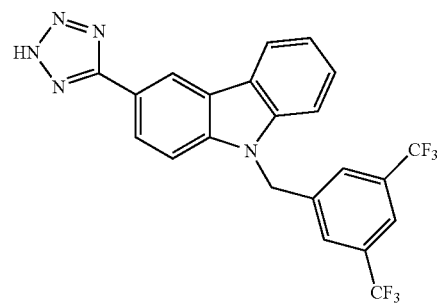

HPLC-MS (Method C): m/z: 462 (M+1); Rt=4.70 min.

Example 542

General Procedure (J)

9-(4-Bromobenzyl)-3-(2H-tetrazol-5-yl)-9H-carbazole

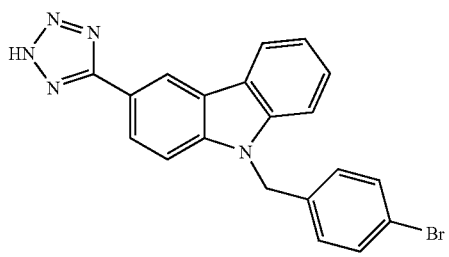

¹H-NMR (DMSO-d₆): δ 8.89 (1H, d), 8.29 (1H, d), 8.11 (1H, dd), 7.88 (1H, d), 7.70 (1H, d), 7.52 (1H, t), 7.49 (2H, d), 7.31 (1H, t), 7.14 (2H, d), 5.74 (2H, s); HPLC-MS (Method C): m/z: 404 (M+1); Rt=4.40 min.

Example 543

General Procedure (J)

9-(Anthracen-9-ylmethyl)-3-(2H-tetrazol-5-yl)-9H-carbazole

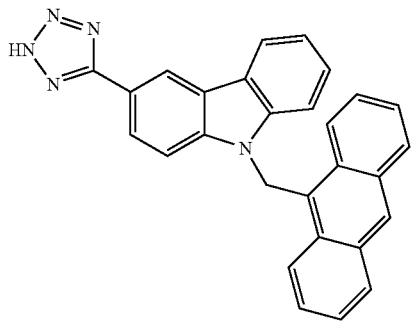

HPLC-MS (Method C): m/z: 426 (M+1); Rt=4.78 min.

Example 544

General Procedure (J)

9-(4-Carboxybenzyl)-3-(2H-tetrazol-5-yl)-9H-carbazole

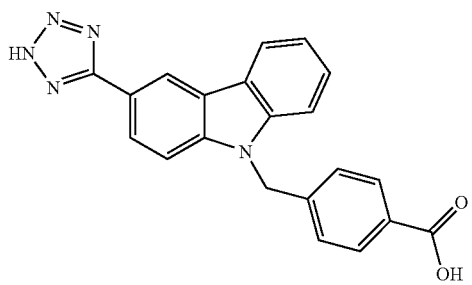

3.6 fold excess sodium hydride was used.

¹H-NMR (DMSO-d₆): δ 12.89 (1H, bs), 8.89 (1H, d), 8.30 (1H, d), 8.10 (1H, dd), 7.87 (1H, d), 7.86 (2H, d), 7.68 (1H, d), 7.51 (1H, t), 7.32 (1H, t), 7.27 (2H, d), 5.84 (2H, s); HPLC-MS (Method C): m/z: 370 (M+1); Rt=3.37 min.

Example 545

General Procedure (J)

9-(2-Chlorobenzyl)-3-(2H-tetrazol-5-yl)-9H-carbazole

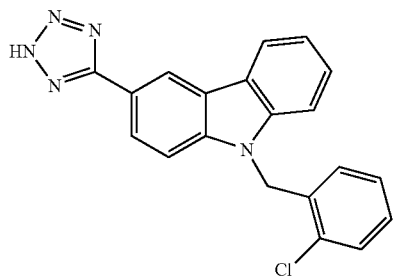

HPLC-MS (Method B): m/z: 360 (M+1); Rt=5.30 min.

Example 546

General Procedure (J)

9-(4-Fluorobenzyl)-3-(2H-tetrazol-5-yl)-9H-carbazole

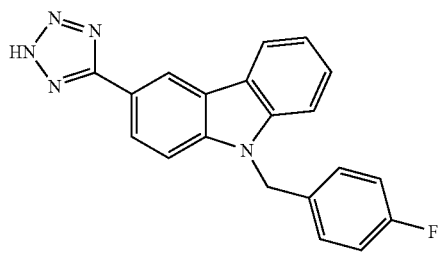

¹H-NMR (DMSO-d₆): δ 8.88 (1H, d), 8.28 (1H, d), 8.10 (1H, dd), 7.89 (1H, d), 7.72 (1H, d), 7.52 (1H, t), 7.31 (1H, t), 7.31-7.08 (4H, m), 5.74 (2H, s); HPLC-MS (Method C): m/z: 344 (M+1); Rt=4.10 min.

Example 547

General Procedure (J)

9-(3-Fluorobenzyl)-3-(2H-tetrazol-5-yl)-9H-carbazole

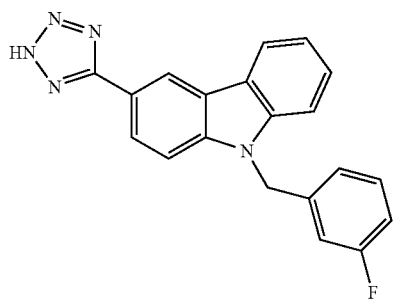

¹H-NMR (DMSO-d₆): δ 8.89 (1H, d), 8.29 (1H, d), 8.12 (1H, dd), 7.90 (1H, d), 7.72 (1H, d), 7.53 (1H, t), 7.37-7.27 (2H, m), 7.12-7.02 (2H, m), 6.97 (1H, d), 5.78 (2H, s); HPLC-MS (Method C): m/z: 344 (M+1); Rt=4.10 min.

Example 548

General Procedure (J)

9-(2-Iodobenzyl)-3-(2H-tetrazol-5-yl)-9H-carbazole

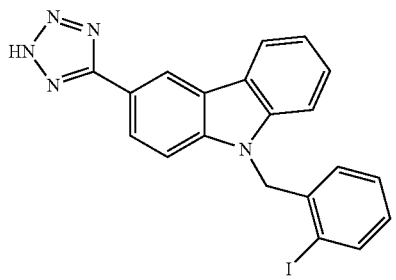

HPLC-MS (Method C): m/z: 452 (M+1); Rt=4.58 min.

Example 549

General Procedure (J)

9-(3-Carboxybenzyl)-3-(2H-tetrazol-5-yl)-9H-carbazole

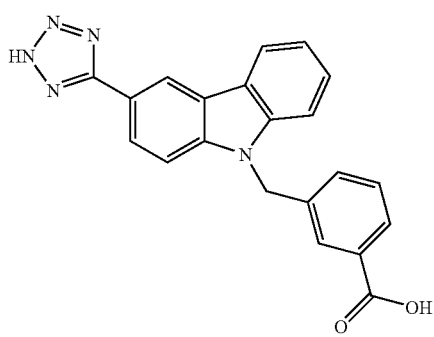

3.6 fold excess sodium hydride was used.

$^1$H-NMR (DMSO-$d_6$): δ 12.97 (1H, bs), 8.90 (1H, bs), 8.30 (1H, d), 8.12 (1H, bd), 7.8 (1H, d), 7.82 (1H, m), 7.77 (1H, bs), 7.71 (1H, d), 7.53 (1H, t), 7.46-7.41 (2H, m), 7.32 (1H, t), 5.84 (2H, s); HPLC-MS (Method C): m/z: 370 (M+1); Rt=3.35 min.

Example 550

General Procedure (J)

9-[4-(2-Propyl)benzyl]-3-(2H-tetrazol-5-yl)-9H-carbazole

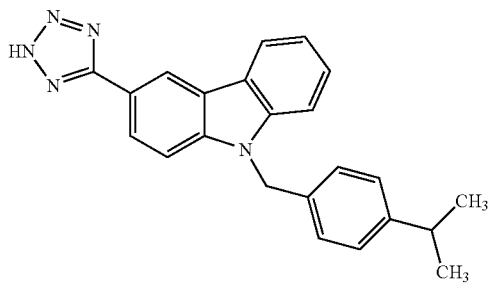

$^1$H-NMR (DMSO-$d_6$): δ 8.87 (1H, d), 8.27 (1H, d), 8.10 (1H, dd), 7.87 (1H, d), 7.71 (1H, d), 7.51 (1H, t), 7.31 (1H, t), 7.15 (2H, d), 7.12 (2H, d), 5.69 (2H, s), 2.80 (1H, sept), 1.12 (6H, d); HPLC-MS (Method C): m/z: 368 (M+1); Rt=4.73 min.

Example 551

General Procedure (J)

9-(3,5-Dimethoxybenzyl)-3-(2H-tetrazol-5-yl)-9H-carbazole

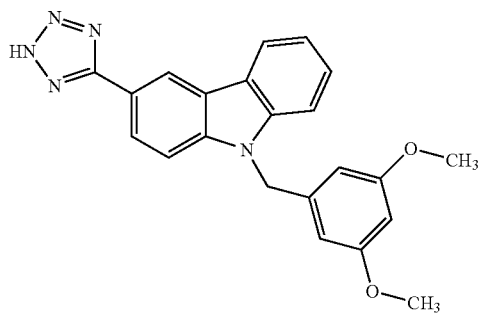

HPLC-MS (Method C): m/z: 386 (M+1); Rt=4.03 min.

Example 552

General Procedure (J)

3-(2H-Tetrazol-5-yl)-9-(2,4,5-trifluorobenzyl)-9H-carbazole

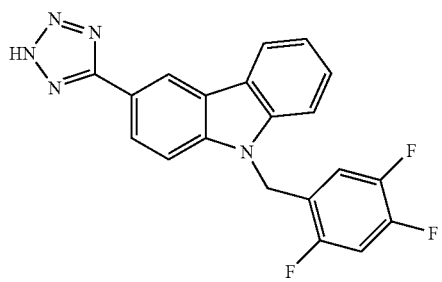

HPLC-MS (Method B): m/z: 380 (M+1); Rt=5.00 min.

Example 553

General Procedure (J)

N-Methyl-N-phenyl-2-[3-(2H-tetrazol-5-yl)carbazol-9-yl]acetamide

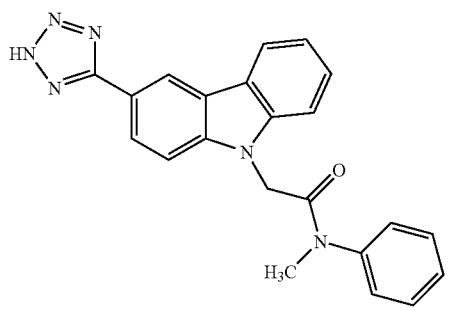

HPLC-MS (Method B): m/z: 383 (M+1); Rt=4.30 min.

Example 554

General Procedure (J)

9-(4-Methoxybenzyl)-3-(2H-tetrazol-5-yl)-9H-carbazole

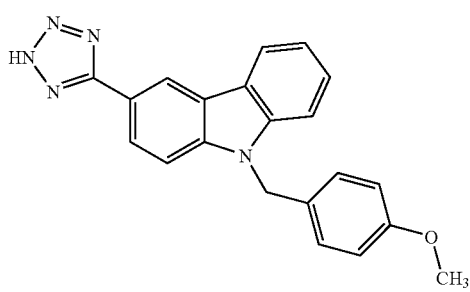

$^1$H-NMR (DMSO-d$_6$): δ 8.86 (1H, d), 8.26 (1H, d), 8.10 (1H, dd), 7.90 (1H, d), 7.73 (1H, d), 7.51 (1H, t), 7.30 (1H, t), 7.18 (2H, d), 6.84 (2H, d), 5.66 (2H, s), 3.67 (3H, s); HPLC-MS (Method B): m/z: 356 (M+1); Rt=4.73 min.

Example 555

General Procedure (J)

9-(2-Methoxybenzyl)-3-(2H-tetrazol-5-yl)-9H-carbazole

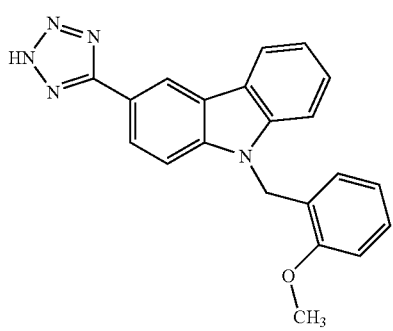

$^1$H-NMR (DMSO-d$_6$): δ 8.87 (1H, d), 8.27 (1H, d), 8.09 (1H, dd), 7.77 (1H, d), 7.60 (1H, d), 7.49 (1H, t), 7.29 (1H, t), 7.23 (1H, bt), 7.07 (1H, bd), 6.74 (1H, bt), 6.61 (1H, bd), 5.65 (2H, s), 3.88 (3H, s); HPLC-MS (Method B): m/z: 356 (M+1); Rt=4.97 min.

Example 556

General Procedure (J)

9-(4-Cyanobenzyl)-3-(2H-tetrazol-5-yl)-9H-carbazole

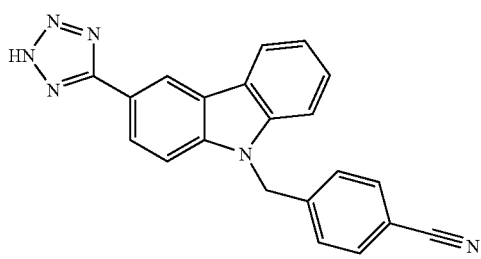

HPLC-MS (Method C): m/z: 351 (M+1); Rt=3.74 min.

Example 557

General Procedure (J)

9-(3-Cyanobenzyl)-3-(2H-tetrazol-5-yl)-9H-carbazole

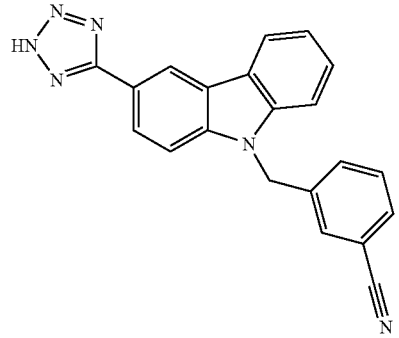

HPLC-MS (Method C): m/z: 351 (M+1); Rt=3.73 min.

Example 558

General Procedure (J)

9-(5-Chloro-2-methoxybenzyl)-3-(2H-tetrazol-5-yl)-9H-carbazole

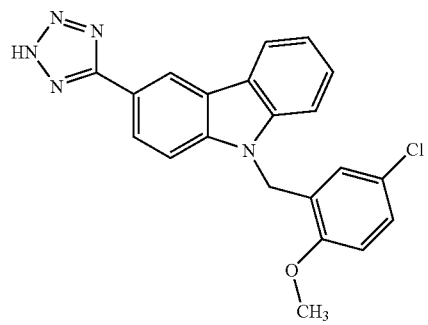

$^1$H-NMR (DMSO-d$_6$): δ 8.87 (1H, d), 8.35 (1H, d), 8.10 (1H, dd), 7.73 (1H, d), 7.59 (1H, d), 7.49 (1H, t), 7.29 (1H, t), 7.27 (1H, dd), 7.11 (1H, d), 6.51 (1H, d), 5.63 (2H, s), 3.88 (3H, s); HPLC-MS (Method C): m/z: 390 (M+1); Rt=4.37 min.

Example 559

General Procedure (J)

N-Phenyl-2-[3-(2H-tetrazol-5-yl)carbazol-9-yl]acetamide

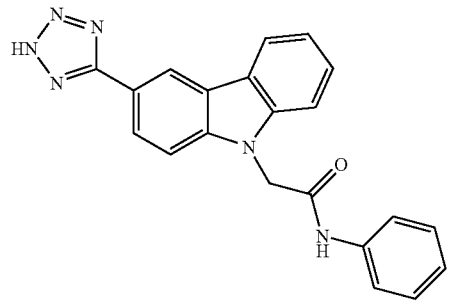

$^1$H-NMR (DMSO-d$_6$): δ 10.54 (1H, s), 8.87 (1H, bs), 8.27 (1H, d), 8.12 (1H, bd), 7.83 (1H, d), 7.66 (1H, d), 7.61 (2H, d), 7.53 (1H, t), 7.32 (1H, t), 7.32 (2H, t), 7.07 (1H, t), 5.36 (2H, s); HPLC-MS (Method C): m/z: 369 (M+1); Rt=3.44 min.

Example 560

General Procedure (J)

N-Butyl-2-[3-(2H-tetrazol-5-yl)carbazol-9-yl]acetamide

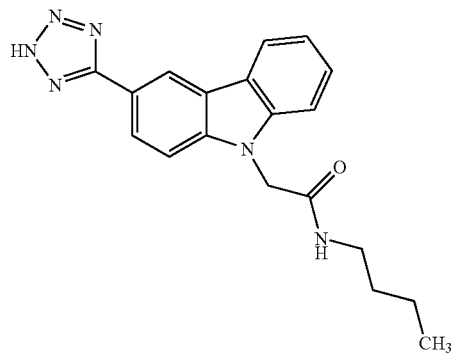

$^1$H-NMR (DMSO-$d_6$): δ 8.85 (1H, d), 8.31 (1H, t), 8.25 (1H, d), 8.10 (1H, dd), 7.75 (1H, d), 7.58 (1H, d), 7.52 (1H, t), 7.30 (1H, t), 5.09 (2H, s), 3.11 (2H, q), 1.42 (2H, quint), 1.30 (2H, sext), 0.87 (3H, t); HPLC-MS (Method C): m/z: 349 (M+1); Rt=3.20 min.

Example 561

General Procedure (J)

9-(2,4-Dichlorobenzyl)-3-(2H-tetrazol-5-yl)-9H-carbazole

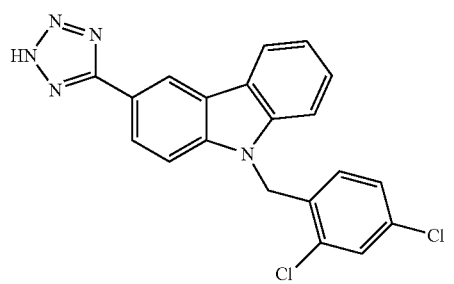

$^1$H-NMR (DMSO-$d_6$): δ 8.92 (1H, d), 8.32 (1H, d), 8.09 (1H, dd), 7.76 (1H, d), 7.74 (1H, d), 7.58 (1H, d), 7.51 (1H, t), 7.33 (1H, t), 7.23 (1H, dd), 6.42 (1H, d), 5.80 (2H, s); HPLC-MS (Method B): m/z: 394 (M+1); Rt=5.87 min.

Example 562

General Procedure (J)

9-(2-Methylbenzyl)-3-(2H-tetrazol-5-yl)-9H-carbazole

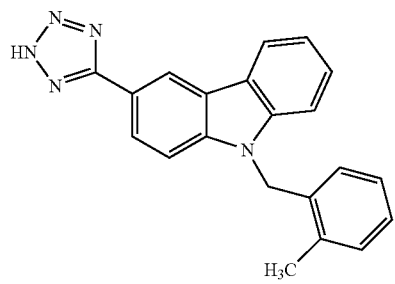

$^1$H-NMR (DMSO-$d_6$): δ 8.92 (1H, d), 8.32 (1H, d), 8.08 (1H, dd), 7.72 (1H, d), 7.55 (1H, d), 7.48 (1H, t), 7.32 (1H, t), 7.26 (1H, d), 7.12 (1H, t), 6.92 (1H, t), 6.17 (1H, d), 5.73 (2H, s), 2.46 (3H, s); HPLC-MS (Method B): m/z: 340 (M+1); Rt=5.30 min.

Example 563

General Procedure (J)

9-(3-Nitrobenzyl)-3-(2H-tetrazol-5-yl)-9H-carbazole

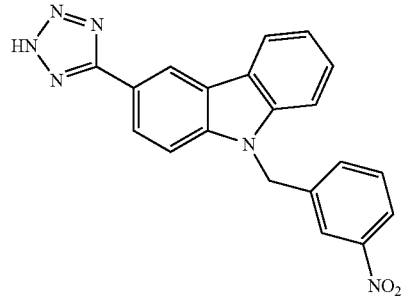

HPLC-MS (Method C): m/z: 371 (M+1); Rt=3.78 min.

Example 564

General Procedure (J)

9-(3,4-Dichlorobenzyl)-3-(2H-tetrazol-5-yl)-9H-carbazole

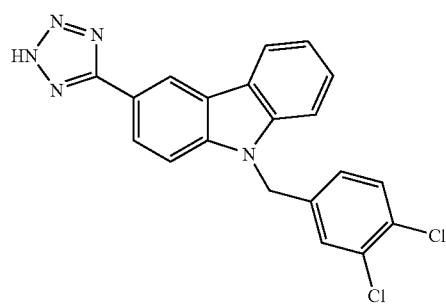

HPLC-MS (Method B): m/z: 394 (M+1); Rt=5.62 min.

Example 565

General Procedure (J)

9-(2,4-Difluorobenzyl)-3-(2H-tetrazol-5-yl)-9H-carbazole

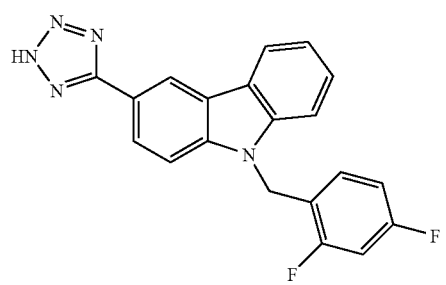

$^1$H-NMR (DMSO-$d_6$): δ 8.89 (1H, d), 8.29 (1H, d), 8.11 (1H, dd), 7.88 (1H, d), 7.69 (1H, d), 7.52 (1H, t), 7.36-7.24 (2H, m), 7.06-6.91 (2H, m), 5.78 (2H, s); HPLC-MS (Method B): m/z: 362 (M+1); Rt=5.17 min.

Example 566

General Procedure (J)

9-(3,5-Difluorobenzyl)-3-(2H-tetrazol-5-yl)-9H-carbazole

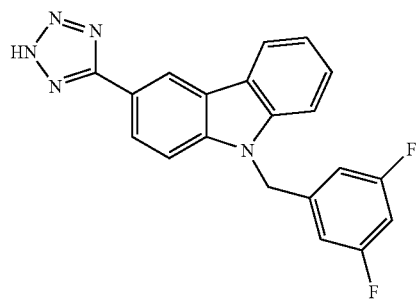

$^1$H-NMR (DMSO-$d_6$): δ 8.90 (1H, bs), 8.31 (1H, d), 8.13 (1H, bd), 7.90 (1H, d), 7.73 (1H, d), 7.54 (1H, t), 7.34 (1H, t), 7.14 (1H, t), 6.87 (2H, bd), 5.80 (2H, s); HPLC-MS (Method B): m/z: 362 (M+1); Rt=5.17 min.

Example 567

General Procedure (J)

9-(3,4-Difluorobenzyl)-3-(2H-tetrazol-5-yl)-9H-carbazole

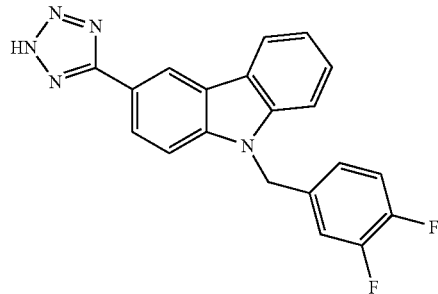

$^1$H-NMR (DMSO-$d_6$): δ 8.89 (1H, bs), 8.29 (1H, d), 8.12 (1H, bd), 7.92 (1H, d), 7.74 (1H, d), 7.54 (1H, t), 7.42-7.25 (3H, m), 6.97 (1H, bm), 5.75 (2H, s); HPLC-MS (Method B): m/z: 362 (M+1); Rt=5.17 min.

Example 568

General Procedure (J)

9-(3-Iodobenzyl)-3-(2H-tetrazol-5-yl)-9H-carbazole

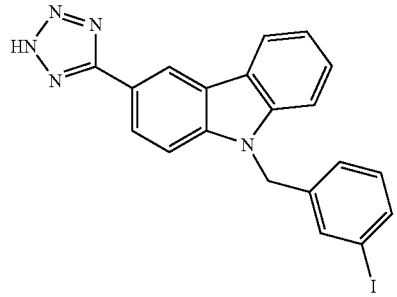

HPLC-MS (Method B): m/z: 452 (M+1); Rt=5.50 min.

Example 569

General Procedure (J)

3-(2H-Tetrazol-5-yl)-9-[3-(trifluoromethyl)benzyl]-9H-carbazole

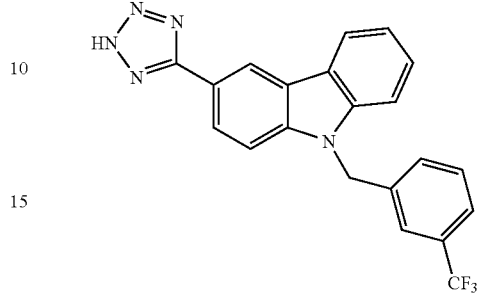

$^1$H-NMR (DMSO-$d_6$): δ 8.89 (1H, d), 8.30 (1H, d), 8.11 (1H, dd), 7.90 (1H, d), 7.72 (1H, d), 7.67 (1H, bs), 7.62 (1H, bd), 7.53 (1H, t), 7.50 (1H, bt), 7.33 (1H, bd), 7.32 (1H, t), 5.87 (2H, s); HPLC-MS (Method B): m/z: 394 (M+1); Rt=5.40 min.

Example 570

General Procedure (J)

N-(4-Carboxyphenyl)-2-[3-(2H-tetrazol-5-yl)carbazol-9-yl]acetamide

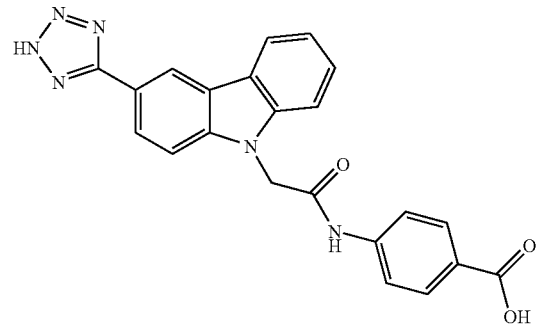

3.6 fold excess sodium hydride was used.
HPLC-MS (Method B): m/z: 413 (M+1); Rt=3.92 min.

Example 571

General Procedure (J)

N-(2-Propyl)-2-[3-(2H-tetrazol-5-yl)carbazol-9-yl]acetamide

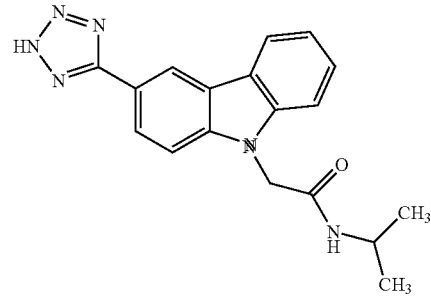

HPLC-MS (Method B): m/z: 335 (M+1); Rt=3.70 min.

Example 572

General Procedure (J)

N-Benzyl-N-phenyl-2-[3-(2H-tetrazol-5-yl)carbazol-9-yl]acetamide

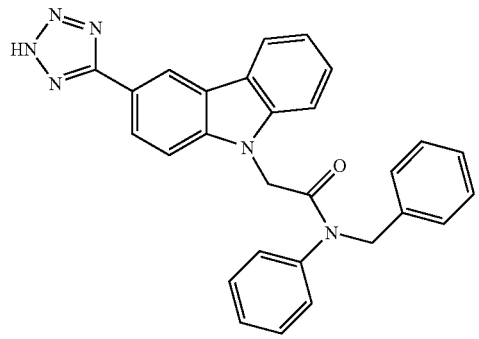

HPLC-MS (Method B): m/z: 459 (M+1); Rt=5.37 min.

Example 573

General Procedure (J)

N-[4-(2-Methyl-2-propyl)phenyl]-2-[3-(2H-tetrazol-5-yl)carbazol-9-yl]acetamide

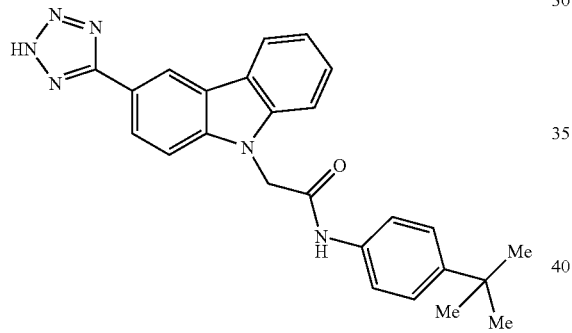

HPLC-MS (Method B): m/z: 425 (M+1); Rt=5.35 min.

Example 574

General Procedure (J)

N-Phenethyl-2-[3-(2H-tetrazol-5-yl)carbazol-9-yl]acetamide

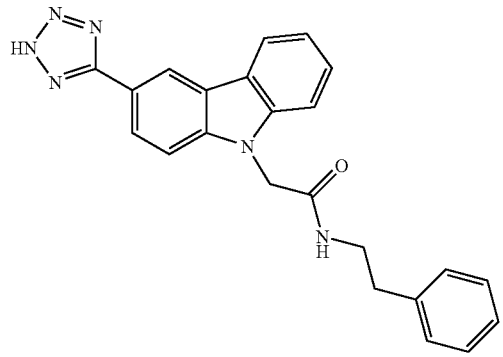

HPLC-MS (Method C): m/z: 397 (M+1); Rt=3.43 min.

Example 575

General Procedure (J)

3-(2H-Tetrazol-5-yl)-9-[2-(trifluoromethyl)benzyl]-9H-carbazole

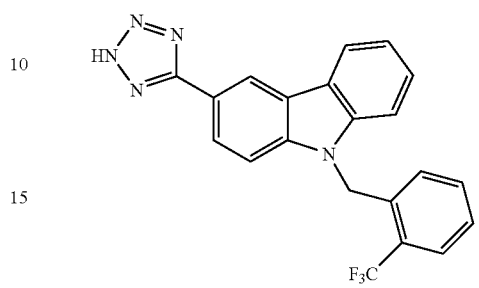

HPLC-MS (Method C): m/z: 394 (M+1); Rt=4.44 min.

Example 576

General Procedure (J)

9-[2-Fluoro-6-(trifluoromethyl)benzyl]-3-(2H-tetrazol-5-yl)-9H-carbazole

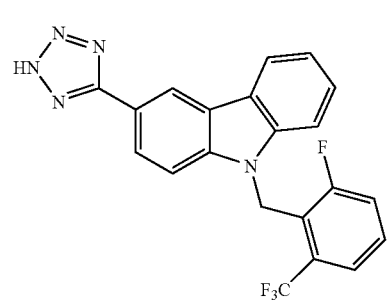

HPLC-MS (Method C): m/z: 412 (M+1); Rt=4.21 min.

Example 577

General Procedure (J)

9-[2,4-Bis(trifluoromethyl)benzyl)]-3-(2H-tetrazol-5-yl)-9H-carbazole

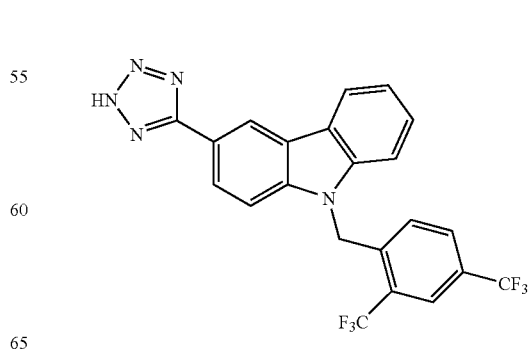

HPLC-MS (Method C): m/z: 462 (M+1); Rt=4.82 min.

Example 578

General Procedure (J)

3-(2H-Tetrazol-5-yl)-9-(2,4,6-trimethylbenzyl)-9H-carbazole

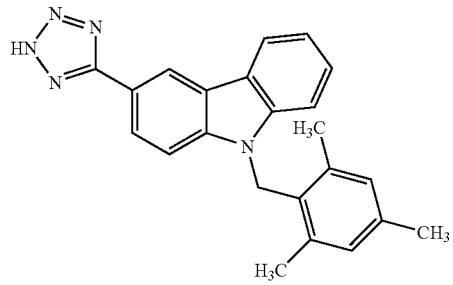

HPLC-MS (Method C): m/z: 368 (M+1); Rt=4.59 min.

Example 579

General Procedure (J)

9-(2,3,5,6-Tetramethylbenzyl)-3-(2H-tetrazol-5-yl)-9H-carbazole

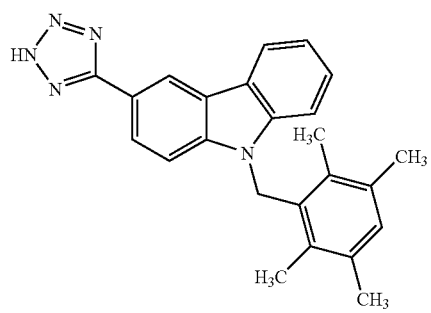

HPLC-MS (Method C): m/z: 382 (M+1); Rt=4.47 min.

Example 580

General Procedure (J)

9-[(Naphthalen-1-yl)methyl]-3-(2H-tetrazol-5-yl)-9H-carbazole

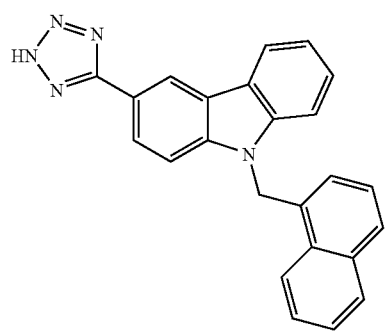

HPLC-MS (Method C): m/z: 376 (M+1); Rt=4.43 min.

Further preferred compounds of the invention that may be prepared according to general procedure (J) includes:

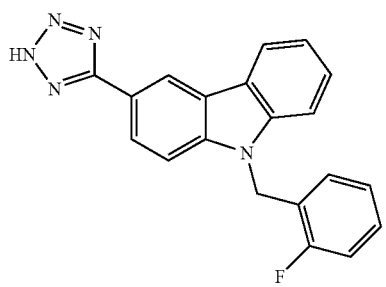

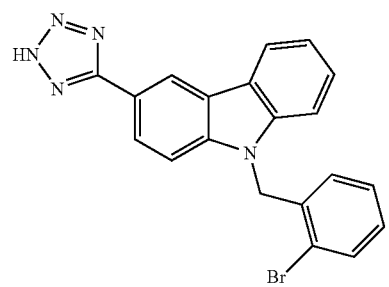

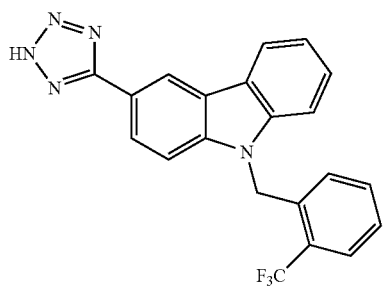

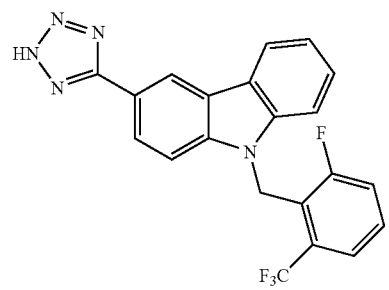

-continued

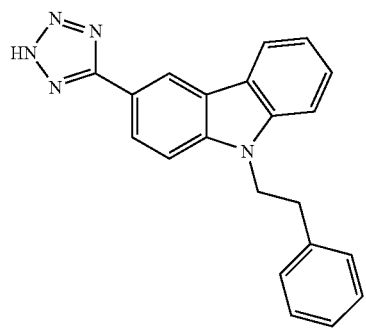
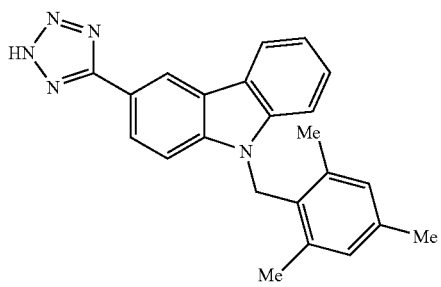

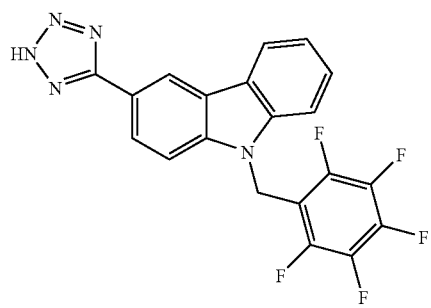
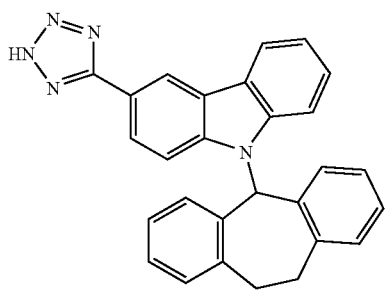

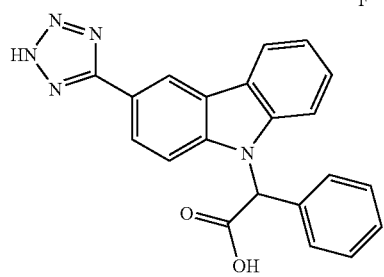
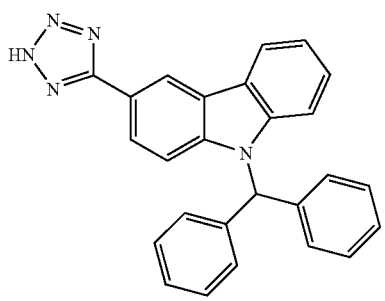

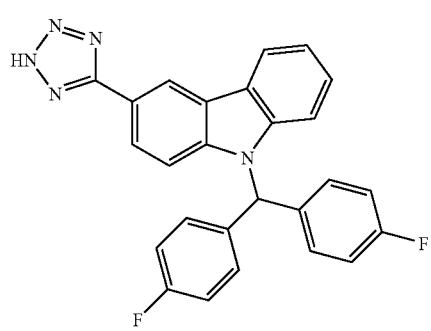
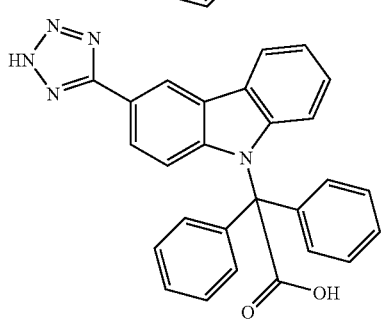

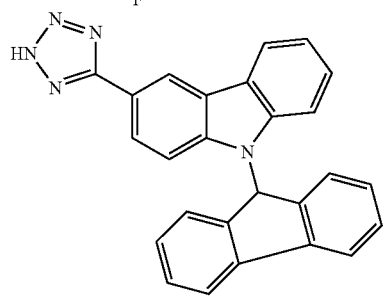

The following preferred compounds of the invention may be prepared eg. from 9-(4-bromobenzyl)-3-(2H-tetrazol-5-yl)-9H-carbazole (example 542) or from 9-(3-bromobenzyl)-3-(2H-tetrazol-5-yl)-9H-carbazole (example 536) and aryl boronic acids via the Suzuki coupling reaction eg as described in Littke, Dai & Fu *J. Am. Chem. Soc.*, 2000, 122, 4020-8 (or references cited therein), or using the methodology described in general procedure (E), optionally changing the palladium catalyst to bis(tri-tert-butylphosphine)palladium (0).

221
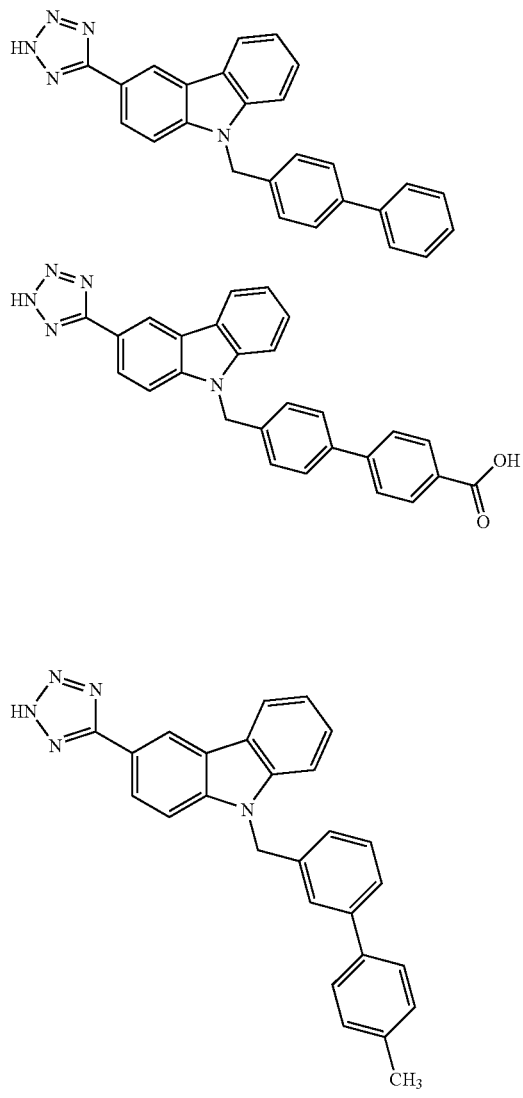
222
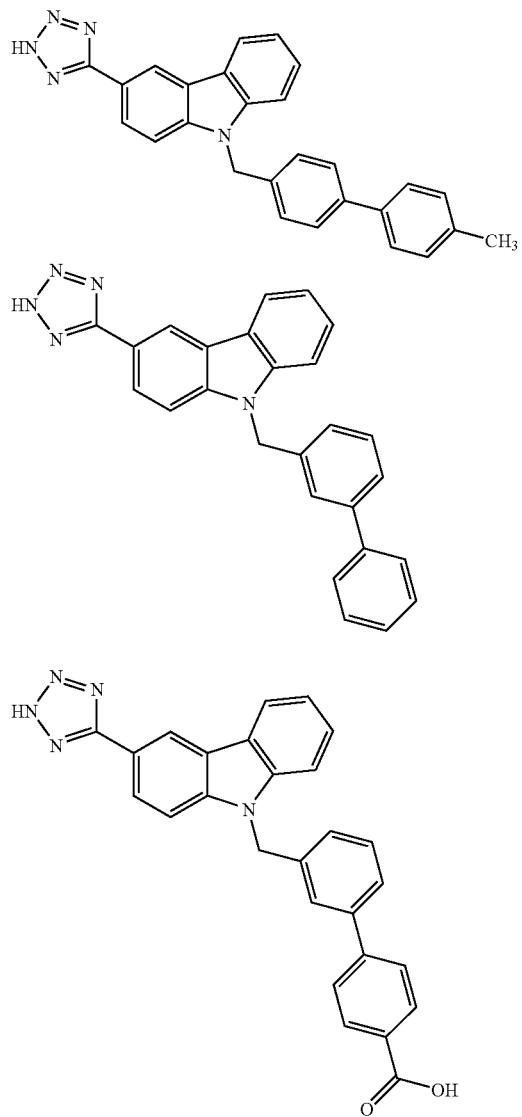
General Procedure (K) for Preparation of Compounds of General Formula I$_{10}$:
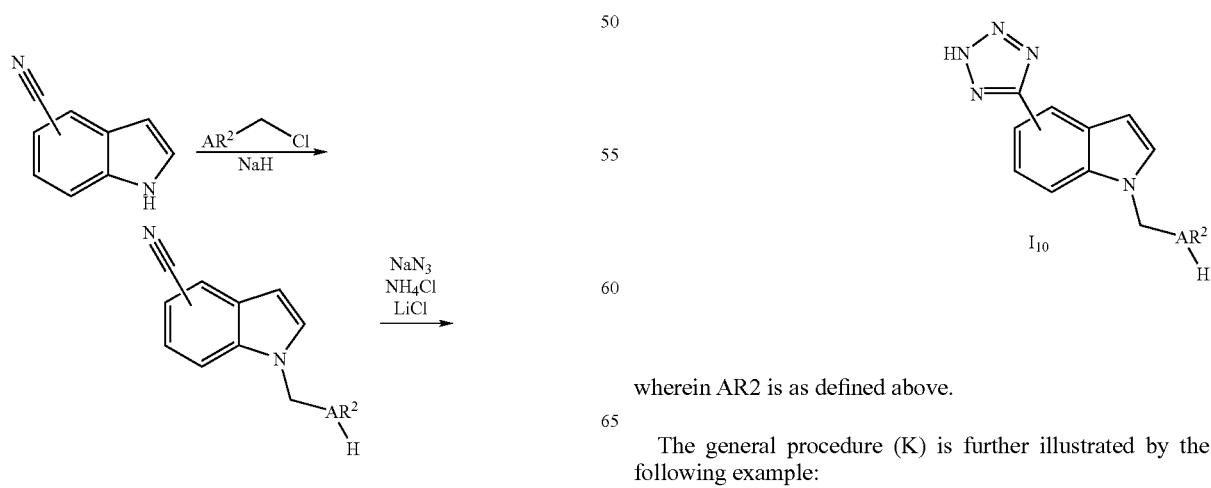
wherein AR2 is as defined above.
The general procedure (K) is further illustrated by the following example:

Example 581

General Procedure (K)

1-Benzyl-5-(2H-tetrazol-5-yl)-1H-indole

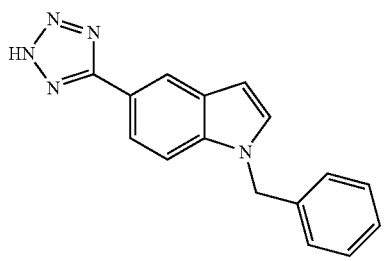

5-Cyanoindole (1.0 g, 7.0 mmol) was dissolved in N,N-dimethylformamide (14 mL) and cooled in an ice-water bath. Sodium hydride (0.31 g, 60%, 7.8 mmol) was added, and the resulting suspension was stirred for 30 min. Benzyl chloride (0.85 mL, 0.94 g, 7.4 mmol) was added, and the cooling was discontinued. The stirring was continued for 65 hours at room temperature. Water (150 mL) was added, and the mixture was extracted with ethyl acetate (3×25 mL). The combined organic phases were washed with brine (30 mL) and dried with sodium sulfate (1 hour). Filtration and concentration yielded the crude material. Purification by flash chromatography on silica gel eluting with ethyl acetate/heptanes=1:3 afforded 1.60 g 1-benzyl-1H-indole-5-carbonitrile.

HPLC-MS (Method C): m/z: 233 (M+1); Rt=4.17 min.

1-Benzyl-1H-indole-5-carbonitrile was transformed into 1-benzyl-5-(2H-tetrazol-5-yl)-1H-indole by the method described in general procedure (J) and in example 401. Purification was done by flash chromatography on silica gel eluting with dichloromethane/methanol=9:1.

HPLC-MS (Method C): m/z: 276 (M+1); Rt=3.35 min.

The compounds in the following examples were prepared by the same procedure.

Example 582

General Procedure (K)

1-(4-Bromobenzyl)-5-(2H-tetrazol-5-yl)-1H-indole

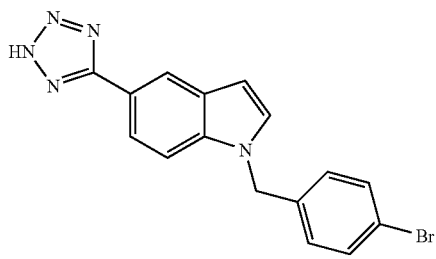

HPLC-MS (Method C): m/z: 354 (M+1); Rt=3.80 min.

Example 583

General Procedure (K)

1-(4-Phenylbenzyl)-5-(2H-tetrazol-5-yl)-1H-indole

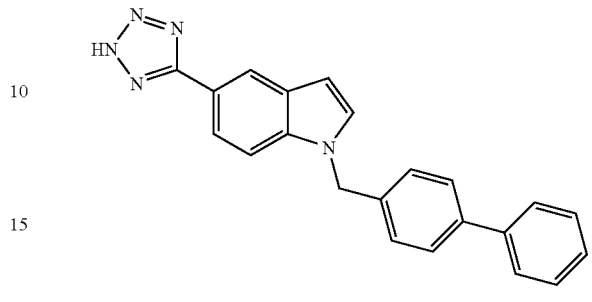

$^1$H-NMR (200 MHz, DMSO-$d_6$): δ=5.52 (2H, s), 6.70 (1H, d), 7.3-7.45 (6H, m), 7.6 (4H, m), 7.7-7.8 (2H, m), 7.85 (1H, dd), 8.35 (1H, d).

Calculated for $C_{22}H_{17}N_5$, $H_2O$: 73.32% C; 5.03% H; 19.43% N. Found: 73.81% C; 4.90% H; 19.31% N.

Example 584

General Procedure (K)

5-(2H-Tetrazol-5-yl)-1H-indole

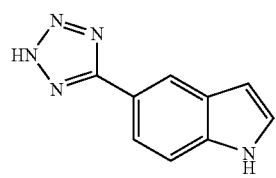

5-(2H-Tetrazol-5-yl)-1H-indole was prepared from 5-cyanoindole according to the method described in example 401.

HPLC-MS (Method C): m/z: 186 (M+1); Rt=1.68 min.

Example 585

General Procedure (K)

1-Benzyl-4-(2H-tetrazol-5-yl)-1H-indole

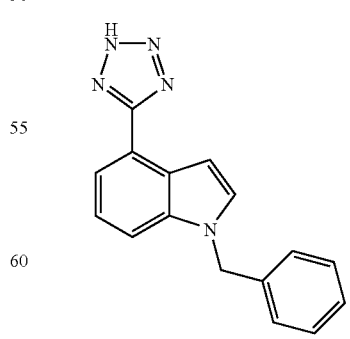

1-Benzyl-1H-indole-4-carbonitrile was prepared from 4-cyanoindole according to the method described in example 581.

225
HPLC-MS (Method C): m/z: 233 (M+1); Rt=4.24 min.
1-Benzyl-4-(2H-tetrazol-5-yl)-1H-indole was prepared from 1-benzyl-1H-indole-4-carbonitrile according to the method described in example 401.
226
HPLC-MS (Method C): m/z: 276 (M+1); Rt=3.44 min.
Further preferred compounds of the invention that may be prepared according to general procedure (K) includes:
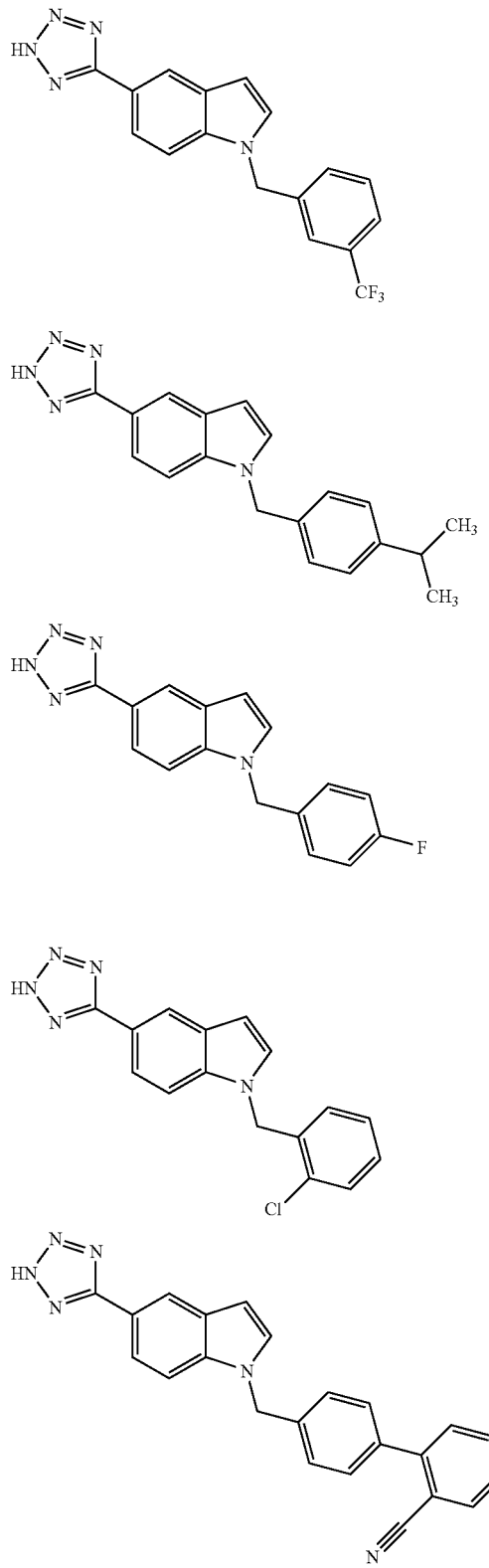

227
228
-continued
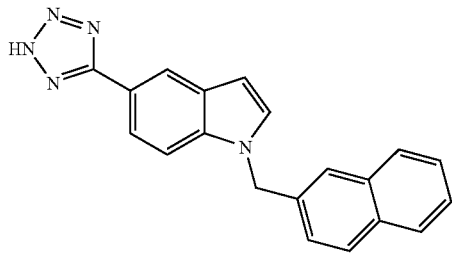
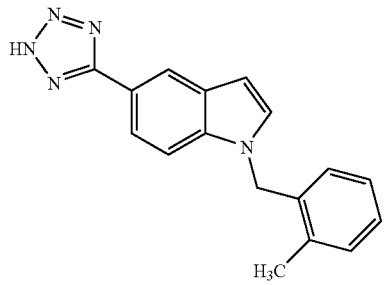
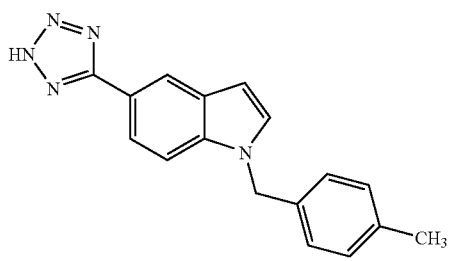
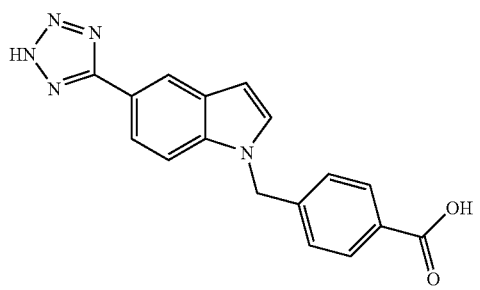
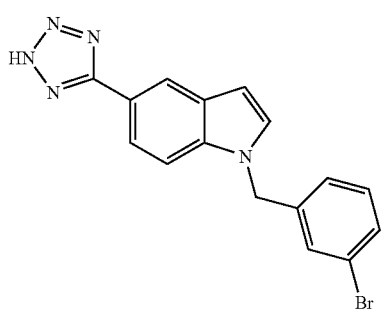
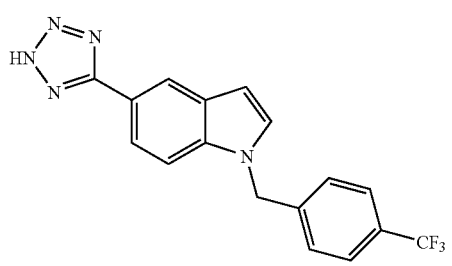
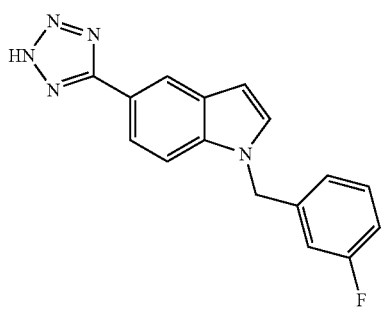
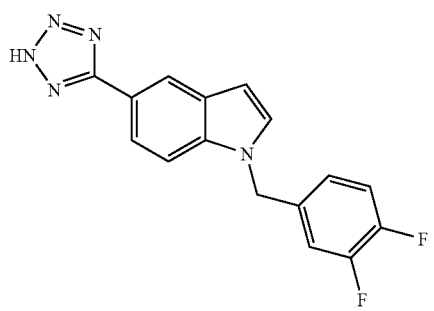
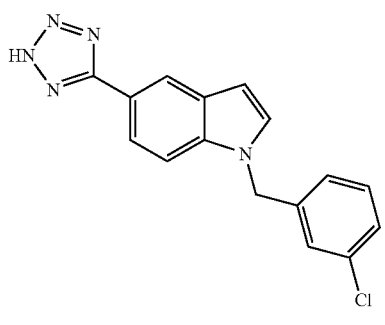
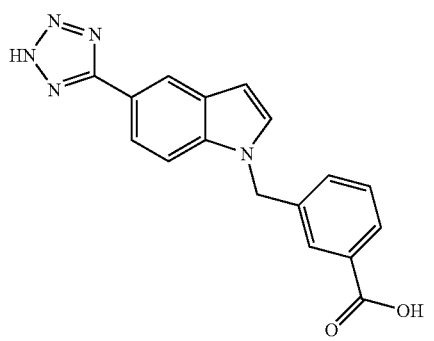

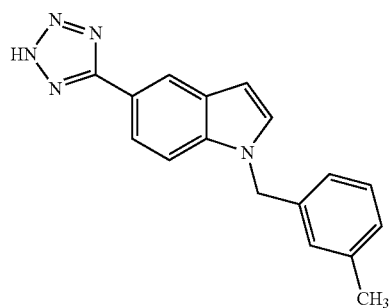

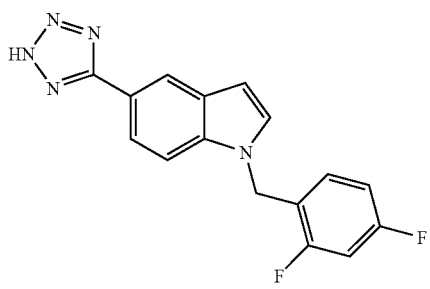

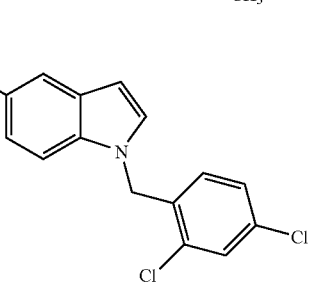

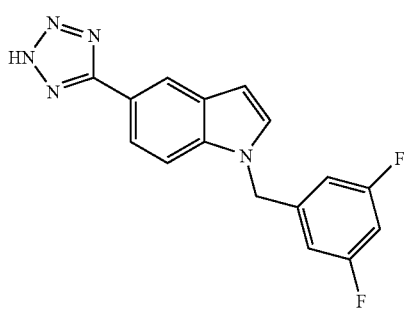

The following preferred compounds of the invention may be prepared eg. from 1-(4-bromobenzyl)-5-(2H-tetrazol-5-yl)-1H-indole (example 532) or from the analogue 1-(3-bromobenzyl)-5-(2H-tetrazol-5-yl)-1H-indole and aryl boronic acids via the Suzuki coupling reaction eg as described in Littke, Dai & Fu *J. Am. Chem. Soc.,* 2000, 122, 4020-8 (or references cited therein), or using the methodology described in general procedure (E), optionally changing the palladium catalyst to bis(tri-tert-butylphosphine)palladium (0).

-continued

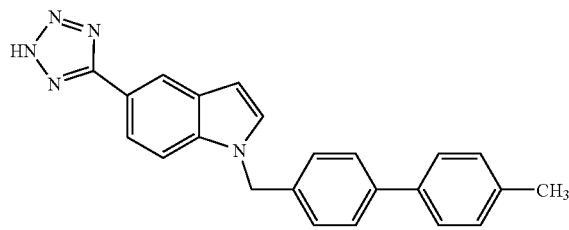

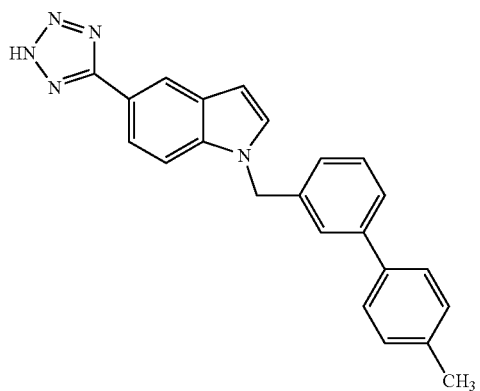

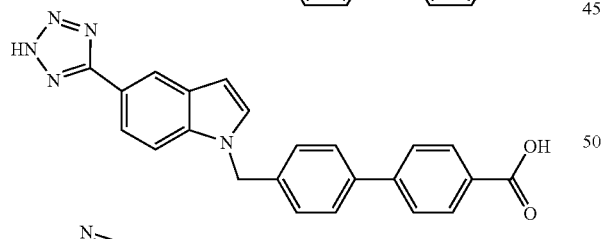

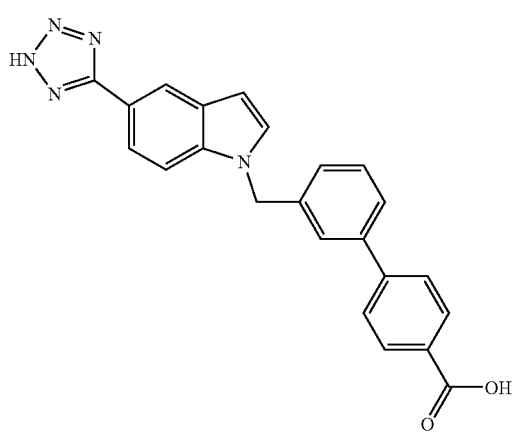

General Procedure (L) for Preparation of Compounds of General Formula I₁₁:

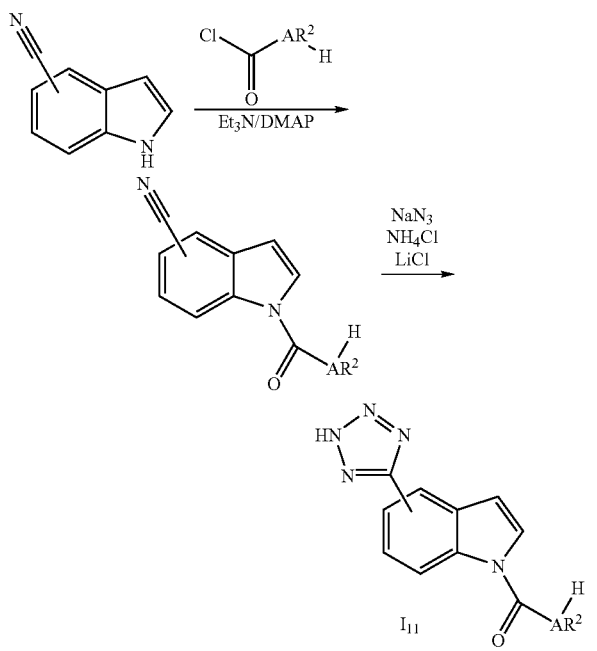

The general procedure (L) is further illustrated by the following example:

Example 586

General Procedure (L)

1-Benzoyl-5-(2H-tetrazol-5-yl)-1H-indole

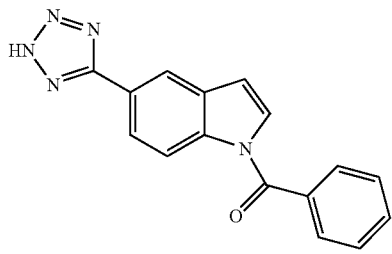

To a solution of 5-cyanoindole (1.0 g, 7.0 mmol) in dichloromethane (8 mL) was added 4-(dimethylamino)pyridine (0.171 g, 1.4 mmol), triethylamine (1.96 mL, 1.42 g, 14 mmol) and benzoyl chloride (0.89 mL, 1.08 g, 7.7 mmol). The resulting mixture was stirred for 18 hours at room temperature. The mixture was diluted with dichloromethane (80 mL) and washed consecutively with a saturated solution of sodium hydrogencarbonate (40 mL) and brine (40 mL). The organic phase was dried with magnesium sulfate (1 hour). Filtration and concentration furnished the crude material which was purified by flash chromatography on silica gel, eluting with ethyl acetate/heptanes=2:3. 1-Benzoyl-1H-indole-5-carbonitrile was obtained as a solid.

HPLC-MS (Method C): m/z: 247 (M+1); Rt=4.07 min.

1-Benzoyl-1H-indole-5-carbonitrile was transformed into 1-benzoyl-5-(2H-tetrazol-5-yl)-1H-indole by the method described in example 401.

HPLC (Method C): Rt=1.68 min.

The compound in the following example was prepared by the same procedure.

Example 587

General Procedure (L)

1-Benzoyl-4-(2H-tetrazol-5-yl)-1H-indole

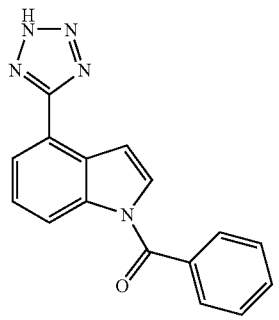

1-Benzoyl-1H-indole-4-carbonitrile was prepared from 4-cyanoindole according to the method described in example 586.

HPLC-MS (Method C): m/z: 247 (M+1); Rt=4.24 min.

1-Benzoyl-4-(2H-tetrazol-5-yl)-1H-indole was prepared from 1-benzoyl-1H-indole-4-carbonitrile according to the method described in example 401.

HPLC (Method C); Rt=1.56 min.

The following known and commercially available compounds do all bind to the His B10 $Zn^{2+}$ site of the insulin hexamer:

Example 588

1-(4-Fluorophenyl)-5-(2H-tetrazol-5-yl)-1H-indole

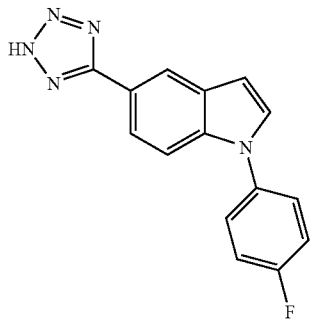

Example 589

1-Amino-3-(2H-tetrazol-5-yl)benzene

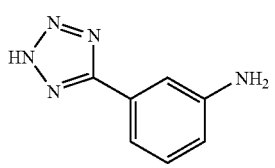

Example 590

1-Amino-4-(2H-tetrazol-5-yl)benzene

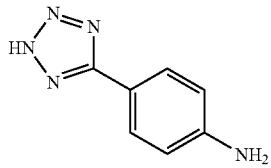

A mixture of 4-aminobenzonitrile (10 g, 84.6 mmol), sodium azide (16.5 g, 254 mmol) and ammonium chloride (13.6 g, 254 mmol) in DMF was heated at 125° C. for 16 hours. The cooled mixture was filtered and the filtrate was concentrated in vacuo. The residue was added water (200 mL) and diethyl ether (200 mL) which resulted in crystallisation. The mixture was filtered and the solid was dried in vacuo at 40° C. for 16 hours to afford 5-(4-aminophenyl)-2H-tetrazole.

$^1$H NMR DMSO-$d_6$): δ=5.7 (3H, bs), 6.69 (2H, d), 7.69 (2H, d). HPLC-MS (Method C): m/z: 162 (M+1); Rt=0.55 min.

Example 591

1-Nitro-4-(2H-tetrazol-5-yl)benzene

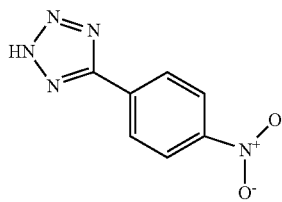

Example 592

1-Bromo-4-(2H-tetrazol-5-yl)benzene

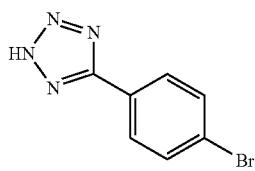

General Procedure (M) for Solution Phase Preparation of Amides of General Formula $I_{12}$:

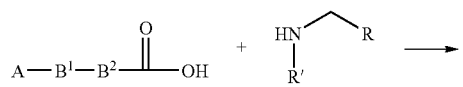

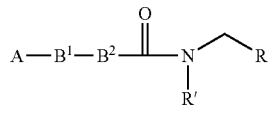

wherein A, $B^1$, $B^2$ are as defined above, R is hydrogen, optionally substituted aryl or $C_{1-8}$-alkyl and R' is hydrogen or $C_{1-4}$-alkyl.

A-$B^1$—$B^2$—$CO_2$H may be prepared eg by general procedure (D) or by other similar procedures described herein, or may be commercially available.

The procedure is further illustrated in the following example 593:

Example 593

General Procedure (M)

N-(4-Chlorobenzyl)-2-[3-(2,4-dioxothiazolidin-5-ylidenemethyl)-1H-indol-1-yl]acetamide

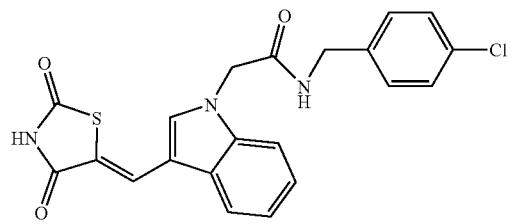

[3-(2,4-Dioxothiazolidin-5-ylidenemethyl)indol-1-yl] acetic acid (example 300, 90.7 mg, 0.3 mmol) was dissolved in NMP (1 mL) and added to a mixture of 1-ethyl-3-(3-dimethylaminopropyl)carbodiimide, hydrochloride (86.4 mg, 0.45 mmol) and 1-hydroxybenzotriazol (68.8 mg, 0.45 mmol) in NMP (1 mL). The resulting mixture was shaken at RT for 2 h. 4-Chlorobenzylamine (51 mg, 0.36 mmol) and DIPEA (46.4 mg, 0.36 mmol) in NMP (1 mL) were added to the mixture resulting mixture shaken at RT for 2 days. Subsequently ethyl acetate (10 mL) was added and the resulting mixture washed with 2×10 mL water followed by saturated ammonium chloride (5 mL). The organic phase was evaporated to dryness giving 75 mg (57%) of the title compound.

HPLC-MS (Method C): m/z: 426 (M+1); Rt.=3.79 min.

Example 594

General Procedure (M)

1H-Benzotriazole-5-carboxylic acid 4-chlorobenzylamide

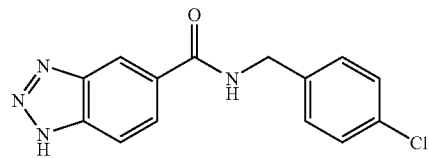

HPLC-MS (Method B): m/z: 287 (M+1); Rt=4.40 min.

Example 595

General Procedure (M)

N-(4-Chlorobenzyl)-4-[2-chloro-4-(2,4-dioxothiazo-lidin-5-ylidenemethyl)phenoxy]butyramide

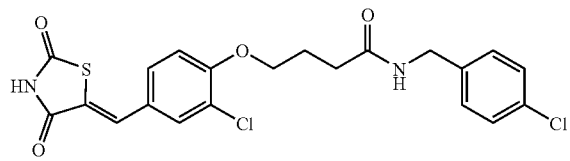

HPLC-MS (Method A): m/z: 465 (M+1); Rt=4.35 min.

Example 596

General Procedure (M)

N-(4-Chlorobenzyl)-4-[4-(2,4-dioxothiazolidin-5-ylidenemethyl)phenoxy]butyramide

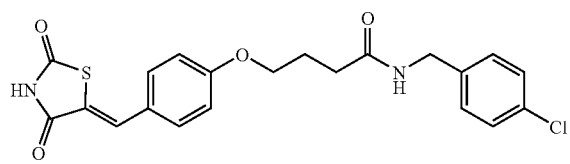

HPLC-MS (Method A): m/z: 431 (M+1); Rt=3.68 min.

Example 597

General Procedure (M)

2-[2-Bromo-4-(2,4-dioxothiazolidin-5-ylidenem-ethyl)phenoxy]-N-(4-chlorobenzyl)acetamide

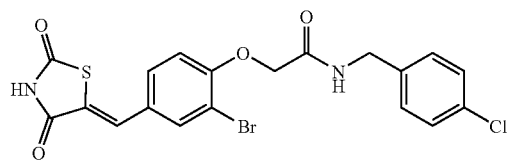

HPLC-MS (Method A): m/z: 483 (M+1); Rt=4.06 min.

Example 598

General Procedure (M)

N-(4-Chlorobenzyl)-2-[3-(2,4-dioxothiazolidin-5-ylidenemethyl)phenoxy]acetamide

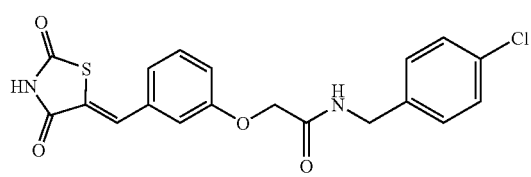

HPLC-MS (Method A): m/z: 403 (M+1); Rt=4.03 min.

Example 599

General Procedure (M)

N-(4-Chlorobenzyl)-3-[4-(2,4-dioxothiazolidin-5-ylidenemethyl)phenyl]acrylamide

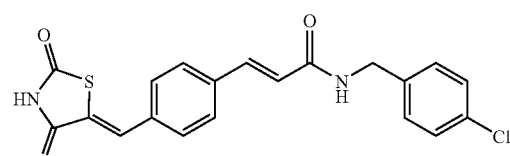

HPLC-MS (Method A): m/z: 399 (M+1); Rt=3.82.

Example 600

General Procedure (M)

N-(4-Chlorobenzyl)-4-[3-(2,4-dioxothiazolidin-5-ylidenemethyl)phenoxy]butyramide

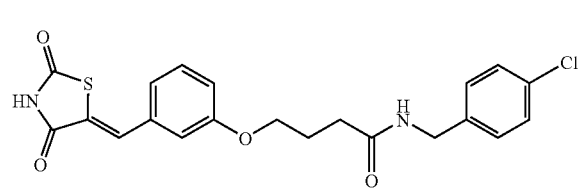

HPLC-MS (Method A): m/z: 431 (M+1); Rt=3.84 min.

Example 601

General Procedure (M)

4-[2-Bromo-4-(2,4-dioxothiazolidin-5-ylidenem-ethyl)phenoxy]-N-(4-chlorobenzyl)butyramide

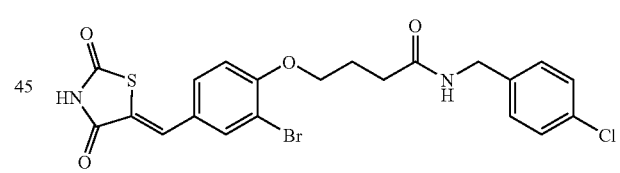

HPLC-MS (Method A): m/z: 511 (M+1)); Rt=4.05 min.

Example 602

General Procedure (M)

4-[2-Bromo-4-(4-oxo-2-thioxothiazolidin-5-yliden-emethyl)-phenoxy]-N-(4-chlorobenzyl)-butyramide

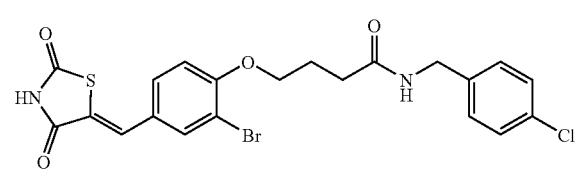

HPLC-MS (Method A): m/z: 527 (M+1); Rt=4.77 min.

Example 603

General Procedure (M)

N-(4-Chlorobenzyl)-2-[4-(2,4-dioxothiazolidin-5-ylidenemethyl)naphthalen-1-yloxy]acetamide

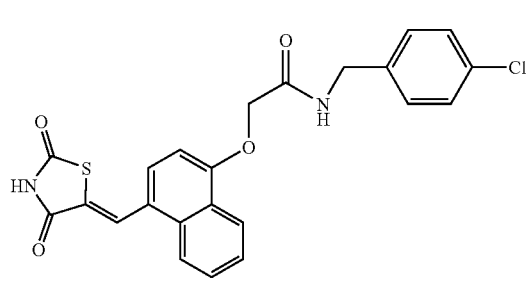

HPLC-MS (Method C): m/z: 431 (M+1); Rt.=4.03 min.

Example 604

General Procedure (M)

N-(4-Chlorobenzyl)-3-[3-(2,4-dioxothiazolidin-5-ylidenemethyl)-1H-indol-1-yl]propionamide

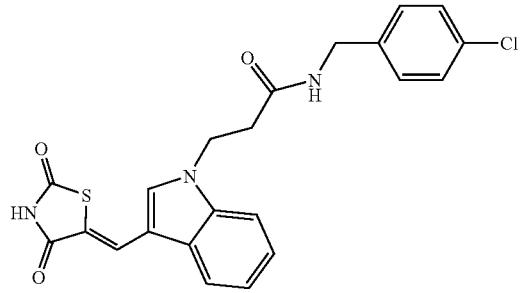

HPLC-MS (Method C): m/z: 440 (M+1); Rt.=3.57 min.

Example 605

General Procedure (M)

N-(4-Chlorobenzyl)-4-[4-(2,4-dioxothiazolidin-5-ylidenemethyl)naphthalen-1-yloxy]butyramide

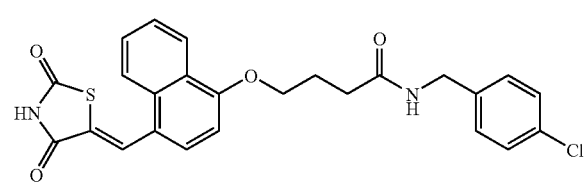

HPLC-MS (Method C): m/z: 481 (M+1); Rt=4.08 min.

Example 606

General Procedure (M)

4-[4-(2,4-Dioxothiazolidin-5-ylidenemethyl)-naphthalen-1-yloxy]-N-hexylbutyramide

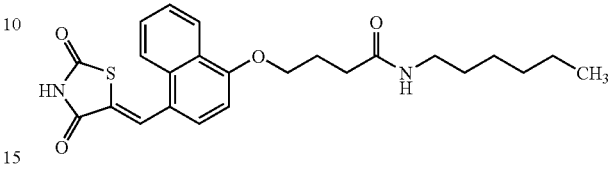

HPLC-MS (Method C): m/z: 441 (M+1); Rt=4.31 min.

Example 607

General Procedure (M)

N-(4-Chlorobenzyl)-4-[3-(2H-tetrazol-5-yl)carbazol-9-ylmethyl]benzamide

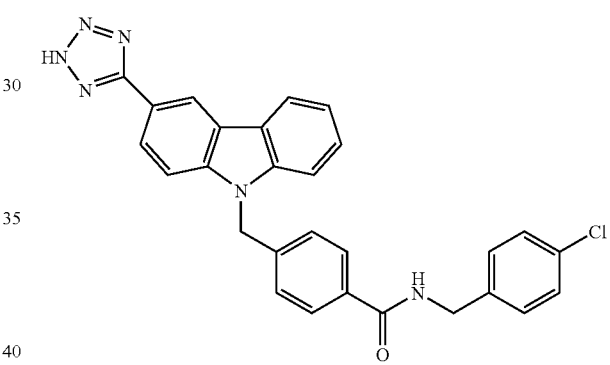

HPLC-MS (Method C): m/z: 493 (M+1); Rt=4.19 min.

Example 608

General Procedure (M)

N-(4-Chlorobenzyl)-3-[3-(2H-tetrazol-5-yl)carbazol-9-ylmethyl]benzamide

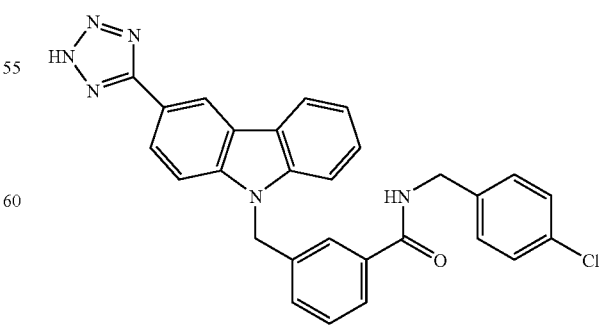

HPLC-MS (Method C): m/z: 493 (M+1); Rt=4.20 min.

Example 609

4-({[3-(2,4-Dioxothiazolidin-5-ylidenemethyl)indole-7-carbonyl]amino}methyl)benzoic acid Methyl Ester

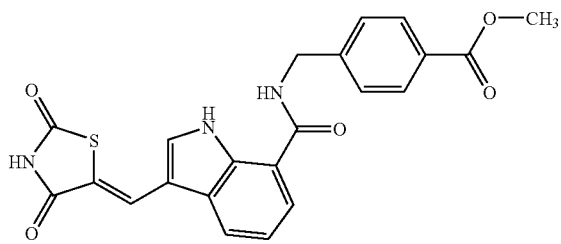

HPLC-MS (Method C): m/z: 436 (M+1); Rt.=3.55 min.

The commercially available compounds in the following examples do all bind to the HisB10 $Zn^{2+}$ site:

Example 610

1-(4-Bromo-3-methylphenyl)-1,4-dihydrotetrazole-5-thione

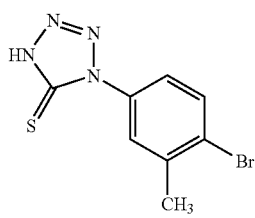

Example 611

1-(4-Iodophenyl)-1,4-dihydrotetrazole-5-thione

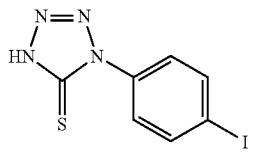

Example 612

1-(2,4,5-Trichlorophenyl)-1H-tetrazole-5-thiol

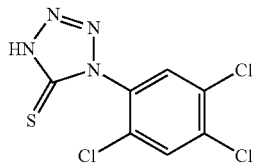

Example 613

1-(2,6-Dimethylphenyl)-1,4-dihydrotetrazole-5-thione

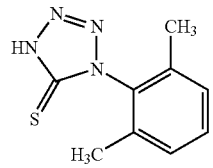

Example 614

1-(2,4,6-Trimethylphenyl)-1,4-dihydrotetrazole-5-thione

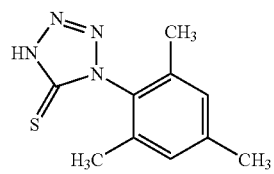

Example 615

1-(4-Dimethylaminophenyl)-1H-tetrazole-5-thiol

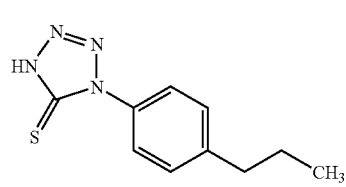

Example 616

1-(3,4-Dichlorophenyl)-1,4-dihydro-1H-tetrazole-5-thione

Example 617

1-(4-Propylphenyl)-1,4-dihydro-1H-tetrazole-5-thione

Example 618

1-(3-Chlorophenyl)-1,4-dihydro-1H-tetrazole-5-thione

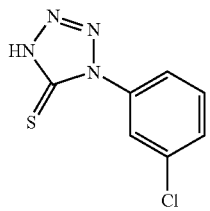

Example 619

1-(2-Fluorophenyl)-1,4-dihydro-1H-tetrazole-5-thione

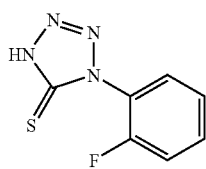

Example 620

1-(2,4-Dichlorophenyl)-1,4-dihydro-1H-tetrazole-5-thione

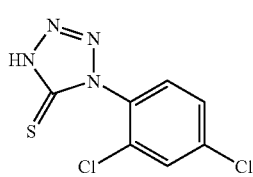

Example 621

1-(4-Trifluoromethoxyphenyl)-1,4-dihydro-1H-tetrazole-5-thione

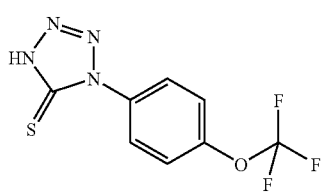

Example 622

N-[4-(5-Mercaptotetrazol-1-yl)-phenyl]-acetamide

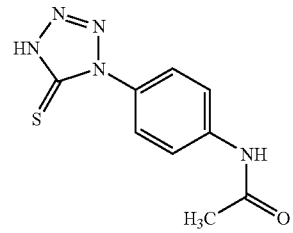

Example 623

1-(4-Chlorophenyl)-1,4-dihydrotetrazole-5-thione

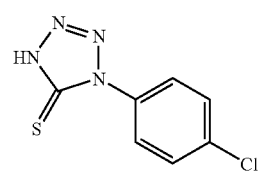

Example 624

1-(4-Methoxyphenyl)-1,4-dihydrotetrazole-5-thione

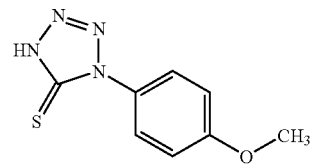

Example 625

1-(3-Fluoro-4-pyrrolidin-1-ylphenyl)-1,4-dihydrotetrazole-5-thione

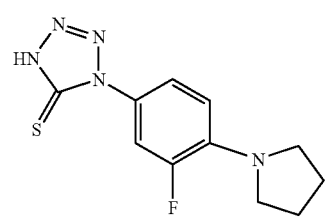

Preparation of 1-aryl-1,4-dihydrotetrazole-5-thiones (or the tautomeric 1-aryltetrazole-5-thiols) is described in the literature (eg. by Kauer & Sheppard, *J. Org. Chem.*, 32, 3580-92 (1967)) and is generally performed eg. by reaction of aryl-isothiocyanates with sodium azide followed by acidification 1-Aryl-1,4-dihydrotetrazole-5-thiones with a carboxylic acid tethered to the aryl group may be prepared as shown in the following scheme:

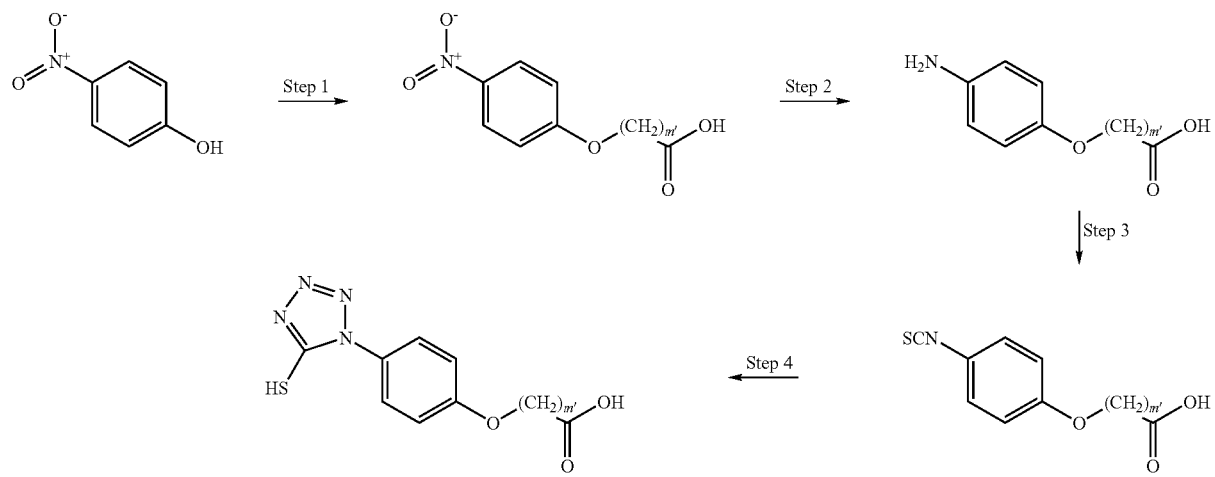

Step 1 is a phenol alkylation and is very similar to steps 1 and 2 of general procedure (D) and may also be prepared similarly as described in example 303.

Step 2 is a reduction of the nitro group. SnCl$_2$, H$_2$ over Pd/C and many other procedures known to those skilled in the art may be utilised.

Step 3 is formation of an arylisothiocyanate from the corresponding aniline. As reagents CS$_2$, CSCl$_2$, or other reagents known to those skilled in the art, may be utilised.

Step 4 is a conversion to mercaptotetrazole as described above.

Preferred compounds of the invention includes:

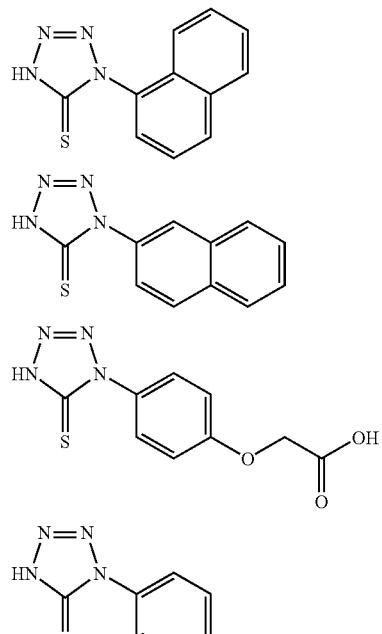

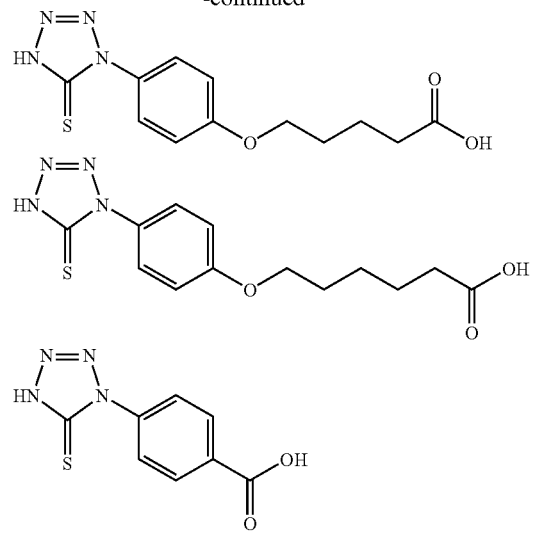

Example 626

4-(4-Hydroxyphenyl)-1H-[1,2,3]triazole-5-carbonitrile

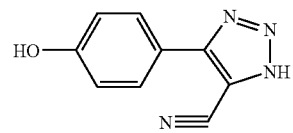

Phenylsulphonyl acetonitrile (2.0 g, 11.04 mmol) was mixed with 4-hydroxybenzaldehyde (1.35 g, 11.04 mmol) in DMF (10 mL) and toluene (20 mL). The mixture was refluxed for 3 hours and subsequently evaporated to dryness in vacuo. The residue was treated with diethyl ether and toluene. The solid formed was filtered to afford 2.08 g (66%) of 2-benzenesulfonyl-3-(4-hydroxyphenyl)acrylonitrile.

HPLC-MS (Method C): m/z: 286 (M+1); Rt.=3.56 min.

A mixture of 2-benzenesulfonyl-3-(4-hydroxyphenyl) acrylonitrile (2.08 g, 7.3 mmol) and sodium azide (0.47 g, 7.3 mmol) in DMF (50 mL) was heated at reflux temperature 2 hours. After cooling, the mixture was poured on ice. The mixture was evaporated in vacuo to almost dryness and toluene was added. After filtration, the organic phase was evaporated in vacuo. The residue was purified by silicagel chromatography eluting with a mixture of ethyl acetate and heptane (1:2). This afforded 1.2 g (76%) of the title compound.

$^1$H NMR (DMSO-$d_6$): 10.2 (broad, 1H); 7.74 (d, 2H); 6.99 (d, 2H); 3.6-3.2 (broad, 1H). HPLC-MS (Method C) m/z:= 187 (M+1); Rt.=1.93 min The compounds in the following examples are commercially available and may be prepared using a similar methodology:

Example 627

4-(4-Trifluoromethoxyphenyl)-1H-[1,2,3]triazole-5-carbonitrile

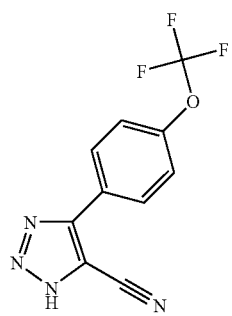

Example 628

4-Benzo[1,3]dioxol-5-yl-1H-[1,2,3]triazole-5-carbonitrile

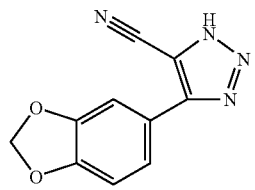

Example 629

4-(3-Trifluoromethylphenyl)-1H-[1,2,3]triazole-5-carbonitrile

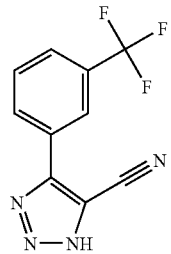

Example 630

4-Pyridin-3-yl-1H-[1,2,3]triazole-5-carbonitrile

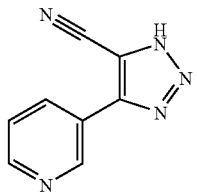

Example 631

4-(2,6-Dichlorophenyl)-1H-[1,2,3]triazole-5-carbonitrile

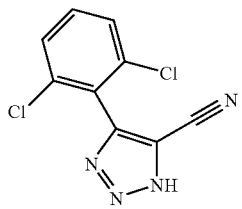

Example 632

4-Thiophen-2-yl-1H-[1,2,3]triazole-5-carbonitrile

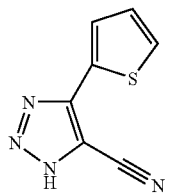

Example 633

3,5-Dimethylisoxazole-4-carboxylic acid 4-(5-cyano-1H-[1,2,3]triazol-4-yl)phenyl Ester

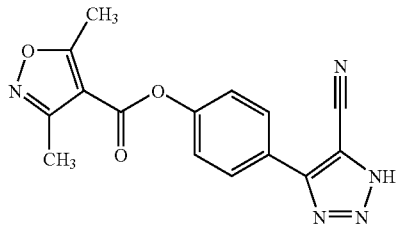

Example 634

3,3-Dimethyl-butyric acid 4-(5-cyano-1H-[1,2,3]triazol-4-yl)phenyl Ester

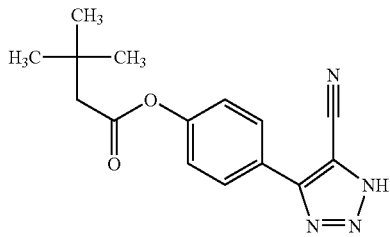

Example 635

4-Methyl-[1,2,3]thiadiazole-5-carboxylic acid 4-(5-cyano-1H-[1,2,3]triazol-4-yl)phenyl Ester

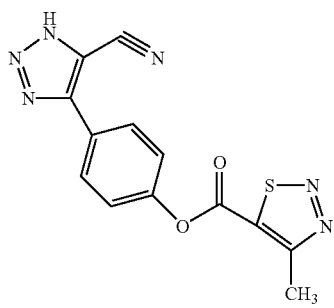

Example 636

4-Chlorobenzoic acid 4-(5-cyano-1H-[1,2,3]triazol-4-yl)phenyl Ester

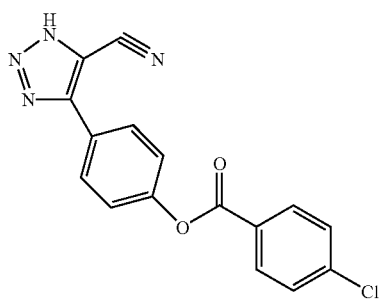

Example 637

4-(3-Phenoxyphenyl)-1H-[1,2,3]triazole-5-carbonitrile

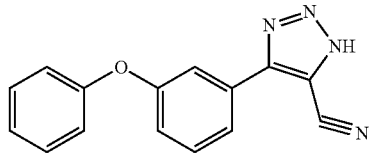

Example 638

4-(5-Bromo-2-methoxyphenyl)-1H-[1,2,3]triazole-5-carbonitrile

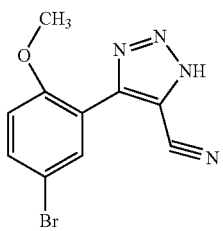

Example 639

4-(2-Chloro-6-fluorophenyl)-1H-[1,2,3]triazole-5-carbonitrile

The following cyanotriazoles are also preferred compounds of the invention:

4-(2-Chloro-6-fluorophenyl)-1H-[1,2,3]triazole-5-carbonitrile.
Terephthalic acid mono[4-(5-cyano-1H-[1,2,3]triazol-4-yl)phenyl] ester.
N-[4-(5-cyano-1H-[1,2,3]triazol-4-yl)-phenyl]terephthalamic acid
4-(4-Octyloxyphenyl)-1H-[1,2,3]triazole-5-carbonitrile
4-(Styrylphenyl))-1H-[1,2,3]triazole-5-carbonitrile.
4-(4'-Trifluoromethylbiphenyl-4-yl)-1H-[1,2,3]triazole-5-carbonitrile.
4-(4'-Chlorobiphenyl-4-yl)-1H-[1,2,3]triazole-5-carbonitrile.
4-(4'-Methoxybiphenyl-4-yl)-1H-[1,2,3]triazole-5-carbonitrile.
4-(1-Naphthyl)-1H-[1,2,3]triazole-5-carbonitrile.
4-(9-Anthranyl)-1H-[1,2,3]triazole-5-carbonitrile.
4-(4-Methoxy-1-naphthyl)-1H-[1,2,3]triazole-5-carbonitrile.
4-(4-Aminophenyl)-1H-[1,2,3]triazole-5-carbonitrile.
4-(2-Naphthyl)-1H-[1,2,3]triazole-5-carbonitrile.

General Procedure (N) for Preparation of Compounds of General Formula $I_{13}$:

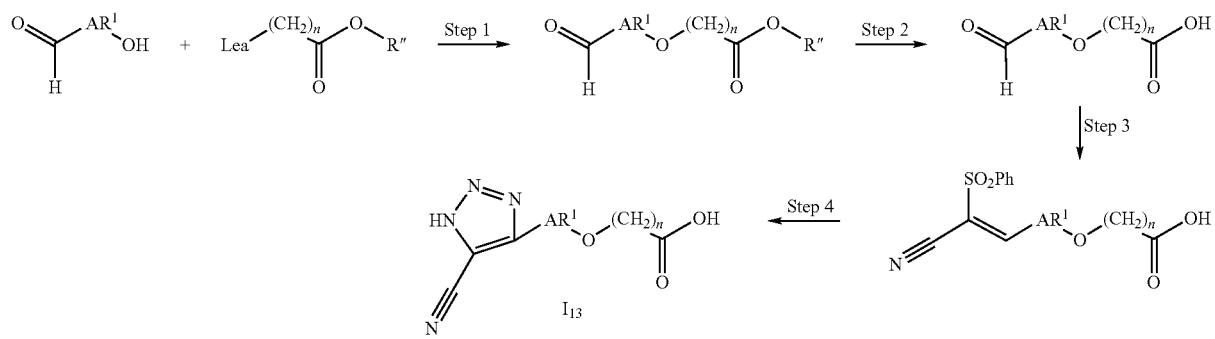

wherein
n is 1 or 3-20,
$AR^1$ is as defined above,
R" is a standard carboxylic acid protecting group, such as $C_1$-$C_6$-alkyl or benzyl and Lea is a leaving group, such as chloro, bromo, iodo, methanesulfonyloxy, toluenesulfonyloxy or the like.

This procedure is very similar to general procedure (D), steps 1 and 2 are identical.

Steps 3 and 4 are described in the literature (eg Beck & Günther, *Chem. Ber.*, 106, 2758-66 (1973))

Step 3 is a Knoevenagel condensation of the aldehyde obtained in step 2 with phenylsulfonylacetonitrile and step 4 is a reaction of the vinylsulfonyl compound obtained in step 3 with sodium azide. This reaction is usually performed in DMF at 90-110° C.

The following compounds may be prepared according to this general procedure (N):
4-(4-(5-Cyano-1H-[1,2,3]triazol-4-yl)phenoxy)butyric acid:

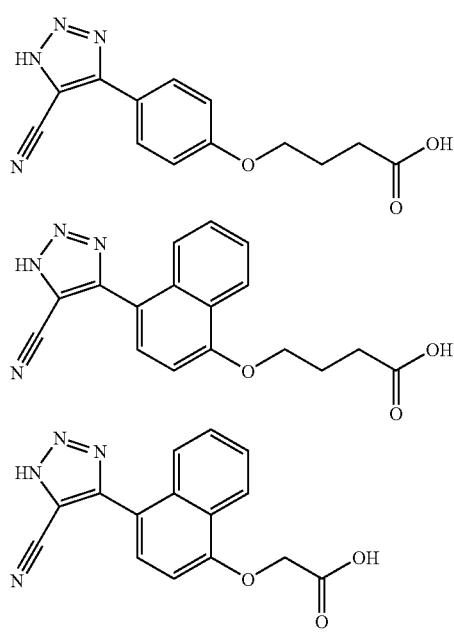

2-(4-(5-Cyano-1H-[1,2,3]triazol-4-yl)phenoxy)acetic acid:

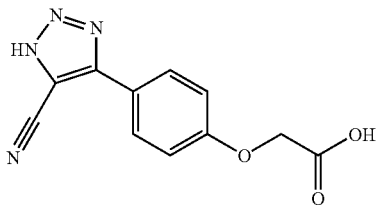

4-(4-(5-Cyano-1H-[1,2,3]triazol-4-yl)phenoxy)butyric acid ethyl ester
5-(4-(5-Cyano-1H-[1,2,3]triazol-4-yl)phenoxy)pentanoic acid
8-(4-(5-Cyano-1H-[1,2,3]triazol-4-yl)phenoxy)octanoic acid
10-(4-(5-Cyano-1H-[1,2,3]triazol-4-yl)phenoxy)decanoic acid
12-(4-(5-Cyano-1H-[1,2,3]triazol-4-yl)phenoxy)dodecanoic acid General Procedure (O) for Preparation of Compounds of General Formula $I_7$:

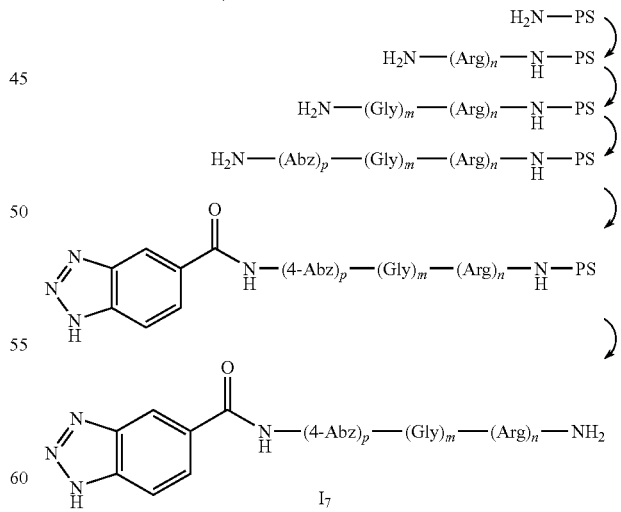

(SEQ ID NOS: 20-23 and 23, respectively, in order or appearance)

wherein PS is polymeric support, a Tentagel S RAM resin, n is 1-20, m is 0-5, and p is 0 or 1.

The compounds of the invention of general formula (I₂) can be prepared by means of standard peptide chemistry (General procedure H), e.g. in 0.5 mmol scale, using Fmoc strategy and HOAt or HOBT activated amino acids. The compounds prepared in the following examples according to General procedure (O) were all isolated as the TFA salts. This procedure is further illustrated in the following:

Typically, 2 gram of Fmoc Tentagel S RAM resin (Rapp Polymere, Tubingen) with substitution 0.25 mmol/g was washed with NMP then treated with 25% piperidine in NMP for 30 min followed by wash with NMP which renders the resin ready for coupling.

Step wise coupling of Fmoc-Arginine (Fmoc-Arg(Pmc)-OH), Fmoc-Glycine (Fmoc-Gly-OH) and Fmoc-4-aminobenzoic acid (Fmoc-4-Abz-OH):

To 2 mmol of Fmoc-L-Arg(Pmc)-OH (Novabiochem) was added 3.33 ml 0.6M HOAt in NMP (Perseptives) or 0.6M HOBT in NMP (Novabiochem) containing 0.2% bromphenolblue as indicator and added 330 µl of diisopropylcarbodiimide DIC (Fluka) and the solution was then added to the resin. After coupling for minimum 1 hour, or when the blue colour disappeared, the resin was washed with NMP and the Fmoc group was deprotected with 25% piperidine in NMP for 20 minutes followed by wash with NMP. This stepwise assembling of the arginine residues was repeated to give 3, 4, 5 or 6 arginines on the resin. The Fmoc-Glycine (Novabiochem) and Fmoc-4-aminobenzoic acid (Fluka and Neosystems) were coupled using the same procedure as described for Fmoc-Arg(Pmc)-OH.

Coupling of A-OH, e.g. 1H-benzotriazole-5-carboxylic acid on Gly.

When A-OH, e.g. 1H-benzotriazole-5-carboxylic acid (Aldrich) was coupled on a glycine or arginine residue the coupling procedure was as described above.

Coupling of A-OH, e.g. 1H-benzotriazole-5-carboxylic acid on Abz or 4-Apac:

Due to the lower nucleophilicity of the amino group in Abz the following procedure was necessary. To 4 mmol of A-OH, e.g. 1H-benzotriazole-5-carboxylic acid was added 6.66 ml of a solution of 0.6M HOAt, 0.2 mmol dimethylaminopyridine (DMAP) and 4-mmol DIC and was then added to the resin and allowed to react overnight.

Introduction of Fragment 4-Apac Instead of 4-Abz:

4-Nitrophenoxyacetic acid may be coupled on a glycine or arginine residue using DIC and HOBT/HOAt as described above. Subsequent reduction of the nitro group may be done using SnCl₂ in NMP or DMF e.g. as described by Tumelty et al. (*Tet. Lett.*, (1998) 7467-70).

Cleavage of the Peptides from the Resin.

After synthesis the resin was washed extensively with diethyl ether and dried. To 1 gram of the peptidyl resin was added 25 ml of a TFA solution containing 5% thioanisole, 5% ethanol, 5% phenol and 2% triisopropylsilane and allowed to react for 2 hours. The TFA solution was filtered and concentrated with argon flow for approximately 30 minutes. Then diethylether ca. 5-7 times the residual volume of TFA was added and the peptide precipitate was extracted in 10% AcOH and washed 5 times with diethyl ether and lyophilized.

RP-HPLC analysis and purification: The crude products were analysed on RP-HPLC C18 column (4.6×250 mm) using one of two gradients (see table 1 and 2), temperature 25° C., wavelength 214 nm and flow rate 1 ml/min with A-buffer 0.15% ($^w/_w$) TFA in H₂O and B-Buffer (87.5% ($^w/_w$) MeCN, 0.13% ($^w/_w$) TFA in H₂O)

The products were purified on preparative RP-HPLC C18 column (2×25 cm) using a gradient (variable, see e.g examples 640 to 643643643), temperature 25° C., wavelength 214 nm and flow rate 6 ml/min with A-buffer 0.15% ($^w/_w$) TFA in H₂O and B-Buffer (87.5% ($^w/_w$) MeCN, 0.13% ($^w/_w$) TFA in H₂O) and verified by mass spectrometry (MALDI).

TABLE 1

| Time (min.) | Flow (ml/min) ( | % A | % B |
|---|---|---|---|
| 0 | 1.00 | 95.0 | 5.0 |
| 30.00 | 1.00 | 80.0 | 20.0 |
| 35.00 | 1.00 | 0.0 | 100.0 |
| 40.00 | 1.00 | 0.0 | 100.0 |
| 45.00 | 1.00 | 95.0 | 5.0 |

TABLE 2

| Time (min.) | Flow (ml/min) | % A | % B |
|---|---|---|---|
| 0 | 1.00 | 95.0 | 5.0 |
| 30.00 | 1.00 | 40.0 | 60.0 |
| 31.00 | 1.00 | 0.00 | 100.0 |
| 35.00 | 1.00 | 0.00 | 100.0 |
| 36.00 | 1.00 | 95.0 | 5.0 |

The following examples were prepared using this general procedure (O).

Example 640

General Procedure (O)

Benzotriazol-5-ylcarbonyl-Gly₂-Arg₃-NH₂ (BT-G₂R₃) (SEQ ID NO: 6)

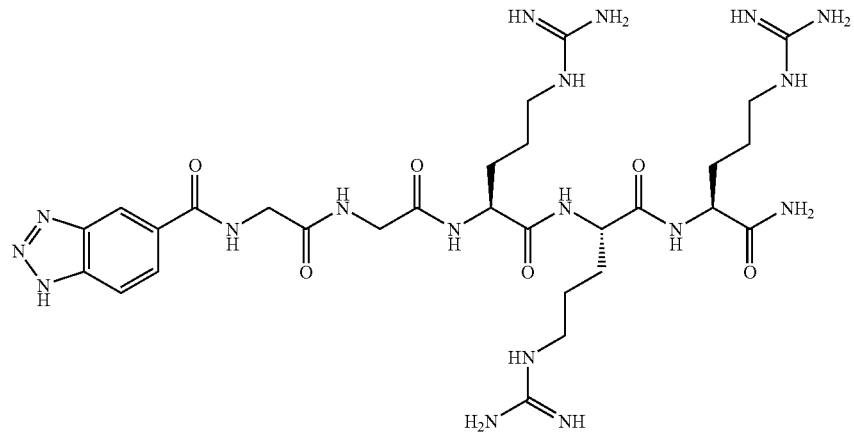

253
MS (MALDI): m/z: 746.7 g/mol; calculated: 744.2 g/mol.
HPLC gradient:
| Time (min) | Flow (ml/min) | % A | % B |
|---|---|---|---|
| 0.00 | 6.00 | 90.0 | 10.0 |
| 120.00 | 6.00 | 90.0 | 10.0 |
| 121.00 | 0.10 | 90.0 | 10.0 |
Example 641
General Procedure (O)
Benzotriazol-5-ylcarbonyl-Gly$_2$-Arg$_4$-NH$_2$ (BT-G$_2$R$_4$) (SEQ ID NO: 2)
254
MS (MALDI): m/z: 903.0 g/mol; calculated: 900.6 g/mol.
HPLC gradient:
| Time (min) | Flow (ml/min) | % A | % B |
|---|---|---|---|
| 0.00 | 6.00 | 95.0 | 5.0 |
| 30.00 | 6.00 | 80.0 | 20.0 |
| 35.00 | 6.00 | 0.0 | 100.0 |
| 40.00 | 6.00 | 0.0 | 100.0 |
| 45.00 | 6.00 | 95.0 | 5.0 |
| 64.00 | 6.00 | 95.0 | 5.0 |
Example 642
General Procedure (O)
Benzotriazol-5-ylcarbonyl-Gly$_2$-Arg$_5$-NH$_2$ (BT-G$_2$R$_5$) (SEQ ID NO: 1)
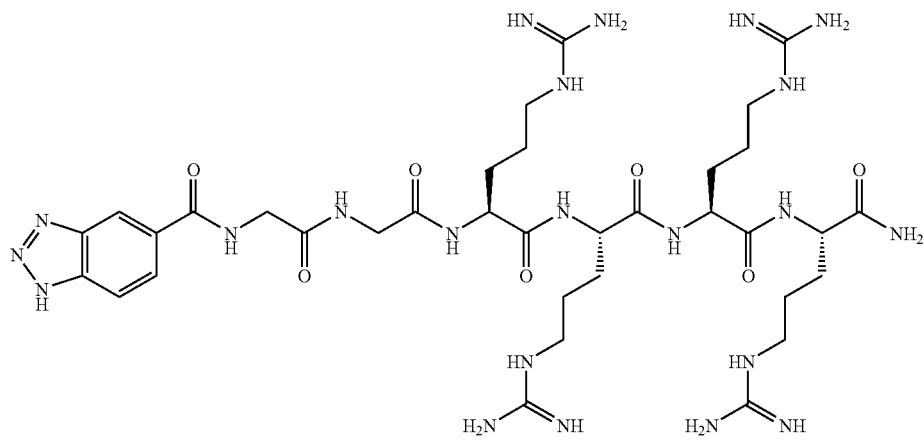
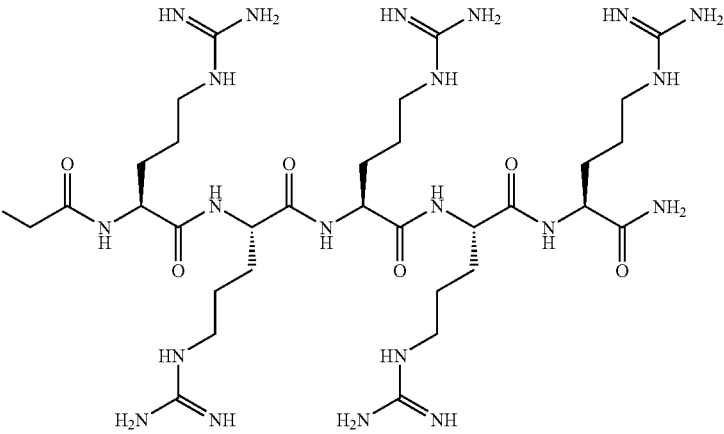

MS (MALDI): m/z: 1060.8 g/mol; calculated: 1057 g/mol.
HPLC gradient
| Time (min) | Flow (ml/min) | % A | % B |
|---|---|---|---|
| 0.00 | 6.00 | 88.0 | 12.0 |
| 120.00 | 6.00 | 88.0 | 12.0 |
| 121.00 | 0.10 | 88.0 | 12.0 |
MS (MALDI): m/z: 1214.8 g/mol; calculated: 1213.4 g/mol.
HPLC gradient:
| Time (min) | Flow (ml/min) | % A | % B |
|---|---|---|---|
| 0.00 | 6.00 | 88.0 | 12.0 |
| 120.00 | 6.00 | 88.0 | 12.0 |
| 121.00 | 0.10 | 88.0 | 12.0 |
Example 643
General Procedure (O)
Benzotriazol-5-ylcarbonyl-Gly$_2$-Arg$_6$-NH$_2$ (BT-G$_2$R$_6$) (SEQ ID NO: 5)
Example 644
General Procedure (O)
Benzotriazol-5-ylcarbonyl-4-Abz-Gly$_2$-Arg$_5$-NH$_2$ (BT-4-Abz-G$_2$R$_5$) (SEQ ID NO: 10)
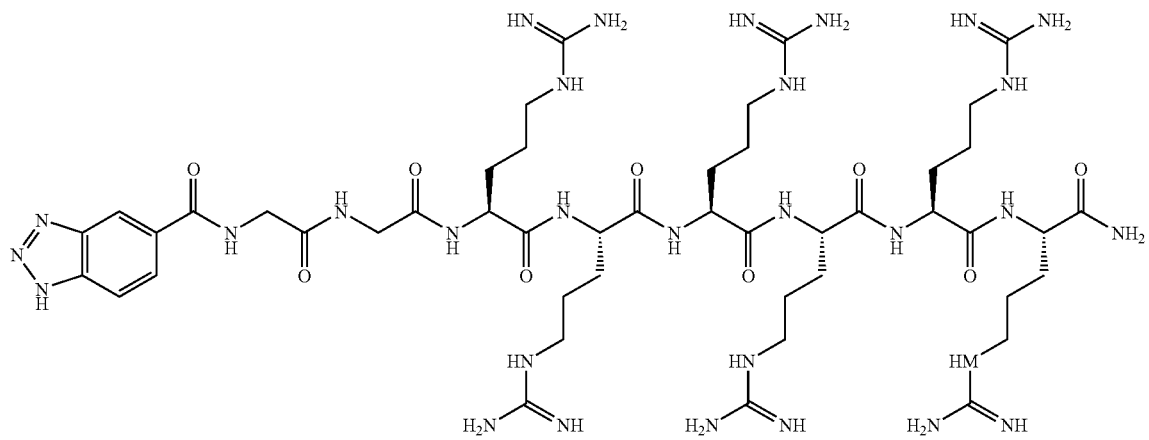
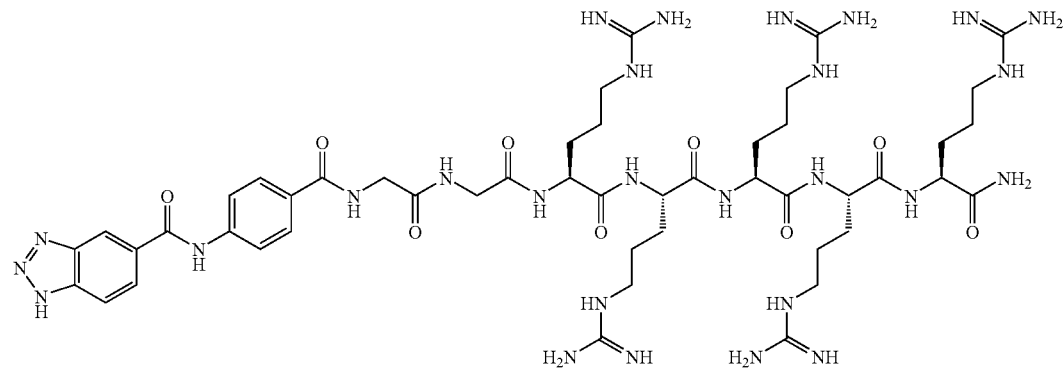

257
MS (MALDI): m/z: 1176.7 g/mol; calculated: 1177.9 g/mol.
HPLC gradient:
| Time (min) | Flow (ml/min) | % A  | % B   |
|------------|---------------|------|-------|
| 0.00       | 6.00          | 95.0 | 5.0   |
| 40.00      | 6.00          | 60.0 | 40.0  |
| 45.00      | 6.00          | 60.0 | 40.0  |
| 50.00      | 6.00          | 0.0  | 100.0 |
| 55.00      | 6.00          | 0.0  | 100.0 |
| 60.00      | 6.00          | 95.0 | 5.0   |
Example 645
General Procedure (O)
Benzotriazol-5-ylcarbonyl-4-Abz-Gly-Arg$_5$-NH$_2$ (BT-4-Abz-GR$_5$) (SEQ ID NO: 24)
258
MS (MALDI): m/z: 1122 g/mol; calculated: 1120.4 g/mol.
HPLC gradient:
| Time (min) | Flow (ml/min) | % A  | % B   |
|------------|---------------|------|-------|
| 0.00       | 6.00          | 95.0 | 5.0   |
| 40.00      | 6.00          | 60.0 | 40.0  |
| 45.00      | 6.00          | 60.0 | 40.0  |
| 50.00      | 6.00          | 0.0  | 100.0 |
| 55.00      | 6.00          | 0.0  | 100.0 |
| 60.00      | 6.00          | 95.0 | 5.0   |
Example 646
General Procedure (O)
Benzotriazol-5-ylcarbonyl-4-Abz-Arg$_5$-NH$_2$ (BT-4-Abz-R$_5$) (SEQ ID NO: 13)
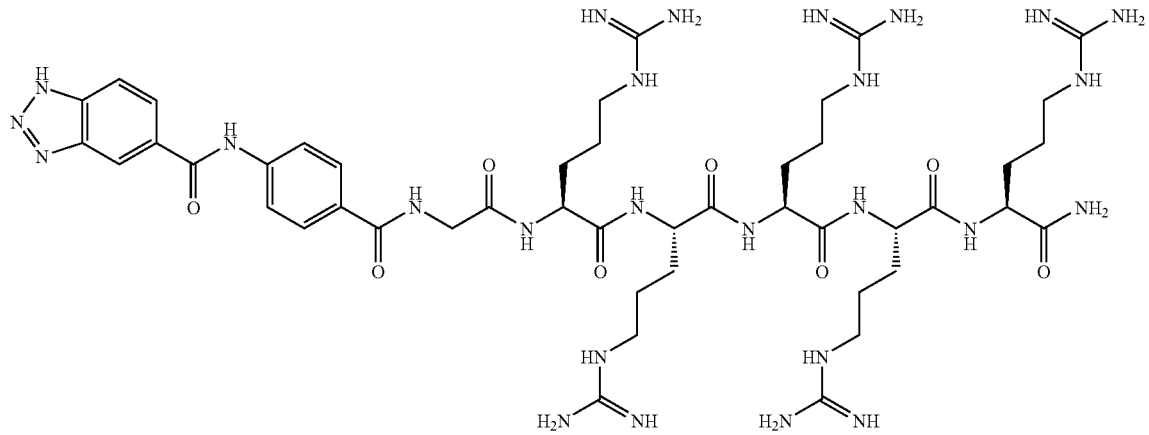
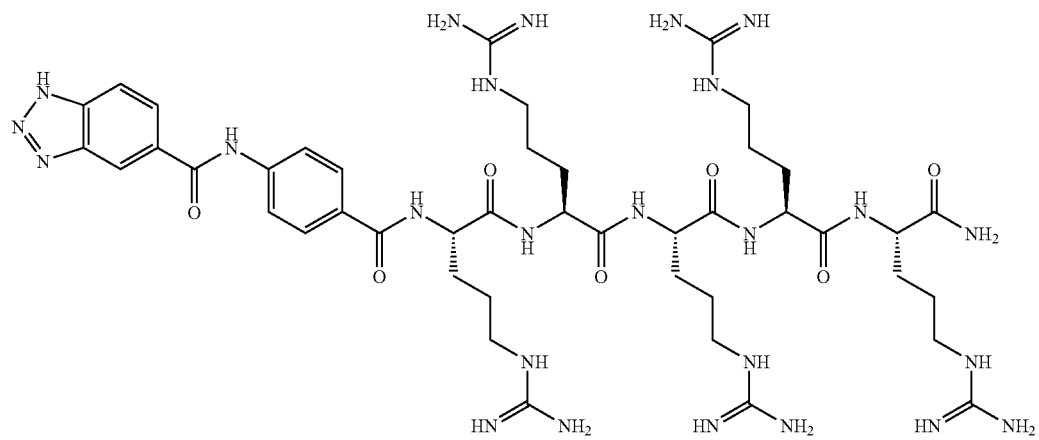

MS (MALDI): m/z: 1064.3 g/mol; calculated: 1063.2 g/mol.

HPLC gradient:

| Time (min) | Flow (ml/min) | % A | % B |
|---|---|---|---|
| 0.00 | 6.00 | 95.0 | 5.0 |
| 40.00 | 6.00 | 60.0 | 40.0 |
| 45.00 | 6.00 | 60.0 | 40.0 |
| 50.00 | 6.00 | 0.0 | 100.0 |
| 55.00 | 6.00 | 0.0 | 100.0 |
| 60.00 | 6.00 | 95.0 | 5.0 |

General Procedure (P) for Preparation of Compounds of General Formula $I_8$:

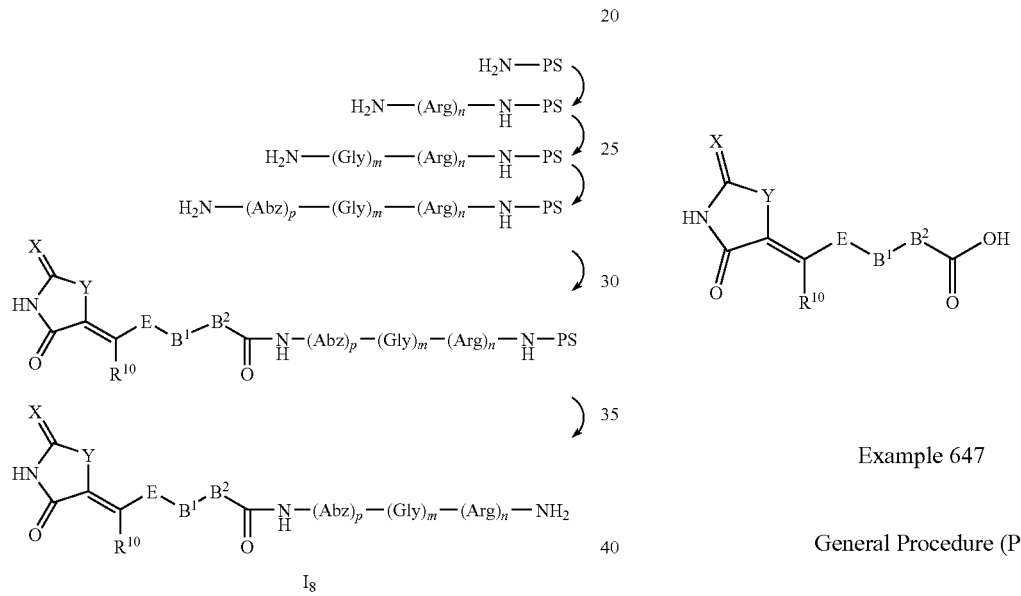

$I_8$ (SEQ ID NOS: 20-22, 22 and 22, respectively, in order or appearance)

wherein X, Y, $R^{10}$, E, $B^1$, $B^2$ are as defined above, p is 0 or 1, m is 0-5 and n is 1-20.

This general procedure is very similar to General procedure (O), where benzotriazole-5-carboxylic acid in the last step before cleavage from the resin is replaced with compounds optionally prepared according to general procedure (D):

Example 647

General Procedure (P)

4-{2-[3-(2,4-Dioxothiazolidin-5-ylidenemethyl)phenoxy]acetylamino}benzoyl-Gly$_2$-Arg$_5$-NH$_2$ (SEQ ID NO: 25)

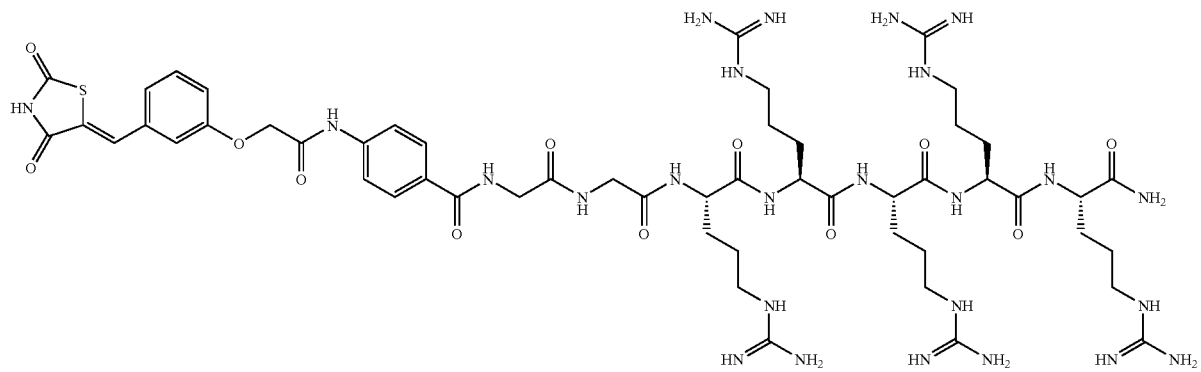

Example 648
General Procedure (P)
3-[4-(2,4-Dioxothiazolidin-5-ylidenemethyl)phenyl]
acryloyl-Arg$_5$-NH$_2$ (SEQ ID NO: 26)
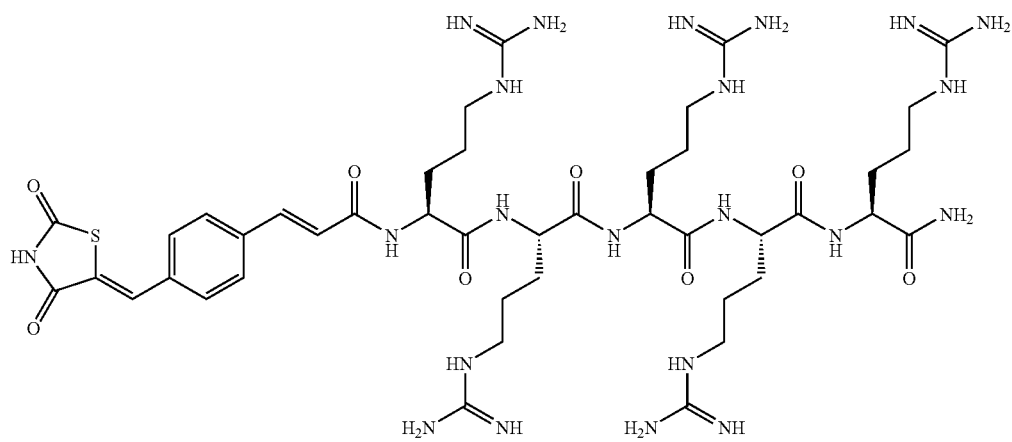
MS (MALDI): m/z: 1057.3 g/mol; calculated: 1055.3 g/mol.
Example 649
General Procedure (P)
3-[4-(2,4-Dioxothiazolidin-5-ylidenemethyl)phenyl]
acryloyl-Arg$_4$-NH$_2$ (SEQ ID NO: 27)
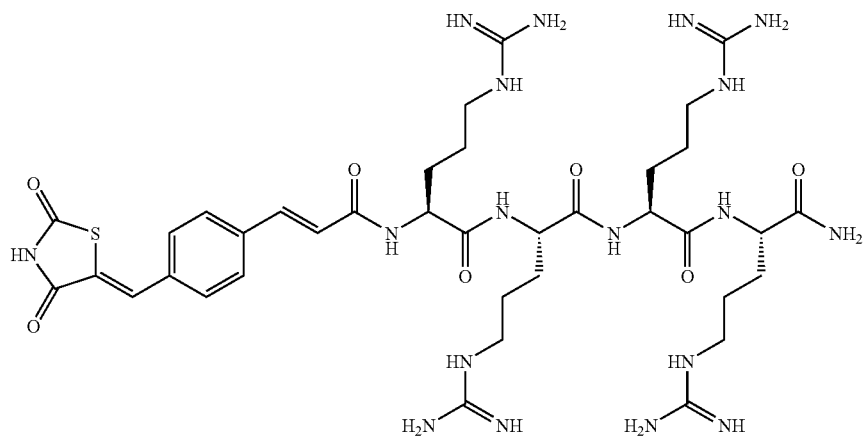
MS (MALDI): m/z: 899.1 g/mol; calculated: 901.6 g/mol.

Example 650
General Procedure (P)
3-[4-(2,4-Dioxothiazolidin-5-ylidenemethyl)phenyl]acryloyl-Arg$_3$-NH$_2$
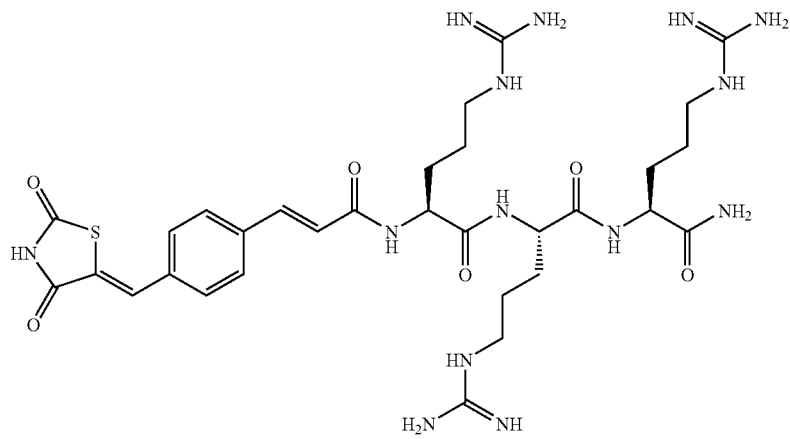
MS (MALDI): m/z: 746.2 g/mol; calculated: 742.9 g/mol.
Example 651
General Procedure (P)
4-[4-(2,4-Dioxothiazolidin-5-ylidenemethyl)phenoxy]butyryl-Arg$_5$-NH$_2$ (SEQ ID NO: 26)
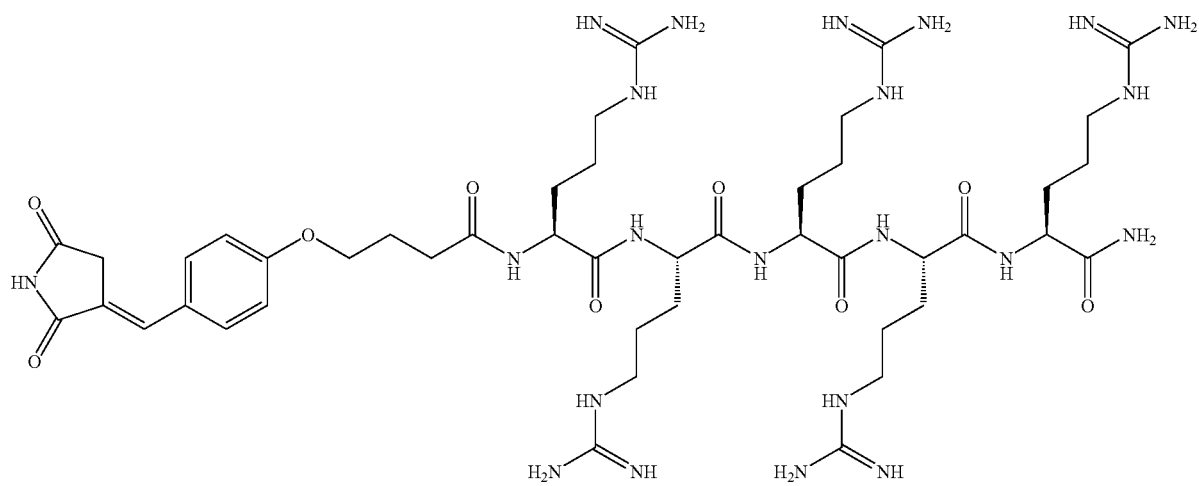
MS (MALDI): m/z: 1088.7 g/mol; calculated: 1087 g/mol.

Example 652
General Procedure (P)
4-[4-(2,4-Dioxothiazolidin-5-ylidenemethyl)phenoxy]butyryl-Arg$_4$-NH$_2$ (SEQ ID NO: 27)
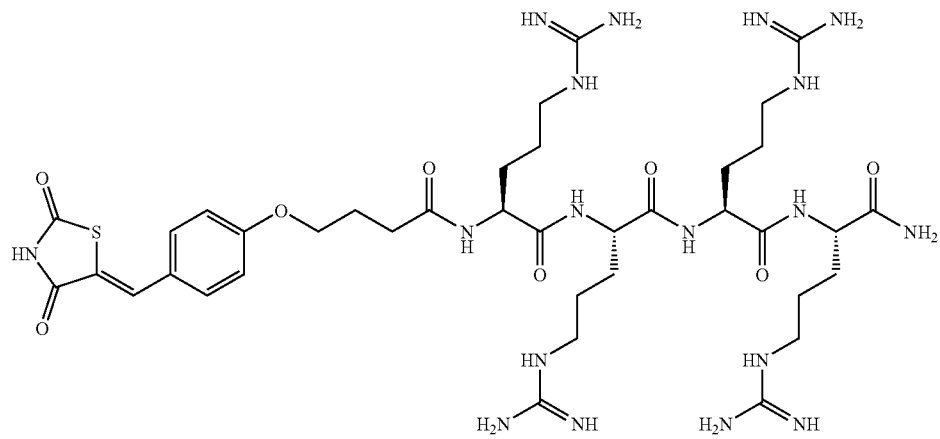
MS (MALDI): m/z: 933.0 g/mol; calculated: 931 g/mol.
Example 653
General Procedure (P)
4-[4-(2,4-Dioxothiazolidin-5-ylidenemethyl)phenoxy]butyryl-Arg$_3$-NH$_2$
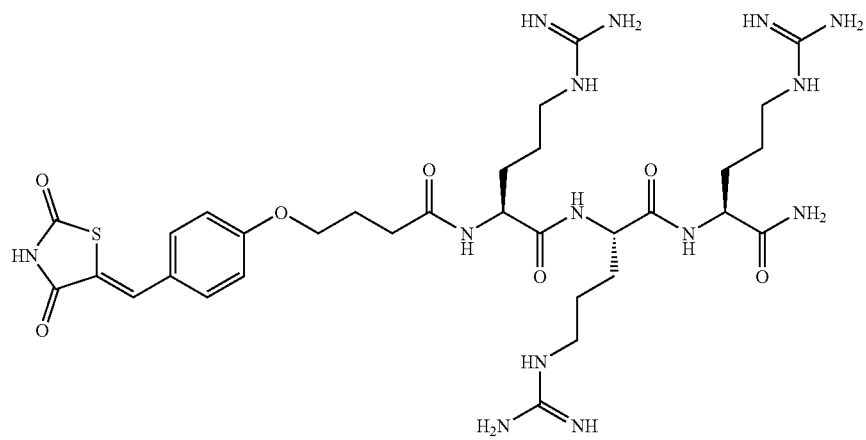
MS (MALDI): m/z: 776.9 g/mol; calculated: 774.0 g/mol.

Example 654
General Procedure (P)
4-[4-(2,4-Dioxothiazolidin-5-ylidenemethyl)naphthalen-1-yloxy]butyryl-Arg$_{12}$-NH$_2$ (SEQ ID NO: 28)
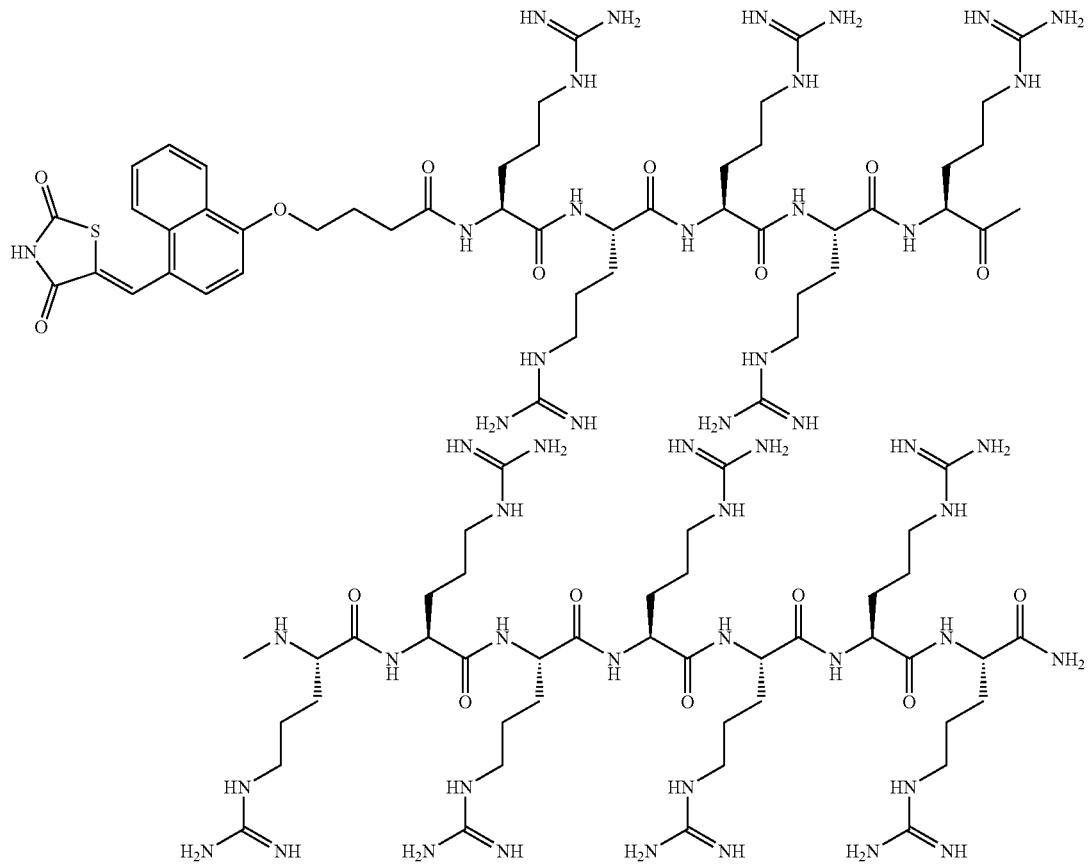
MS (MALDI): m/z: 2232.9.4 g/mol; calculated: 2230.3 g/mol.
Example 655
General Procedure (P)
4-[4-(2,4-Dioxothiazolidin-5-ylidenemethyl)naphthalen-1-yloxy]butyryl-Arg$_8$-NH$_2$ (SEQ ID NO: 29)
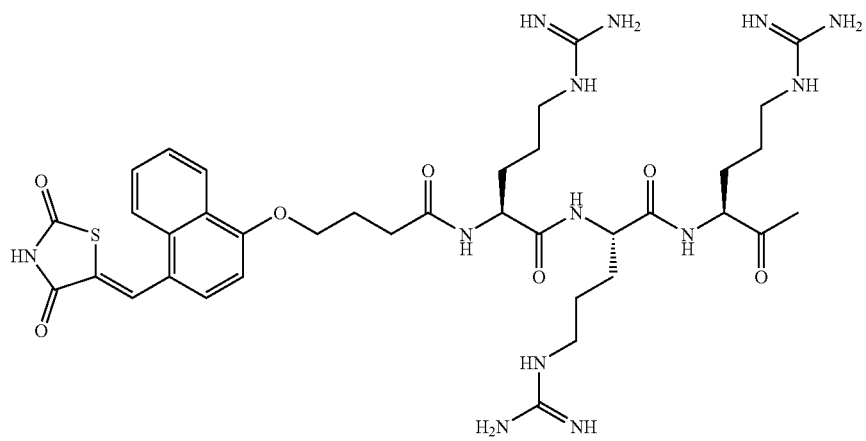

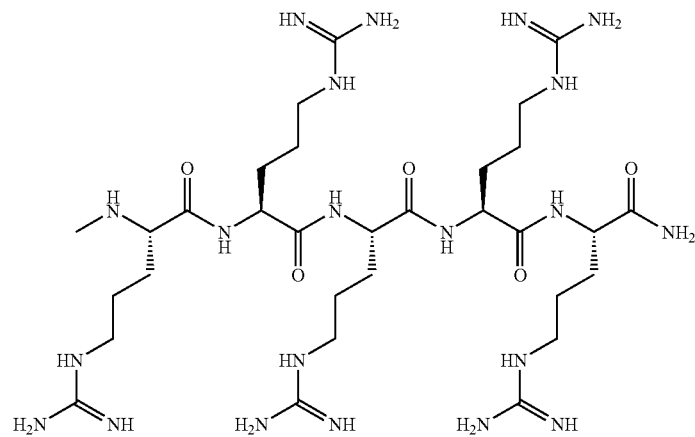
MS (MALDI): m/z: 1607.4 g/mol; calculated: 1605.5 g/mol.
Example 656
General Procedure (P)
4-[4-(2,4-Dioxothiazolidin-5-ylidenemethyl)naphthalen-1-yloxy]butyryl-Arg$_5$-NH$_2$ (SEQ ID NO: 26)
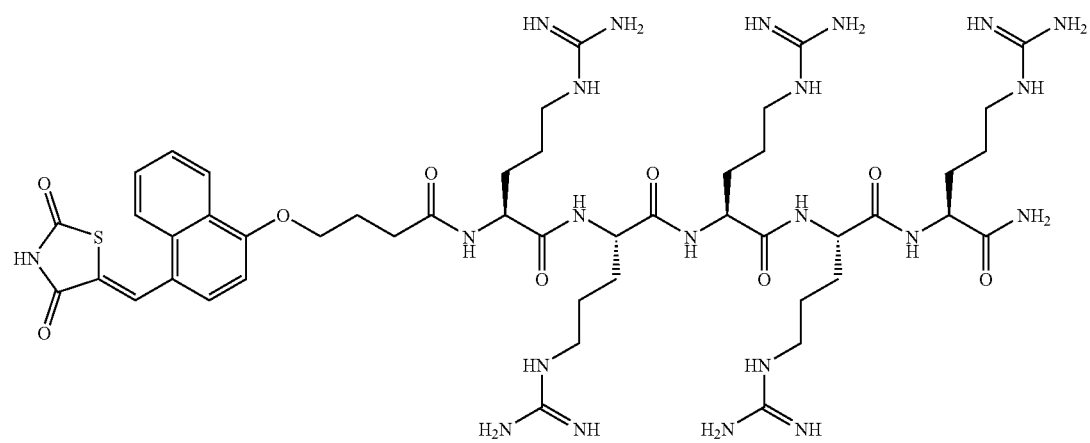

MS (MALDI): m/z: 1141.9 g/mol; calculated: 1137.4 g/mol.
Example 657
General Procedure (P)
4-[4-(2,4-Dioxothiazolidin-5-ylidenemethyl)naphthalen-1-yloxy]butyryl-Arg$_4$-NH$_2$ (SEQ ID NO: 27)
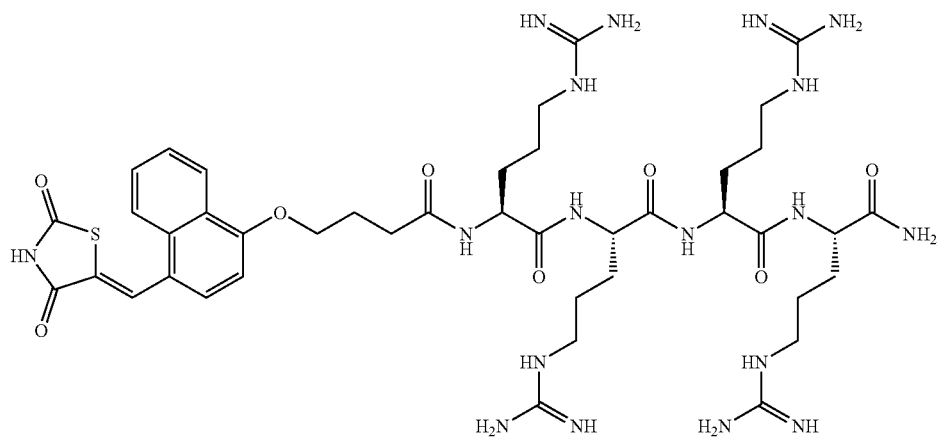
MS (MALDI): m/z: 985.4 g/mol; calculated: 981.2 g/mol.
Example 658
General Procedure (P)
4-[4-(2,4-Dioxothiazolidin-5-ylidenemethyl)naphthalen-1-yloxy]butyryl-Arg$_3$-NH$_2$
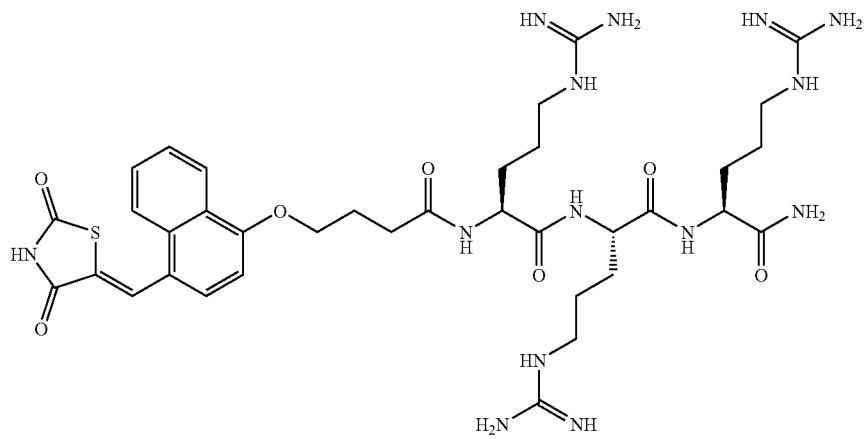

MS (MALDI): m/z: 828.5 g/mol; calculated: 825.0 g/mol.
The following compounds were prepared according to the methodology described in general procedure (O) and (P):
Example 659
4-(2H-Tetrazol-5-yl)benzoyl-4-Abz-Gly$_2$-Arg$_5$-NH$_2$
(SEQ ID NO: 19)
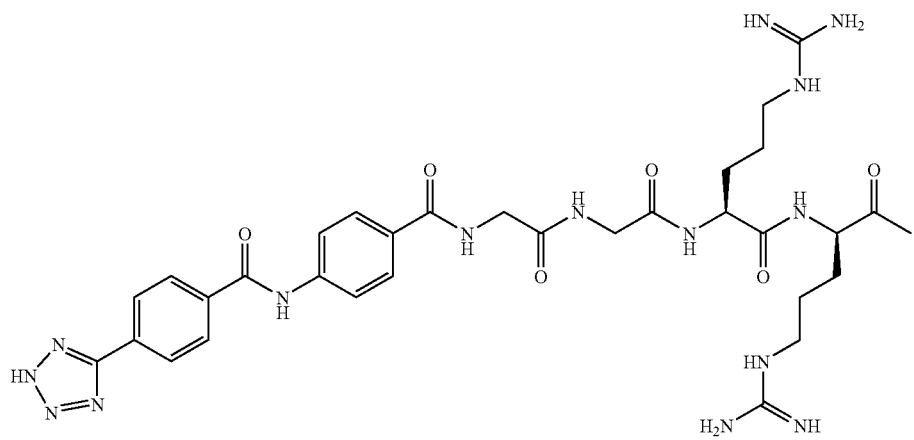
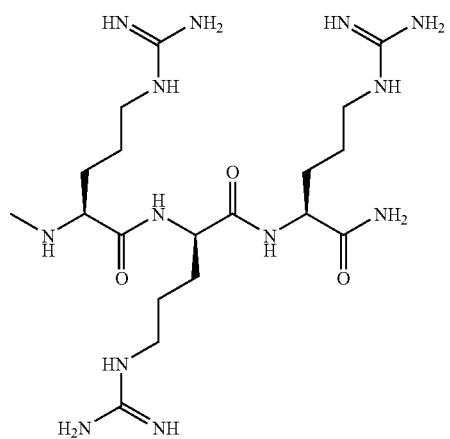

MS (MALDI): m/z: 1203.8 g/mol; calculated: 1203.8 g/mol.
Example 660
4-[3-(2H-Tetrazol-5-yl)carbazol-9-ylmethyl]benzoyl-Arg$_5$-NH$_2$ (SEQ ID NO: 26)
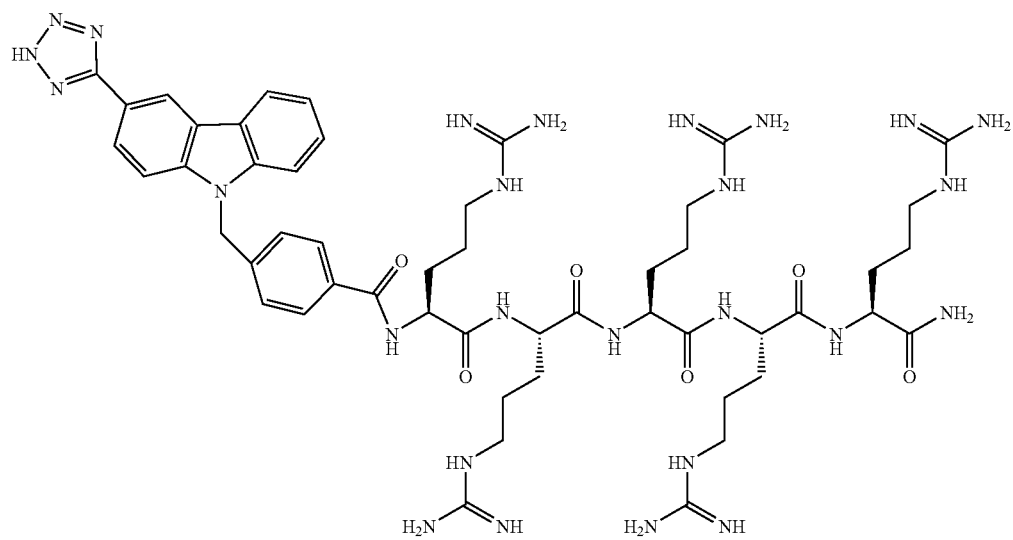
MS (MALDI): m/z: 1152.5 g/mol; calculated: 1149.3 g/mol.
Example 661
4-[3-(2H-Tetrazol-5-yl)carbazol-9-ylmethyl]benzoyl-Arg$_8$-NH$_2$ (SEQ ID NO: 29)
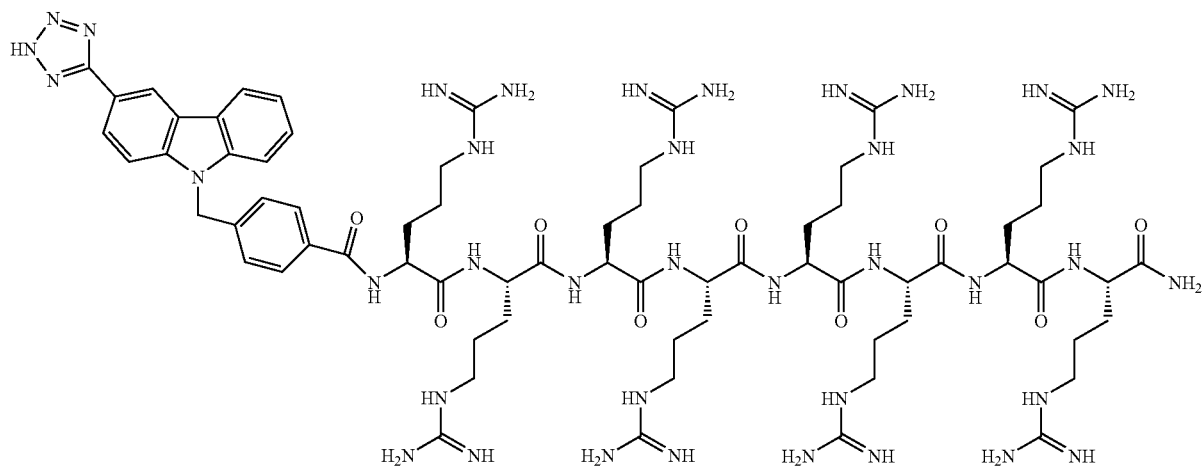

MS (MALDI): m/z: 1621.0 g/mol; calculated: 1617.5 g/mol.
Example 662
4-[3-(2H-Tetrazol-5-yl)carbazol-9-ylmethyl]benzoyl-Arg$_{12}$-NH$_2$ (SEQ ID NO: 28)
MS (MALDI): m/z: 2247.9 g/mol; calculated: 2242.3 g/mol.
Other preferred compounds of the invention that may be prepared according to general procedure (O) and/or general procedure (P) includes:
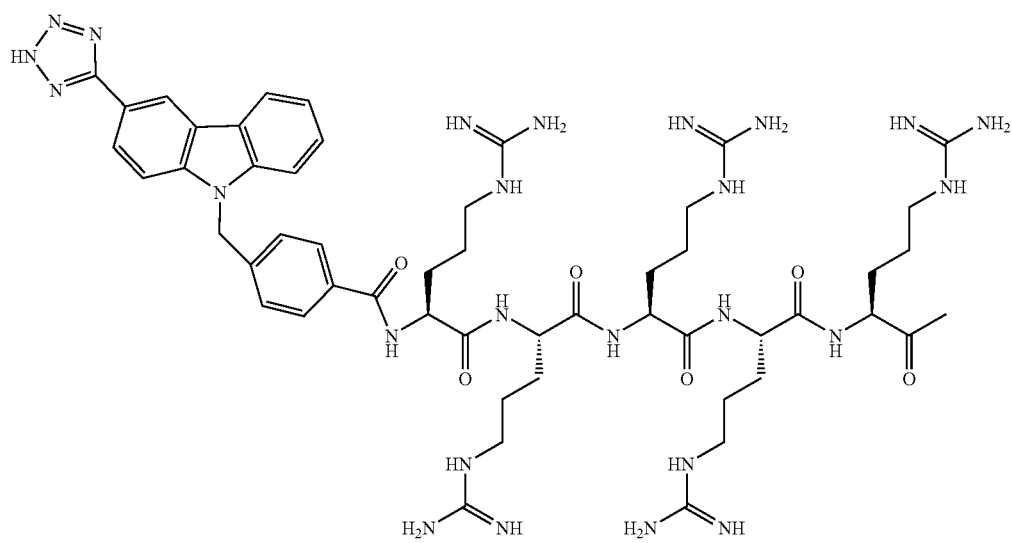
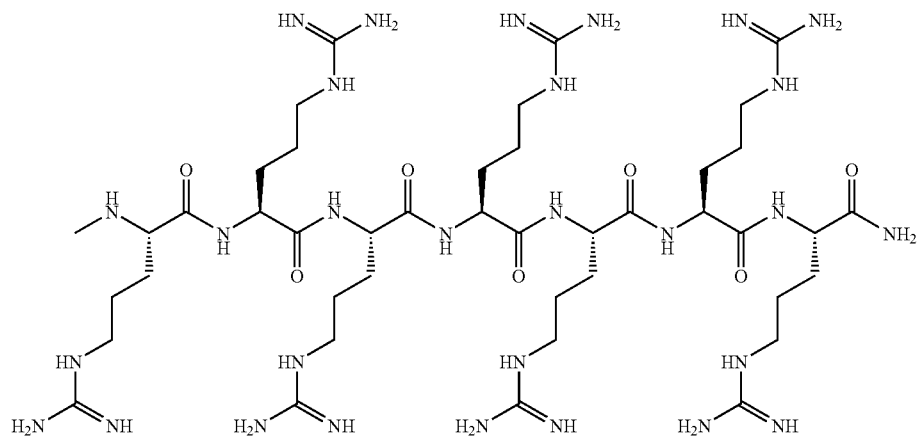

| Building block from example 291: |
|---|

4-[4-(2,4-Dioxothiazolidin-5-ylidenemethyl)naphthalen-1-yloxy]butyryl-Arg$_{10}$-NH$_2$
(SEQ ID NO: 30)
4-[4-(2,4-Dioxothiazolidin-5-ylidenemethyl)naphthalen-1-yloxy]butyryl-Arg$_9$-NH$_2$
(SEQ ID NO: 31)
4-[4-(2,4-Dioxothiazolidin-5-ylidenemethyl)naphthalen-1-yloxy]butyryl-Arg$_8$-NH$_2$
(SEQ ID NO: 29)
4-[4-(2,4-Dioxothiazolidin-5-ylidenemethyl)naphthalen-1-yloxy]butyryl-Arg$_7$-NH$_2$
(SEQ ID NO: 32)
4-[4-(2,4-Dioxothiazolidin-5-ylidenemethyl)naphthalen-1-yloxy]butyryl-Arg$_{11}$-NH$_2$
(SEQ ID NO: 33)
4-[4-(2,4-Dioxothiazolidin-5-ylidenemethyl)naphthalen-1-yloxy]butyryl-Arg$_{12}$-NH$_2$
(SEQ ID NO: 28)
4-[4-(2,4-Dioxothiazolidin-5-ylidenemethyl)naphthalen-1-yloxy]butyryl-Arg$_{13}$-NH$_2$
(SEQ ID NO: 34)
4-[4-(2,4-Dioxothiazolidin-5-ylidenemethyl)naphthalen-1-yloxy]butyryl-Arg$_{14}$-NH$_2$
(SEQ ID NO: 35)
4-[4-(2,4-Dioxothiazolidin-5-ylidenemethyl)naphthalen-1-yloxy]butyryl-Arg$_{15}$-NH$_2$
(SEQ ID NO: 36)
4-[4-(2,4-Dioxothiazolidin-5-ylidenemethyl)naphthalen-1-yloxy]butyryl-Arg$_{16}$-NH$_2$
(SEQ ID NO: 37)
4-[4-(2,4-Dioxothiazolidin-5-ylidenemethyl)naphthalen-1-yloxy]butyryl-Arg$_{17}$-NH$_2$
(SEQ ID NO: 38)
4-[4-(2,4-Dioxothiazolidin-5-ylidenemethyl)naphthalen-1-yloxy]butyryl-Arg$_{18}$-NH$_2$
(SEQ ID NO: 39)
4-[4-(2,4-Dioxothiazolidin-5-ylidenemethyl)naphthalen-1-yloxy]butyryl-Arg$_{19}$-NH$_2$
(SEQ ID NO: 40)
4-[4-(2,4-Dioxothiazolidin-5-ylidenemethyl)naphthalen-1-yloxy]butyryl-Arg$_{20}$-NH$_2$
(SEQ ID NO: 41)
4-[4-(2,4-Dioxothiazolidin-5-ylidenemethyl)naphthalen-1-yloxy]butyryl-Lys$_6$-NH$_2$
(SEQ ID NO: 42)
4-[4-(2,4-Dioxothiazolidin-5-ylidenemethyl)naphthalen-1-yloxy]butyryl-Lys$_5$-NH$_2$
(SEQ ID NO: 43)
4-[4-(2,4-Dioxothiazolidin-5-ylidenemethyl)naphthalen-1-yloxy]butyryl-Lys$_4$-NH$_2$
(SEQ ID NO: 44)
4-[4-(2,4-Dioxothiazolidin-5-ylidenemethyl)naphthalen-1-yloxy]butyryl-Lys$_3$-NH$_2$
4-[4-(2,4-Dioxothiazolidin-5-ylidenemethyl)naphthalen-1-yloxy]butyryl-Lys$_7$-NH$_2$
(SEQ ID NO: 45)
4-[4-(2,4-Dioxothiazolidin-5-ylidenemethyl)naphthalen-1-yloxy]butyryl-Lys$_8$-NH$_2$
(SEQ ID NO: 46)
4-[4-(2,4-Dioxothiazolidin-5-ylidenemethyl)naphthalen-1-yloxy]butyryl-Lys$_9$-NH$_2$
(SEQ ID NO: 47)
4-[4-(2,4-Dioxothiazolidin-5-ylidenemethyl)naphthalen-1-yloxy]butyryl-Lys$_{10}$-NH$_2$
(SEQ ID NO: 48)
4-[4-(2,4-Dioxothiazolidin-5-ylidenemethyl)naphthalen-1-yloxy]butyryl-Lys$_{11}$-NH$_2$
(SEQ ID NO: 49)
4-[4-(2,4-Dioxothiazolidin-5-ylidenemethyl)naphthalen-1-yloxy]butyryl-Lys$_{12}$-NH$_2$
(SEQ ID NO: 50)
4-[4-(2,4-Dioxothiazolidin-5-ylidenemethyl)naphthalen-1-yloxy]butyryl-Lys$_{13}$-NH$_2$
(SEQ ID NO: 51)
4-[4-(2,4-Dioxothiazolidin-5-ylidenemethyl)naphthalen-1-yloxy]butyryl-Lys$_{14}$-NH$_2$
(SEQ ID NO: 52)
4-[4-(2,4-Dioxothiazolidin-5-ylidenemethyl)naphthalen-1-yloxy]butyryl-Lys$_{15}$-NH$_2$
(SEQ ID NO: 53)
4-[4-(2,4-Dioxothiazolidin-5-ylidenemethyl)naphthalen-1-yloxy]butyryl-Lys$_{16}$-NH$_2$
(SEQ ID NO: 54)
4-[4-(2,4-Dioxothiazolidin-5-ylidenemethyl)naphthalen-1-yloxy]butyryl-Lys$_{17}$-NH$_2$
(SEQ ID NO: 55)
4-[4-(2,4-Dioxothiazolidin-5-ylidenemethyl)naphthalen-1-yloxy]butyryl-Lys$_{18}$-NH$_2$
(SEQ ID NO: 56)
4-[4-(2,4-Dioxothiazolidin-5-ylidenemethyl)naphthalen-1-yloxy]butyryl-Lys$_{19}$-NH$_2$
(SEQ ID NO: 57)
4-[4-(2,4-Dioxothiazolidin-5-ylidenemethyl)naphthalen-1-yloxy]butyryl-Lys$_{20}$-NH$_2$
(SEQ ID NO: 58)

Building block from example 292:

5-[4-(2,4-Dioxothiazolidin-5-ylidenemethyl)naphthalen-1-yloxy]pentanoyl-Arg$_6$-NH$_2$
(SEQ ID NO: 59)
5-[4-(2,4-Dioxothiazolidin-5-ylidenemethyl)naphthalen-1-yloxy]pentanoyl-Arg$_5$-NH$_2$
(SEQ ID NO: 26)
5-[4-(2,4-Dioxothiazolidin-5-ylidenemethyl)naphthalen-1-yloxy]pentanoyl-Arg$_4$-NH$_2$
(SEQ ID NO: 27)
5-[4-(2,4-Dioxothiazolidin-5-ylidenemethyl)naphthalen-1-yloxy]pentanoyl-Arg$_3$-NH$_2$ Building block from page 164:

6-[4-(2,4-Dioxothiazolidin-5-ylidenemethyl)naphthalen-1-yloxy]hexanoyl-Arg$_3$-NH$_2$
6-[4-(2,4-Dioxothiazolidin-5-ylidenemethyl)naphthalen-1-yloxy]hexanoyl-Arg$_4$-NH$_2$
(SEQ ID NO: 27)

-continued

6-[4-(2,4-Dioxothiazolidin-5-ylidenemethyl)naphthalen-1-yloxy]hexanoyl-Arg$_5$-NH$_2$
(SEQ ID NO: 26)
Building block from page 164:

7-[4-(2,4-Dioxothiazolidin-5-ylidenemethyl)naphthalen-1-yloxy]heptanoyl-Arg$_3$-NH$_2$
7-[4-(2,4-Dioxothiazolidin-5-ylidenemethyl)naphthalen-1-yloxy]heptanoyl-Arg$_4$-NH$_2$
(SEQ ID NO: 27)
7-[4-(2,4-Dioxothiazolidin-5-ylidenemethyl)naphthalen-1-yloxy]heptanoyl-Arg$_5$-NH$_2$
(SEQ ID NO: 26)
Building block from page 164:

8-[4-(2,4-Dioxothiazolidin-5-ylidenemethyl)naphthalen-1-yloxy]octanoyl-Arg$_3$-NH$_2$
8-[4-(2,4-Dioxothiazolidin-5-ylidenemethyl)naphthalen-1-yloxy]octanoyl-Arg$_4$-NH$_2$
(SEQ ID NO: 27)
8-[4-(2,4-Dioxothiazolidin-5-ylidenemethyl)naphthalen-1-yloxy]octanoyl-Arg$_5$-NH$_2$
(SEQ ID NO: 26)
Building block from page 164:

10-[4-(2,4-Dioxothiazolidin-5-ylidenemethyl)naphthalen-1-yloxy]decanoyl-Arg$_3$-NH$_2$
10-[4-(2,4-Dioxothiazolidin-5-ylidenemethyl)naphthalen-1-yloxy]decanoyl-Arg$_4$-NH$_2$
(SEQ ID NO: 27)
10-[4-(2,4-Dioxothiazolidin-5-ylidenemethyl)naphthalen-1-yloxy]decanoyl-Arg$_5$-NH$_2$
(SEQ ID NO: 26)
Building block from page 164:

11-[4-(2,4-Dioxothiazolidin-5-ylidenemethyl)naphthalen-1-yloxy]undecanoyl-Arg$_3$-NH$_2$
11-[4-(2,4-Dioxothiazolidin-5-ylidenemethyl)naphthalen-1-yloxy]undecanoyl-Arg$_4$-NH$_2$
(SEQ ID NO: 27)
11-[4-(2,4-Dioxothiazolidin-5-ylidenemethyl)naphthalen-1-yloxy]undecanoyl-Arg$_5$-NH$_2$
(SEQ ID NO: 26)
Building block from page 164:

12-[4-(2,4-Dioxothiazolidin-5-ylidenemethyl)naphthalen-1-yloxy]dodecanoyl-Arg$_3$-NH$_2$
12-[4-(2,4-Dioxothiazolidin-5-ylidenemethyl)naphthalen-1-yloxy]dodecanoyl-Arg$_4$-NH$_2$
(SEQ ID NO: 27)
12-[4-(2,4-Dioxothiazolidin-5-ylidenemethyl)naphthalen-1-yloxy]dodecanoyl-Arg$_5$-NH$_2$
(SEQ ID NO: 26)
Building block from page 164:

15-[4-(2,4-Dioxothiazolidin-5-ylidenemethyl)naphthalen-1-yloxy]pentadecanoyl-Arg$_3$-NH$_2$
15-[4-(2,4-Dioxothiazolidin-5-ylidenemethyl)naphthalen-1-yloxy]pentadecanoyl-Arg$_4$-NH$_2$
(SEQ ID NO: 27)
15-[4-(2,4-Dioxothiazolidin-5-ylidenemethyl)naphthalen-1-yloxy]pentadecanoyl-Arg$_5$-NH$_2$
(SEQ ID NO: 26)
Building block from example 298:

2-[4-(2,4-Dioxothiazolidin-5-ylidenemethyl)naphthalen-1-yloxy]acetyl-Arg$_6$-NH$_2$
(SEQ ID NO: 59)
2-[4-(2,4-Dioxothiazolidin-5-ylidenemethyl)naphthalen-1-yloxy]acetyl-Arg$_5$-NH$_2$
(SEQ ID NO: 26)
2-[4-(2,4-Dioxothiazolidin-5-ylidenemethyl)naphthalen-1-yloxy]acetyl-Arg$_4$-NH$_2$
(SEQ ID NO: 27)
2-[4-(2,4-Dioxothiazolidin-5-ylidenemethyl)naphthalen-1-yloxy]acetyl-Arg$_3$-NH$_2$
Building block from example 302:

2-{5-[4-(2,4-Dioxothiazolidin-5-ylidenemethyl)benzylidene]-4-oxo-2-thioxothiazolidin-3-yl}acetyl-Arg$_6$-NH$_2$
(SEQ ID NO: 59)
2-{5-[4-(2,4-Dioxothiazolidin-5-ylidenemethyl)benzylidene]-4-oxo-2-thioxothiazolidin-3-yl}acetyl-Arg$_5$-NH$_2$
(SEQ ID NO: 26)
2-{5-[4-(2,4-Dioxothiazolidin-5-ylidenemethyl)benzylidene]-4-oxo-2-thioxothiazolidin-3-yl}acetyl-Arg$_4$-NH$_2$
(SEQ ID NO: 27)
2-{5-[4-(2,4-Dioxothiazolidin-5-ylidenemethyl)benzylidene]-4-oxo-2-thioxothiazolidin-3-yl}acetyl-Arg$_3$-NH$_2$
4-[6-(2,4-Dioxothiazolidin-5-ylidenemethyl)naphthalen-2-yloxy]butyryl-Arg$_6$-NH$_2$
(SEQ ID NO: 59)
4-[6-(2,4-Dioxothiazolidin-5-ylidenemethyl)naphthalen-2-yloxy]butyryl-Arg$_5$-NH$_2$
(SEQ ID NO: 26)
4-[6-(2,4-Dioxothiazolidin-5-ylidenemethyl)naphthalen-2-yloxy]butyryl-Arg$_4$-NH$_2$
(SEQ ID NO: 27)
4-[6-(2,4-Dioxothiazolidin-5-ylidenemethyl)naphthalen-2-yloxy]butyryl-Arg$_3$-NH$_2$
15-[6-(2,4-Dioxothiazolidin-5-ylidenemethyl)naphthalen-2-yloxy]pentadecanoyl-Arg$_6$-NH$_2$
(SEQ ID NO: 59)
15-[6-(2,4-Dioxothiazolidin-5-ylidenemethyl)naphthalen-2-yloxy]pentadecanoyl-Arg$_5$-NH$_2$
(SEQ ID NO: 26)
15-[6-(2,4-Dioxothiazolidin-5-ylidenemethyl)naphthalen-2-yloxy]pentadecanoyl-Arg$_4$-NH$_2$
(SEQ ID NO: 27)

-continued

15-[6-(2,4-Dioxothiazolidin-5-ylidenemethyl)naphthalen-2-yloxy]pentadecanoyl-Arg$_3$-NH$_2$
5-[2-Bromo-4-(2,4-dioxothiazolidin-5-ylidenemethyl)naphthalen-1-yloxy]pentanoyl-Arg$_6$-NH$_2$
(SEQ ID NO: 59)
5-[2-Bromo-4-(2,4-dioxothiazolidin-5-ylidenemethyl)naphthalen-1-yloxy]pentanoyl-Arg$_5$-NH$_2$
(SEQ ID NO: 26)
5-[2-Bromo-4-(2,4-dioxothiazolidin-5-ylidenemethyl)naphthalen-1-yloxy]pentanoyl-Arg$_4$-NH$_2$
(SEQ ID NO: 27)
5-[2-Bromo-4-(2,4-dioxothiazolidin-5-ylidenemethyl)naphthalen-1-yloxy]pentanoyl-Arg$_3$-NH$_2$
Building block from example 284:

3-[4-(2,4-Dioxothiazolidin-5-ylidenemethyl)phenyl]acryloyl-Arg$_6$-NH$_2$
(SEQ ID NO: 59)
Building block from example 295:

2-[2-Bromo-4-(2,4-dioxothiazolidin-5-ylidenemethyl)phenoxy]acetyl-Arg$_6$-NH$_2$
(SEQ ID NO: 59)
2-[2-Bromo-4-(2,4-dioxothiazolidin-5-ylidenemethyl)phenoxy]acetyl-Arg$_5$-NH$_2$
(SEQ ID NO: 26)
2-[2-Bromo-4-(2,4-dioxothiazolidin-5-ylidenemethyl)phenoxy]acetyl-Arg$_4$-NH$_2$
(SEQ ID NO: 27)
2-[2-Bromo-4-(2,4-dioxothiazolidin-5-ylidenemethyl)phenoxy]acetyl-Arg$_3$-NH$_2$
8-[6-(2,4-Dioxothiazolidin-5-ylidenemethyl)naphthalen-2-yloxy]octanoyl-Arg$_6$-NH$_2$
(SEQ ID NO: 59)
8-[6-(2,4-Dioxothiazolidin-5-ylidenemethyl)naphthalen-2-yloxy]octanoyl-Arg$_5$-NH$_2$
(SEQ ID NO: 26)
8-[6-(2,4-Dioxothiazolidin-5-ylidenemethyl)naphthalen-2-yloxy]octanoyl-Arg$_4$-NH$_2$
(SEQ ID NO: 27)
8-[6-(2,4-Dioxothiazolidin-5-ylidenemethyl)naphthalen-2-yloxy]octanoyl-Arg$_3$-NH$_2$
6-[6-(2,4-Dioxothiazolidin-5-ylidenemethyl)naphthalen-2-yloxy]hexanoyl-Arg$_6$-NH$_2$
(SEQ ID NO: 59)
6-[6-(2,4-Dioxothiazolidin-5-ylidenemethyl)naphthalen-2-yloxy]hexanoyl-Arg$_5$-NH$_2$
(SEQ ID NO: 26)
6-[6-(2,4-Dioxothiazolidin-5-ylidenemethyl)naphthalen-2-yloxy]hexanoyl-Arg$_4$-NH$_2$
(SEQ ID NO: 27)
6-[6-(2,4-Dioxothiazolidin-5-ylidenemethyl)naphthalen-2-yloxy]hexanoyl-Arg$_3$-NH$_2$
Building block from example 288:

4-[2-Chloro-4-(2,4-dioxothiazolidin-5-ylidenemethyl)phenoxy]butyryl-Arg$_6$-NH$_2$
(SEQ ID NO: 59)
4-[2-Chloro-4-(2,4-dioxothiazolidin-5-ylidenemethyl)phenoxy]butyryl-Arg$_5$-NH$_2$
(SEQ ID NO: 26)
4-[2-Chloro-4-(2,4-dioxothiazolidin-5-ylidenemethyl)phenoxy]butyryl-Arg$_4$-NH$_2$
(SEQ ID NO: 27)
4-[2-Chloro-4-(2,4-dioxothiazolidin-5-ylidenemethyl)phenoxy]butyryl-Arg$_3$-NH$_2$
Building block from example 282:

4-[4-(2,4-Dioxothiazolidin-5-ylidenemethyl)phenoxy]butyryl-Arg$_6$-NH$_2$
(SEQ ID NO: 59)
Building block from example 289:

4-[2-Bromo-4-(2,4-dioxothiazolidin-5-ylidenemethyl)phenoxy]butyryl-Arg$_6$-NH$_2$
(SEQ ID NO: 59)
4-[2-Bromo-4-(2,4-dioxothiazolidin-5-ylidenemethyl)phenoxy]butyryl-Arg$_5$-NH$_2$
(SEQ ID NO: 26)
4-[2-Bromo-4-(2,4-dioxothiazolidin-5-ylidenemethyl)phenoxy]butyryl-Arg$_4$-NH$_2$
(SEQ ID NO: 27)
4-[2-Bromo-4-(2,4-dioxothiazolidin-5-ylidenemethyl)phenoxy]butyryl-Arg$_3$-NH$_2$
11-[6-(2,4-Dioxothiazolidin-5-ylidenemethyl)naphthalen-2-yloxy]undecanoyl-Arg$_6$-NH$_2$
(SEQ ID NO: 59)
11-[6-(2,4-Dioxothiazolidin-5-ylidenemethyl)naphthalen-2-yloxy]undecanoyl-Arg$_5$-NH$_2$
(SEQ ID NO: 26)
11-[6-(2,4-Dioxothiazolidin-5-ylidenemethyl)naphthalen-2-yloxy]undecanoyl-Arg$_4$-NH$_2$
(SEQ ID NO: 27)
11-[6-(2,4-Dioxothiazolidin-5-ylidenemethyl)naphthalen-2-yloxy]undecanoyl-Arg$_3$-NH$_2$
4-[2-Bromo-4-(2,4-dioxothiazolidin-5-ylidenemethyl)naphthalen-1-yloxy]butyryl-Arg$_6$-NH$_2$
(SEQ ID NO: 59)
4-[2-Bromo-4-(2,4-dioxothiazolidin-5-ylidenemethyl)naphthalen-1-yloxy]butyryl-Arg$_5$-NH$_2$
(SEQ ID NO: 26)
4-[2-Bromo-4-(2,4-dioxothiazolidin-5-ylidenemethyl)naphthalen-1-yloxy]butyryl-Arg$_4$-NH$_2$
(SEQ ID NO: 27)
4-[2-Bromo-4-(2,4-dioxothiazolidin-5-ylidenemethyl)naphthalen-1-yloxy]butyryl-Arg$_3$-NH$_2$
Building block from example 286:

4-(2,4-Dioxothiazolidin-5-ylidenemethyl)benzoyl-Arg$_6$-NH$_2$
(SEQ ID NO: 59)
4-(2,4-Dioxothiazolidin-5-ylidenemethyl)benzoyl-Arg$_5$-NH$_2$
(SEQ ID NO: 26)
4-(2,4-Dioxothiazolidin-5-ylidenemethyl)benzoyl-Arg$_4$-NH$_2$
(SEQ ID NO: 27)

-continued 4-(2,4-Dioxothiazolidin-5-ylidenemethyl)benzoyl-Arg$_3$-NH$_2$
Building block from example 285:

2-[4-(2,4-Dioxothiazolidin-5-ylidenemethyl)phenoxy]acetyl-Arg$_6$-NH$_2$
(SEQ ID NO: 59)
2-[4-(2,4-Dioxothiazolidin-5-ylidenemethyl)phenoxy]acetyl-Arg$_5$-NH$_2$
(SEQ ID NO: 26)
2-[4-(2,4-Dioxothiazolidin-5-ylidenemethyl)phenoxy]acetyl-Arg$_4$-NH$_2$
(SEQ ID NO: 27)
2-[4-(2,4-Dioxothiazolidin-5-ylidenemethyl)phenoxy]acetyl-Arg$_3$-NH$_2$
Building block from example 283:

2-[3-(2,4-Dioxothiazolidin-5-ylidenemethyl)phenoxy]acetyl-Arg$_6$-NH$_2$
(SEQ ID NO: 59)
2-[3-(2,4-Dioxothiazolidin-5-ylidenemethyl)phenoxy]acetyl-Arg$_5$-NH$_2$
(SEQ ID NO: 26)
2-[3-(2,4-Dioxothiazolidin-5-ylidenemethyl)phenoxy]acetyl-Arg$_4$-NH$_2$
(SEQ ID NO: 27)
2-[3-(2,4-Dioxothiazolidin-5-ylidenemethyl)phenoxy]acetyl-Arg$_3$-NH$_2$
Building block from example 296:

4-[3-(2,4-Dioxothiazolidin-5-ylidenemethyl)phenoxy]butyryl-Arg$_6$-NH$_2$
(SEQ ID NO: 59)
4-[3-(2,4-Dioxothiazolidin-5-ylidenemethyl)phenoxy]butyryl-Arg$_5$-NH$_2$
(SEQ ID NO: 26)
4-[3-(2,4-Dioxothiazolidin-5-ylidenemethyl)phenoxy]butyryl-Arg$_4$-NH$_2$
(SEQ ID NO: 27)
4-[3-(2,4-Dioxothiazolidin-5-ylidenemethyl)phenoxy]butyryl-Arg$_3$-NH$_2$
Building block from example 290:

4-[2-Bromo-4-(4-oxo-2-thioxothiazolidin-5-ylidenemethyl)phenoxy]butyryl-Arg$_6$-NH$_2$
(SEQ ID NO: 59)
4-[2-Bromo-4-(4-oxo-2-thioxothiazolidin-5-ylidenemethyl)phenoxy]butyryl-Arg$_5$-NH$_2$
(SEQ ID NO: 26)
4-[2-Bromo-4-(4-oxo-2-thioxothiazolidin-5-ylidenemethyl)phenoxy]butyryl-Arg$_4$-NH$_2$
(SEQ ID NO: 27)
4-[2-Bromo-4-(4-oxo-2-thioxothiazolidin-5-ylidenemethyl)phenoxy]butyryl-Arg$_3$-NH$_2$
Building block from example 544:

4-[3-(2H-Tetrazol-5-yl)carbazol-9-ylmethyl]benzoyl-Arg$_6$-NH$_2$
(SEQ ID NO: 59)
4-[3-(2H-Tetrazol-5-yl)carbazol-9-ylmethyl]benzoyl-Arg$_4$-NH$_2$
(SEQ ID NO: 27)
4-[3-(2H-Tetrazol-5-yl)carbazol-9-ylmethyl]benzoyl-Arg$_3$-NH$_2$
4-[3-(2H-Tetrazol-5-yl)carbazol-9-ylmethyl]benzoyl-Arg$_7$-NH$_2$
(SEQ ID NO: 32)
4-[3-(2H-Tetrazol-5-yl)carbazol-9-ylmethyl]benzoyl-Arg$_8$-NH$_2$
(SEQ ID NO: 29)
4-[3-(2H-Tetrazol-5-yl)carbazol-9-ylmethyl]benzoyl-Arg$_9$-NH$_2$
(SEQ ID NO: 31)
4-[3-(2H-Tetrazol-5-yl)carbazol-9-ylmethyl]benzoyl-Arg$_{10}$-NH$_2$
(SEQ ID NO: 30)
4-[3-(2H-Tetrazol-5-yl)carbazol-9-ylmethyl]benzoyl-Arg$_{11}$-NH$_2$
(SEQ ID NO: 33)
4-[3-(2H-Tetrazol-5-yl)carbazol-9-ylmethyl]benzoyl-Arg$_{12}$-NH$_2$
(SEQ ID NO: 28)
4-[3-(2H-Tetrazol-5-yl)carbazol-9-ylmethyl]benzoyl-Arg$_{13}$-NH$_2$
(SEQ ID NO: 34)
4-[3-(2H-Tetrazol-5-yl)carbazol-9-ylmethyl]benzoyl-Arg$_{14}$-NH$_2$
(SEQ ID NO: 35)
4-[3-(2H-Tetrazol-5-yl)carbazol-9-ylmethyl]benzoyl-Arg$_{15}$-NH$_2$
(SEQ ID NO: 36)
4-[3-(2H-Tetrazol-5-yl)carbazol-9-ylmethyl]benzoyl-Arg$_{16}$-NH$_2$
(SEQ ID NO: 37)
4-[3-(2H-Tetrazol-5-yl)carbazol-9-ylmethyl]benzoyl-Arg$_{17}$-NH$_2$
(SEQ ID NO: 38)
4-[3-(2H-Tetrazol-5-yl)carbazol-9-ylmethyl]benzoyl-Arg$_{18}$-NH$_2$
(SEQ ID NO: 39)
4-[3-(2H-Tetrazol-5-yl)carbazol-9-ylmethyl]benzoyl-Arg$_{19}$-NH$_2$
(SEQ ID NO: 40)
4-[3-(2H-Tetrazol-5-yl)carbazol-9-ylmethyl]benzoyl-Arg$_{20}$-NH$_2$
(SEQ ID NO: 41)
Building block from page 251:

4'-[3-(2H-Tetrazol-5-yl)carbazol-9-ylmethyl]biphenyl-4-carbonyl-Arg$_6$-NH$_2$
(SEQ ID NO: 59)
4'-[3-(2H-Tetrazol-5-yl)carbazol-9-ylmethyl]biphenyl-4-carbonyl-Arg$_5$-NH$_2$
(SEQ ID NO: 26)
4'-[3-(2H-Tetrazol-5-yl)carbazol-9-ylmethyl]biphenyl-4-carbonyl-Arg$_4$-NH$_2$ -continued (SEQ ID NO: 27)
4'-[3-(2H-Tetrazol-5-yl)carbazol-9-ylmethyl]biphenyl-4-carbonyl-$Arg_3$-$NH_2$
Building block from example 549:

3-[3-(2H-Tetrazol-5-yl)carbazol-9-ylmethyl]benzoyl-$Arg_6$-$NH_2$
(SEQ ID NO: 59)
3-[3-(2H-Tetrazol-5-yl)carbazol-9-ylmethyl]benzoyl-$Arg_5$-$NH_2$
(SEQ ID NO: 26)
3-[3-(2H-Tetrazol-5-yl)carbazol-9-ylmethyl]benzoyl-$Arg_4$-$NH_2$
(SEQ ID NO: 27)
3-[3-(2H-Tetrazol-5-yl)carbazol-9-ylmethyl]benzoyl-$Arg_3$-$NH_2$
Building block from page 252:

4'-[5-(2H-Tetrazol-5-yl)indol-1-ylmethyl]biphenyl-4-carbonyl-$Arg_6$-$NH_2$
(SEQ ID NO: 59)
4'-[5-(2H-Tetrazol-5-yl)indol-1-ylmethyl]biphenyl-4-carbonyl-$Arg_5$-$NH_2$
(SEQ ID NO: 26)
4'-[5-(2H-Tetrazol-5-yl)indol-1-ylmethyl]biphenyl-4-carbonyl-$Arg_4$-$NH_2$
(SEQ ID NO: 27)
4'-[5-(2H-Tetrazol-5-yl)indol-1-ylmethyl]biphenyl-4-carbonyl-$Arg_3$-$NH_2$
Building block from example 412:

4-(2H-Tetrazol-5-yl)benzoyl-$Gly_2$-$Arg_6$-$NH_2$
(SEQ ID NO: 59)
4-(2H-Tetrazol-5-yl)benzoyl-$Gly_2$-$Arg_5$-$NH_2$
(SEQ ID NO: 26)
4-(2H-Tetrazol-5-yl)benzoyl-$Gly_2$-$Arg_4$-$NH_2$
(SEQ ID NO: 27)
4-(2H-Tetrazol-5-yl)benzoyl-$Gly_2$-$Arg_3$-$NH_2$
Building block from example 355:

[4-(7-Carboxy-6-hydroxynaphthalen-2-yl)phenyl]methyl-$Arg_6$-$NH_2$
(SEQ ID NO: 59)
[4-(7-Carboxy-6-hydroxynaphthalen-2-yl)phenyl]methyl-$Arg_5$-$NH_2$
(SEQ ID NO: 26)
[4-(7-Carboxy-6-hydroxynaphthalen-2-yl)phenyl]methyl-$Arg_4$-$NH_2$
(SEQ ID NO: 27)
[4-(7-Carboxy-6-hydroxynaphthalen-2-yl)phenyl]methyl-$Arg_3$-$NH_2$
Building block from example 342:

(7-Carboxy-6-hydroxynaphthalen-2-yl)methyl-$Arg_6$-$NH_2$
(SEQ ID NO: 59)
(7-Carboxy-6-hydroxynaphthalen-2-yl)methyl-$Arg_5$-$NH_2$
(SEQ ID NO: 26)
(7-Carboxy-6-hydroxynaphthalen-2-yl)methyl-$Arg_4$-$NH_2$
(SEQ ID NO: 27)
(7-Carboxy-6-hydroxynaphthalen-2-yl)methyl-$Arg_3$-$NH_2$
Building block from example 342:

4-[(7-Carboxy-6-hydroxynaphthalen-2-ylmethyl)amino]benzoyl-$Arg_6$-$NH_2$
(SEQ ID NO: 59)
4-[(7-Carboxy-6-hydroxynaphthalen-2-ylmethyl)amino]benzoyl-$Arg_5$-$NH_2$
(SEQ ID NO: 26)
4-[(7-Carboxy-6-hydroxynaphthalen-2-ylmethyl)amino]benzoyl-$Arg_4$-$NH_2$
(SEQ ID NO: 27)
4-[(7-Carboxy-6-hydroxynaphthalen-2-ylmethyl)amino]benzoyl-$Arg_3$-$NH_2$
4-[4-(5-Mercaptotetrazol-1-yl)benzoylamino]benzoyl-$Arg_6$-$NH_2$
(SEQ ID NO: 59)
4-[4-(5-Mercaptotetrazol-1-yl)benzoylamino]benzoyl-$Arg_5$-$NH_2$
(SEQ ID NO: 26)
4-[4-(5-Mercaptotetrazol-1-yl)benzoylamino]benzoyl-$Arg_4$-$NH_2$
(SEQ ID NO: 27)
4-[4-(5-Mercaptotetrazol-1-yl)benzoylamino]benzoyl-$Arg_3$-$NH_2$
4-[4-(5-Mercaptotetrazol-1-yl)phenoxy]butyryl-$Arg_6$-$NH_2$
(SEQ ID NO: 59)
4-[4-(5-Mercaptotetrazol-1-yl)phenoxy]butyryl-$Arg_5$-$NH_2$
(SEQ ID NO: 26)
4-[4-(5-Mercaptotetrazol-1-yl)phenoxy]butyryl-$Arg_4$-$NH_2$
(SEQ ID NO: 27)
4-[4-(5-Mercaptotetrazol-1-yl)phenoxy]butyryl-$Arg_3$-$NH_2$
4-[4-(5-Mercaptotetrazol-1-yl)naphthalen-1-yloxy]butyryl-$Arg_6$-$NH_2$
(SEQ ID NO: 59)
4-[4-(5-Mercaptotetrazol-1-yl)naphthalen-1-yloxy]butyryl-$Arg_5$-$NH_2$
(SEQ ID NO: 26)
4-[4-(5-Mercaptotetrazol-1-yl)naphthalen-1-yloxy]butyryl-$Arg_4$-$NH_2$
(SEQ ID NO: 27)
4-[4-(5-Mercaptotetrazol-1-yl)naphthalen-1-yloxy]butyryl-$Arg_3$-$NH_2$
Benzotriazol-5-ylcarbonyl-4-Abz-$Gly_2$-$Arg_6$-$NH_2$
(SEQ ID NO: 60)

-continued

Benzotriazol-5-ylcarbonyl-4-Abz-Gly$_2$-Arg$_4$-NH$_2$
(SEQ ID NO: 61)
Benzotriazol-5-ylcarbonyl-4-Abz-Gly$_2$-Arg$_3$-NH$_2$
(SEQ ID NO: 62)
4-[5-Bromo-6-(2,4-dioxothiazolidin-5-ylidenemethyl)naphthalen-2-yloxymethyl]benzoyl-Arg$_3$-NH$_2$
4-[5-Bromo-6-(2,4-dioxothiazolidin-5-ylidenemethyl)naphthalen-2-yloxymethyl]benzoyl-Arg$_4$-NH$_2$
(SEQ ID NO: 27)
4-[5-Bromo-6-(2,4-dioxothiazolidin-5-ylidenemethyl)naphthalen-2-yloxymethyl]benzoyl-Arg$_5$-NH$_2$
(SEQ ID NO: 26)
3',5'-Dichloro-4'-(2,4-dioxothiazolidin-5-ylidenemethyl)biphenyl-4-oyl-Arg$_3$-NH$_2$
3',5'-Dichloro-4'-(2,4-dioxothiazolidin-5-ylidenemethyl)biphenyl-4-oyl-Arg$_4$-NH$_2$
(SEQ ID NO: 27)
3',5'-Dichloro-4'-(2,4-dioxothiazolidin-5-ylidenemethyl)biphenyl-4-oyl-Arg$_5$-NH$_2$
(SEQ ID NO: 26)
2-(4-(5-Cyano-1H-[1,2,3]triazol-4-yl)phenoxy)acetyl-Arg$_3$-NH$_2$
2-(4-(5-Cyano-1H-[1,2,3]triazol-4-yl)phenoxy)acetyl-Arg$_4$-NH$_2$
(SEQ ID NO: 27)
2-(4-(5-Cyano-1H-[1,2,3]triazol-4-yl)phenoxy)acetyl-Arg$_5$-NH$_2$
(SEQ ID NO: 26)
4-(4-(5-Cyano-1H-[1,2,3]triazol-4-yl)phenoxy)butyryl-Arg$_5$-NH$_2$
(SEQ ID NO: 26)
4-(4-(5-Cyano-1H-[1,2,3]triazol-4-yl)phenoxy)butyryl-Arg$_4$-NH$_2$
(SEQ ID NO: 27)
4-(4-(5-Cyano-1H-[1,2,3]triazol-4-yl)phenoxy)butyryl-Arg$_3$-NH$_2$
5-(4-(5-Cyano-1H-[1,2,3]triazol-4-yl)phenoxy)pentanoyl-Arg$_5$-NH$_2$
(SEQ ID NO: 26)
5-(4-(5-Cyano-1H-[1,2,3]triazol-4-yl)phenoxy)pentanoyl-Arg$_4$-NH$_2$
(SEQ ID NO: 27)
5-(4-(5-Cyano-1H-[1,2,3]triazol-4-yl)phenoxy)pentanoyl-Arg$_3$-NH$_2$
8-(4-(5-Cyano-1H-[1,2,3]triazol-4-yl)phenoxy)octanoyl-Arg$_5$-NH$_2$
(SEQ ID NO: 26)
8-(4-(5-Cyano-1H-[1,2,3]triazol-4-yl)phenoxy)octanoyl-Arg$_4$-NH$_2$
(SEQ ID NO: 27)
8-(4-(5-Cyano-1H-[1,2,3]triazol-4-yl)phenoxy)octanoyl-Arg$_3$-NH$_2$
4-[4-(5-Cyano-1H-[1,2,3]triazol-4-yl)benzoylamino]-benzoyl-Arg$_6$-NH$_2$
(SEQ ID NO: 59)
4-[4-(5-Cyano-1H-[1,2,3]triazol-4-yl)benzoylamino]-benzoyl-Arg$_5$-NH$_2$
(SEQ ID NO: 26)
4-[4-(5-Cyano-1H-[1,2,3]triazol-4-yl)benzoylamino]-benzoyl-Arg$_4$-NH$_2$
(SEQ ID NO: 27)
4-[4-(5-Cyano-1H-[1,2,3]triazol-4-yl)benzoylamino]-benzoyl-Arg$_3$-NH$_2$
N-[4-(5-Cyano-1H-[1,2,3]triazol-4-yl)phenyl]terephthalamoyl-Arg$_5$-NH$_2$
(SEQ ID NO: 26)
N-[4-(5-Cyano-1H-[1,2,3]triazol-4-yl)phenyl]terephthalamoyl-Arg$_4$-NH$_2$
(SEQ ID NO: 27)
N-[4-(5-Cyano-1H-[1,2,3]triazol-4-yl)phenyl]terephthalamoyl-Arg$_3$-NH$_2$ Example 663

Equilibrium Solubility. For pH-solubility profiles, a 0.6 mM human insulin stock solution containing 0.2 mM $Zn^{2+}$, 30 mM phenol, 0.2 M mannitol, 2 mM phosphate and $Zn^{2+}$-binding ligand as required were prepared and the pH was adjusted to the desired value corresponding to the alkaline endpoint of the pH-solubility profile. From these stock solutions samples were withdrawn, the pH adjusted to the desired value in the pH 3-8 range, and samples were incubated at 23 C for 24 hours. After centrifugation (20,000 g in 20 min at 23 C) of each sample, pH was measured and the solubility was determined by quantitation of insulin contents in the supernatant by SEC HPLC analysis The effect of various concentration of the ligand BTG$_2$R$_5$ (SEQ ID NO: 1) on the pH-dependence of insulin solubility is illustrated in FIG. 1.

Example 664

Figure 2:
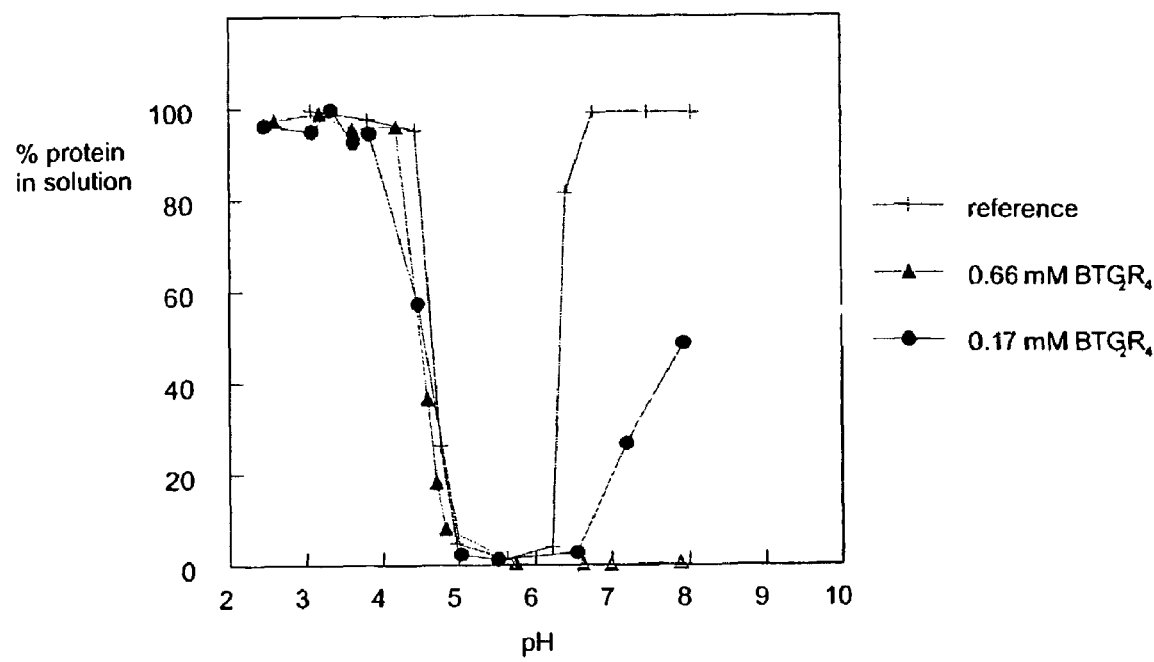
FIG. 2: Effect of BTG$_2$R$_4$—NH$_2$ (SEQ ID NO: 2) on the pH-solubility profile of an insulin preparation.
Figure 3:
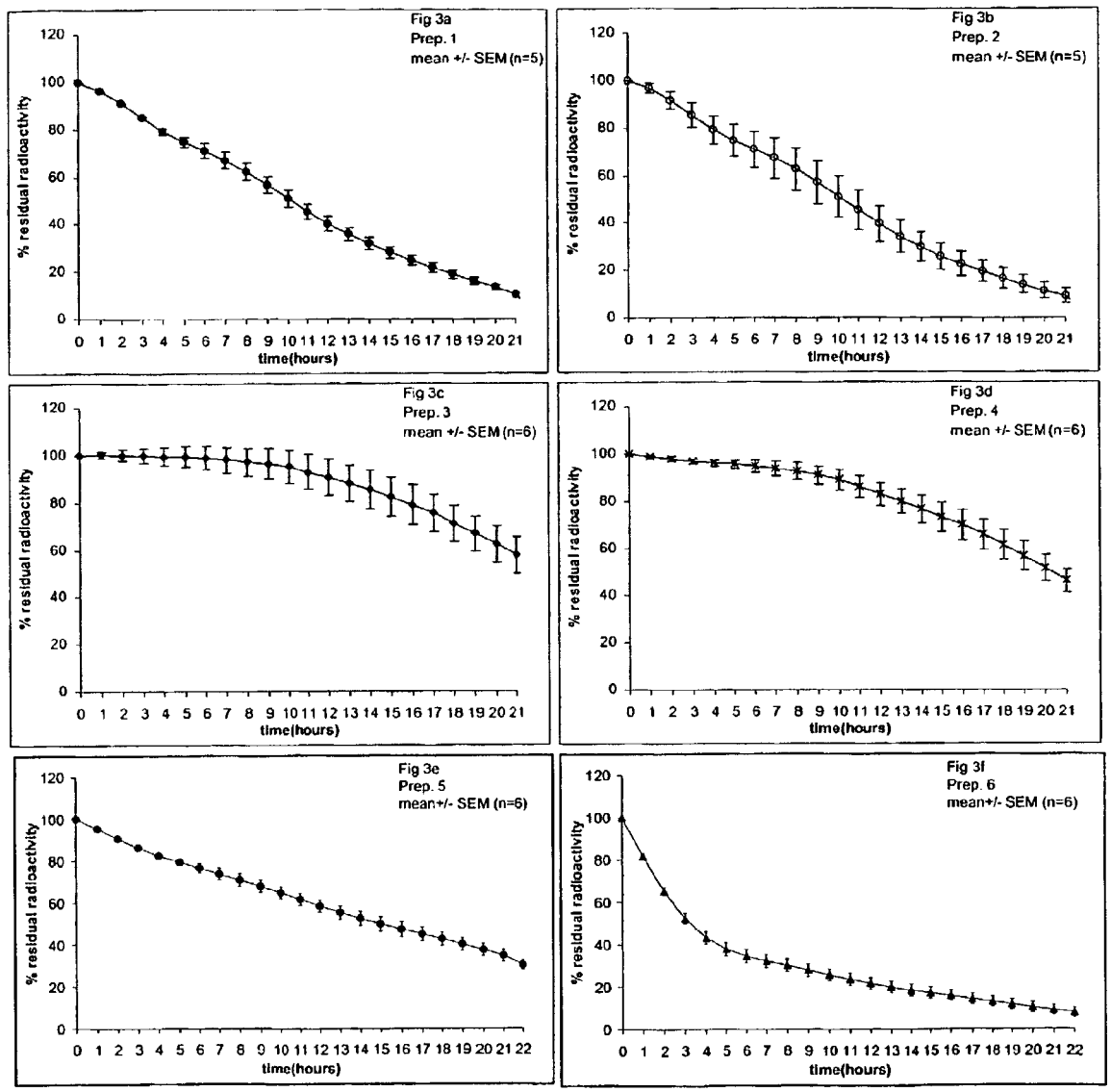
FIG. 3: Disappearance from the subcutaneous depot (pig model) of insulin preparations in the presence of BT-AbzG$_2$R$_5$—NH$_2$ (SEQ ID NO: 3) with phenol and 7-hydroxy indole (a-b); and BT-G$_2$R$_5$—NH$_2$ (SEQ ID NO: 1) and BT-G$_2$R$_4$ (SEQ ID NO: 2) with phenol (c-d). The bottom panels (e-f) show slow- and dual release profiles, respectively, obtained from Asp$^{B28}$ human insulin formulated with variable concentration of TZD-Abz-G$_2$R$_5$ (SEQ ID NO: 4)

The effect of increasing concentrations of the ligand BTG$_2$R$_4$ (SEQ ID NO: 2) on the pH-dependence of insulin solubility is illustrated in FIG. 2. The solubility was determined as in example 24. Solution conditions: 0.6 mM human insulin, 0.2 mM mM $Zn^{2+}$, 30 mM phenol, 0.2 M mannitol, 2 mM phosphate, 23 C.

Example 665

The slow release (prolonged action) properties of certain formulations of the present invention was characterized by the disappearance rate from the subcutaneous depot following subcutaneous injections in pigs. $T_{50\%}$ is the time when 50% of the A14 Tyr($^{125}$I) insulin has disappeared from the site of injection as measured with an external γ-counter (Ribel et al., The Pig as a Model for Subcutaneous Absorption in Man. In: M. Serrano-Rtios and P. J. Lefebre (Eds): Diabetes (1985) Proceedings of the 12$^{th}$ congress of the International Diabetes Federation, Madrid, Spain, 1985 (Excerpta Medica, Amsterdam (1986), 891-896). The composition of a series of protracted formulations is given in the table below together with the $T_{50\%}$ values. The disappearance curves are illustrated in FIG. 3a-d. For comparison, the $T_{50\%}$ for the corresponding insulin preparations formulated without the ligands would be about 2 hours.

The induction of slow release by addition of exogenous ligands of the invention affords further advantages in terms of versatility regarding the choice of insulin species and release patterns. Consequently, human or mutant insulins such as $Asp^{B28}$, $Lys^{B28}Pro^{B29}$, or $Gly^{A21}Lys^{B3}Glu^{B29}$ may be formulated as slow- or dual-release preparations by adding variable amounts of $His^{B10}Zn^{2+}$-site ligand. This is illustrated below for $Asp^{B28}$ human insulin employing two different levels of the ligand TZD-Abz-$G_2R_5$ (SEQ ID NO: 4) (example 647). As shown in the table and in FIG. 3 panels e-f, addition of this ligand in slight excess of the $Zn^{2+}$ concentration produces a slow release preparation with $T_{50\%}$ about 14.8. In contrast, when the ligand is added in concentrations lower than that of $Zn^{2+}$, a distinctly dual-release formulation results.

TABLE 3

| ligand addition (μl) | ligand conc. (mM) | dilution factor |
|---|---|---|
| 1 | 0.010 | 1.0005 |
| 1 | 0.020 | 1.0010 |
| 1 | 0.030 | 1.0015 |
| 2 | 0.050 | 1.0025 |
| 5 | 0.100 | 1.0050 |
| 10 | 0.198 | 1.0100 |
| 20 | 0.392 | 1.0200 |
| 20 | 0.583 | 1.0300 |
| 20 | 0.769 | 1.0400 |
| 20 | 0.952 | 1.0500 |

| | $^{125}$I-Prep. 1 | $^{125}$I-Prep. 2 | $^{125}$I-Prep. 3 | $^{125}$I-Prep. 4 | $^{125}$I-Prep. 5 | $^{125}$I-Prep. 6 |
|---|---|---|---|---|---|---|
| Insulin (mM) | 0.6 human insulin | 0.6 human insulin | 0.6 human insulin | 0.6 human insulin | 0.6 $Asp^{B28}$ insulin | 0.6 $Asp^{B28}$ insulin |
| $Zn^{2+}$ (mM) | 0.3 | 0.3 | 0.3 | 0.3 | 0.3 | 0.3 |
| Phenolic ligand | 30 mM phenol | 30 mM phenol | 30 mM phenol | 30 mM 7-hydroxyindole | 30 mM phenol | 30 mM phenol |
| $Zn^{2+}$ ligand | 6 mM $BTG_2R_4$ (Ex. 641) (SEQ ID NO: 2) | 6 mM $BTG_2R_6$ (Ex. 643) (SEQ ID NO: 5) | 2 mM BT-$AbzG_2R_5$ (Ex. 644) (SEQ ID NO: 3) | 2 mM BT-$AbzG_2R_5$ (Ex. 644) (SEQ ID NO: 3) | 0.4 mM TZD-$AbzG_2R_5$ (Ex. 647) (SEQ ID NO: 4) | 0.15 mM TZD-$AbzG_2R_5$ (Ex. 647) (SEQ ID NO: 4) |
| Mannitol (mM) | 112 | 112 | 150 | 150 | 154 | 176 |
| Phosphate buffer (mM) | 2 | 2 | 2 | 2 | 2 | 2 |
| pH | 7.4 | 7.4 | 7.4 | 7.4 | 7.4 | 7.4 |
| $T_{50\%}$ (hrs) | 10.2 | 10.3 | >22 | 20.2 | 14.8 | biphasic |

ANALYTICAL METHODS

Assays to quantify the binding affinity of ligands to the metal site of the insulin $R_6$ hexamers:

4H3N-Assay:

The binding affinity of ligands to the metal site of insulin $R_6$ hexamers are measured in a UV/vis based displacement assay. The UV/vis spectrum of 3-hydroxy-4-nitro benzoic acid (4H3N) which is a known ligand for the metal site of insulin $R_6$ shows a shift in absorption maximum upon displacement from the metal site to the solution (Huang et al., 1997, Bio-chemistry 36, 9878-9888). Titration of a ligand to a solution of insulin $R_6$ hexamers with 4H3N mounted in the metal site allows the binding affinity of these ligands to be determined following the reduction of absorption at 444 nm.

A stock solution with the following composition 0.2 mM human insulin, 0.067 mM Zn-acetate, 40 mM phenol, 0.101 mM 4H3N is prepared in a 10 mL quantum as described below. Buffer is always 50 mM tris buffer adjusted to pH=8.0 with NaOH/$ClO_4^-$.

1000 μL of 2.1 mM human insulin in buffer
66.7 μL of 10 mM Zn-acetate in buffer
800 μL of 500 mM phenol in $H_2O$
201 μL of 4H3N in $H_2O$
7.93 ml buffer The ligand is dissolved in DMSO to a concentration of 20 mM.

The ligand solution is titrated to a cuvette containing 2 mL stock solution and after each addition the UV/vis spectrum is measured. The titration points are listed in Table 3 below.

The UV/vis spectra resulting from a titration of the compound 3-hydroxy-2-naphthoic acid is shown in FIG. 5. Inserted in the upper right corner is the absorbance at 444 nm vs. the concentration of ligand.

The following equation is fitted to these datapoints to determine the two parameters $K_D$ (obs), the observed dissociation constant, and $abs_{max}$ the absorbance at maximal ligand concentration.

$$abs([ligand]_{free}) = (abs_{max} * [ligand]_{free})/(K_D(obs) + [ligand]_{free})$$

The observed dissociation constant is recalculated to obtain the apparent dissociation constant $$K_D(app) = K_D(obs)/(1 + [4H3N]/K_{4H3N})$$

The value of $K_{4H3N} = 50$ μM is taken from Huang et al., 1997, Biochemistry 36, 9878-9888.

TZD-Assay:

The binding affinity of ligands to the metal site of insulin R6 hexamers are measured in a fluorescense based displacement assay. The fluorescence of 5-(4-dimethylaminobenzylidene)thiazolidine-2,4-dione (TZD) which is a ligand for the metal site of insulin $R_6$ is quenched upon displacement from the metal site to the solution. Titration of a ligand to a stock solution of insulin $R_6$ hexamers with this compound mounted in the metal site allows the binding affinity of these ligands to be determined measuring the fluorescence at 455 nm upon excitation at 410 nm.

Preparation

Stock solution: 0.02 mM human insulin, 0.007 mM Zn-acetate, 40 mM phenol, 0.01 mM TZD in 50 mM tris buffer adjusted to pH=8.0 with NaOH/ClO$_4^-$. The ligand is dissolved in DMSO to a concentration of 5 mM and added in aliquots to the stock solution to final concentrations of 0-250 mM.

Measurements

Fluorescence measurements were carried out on a Perkin Elmer Spectrofluorometer LS50B. The main absorption band was excited at 410 nm and emission was detected at 455 nm. The resolution was 10 nm and 2.5 nm for excitation and emission, respectively.

Data Analysis

This equation is fitted to the datapoints $$\Delta F(455\ \text{nm}) = \Delta F_{max} * [\text{ligand}]_{free}/(K_D(\text{app})*(1+[TZD]/K_{TZD}) + [\text{ligand}]_{free}))$$

$K_D(\text{app})$ is the apparent dissociation constant and $F_{max}$ is the fluorescence at maximal ligand concentration. The value of $K_{TZD}$ is measured separately to 230 nM Two different fitting-procedures can be used. One in which both parameters, $K_D(\text{app})$ and $F_{max}$, are adjusted to best fit the data and a second in which the value of $F_{max}$ is fixed ($F_{max}=1$) and only $K_D(\text{app})$ is adjusted. The given data are from the second fitting procedure. The Solver module of Microsoft Excel can be used to generate the fits from the datapoints.

---

The invention claimed is:
1. A zinc-binding ligand of the following formula (III)

A-B-C-D-X  (III)

wherein:
A is a chemical group of the following formula which reversibly binds to a $His^{B10}$ $Zn^{2+}$ site of an insulin hexamer;

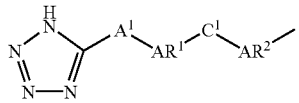

wherein $A^1$ is a valence bond;
$AR^1$ is the group

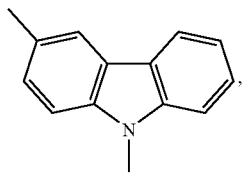

where C1 is attached to the nitrogen;
$C^1$ is CH2;
$AR^2$ is phenyl;
B is a linker selected from the group consisting of
  A valence bond and
  A chemical group $G^B$ of the formula —$B^1$—$B^2$—C(O)—, —$B^1$—$B^2$—$SO_2$—, —$B^1$—$B^2$—$CH_2$—, or —$B^1$—$B^2$—NH—; wherein $B^1$ is a valence bond, —O—, —S—, or —$NR^6$—,
  $B^2$ is a valence bond, $C_1$-$C_{18}$-alkylene, $C_2$-$C_{18}$-alkenylene, $C_2$-$C_{18}$-alkynylene, arylene, heteroarylene, —$C_1$-$C_{18}$-alkyl-aryl-, —$C_2$-$C_{18}$-alkenyl-aryl-, —$C_2$-$C_{18}$-alkynyl-aryl-, —C(=O)—$C_1$-$C_{18}$-alkyl-C(=O)—, —C(=O)—$C_1$-$C_{18}$-alkenyl-C(=O)—, —C(=O)—$C_1$-$C_{18}$-alkyl-O—$C_1$-$C_{18}$-alkyl-C(=O)—, —C(=O)—$C_1$-$C_{18}$-alkyl-S—$C_1$-$C_{18}$-alkyl-C(=O)—, —C(=O)—$C_1$-$C_{18}$-alkyl-$NR^6$—$C_1$-$C_{18}$-alkyl-C(=O)—, —C(=O)-aryl-C(=O)—, —C(=O)-heteroaryl-C(=O)—;
  wherein the alkylene, alkenylene, and alkynylene moieties are optionally substituted with —CN, —$CF_3$, —$OCF_3$, —$OR^6$, or —$NR^6R^7$ and the arylene and heteroarylene moieties are optionally substituted with halogen, —C(O)$OR^6$, —C(O)H, $OCOR^6$, —$SO_2$, —CN, —$CF_3$, —$OCF_3$, —$NO_2$, —$OR^6$, —$NR^6R^7$, $C_1$-$C_{18}$-alkyl, or $C_1$-$C_{18}$-alkanoyl;
  $R^6$ and $R^7$ are independently H, $C_1$-$C_4$-alkyl;
C is a fragment consisting of 0 to 5 neutral amino acids, wherein the individual neutral amino acids are the same or different
D is a fragment consisting of 1 to 20 basic amino acids independently selected from the group consisting of Lys and Arg or D-isomers thereof; and
X is —OH, —$NH_2$ or a diamino group,
or a salt thereof with a pharmaceutically acceptable acid or base, or any optical isomer or mixture of optical isomers, racemic mixture, or tautomeric forms thereof.

2. A zinc-binding ligand according to claim 1 wherein $A^1$ is a valence bond, $C_1$-$C_6$-alkylene, —NH—C(=O)-$A^2$-, —$C_1$-$C_6$-alkyl-S—, —$C_1$-$C_6$-alkyl-O—, or —C(=O)—, wherein any $C_1$-$C_6$-alkyl moiety is optionally substituted by $R^{1A}$.

3. A zinc-binding ligand according to claim 2 wherein $A^1$ is a valence bond, $C_1$-$C_6$-alkylene, —NH—C(=O)-$A^2$-, —$C_1$-$C_6$-alkyl-S—, or —$C_1$-$C_6$-alkyl-O, wherein any $C_1$-$C_6$-alkyl moiety is optionally substituted by $R^{1A}$.

4. A zinc-binding ligand according to claim 3 wherein $A^1$ is a valence bond, $C_1$-$C_6$-alkylene, or —NH—C(=O)-$A^2$, wherein any $C_1$-$C_6$-alkyl moiety is optionally substituted by $R^{1A}$.

5. A zinc-binding ligand according to claim 4 wherein $A^1$ is a valence bond or $C_1$-$C_6$-alkylene, wherein any $C_1$-$C_6$-alkyl moiety is optionally substituted by $R^{1A}$.

6. A zinc-binding ligand according to claim 5 wherein $A^1$ is a valence bond.

7. A zinc-binding ligand according to claim 1 wherein $A^2$ is a valence bond or —$C_1$-$C_6$-alkyl-O—.

8. A zinc-binding ligand according to claim 7 wherein $A^2$ is a valence bond.

9. A zinc-binding ligand according to claim 1 wherein $AR^1$ is arylene or heteroarylene, wherein the aryl or heteroaryl moieties are optionally substituted by one or more $R^{1B}$ independently.

10. A zinc-binding ligand according to claim 9 wherein $AR^1$ is selected from the group of compounds consisting of phenylene, biphenylylene, naphthylene, anthra-cenylene, phenanthrenylene, fluorenylene, indenylene, azulenylene, furylene, thienylene, pyrrolylene, oxazolylene, thiazolylene, imidazolylene, isoxazolylene, isothiazolylene, 1,2,3-triazolylene, 1,2,4-triazolylene, pyranylene, pyridylene, pyridazinylene, pyrimidinylene, pyrazinylene, 1,2,3-triazinylene, 1,2,4-triazinylene, 1,3,5-triazinylene, 1,2,3-oxadiazolylene, 1,2,4-oxadiazolylene, 1,2,5-oxadiazolylene, 1,3,4-oxadiazolylene, 1,2,3-thiadiazolylene, 1,2,4-thiadiazolylene, 1,2,5-thiadiazolylene, 1,3,4-thiadiazolylene, tetrazolylene, thiadiazinylene, indolylene, isoindolylene, benzofurylene, benzothienylene, indazolylene, benzimidazolylene, benzthiazolylene, benzisothiazolylene, benzoxazolylene, benzisoxazolylene, purinylene, quinazolinylene, quinolizinylene, quinolinylene, isoquinolinylene, quinoxalinylene, naphthyridinylene, pteridinylene, carbazolylene, azepinylene, diazepinylene, and acridinylene, optionally substituted by one or more $R^{1B}$ independently.

11. A zinc-binding ligand according to claim 10 wherein $AR^1$ is selected from the group of compounds consisting of phenylene, biphenylylene, naphthylene, pyridinylene, fyrylene, indolylene and carbazolylene, optionally substituted by one or more $R^{1B}$ independently.

12. A zinc-binding ligand according to claim 11 wherein $AR^1$ is selected from the group of compounds consisting of phenylene, indolylene and carbazolylene, optionally substituted by one or more $R^{1B}$ independently.

13. A zinc-binding ligand according to claim 12 wherein $AR^1$ is phenylene optionally substituted by one or more $R^{1B}$ independently.

14. A zinc-binding ligand according to claim 12 wherein $AR^1$ is indolylene optionally substituted by one or more $R^{1B}$ independently.

15. A zinc-binding ligand according to claim 14 wherein AR$^1$ is

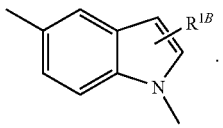

16. A zinc-binding ligand according to claim 12 wherein AR$^1$ is carbazolylene optionally substituted by one or more R$^{1B}$ independently.

17. A zinc-binding ligand according to claim 16 wherein AR$^1$ is

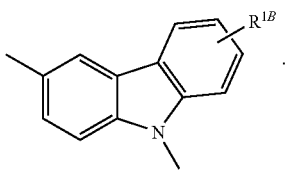

18. A zinc-binding ligand according to claim 1 wherein R$^{1B}$ is selected from the group consisting of
hydrogen, halogen, —CN, —CF$_3$, —OCF$_3$, —NO$_2$, —OR$^{1C}$, —NR$^{1C}$R$^{1D}$, —SR$^{1C}$, —S(O)$_2$R$^{1C}$, —NR$^{1C}$C(O)R$^{1D}$, —OC$_1$-C$_6$-alkyl-C(O)NR$^{1C}$R$^{1D}$, —C$_2$-C$_6$-alkenyl-C(=O)OR$^{1C}$, —C(O)OR$^{1C}$, =O, —NH—C(=O)—O—C$_1$-C$_6$-alkyl, or —NH—C(=O)—C(=O)—O—C$_1$-C$_6$-alkyl
C$_1$-C$_6$-alkyl or C$_2$-C$_6$-alkenyl
which is optionally substituted with one or more substituents selected from the group consisting of halogen, —CN, —CF$_3$, —OCF$_3$, —OR$^{1C}$, and —NR$^{1C}$R$^{1D}$ and
aryl, aryloxy, aryl-C$_1$-C$_6$-alkoxy, aryl-C$_1$-C$_6$-alkyl, aryl-C$_2$-C$_6$-alkenyl, heteroaryl, heteroaryl-C$_1$-C$_6$-alkyl, or heteroaryl-C$_2$-C$_6$-alkenyl
of which the cyclic moieties are optionally substituted with one or more substituents selected from halogen, —C(O)OR$^{1C}$, —CN, —CF$_3$, —OCF$_3$, —NO$_2$, —OR$^{1C}$, —NR$^{1C}$R$^{1D}$ and C$_1$-C$_6$-alkyl.

19. A zinc-binding ligand according to claim 18 wherein R$^{1B}$ is selected from the group consisting of
hydrogen, halogen, —CF$_3$, —NO$_2$, —OR$^{1C}$, —NR$^{1C}$R$^{1D}$, —C(O)OR$^{1C}$, =O, —NH—C(=O)—O—C$_1$-C$_6$-alkyl, or —NH—C(=O)—C(=O)—O—C$_1$-C$_6$-alkyl and
C$_1$-C$_6$-alkyl.

20. A zinc-binding ligand according to claim 1 wherein R$^{1C}$ and R$^{1D}$ independently are hydrogen, C$_1$-C$_6$-alkyl, or aryl, wherein the aryl moieties may optionally be substituted by halogen or —COOH.

21. A zinc-binding ligand according to claim 20 wherein R$^{1C}$ and R$^{1D}$ independently are hydrogen, methyl, ethyl, or phenyl, wherein the phenyl moieties may optionally be substituted by halogen or —COOH.

22. A zinc-binding ligand according to claim 1 wherein C$^1$ is a valence bond, C$_1$-C$_6$-alkylene, —NH—C(=O)—, —C(=O)—NH—, —C(=O)—, or —C$_1$-C$_6$-alkyl-C(=O)—N(R$^{1E}$)— wherein the alkyl moieties are optionally substituted by one or more R$^{1F}$ independently.

23. A zinc-binding ligand according to claim 22 wherein C$^1$ is a valence bond, —CH$_2$—, —CH$_2$—CH$_2$—, —CH$_2$—O—, —CH$_2$—CH$_2$—O—, —CH$_2$—NH—, —CH$_2$—CH$_2$—NH—, —NH—CH$_2$—, —NH—CH$_2$—CH$_2$—, —NH—C(=O)—, —C(=O)—NH—, —O—CH$_2$—, —O—CH$_2$—CH$_2$—, or —C(=O)—.

24. A zinc-binding ligand according to claim 1 wherein R$^{1E}$ and R$^{1F}$ are independently selected from C$_1$-C$_6$-alkyl.

25. A zinc-binding ligand according to claim 1 wherein AR$^2$ is
a valence bond
C$_1$-C$_6$-alkylene, wherein the alkyl is optionally substituted by one or more R$^{2A}$ independently
arylene, aryl-C$_1$-C$_6$-alkyl, heteroarylene, wherein the arylene and heteroarylene moieties are optionally substituted by one or more R$^{2A}$ independently.

26. A zinc-binding ligand according to claim 25 wherein AR$^2$ is
a valence bond
C$_1$-C$_6$-alkylene, wherein the alkyl is optionally substituted by one or more R$^{2A}$ independently
phenyl, phenyl-C$_1$-C$_6$-alkyl, wherein the phenyl moieties are optionally substituted by one or more R$^{2A}$ independently.

27. A zinc-binding ligand according to claim 1 wherein R$^{2A}$ is C$_1$-C$_6$-alkyl, C$_1$-C$_6$-alkoxy, aryl, aryloxy, heteroaryl, —C$_1$-C$_6$-alkyl-COOH, —O—C$_1$-C$_6$-alkyl-COOH, —S(O)$_2$R$^{2B}$, —C$_2$-C$_6$-alkenyl-COOH, —OR$^{2B}$, —NO$_2$, halogen, —COOH, —CF$_3$, —CN, —N(R$^{2B}$R$^{2C}$), wherein the aryl or heteroaryl moieties are optionally substituted by one or more C$_1$-C$_6$-alkyl, C$_1$-C$_6$-alkoxy, —C$_1$-C$_6$-alkyl-COOH, —C$_2$-C$_6$-alkenyl-COOH, —OR$^{2B}$, —NO$_2$, halogen, —COOH, —CF$_3$, —CN, or —N(R$^{2B}$R$^{2C}$).

28. A zinc-binding ligand according to claim 27 wherein R$^{2A}$ is C$_1$-C$_6$-alkyl, C$_1$-C$_6$-alkoxy, aryl, —OR$^{2B}$, —NO$_2$, halogen, —COOH, —CF$_3$, —CN, —N(R$^{2B}$R$^{2C}$), wherein the aryl is optionally substituted by one or more C$_1$-C$_6$-alkyl, C$_1$-C$_6$-alkoxy, —OR$^{2B}$, —NO$_2$, halogen, —COOH, —CF$_3$, —CN, or —N(R$^{2B}$R$^{2C}$).

29. A zinc-binding ligand according to claim 28 wherein R$^{2A}$ is C$_1$-C$_6$-alkyl, C$_1$-C$_6$-alkoxy, aryl, halogen, —CF$_3$, wherein the aryl is optionally substituted by one or more C$_1$-C$_6$-alkyl, halogen, —COOH, —CF$_3$, or —CN.

30. A zinc-binding ligand according to claim 29 wherein R$^{2A}$ is C$_1$-C$_6$-alkyl, C$_1$-C$_6$-alkoxy, phenyl, halogen, —CF$_3$, wherein the phenyl is optionally substituted by one or more C$_1$-C$_6$-alkyl, halogen, —COOH, —CF$_3$, or —CN.

31. A zinc-binding ligand according to claim 1, wherein G$^B$ is of the formula B$^1$—B$^2$—C(O)—, B$^1$—B$^2$—SO$_2$— or —B$^1$—B$^2$—CH$_2$—.

32. A zinc-binding ligand according to claim 1, wherein G$^B$ is of the formula B$^1$—B$^2$—C(O)—, B$^1$—B$^2$—SO$_2$— or B$^1$—B$^2$—NH—.

33. A zinc-binding ligand according to claim 1, wherein G$^B$ is of the formula B$^1$—B$^2$—C(O)—, —B$^1$—B$^2$—CH$_2$— or B$^1$—B$^2$—NH.

34. A zinc-binding ligand according to claim 31, wherein G$^B$ is of the formula B$^1$—B$^2$—C(O)— or B$^1$—B$^2$—SO$_2$.

35. A zinc-binding ligand according to claim 31, wherein G$^B$ is of the formula B$^1$—B$^2$—C(O)— or —B$^1$—B$^2$—CH$_2$—.

36. A zinc-binding ligand according to claim 32 wherein G$^B$ is of the formula B$^1$—B$^2$—C(O)— or B$^1$—B$^2$—NH—.

37. A zinc-binding ligand according to claim 34, wherein G$^B$ is of the formula B$^1$—B$^2$—C(O)—.

38. A zinc-binding ligand according to claim 1 wherein B$^1$ is a valence bond, —O—, or —S—.

39. A zinc-binding ligand according to claim 1 wherein B$^1$ is a valence bond, —O—, or —N(R$^6$)—.

40. A zinc-binding ligand according to claim 1 wherein $B^1$ is a valence bond, —S—, or —N($R^6$)—.

41. A zinc-binding ligand according to claim 1 wherein $B^1$ is —O—, —S— or —N($R^6$)—.

42. A zinc-binding ligand according to claim 38 wherein $B^1$ is a valence bond or —O—.

43. A zinc-binding ligand according to claim 38 wherein $B^1$ is —O— or —S—.

44. A zinc-binding ligand according to claim 39 wherein $B^1$ is —O— or —N($R^6$)—.

45. A zinc-binding ligand according to claim 42, wherein $B^1$ is —O—.

46. A zinc-binding ligand according to claim 1, wherein $B^2$ is a valence bond, $C_1$-$C_{18}$-alkylene, $C_2$-$C_{18}$-alkenylene, $C_2$-$C_{18}$-alkynylene, arylene, heteroarylene, —$C_1$-$C_{18}$-alkyl-aryl-, —C(=O)—$C_1$-$C_{18}$-alkyl-C(=O)—, —C(=O)—$C_1$-$C_{18}$-alkyl-$NR^6$—$C_1$-$C_{18}$-alkyl-C(=O)—; and the alkylene moieties are optionally substituted with —CN, —$CF_3$, —$OCF_3$, —$OR^6$, or —$NR^6R^7$ and the arylene moieties are optionally substituted with halogen, —C(O)$OR^6$, —C(O)H, $OCOR^6$, —$SO_2$, —CN, —$CF_3$, —$OCF_3$, —$NO_2$, —$OR^6$, —$NR^6R^7$, $C_1$-$C_{18}$-alkyl, or $C_1$-$C_{18}$-alkanoyl.

47. A zinc-binding ligand according to claim 46, wherein $B^2$ is a valence bond, $C_1$-$C_{18}$-alkylene, $C_2$-$C_{18}$-alkenylene, $C_2$-$C_{18}$-alkynylene, arylene, heteroarylene, —$C_1$-$C_{18}$-alkyl-aryl-, —C(=O)—$C_1$-$C_{18}$-alkyl-C(=O)—, —C(=O)—$C_1$-$C_{18}$-alkyl-O—$C_1$-$C_{18}$-alkyl-C(=O)—, and the alkylene moieties are optionally substituted with —CN, —$CF_3$, —$OCF_3$, —$OR^6$, or —$NR^6R^7$ and the arylene moieties are optionally substituted with halogen, —C(O)$OR^6$, —C(O)H, $OCOR^6$, —$SO^2$, —CN, —$CF_3$, —$OCF_3$, —$NO_2$, —$OR^6$, —$NR^6R^7$, $C_1$-$C_{18}$-alkyl, or $C_1$-$C_{18}$-alkanoyl.

48. A zinc-binding ligand according to claim 47, wherein $B^2$ is a valence bond, $C_1$-$C_{18}$-alkylene, $C_2$-$C_{18}$-alkenylene, $C_2$-$C_{18}$-alkynylene, arylene, heteroarylene, —$C_1$-$C_{18}$-alkyl-aryl-, —C(=O)—$C_1$-$C_{18}$-alkyl-C(=O)—, and the alkylene moieties are optionally substituted with —CN, —$CF_3$, —$OCF_3$, —$OR^6$, or —$NR^6R^7$ and the arylene moieties are optionally substituted with halogen, —C(O)$OR^6$, —C(O)H, $OCOR^6$, —$SO_2$, —CN, —$CF_3$, —$OCF_3$, —$NO_2$, —$OR^6$, —$NR^6R^7$, $C_1$-$C_{18}$-alkyl, or $C_1$-$C_{18}$-alkanoyl.

49. A zinc-binding ligand according to claim 48, wherein $B^2$ is a valence bond, $C_1$-$C_{18}$-alkylene, arylene, heteroarylene, —$C_1$-$C_{18}$-alkyl-aryl-, —C(=O)—$C_1$-$C_{18}$-alkyl-C(=O)—, and the alkylene moieties are optionally substituted with —CN, —$CF_3$, —$OCF_3$, —$OR^6$, or —$NR^6R^7$ and the arylene moieties are optionally substituted with halogen, —C(O)$OR^6$, —C(O)H, $OCOR^6$, —$SO_2$, —CN, —$CF_3$, —$OCF_3$, —$NO_2$, —$OR^6$, —$NR^6R^7$, $C_1$-$C_{18}$-alkyl, or $C_1$-$C_{18}$-alkanoyl.

50. A zinc-binding ligand according to claim 49 wherein $B^2$ is a valence bond, $C_1$-$C_{18}$-alkylene, arylene, heteroarylene, —$C_1$-$C_{18}$-alkyl-aryl-, and the alkylene moieties are optionally substituted with —CN, —$CF_3$, —$OCF_3$, —$OR^6$, or —$NR^6R^7$ and the arylene moieties are optionally substituted with halogen, —C(O)$OR^6$, —C(O)H, $OCOR^6$, —$SO_2$, —CN, —$CF_3$, —$OCF_3$, —$NO_2$, —$OR^6$, —$NR^6R^7$, $C_1$-$C_{18}$-alkyl, or $C_1$-$C_{18}$-alkanoyl.

51. A zinc-binding ligand according to claim 50, wherein $B^2$ is a valence bond, $C_1$-$C_{18}$-alkylene, arylene, —$C_1$-$C_{18}$-alkyl-aryl-, and the alkylene moieties are optionally substituted with —CN, —$CF_3$, —$OCF_3$, —$OR^6$, or —$NR^6R^7$ and the arylene moieties are optionally substituted with halogen, —C(O)$OR^6$, —C(O)H, $OCOR^6$, —$SO_2$, —CN, —$CF_3$, —$OCF_3$, —$NO_2$, —$OR^6$, —$NR^6R^7$, $C_1$-$C_{18}$-alkyl, or $C_1$-$C_{18}$-alkanoyl.

52. A zinc-binding ligand according to claim 51, wherein $B^2$ is a valence bond or —$C_1$-$C_{18}$-alkylene, and the alkylene moieties are optionally substituted moieties are optionally substituted with —CN, —$CF_3$, —$OCF_3$, —$OR^6$, or —$NR^6R^7$ and the arylene moieties are optionally substituted with halogen, —C(O)$OR^6$, —C(O)H, $OCOR^6$, —$SO_2$, —CN, —$CF_3$, —$OCF_3$, —$NO_2$, —$OR^6$, —$NR^6R^7$, $C_1$-$C_{18}$-alkyl, or $C_1$-$C_{18}$-alkanoyl.

53. A zinc-binding ligand according to claim 1, wherein C consists of 0 to 5 neutral amino acids independently selected from the group consisting of Abz, Gly, Ala, Thr, and Ser.

54. A zinc-binding ligand according to claim 53, wherein C consists of 0 to 5 Gly.

55. A zinc-binding ligand according to claim 54, wherein C consists of 1 Gly.

56. A zinc-binding ligand according to claim 54, wherein C consists of 2 Gly.

57. A zinc-binding ligand according to claim 54, wherein C consists of 3 Gly.

58. A zinc-binding ligand according to claim 54 wherein C consists of 4 Gly.

59. A zinc-binding ligand according to claim 54, wherein C consists of 5 Gly.

60. A zinc-binding ligand according to claim 1, wherein the positively charged groups of D number from 1 to 16.

61. A zinc-binding ligand according to claim 60, wherein the positively charged groups of D number from 1 to 12.

62. A zinc-binding ligand according to claim 61, wherein the positively charged groups of D number from 1 to 10.

63. A zinc-binding ligand according to claim 1, wherein the basic amino acid is Arg.

64. A zinc-binding ligand according to claim 1, wherein X is —OH or —$NH_2$.

65. A zinc-binding ligand according to claim 64, wherein X is —$NH_2$.

66. Method of prolonging the action of an insulin preparation which comprises adding a zinc-binding ligand according to claim 1 to the insulin preparation.

67. A method of preparing a zinc-binding ligand according to claim 1 comprising the steps of
Identifying starter compounds that are able to displace a ligand from the R-state $His^{B10}$-$Zn^{2+}$ site
optionally attaching a fragment consisting of 0 to 5 neutral α- or β-amino acids attaching a fragment comprising 1 to 20 positively charged groups independently selected from amino or guanidino groups.

* * * * *

UNITED STATES PATENT AND TRADEMARK OFFICE
CERTIFICATE OF CORRECTION

PATENT NO. : 7,879,893 B2  
APPLICATION NO. : 10/332541  
DATED : February 1, 2011  
INVENTOR(S) : Olsen et al.

Page 1 of 1

It is certified that error appears in the above-identified patent and that said Letters Patent is hereby corrected as shown below:

Column 323, Claim 22, Line 61: after "alkylene," please insert the following:
-- -$C_1$-$C_6$-alkyl-O-, -$C_1$-$C_6$-alkyl-NH-, -NH-$C_1$-$C_6$-alkyl, --

Signed and Sealed this
Ninth Day of August, 2011

David J. Kappos
*Director of the United States Patent and Trademark Office*